(12) United States Patent
Kang et al.

(10) Patent No.: US 12,122,777 B2
(45) Date of Patent: Oct. 22, 2024

(54) COMPOUND FOR ORGANIC OPTOELECTRONIC DEVICE, COMPOSITION FOR ORGANIC OPTOELECTRONIC DEVICE, ORGANIC OPTOELECTRONIC DEVICE, AND DISPLAY DEVICE

(71) Applicants: SAMSUNG SDI CO., LTD., Yongin-si (KR); SAMSUNG ELECTRONICS CO., LTD., Suwon-si (KR)

(72) Inventors: Dong Min Kang, Suwon-si (KR); Chang Ju Shin, Suwon-si (KR); Jun Seok Kim, Suwon-si (KR); Hyunjung Kim, Suwon-si (KR); Jongwoo Won, Suwon-si (KR); Byoungkwan Lee, Suwon-si (KR); Sangshin Lee, Suwon-si (KR); Sung-Hyun Jung, Suwon-si (KR); Ho Kuk Jung, Suwon-si (KR); Pyeongseok Cho, Suwon-si (KR)

(73) Assignees: Samsung SDI Co., Ltd., Yongin-si (KR); Samsung Electronics Co., Ltd., Suwon-Si (KR)

( * ) Notice: Subject to any disclaimer, the term of this patent is extended or adjusted under 35 U.S.C. 154(b) by 939 days.

(21) Appl. No.: 16/972,663

(22) PCT Filed: Mar. 11, 2019

(86) PCT No.: PCT/KR2019/002807
§ 371 (c)(1),
(2) Date: Dec. 7, 2020

(87) PCT Pub. No.: WO2019/235725
PCT Pub. Date: Dec. 12, 2019

(65) Prior Publication Data
US 2021/0269445 A1    Sep. 2, 2021

(30) Foreign Application Priority Data

Jun. 8, 2018 (KR) .................. 10-2018-0066251

(51) Int. Cl.
*H01L 51/50* (2006.01)
*C07D 487/00* (2006.01)
(Continued)

(52) U.S. Cl.
CPC ......... *C07D 487/00* (2013.01); *C07D 493/00* (2013.01); *C07D 495/00* (2013.01);
(Continued)

(58) Field of Classification Search
None
See application file for complete search history.

(56) References Cited

U.S. PATENT DOCUMENTS

2004/0164292 A1* 8/2004 Tung et al. ............. H01L 35/24
2014/0117331 A1* 5/2014 Kim et al. .............. H10L 51/00
(Continued)

FOREIGN PATENT DOCUMENTS

CN    103804333 A    5/2014
CN    106029831 A    10/2016
(Continued)

OTHER PUBLICATIONS

International Search Report dated Jun. 20, 2019 for PCT/KR2019/002807.
(Continued)

*Primary Examiner* — Gregory D Clark
(74) *Attorney, Agent, or Firm* — Lee IP Law, P.C.

(57) ABSTRACT

The present invention relates to a compound for an organic optoelectronic device, represented by Chemical Formula 1; a composition for an organic optoelectronic device, including same; an organic optoelectronic device; and a display
(Continued)

device. The description of Chemical Formula 1 is the same as that defined in the specification.

19 Claims, 1 Drawing Sheet

(51) Int. Cl.
  *C07D 493/00* (2006.01)
  *C07D 495/00* (2006.01)
  *H10K 85/60* (2023.01)
  *H10K 50/11* (2023.01)
  *H10K 50/15* (2023.01)
(52) U.S. Cl.
  CPC ......... *H10K 85/623* (2023.02); *H10K 85/636* (2023.02); *H10K 85/6572* (2023.02); *H10K 85/6574* (2023.02); *H10K 85/6576* (2023.02); *H10K 50/11* (2023.02); *H10K 50/15* (2023.02)

(56) References Cited

U.S. PATENT DOCUMENTS

| | | |
|---|---|---|
| 2014/0225073 A1 | 8/2014 | Lee et al. |
| 2017/0317293 A1 | 11/2017 | Kim et al. |
| 2017/0373255 A1 | 12/2017 | Lee et al. |

FOREIGN PATENT DOCUMENTS

| | | | | |
|---|---|---|---|---|
| CN | 107337650 A | 11/2017 | | |
| CN | 107540620 A | 1/2018 | | |
| KR | 10-2012-0116881 A | 10/2012 | | |
| KR | 10-2012-0122897 A | 11/2012 | | |
| KR | 10-2014-0057439 A | 5/2014 | | |
| KR | 10-2014-0101224 A | 8/2014 | | |
| KR | 10-2014-0101225 | * 8/2014 | ............. | H10K 50/00 |
| KR | 10-2014-0101225 A | 8/2014 | | |
| KR | 10-2014-0102089 A | 8/2014 | | |
| KR | 10-2016-0055375 A | 5/2016 | | |
| KR | 10-2017-0086211 A | 7/2017 | | |

OTHER PUBLICATIONS

Chinese Office Action (including a search report) dated Mar. 15, 2024, of the corresponding Chinese Patent Application No. 201980044883.7.

* cited by examiner

【Figure 1】
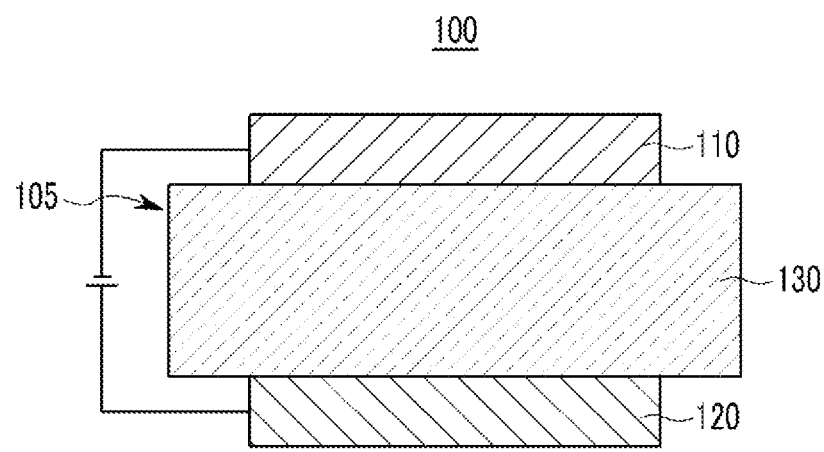
【Figure 2】
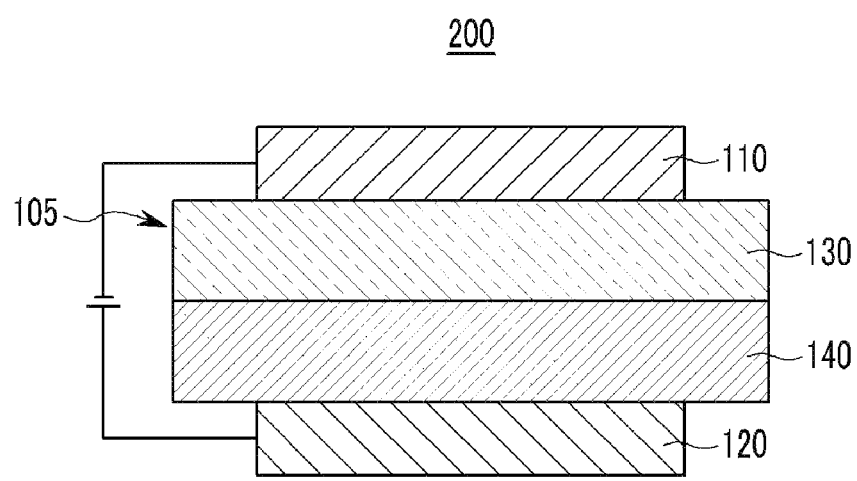

COMPOUND FOR ORGANIC OPTOELECTRONIC DEVICE, COMPOSITION FOR ORGANIC OPTOELECTRONIC DEVICE, ORGANIC OPTOELECTRONIC DEVICE, AND DISPLAY DEVICE

CROSS REFERENCE TO RELATED APPLICATIONS

This is the U.S. national phase application for PCT/KR2019/002807, filed Mar. 11, 2019, which is based on Korean Patent Application No. 10-2018-0066251, filed Jun. 8, 2018, the entire contents of all of which are hereby incorporated by reference.

TECHNICAL FIELD

A compound for an organic optoelectronic device, a composition for an organic optoelectronic device, an organic optoelectronic device, and a display device are disclosed.

BACKGROUND ART

An organic optoelectronic device (organic optoelectronic diode) is a device capable of converting electrical energy and optical energy to each other.

Organic optoelectronic devices may be largely divided into two types according to a principle of operation. One is a photoelectric device that generates electrical energy by separating excitons formed by light energy into electrons and holes, and transferring the electrons and holes to different electrodes, respectively and the other is light emitting device that generates light energy from electrical energy by supplying voltage or current to the electrodes.

Examples of the organic optoelectronic device include an organic photoelectric element, an organic light emitting diode, an organic solar cell, and an organic photo conductor drum.

Among them, organic light emitting diodes (OLEDs) are attracting much attention in recent years due to increasing demands for flat panel display devices. The organic light emitting diode is a device that converts electrical energy into light, and the performance of the organic light emitting diode is greatly influenced by an organic material between electrodes.

DISCLOSURE

Technical Problem

An embodiment provides a compound for an organic optoelectronic device capable of implementing a high efficiency and long life-span organic optoelectronic device.

Another embodiment provides a composition for an organic optoelectronic device including the compound.

Another embodiment provides an organic optoelectronic device including the compound for an organic optoelectronic device or the composition for an organic optoelectronic device.

Another embodiment provides a display device including the organic optoelectronic device.

Technical Solution

According to an embodiment, a compound for an organic optoelectronic device represented by Chemical Formula 1 is provided.

[Chemical Formula 1]

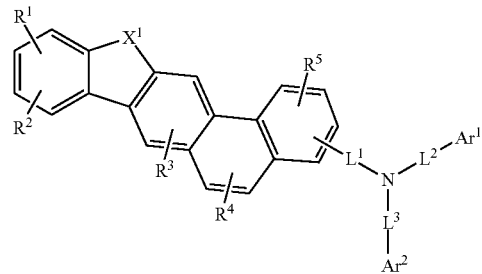

In Chemical Formula 1, $X^1$ is O, S, or $NR^a$, $L^1$ to $L^3$ are independently a single bond, a substituted or unsubstituted C6 to C30 arylene group, a substituted or unsubstituted C2 to C20 heterocyclic group, or a combination thereof, $R^a$ and $R^1$ to $R^3$ are independently hydrogen, deuterium, a cyano group, a substituted or unsubstituted C1 to C30 alkyl group, a substituted or unsubstituted C6 to C30 aryl group, or a combination thereof, and $Ar^1$ and $Ar^2$ are independently a substituted or unsubstituted C6 to C30 aryl group, a substituted or unsubstituted C2 to C30 heterocyclic group, a substituted or unsubstituted C6 to C30 arylamine group, or a combination thereof.

According to another embodiment, a composition for an organic optoelectronic device includes the aforementioned compound for an organic optoelectronic device and a second compound for an organic optoelectronic device represented by Chemical Formula 2.

[Chemical Formula 2]

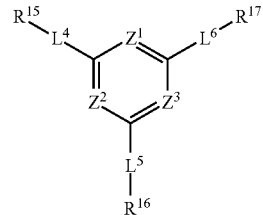

In Chemical Formula 2, $Z^1$ to $Z^3$ are independently N or $C\text{-}L^a\text{-}R^e$, at least two of $Z^1$ to $Z^3$ are N, $L^a$ and $L^4$ to $L^6$ are independently a single bond, a substituted or unsubstituted C6 to C30 arylene group, a substituted or unsubstituted C2 to C30 heterocyclic group, or a combination thereof, $R^e$ and $R^{15}$ to $R^{17}$ are independently hydrogen, deuterium, a cyano group, a substituted or unsubstituted C1 to C30 alkyl group, a substituted or unsubstituted C6 to C30 aryl group, a substituted or unsubstituted C2 to C30 heterocyclic group, or a combination thereof, and at least one of $R^{15}$ to $R^{17}$ is a substituted or unsubstituted carbazolyl group, a substituted or unsubstituted dibenzofuranyl group, a substituted or unsubstituted dibenzothiophenyl group, or a substituted or unsubstituted triphenylene group.

According to another embodiment, an organic optoelectronic device includes an anode and a cathode facing each other, and at least one organic layer between the anode and the cathode, and the organic layer includes the compound or the composition.

According to another embodiment, a display device including the organic optoelectronic device is provided.

Advantageous Effects

High efficiency and long life-span organic optoelectronic devices may be implemented.

DESCRIPTION OF THE DRAWINGS

FIGS. 1 and 2 are cross-sectional views each illustrating an organic light emitting diode according to embodiments.

DESCRIPTION OF SYMBOLS

100, 200: organic light emitting diode
105: organic layer
110: cathode
120: anode
130: light emitting layer
140: hole auxiliary layer

MODE FOR INVENTION

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example of the present invention, "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heteroaryl group. In addition, in specific examples of the present invention, "substituted" refers to replacement of at least one hydrogen of a substituent or a compound by deuterium, a C1 to C20 alkyl group, a C6 to C30 aryl group, or C2 to C30 heteroaryl group. In addition, in specific examples of the present invention, "substituted" refers to replacement of at least one hydrogen of a substituent or a compound by deuterium, a C1 to C5 alkyl group, a C6 to C18 aryl group, a pyridinyl group, a quinolinyl group, an isoquinolinyl group, a dibenzofuranyl group, a dibenzothiophenyl group, or a carbazolyl group. In addition, in specific examples of the present invention, "substituted" refers to replacement of at least one hydrogen of a substituent or a compound by deuterium, a C1 to C5 alkyl group, a C6 to C18 aryl group, a dibenzofuranyl group, or a dibenzothiophenyl group. In addition, in specific examples of the present invention, "substituted" refers to replacement of at least one hydrogen of a substituent or a compound by deuterium, a methyl group, an ethyl group, a propyl group, a butyl group, a phenyl group, a biphenyl group, a terphenyl group, a naphthyl group, a triphenylenyl group, a dibenzofuranyl group, or a dibenzothiophenyl group.

In the present specification, when a definition is not otherwise provided, "hetero" refers to one including one to three heteroatoms selected from N, O, S, P, and Si, and remaining carbons in one functional group.

In the present specification, "aryl group" refers to a group including at least one hydrocarbon aromatic moiety, and may include a group in which all elements of the hydrocarbon aromatic moiety have p-orbitals which form conjugation, for example a phenyl group, a naphthyl group, and the like, a group in which two or more hydrocarbon aromatic moieties may be linked by a sigma bond, for example a biphenyl group, a terphenyl group, a quarterphenyl group, and the like, and a group in which two or more hydrocarbon aromatic moieties are fused directly or indirectly to provide a non-aromatic fused ring, for example, a fluorenyl group, and the like. The aryl group may include a monocyclic, polycyclic or fused ring polycyclic (i.e., rings sharing adjacent pairs of carbon atoms) functional group.

In the present specification, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" refers to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

Specific examples of the heterocyclic group may be a pyridinyl group, a pyrimidinyl group, a pyrazinyl group, a pyridazinyl group, a triazinyl group, a quinolinyl group, an isoquinolinyl group, and the like.

More specifically, the substituted or unsubstituted C6 to C30 aryl group and/or a substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylenyl group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, or a substituted or unsubstituted dibenzothiophenyl group, or a combination thereof, but are not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to the highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to the lowest unoccupied molecular orbital (LUMO) level.

Hereinafter, a compound for an organic optoelectronic device according to an embodiment is described.

The compound for an organic optoelectronic device according to an embodiment is represented by Chemical Formula 1.

[Chemical Formula 1]

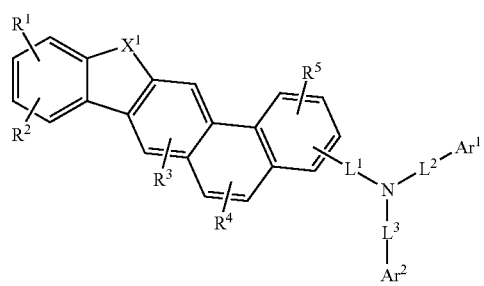

In Chemical Formula 1,
X$^1$ is O, S, or NR$^a$,
L$^1$ to L$^3$ are independently a single bond, a substituted or unsubstituted C6 to C30 arylene group, a substituted or unsubstituted C2 to C20 heterocyclic group, or a combination thereof,
R$^a$ and R$^1$ to R$^3$ are independently hydrogen, deuterium, a cyano group, a substituted or unsubstituted C1 to C30 alkyl group, a substituted or unsubstituted C6 to C30 aryl group, or a combination thereof, and
Ar$^1$ and Ar$^2$ are independently a substituted or unsubstituted C6 to C30 aryl group, a substituted or unsubstituted C2 to C30 heterocyclic group, a substituted or unsubstituted C6 to C30 arylamine group, or a combination thereof.

The compound represented by Chemical Formula 1 has a linear structure in which the 2,3-position of dibenzofuran, dibenzothiophene, or carbazole is further fused. Such a structure may implement a device having high efficiency by increasing a refractive index.

In addition, since the terminal ring to be further fused is substituted with one amine group, a linear structure may be maintained, heat resistance stability may be improved, and a device with an appropriate HOMO energy may be provided, thereby implementing a device with improved lifespan. By maintaining a linear backbone structure, a high Tg may be provided, and when applied to a device, high heat resistance may be provided.

For example, the compound may be represented by any one of Chemical Formula 1-1 to Chemical Formula 1-4, depending on the specific substitution position of the amine group.

[Chemical Formula 1-1]

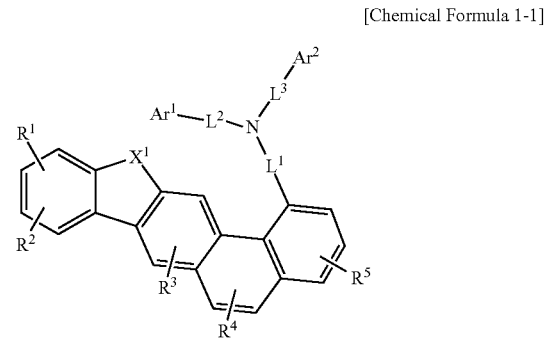

[Chemical Formula 1-2]

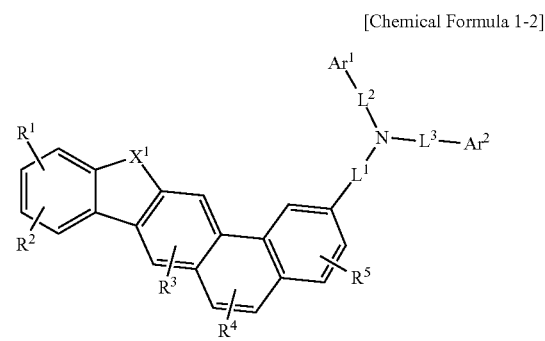

[Chemical Formula 1-3]

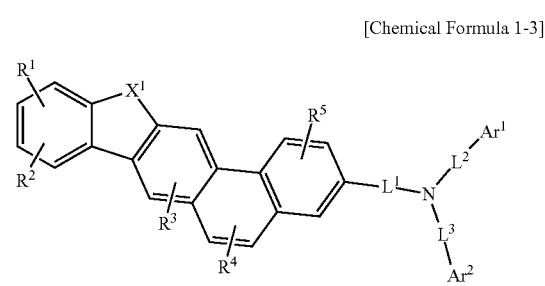

[Chemical Formula 1-4]

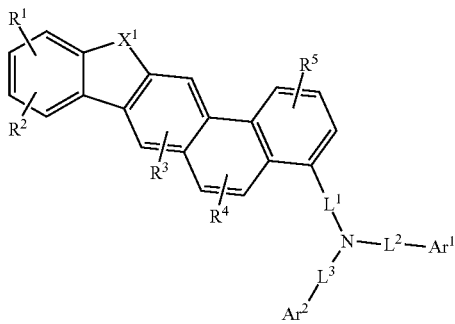

In Chemical Formula 1-1 to Chemical Formula 1-4, $X^1$, $L^1$ to $L^3$, $R^1$ to $R^5$, $Ar^1$ and $Ar^2$ are the same as described above.

According to an embodiment of the present invention, Chemical Formula 1 may be represented by Chemical Formula 1-3.

The compound represented by Chemical Formula 1-3 is the closest to a linear structure and is particularly advantageous in terms of efficiency when applied to a device.

For example, $X^1$ may be O or S.

For example, $X^1$ may be $NR^a$, wherein $R^a$ may be a substituted or unsubstituted C6 to C30 aryl group, specifically $R^a$ may be a substituted or unsubstituted C6 to C20 aryl group, for example, $R^a$ may be a substituted or unsubstituted It may be a phenyl group, a substituted or unsubstituted biphenyl group, or a substituted or unsubstituted naphthyl group.

$L^1$ to $L^3$ may be a single bond or a substituted or unsubstituted C6 to C30 arylene group, and specifically, a single bond or a substituted or unsubstituted C6 to C20 arylene group.

According to an embodiment of the present invention, $L^1$ to $L^3$ may be a single bond or a substituted or unsubstituted phenylene group.

For example, $R^1$ to $R^5$ may independently be hydrogen, deuterium, a cyano group, a substituted or unsubstituted C1 to C10 alkyl group, a substituted or unsubstituted C6 to C20 aryl group, and specifically, $R^1$ to $R^5$ may be hydrogen, deuterium, a cyano group, a substituted or unsubstituted C1 to C10 alkyl group, a substituted or unsubstituted phenyl group, a substituted or unsubstituted biphenyl group, or a substituted or unsubstituted naphthyl group.

According to an embodiment of the present invention, each of $R^1$ to $R^5$ may be hydrogen, but is not limited thereto.

For example, $Ar^1$ and $Ar^2$ may independently be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted fluorenyl group, a substituted or unsubstituted carbazolyl group, a substituted or unsubstituted dibenzofuranyl group, a substituted or unsubstituted dibenzothiophenyl group, or a substituted or unsubstituted C6 to C30 arylamine group.

Specifically, $Ar^1$ and $Ar^2$ may independently be a substituted or unsubstituted phenyl group, a substituted or unsubstituted biphenyl group, a substituted or unsubstituted naphthyl group, a substituted or unsubstituted fluorenyl group, a substituted or unsubstituted dibenzofuranyl group, a substituted or unsubstituted dibenzothiophenyl group, or a substituted or unsubstituted C6 to C30 arylamine group.

According to an embodiment of the present invention, $Ar^1$ and $Ar^2$ may independently be selected from the groups of Group I.

[Group I]

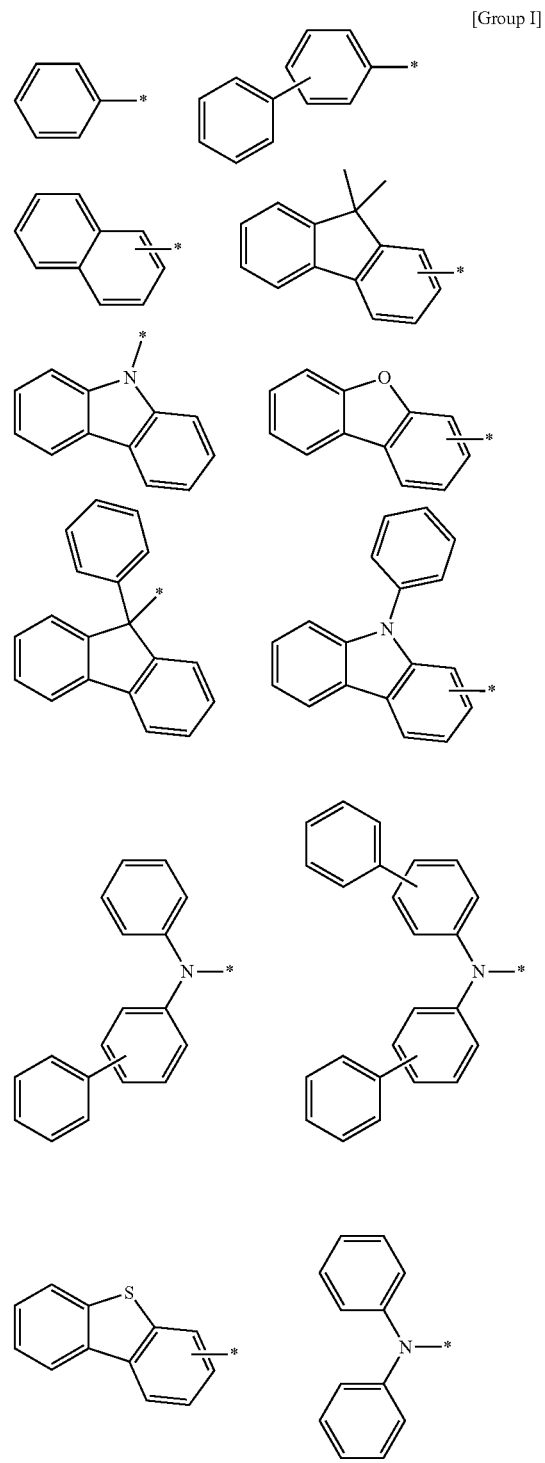

Meanwhile, Chemical Formula 1 may be represented by any one of Chemical Formula 1a to Chemical Formula 1d, for example, depending on the specific types of $Ar^1$ and $Ar^2$.

[Chemical Formula 1a]

[Chemical Formula 1b]

[Chemical Formula 1c]

[Chemical Formula 1d]

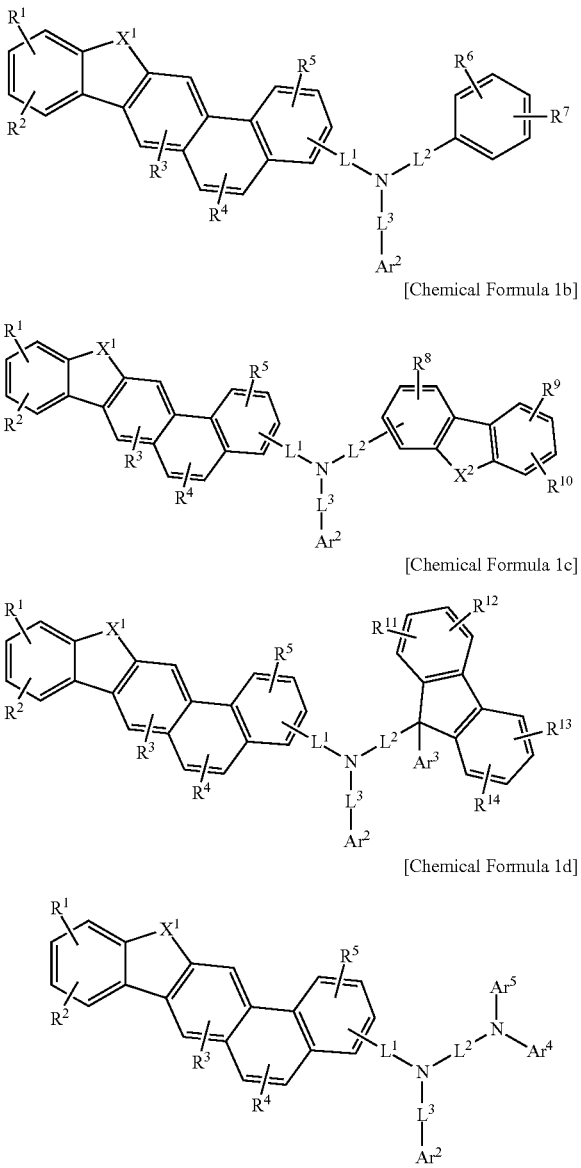

In Chemical Formula 1a to Chemical Formula 1d,
X may be O, S, or NR$^a$
X$^2$ may be O, S, CR$^b$R$^c$, or NR$^d$,
L$^1$ to L$^3$ may independently be a single bond, a substituted or unsubstituted C6 to C30 arylene group, a substituted or unsubstituted C2 to C20 heterocyclic group, or a combination thereof,
R$^a$, R$^b$, R$^c$, R$^d$, and R$^1$ to R$^{14}$ may independently be hydrogen, deuterium, a cyano group, a substituted or unsubstituted C1 to C30 alkyl group, a substituted or unsubstituted C6 to C30 aryl group, or a combination thereof, and
Ar$^2$ to Ar$^5$ may independently be a substituted or unsubstituted C6 to C30 aryl group, a substituted or unsubstituted dibenzofuranyl group, or a substituted or unsubstituted dibenzothiophenyl group.
For example, Ar$^2$ of Chemical Formula 1a to Chemical Formula 1c may be a substituted or unsubstituted C6 to C30 aryl group.

For example, Ar$^2$ of Chemical Formula 1d may be a substituted or unsubstituted C6 to C30 aryl group, a substituted or unsubstituted dibenzofuranyl group, or a substituted or unsubstituted dibenzothiophenyl group, and Ar$^4$ and Ar$^5$ may be a substituted or unsubstituted C6 to C30 aryl group.

As a specific example, Ar$^4$ and Ar$^5$ may be independently present or linked to each other to form a substituted or unsubstituted heteroaromatic polycyclic ring.

For example, the heteroaromatic polycyclic ring may be a carbazolyl group, and may be linked to L$^2$ of Chemical Formula 1d at position 9.

For example, Ar$^2$ in Chemical Formula 1a to Chemical Formula 1c may be a substituted or unsubstituted phenyl group, a substituted or unsubstituted biphenyl group, a substituted or unsubstituted naphthyl group, or a substituted or unsubstituted fluorenyl group,
Ar$^3$ to Ar$^5$ in Chemical Formula 1c and Chemical Formula 1d may independently be a substituted or unsubstituted phenyl group, or a substituted or unsubstituted biphenyl group,
Ar$^2$ of Chemical Formula 1d may be a substituted or unsubstituted phenyl group, a substituted or unsubstituted biphenyl group, a substituted or unsubstituted naphthyl group, a substituted or unsubstituted fluorenyl group, a substituted or unsubstituted dibenzofuranyl group, or a substituted or unsubstituted dibenzothiophenyl group.

According to an embodiment of the present invention, Ar$^2$ of Chemical Formulas 1a to 1c may be a substituted or unsubstituted phenyl group, a substituted or unsubstituted biphenyl group, or a substituted or unsubstituted fluorenyl group, Ar$^2$ of Chemical Formula 1d may be a substituted or unsubstituted phenyl group, a substituted or unsubstituted biphenyl group, a substituted or unsubstituted dibenzofuranyl group, or a substituted or unsubstituted dibenzothiophenyl group, and Ar$^3$ to Ar$^5$ may independently be a substituted or unsubstituted phenyl group, or a substituted or unsubstituted biphenyl group.

According to an embodiment of the present invention, Chemical Formula 1 may be represented by Chemical Formula 1a or Chemical Formula 1d.

The aforementioned compound for an organic optoelectronic device may be, for example, one selected from compounds of Group 1, but is not limited thereto.

H-1

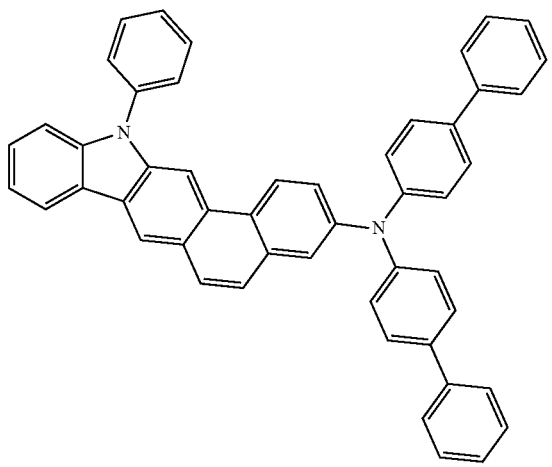

H-2
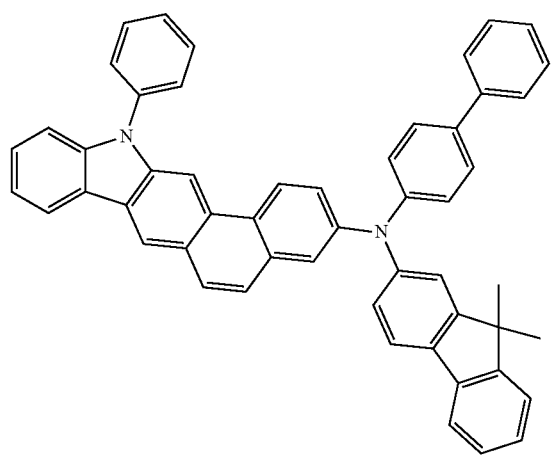
H-3
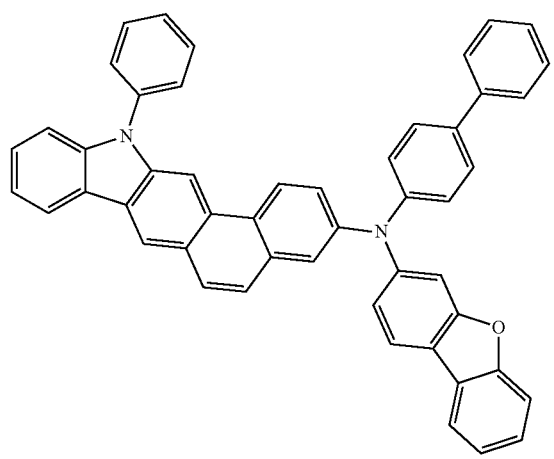
H-4
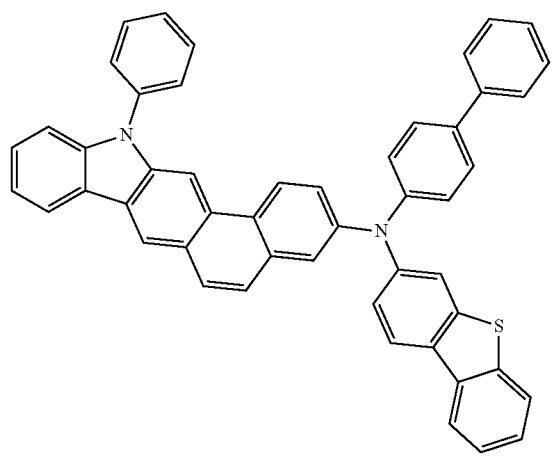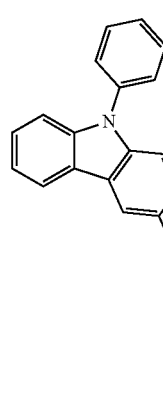
H-5
H-6
H-7
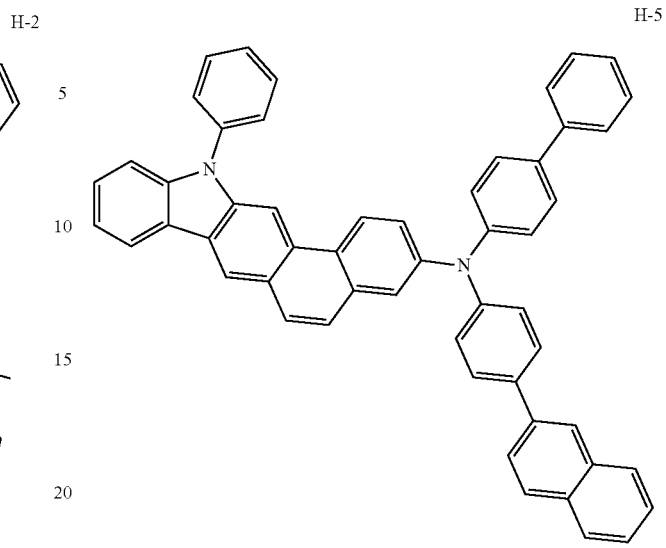

H-8
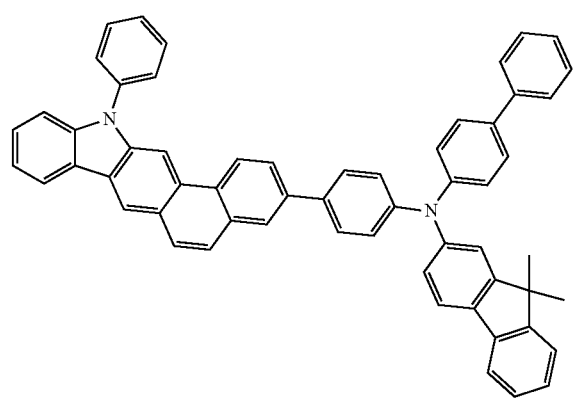
H-9
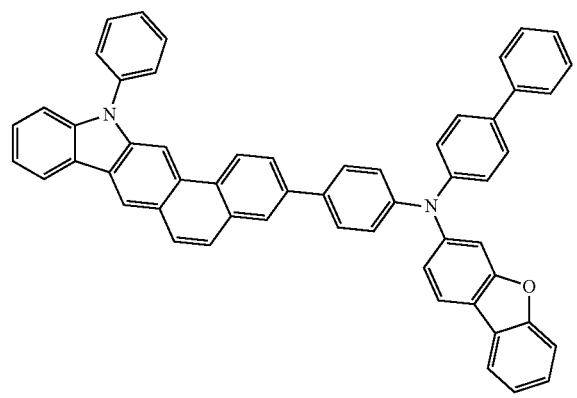
H-10
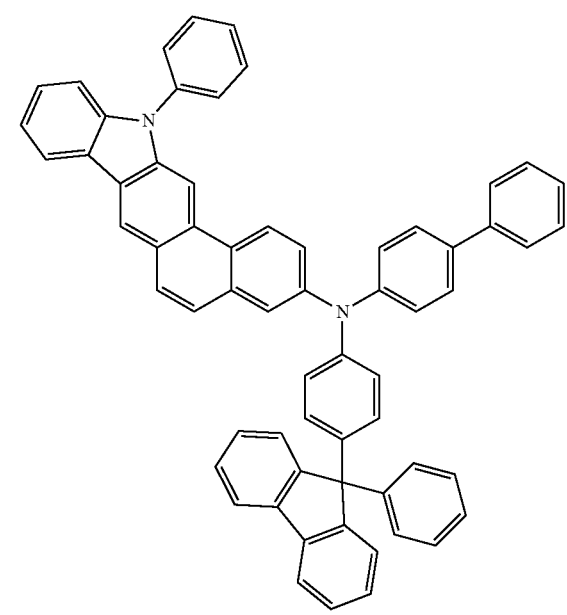
H-11
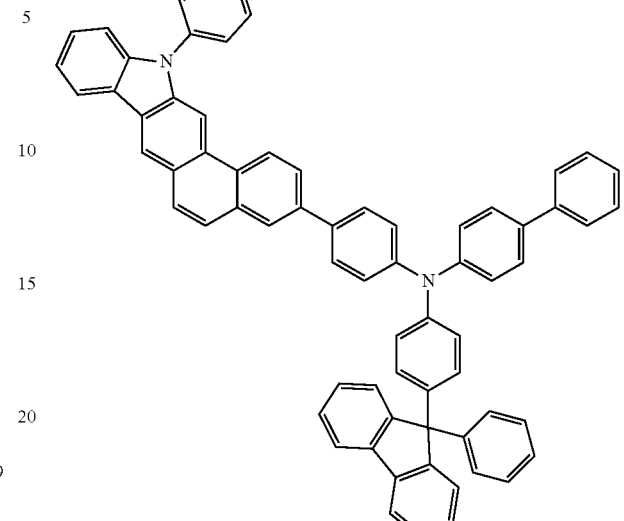
H-12
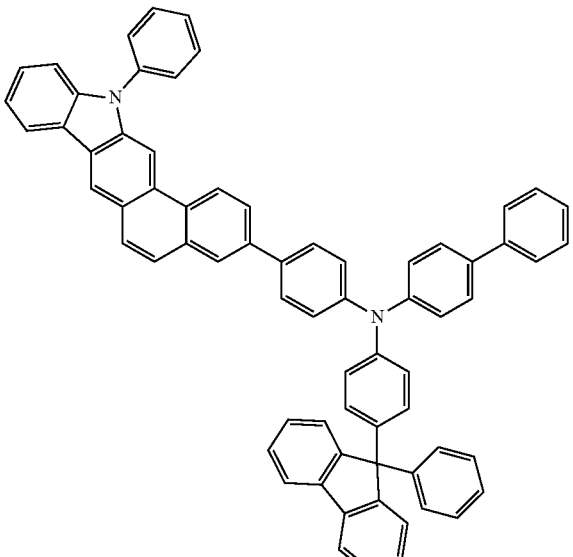
H-13
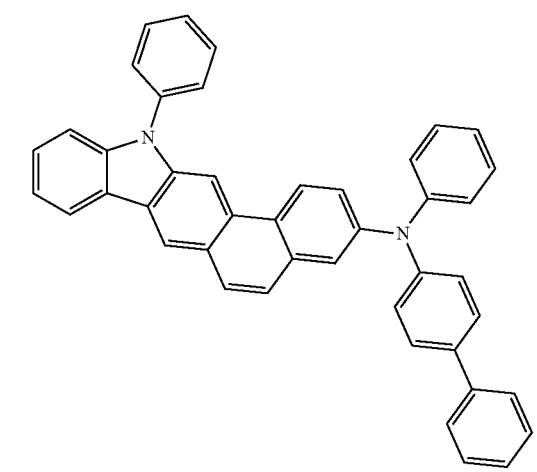

H-14
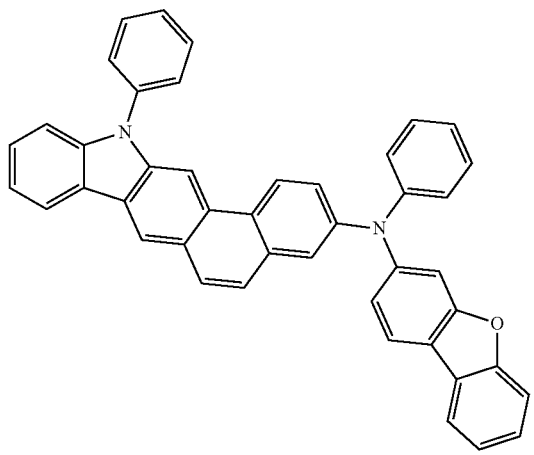
H-15
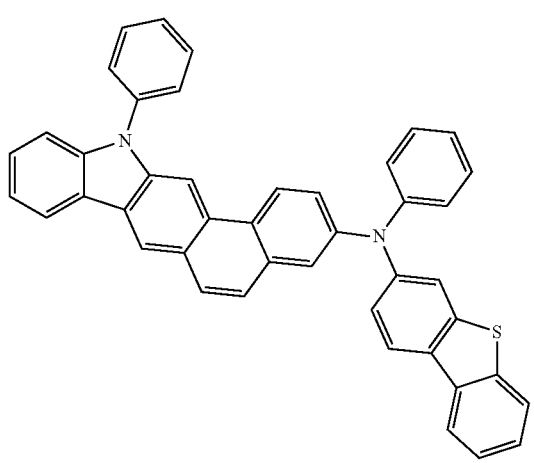
H-16
H-17
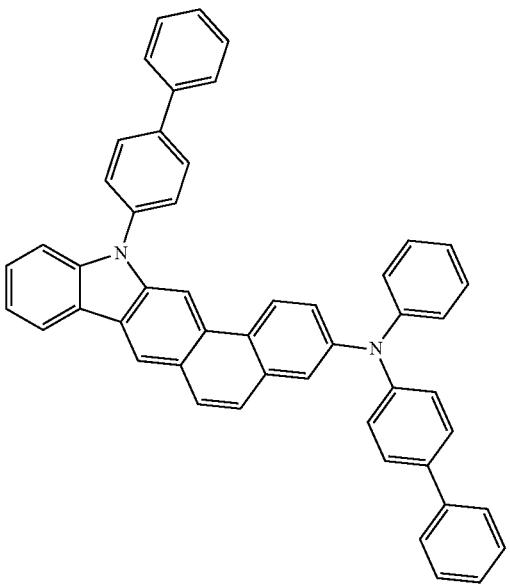
H-18
H-19
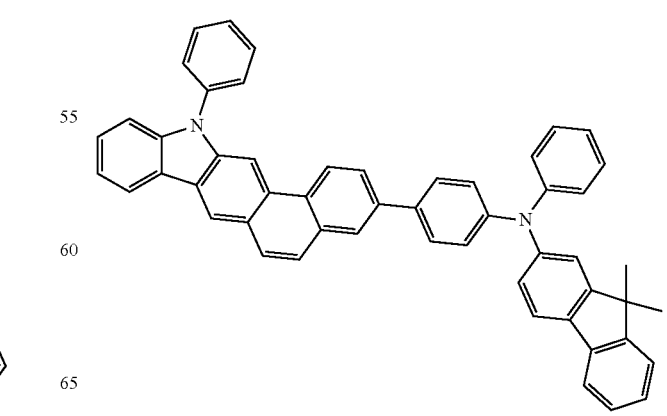

H-20
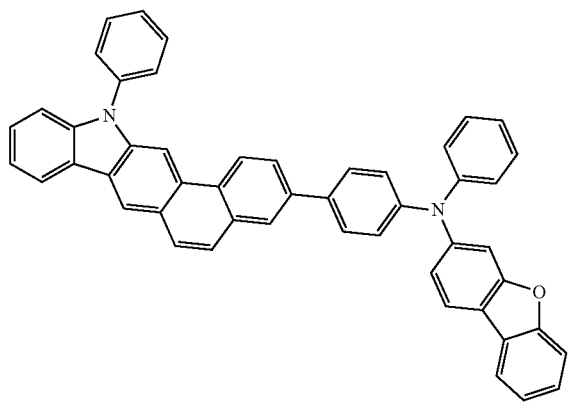
H-21
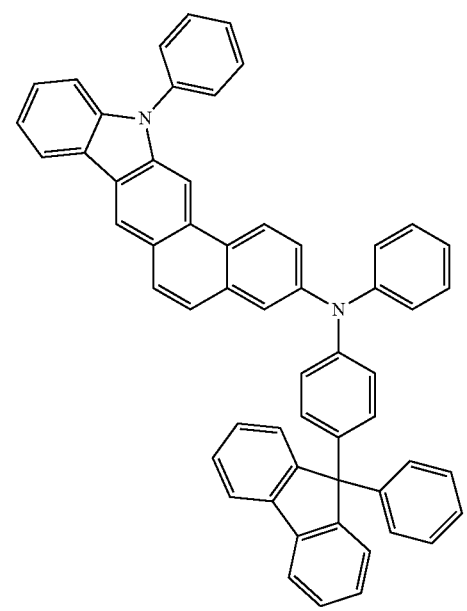
H-22
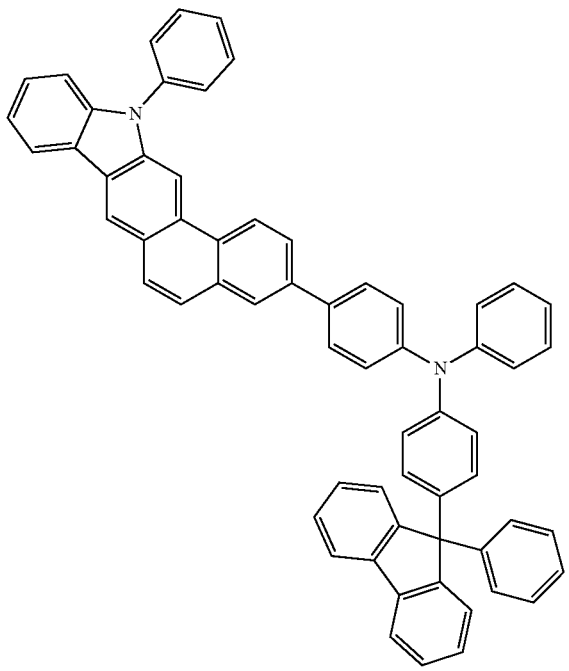
H-23
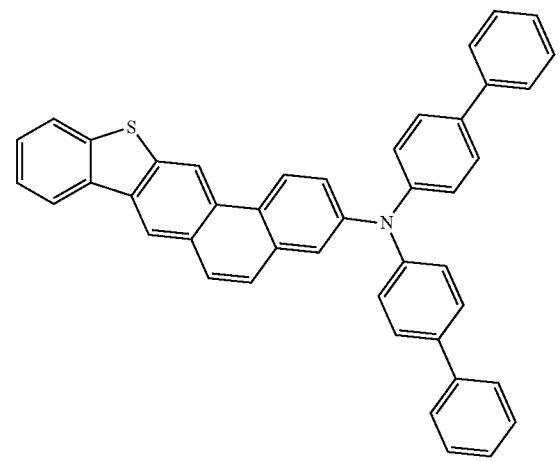
H-24
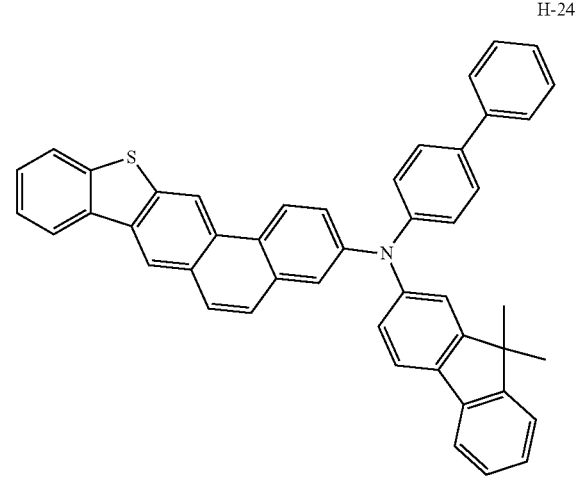

H-25
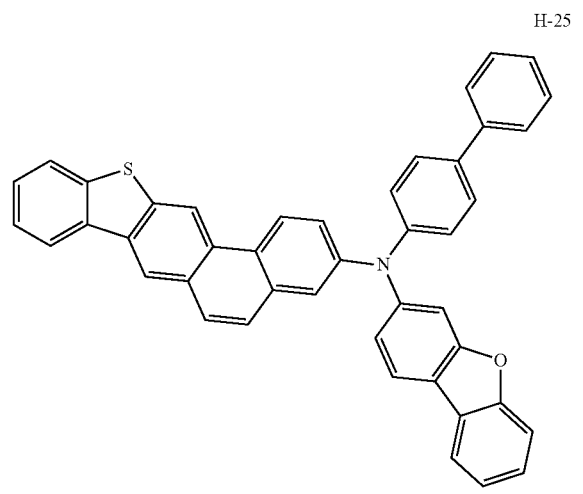
H-26
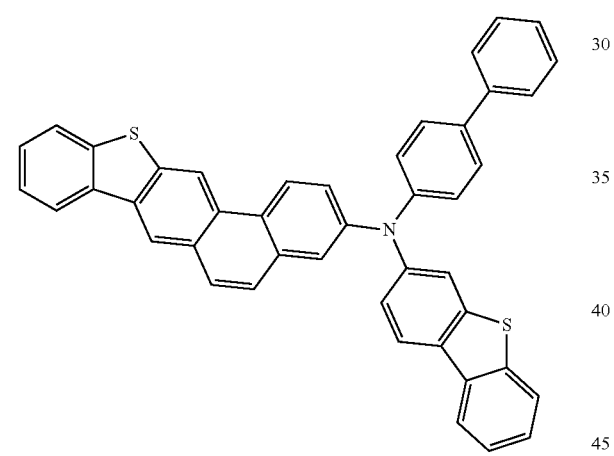
H-27
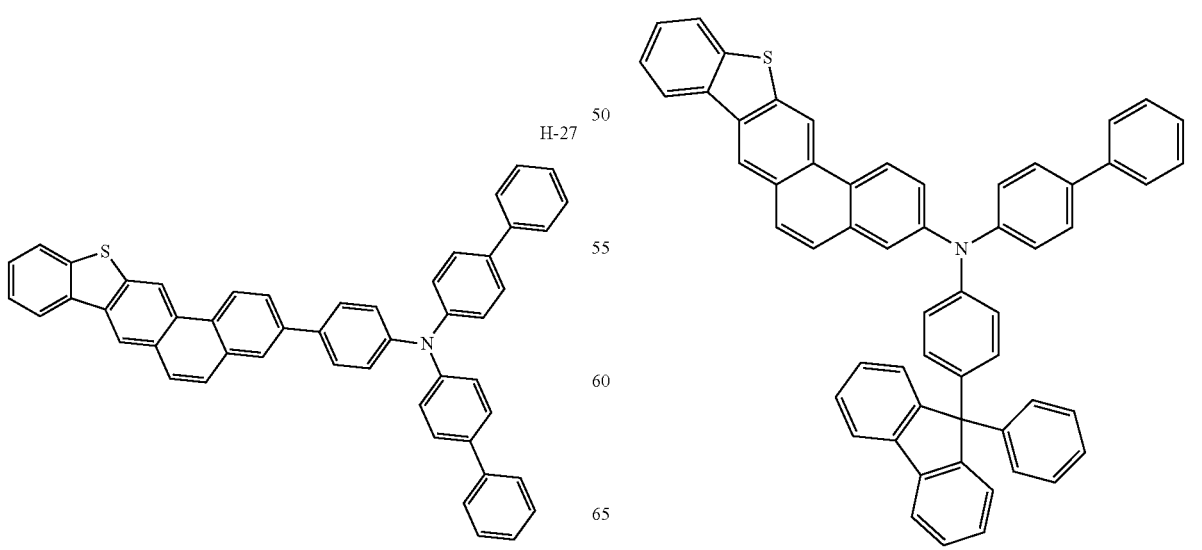
H-28
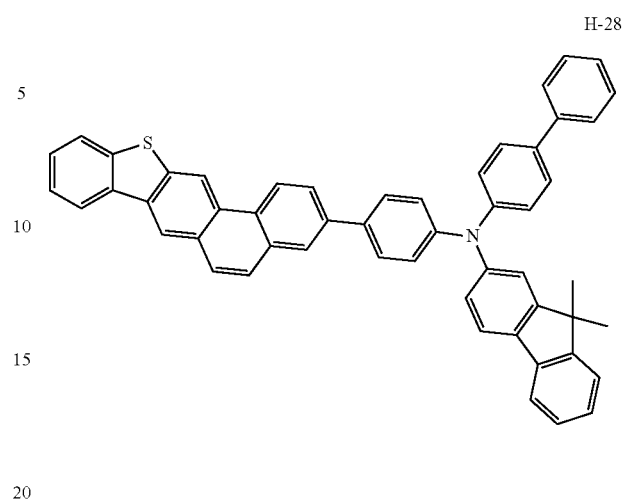
H-29
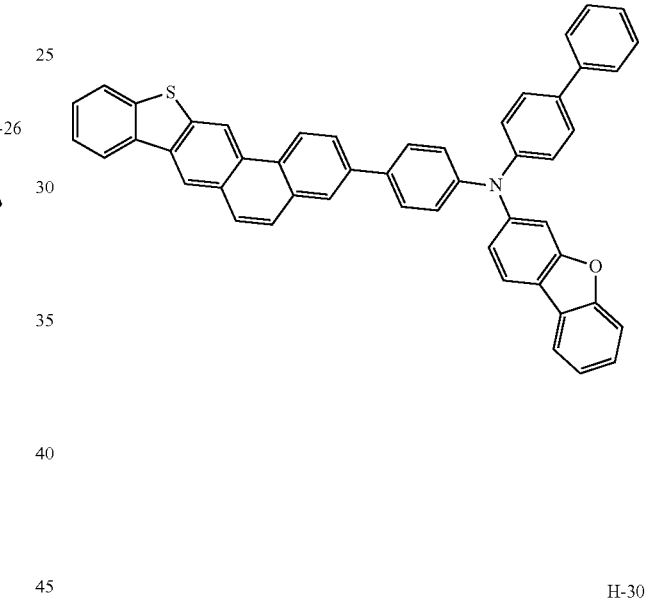
H-30

-continued
H-31
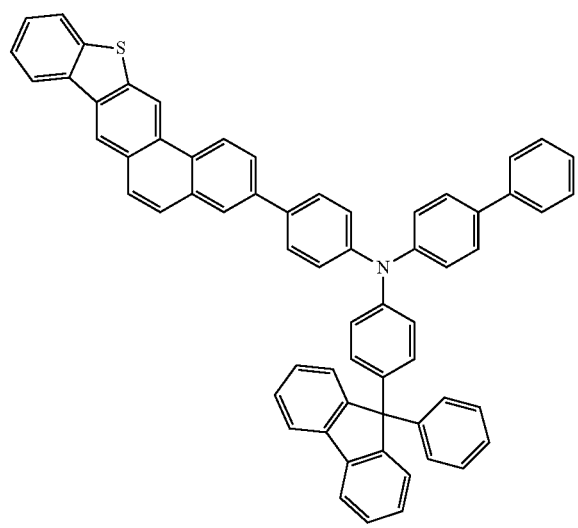
H-32
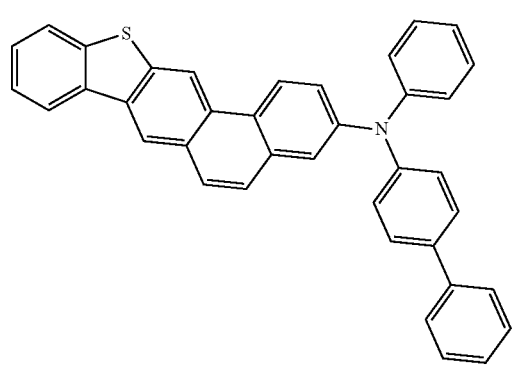
H-33
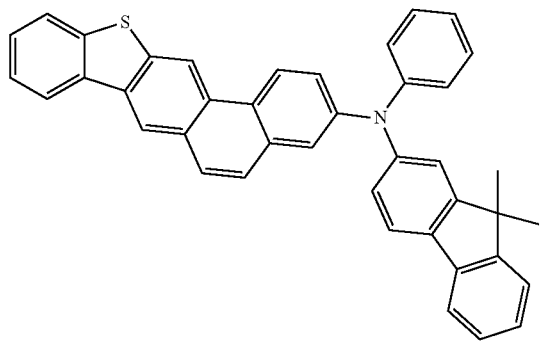
H-34
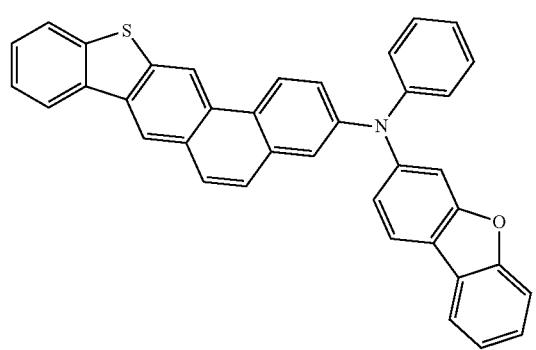
-continued
H-35
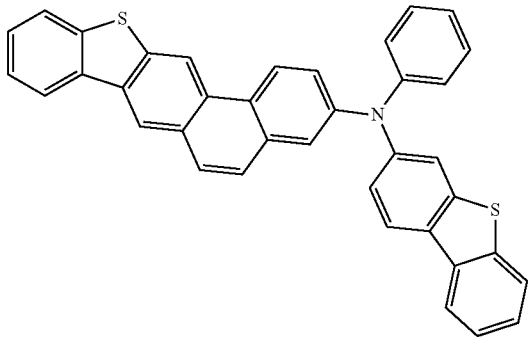
H-36
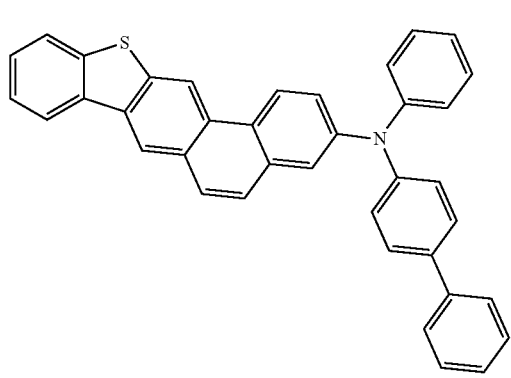
H-37
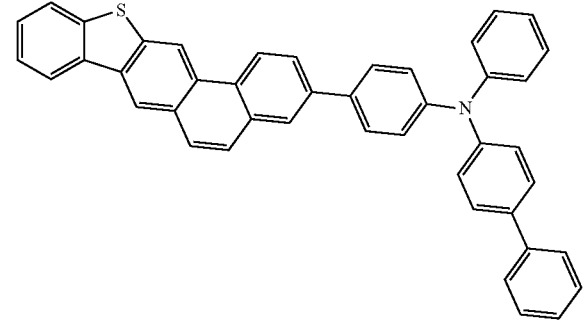
H-38
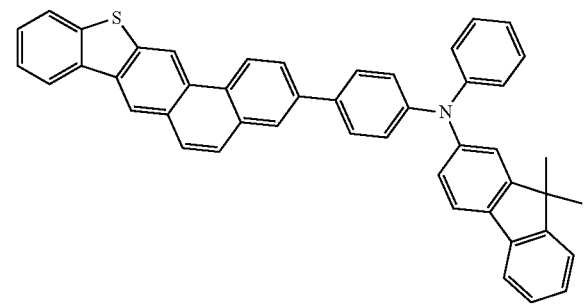

H-39
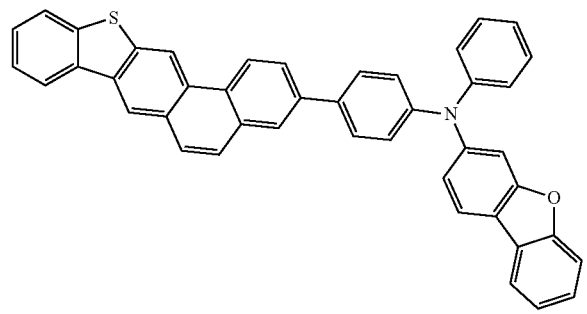
H-40
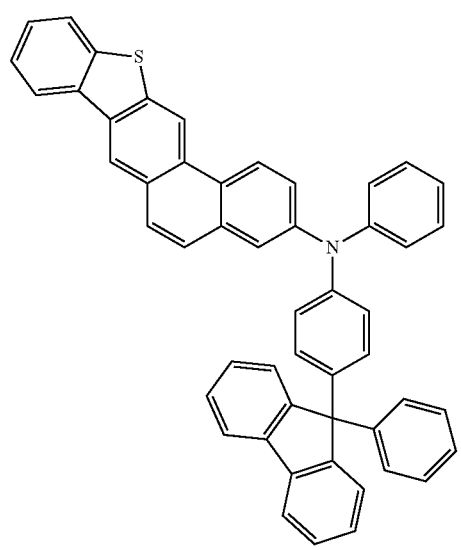
H-41
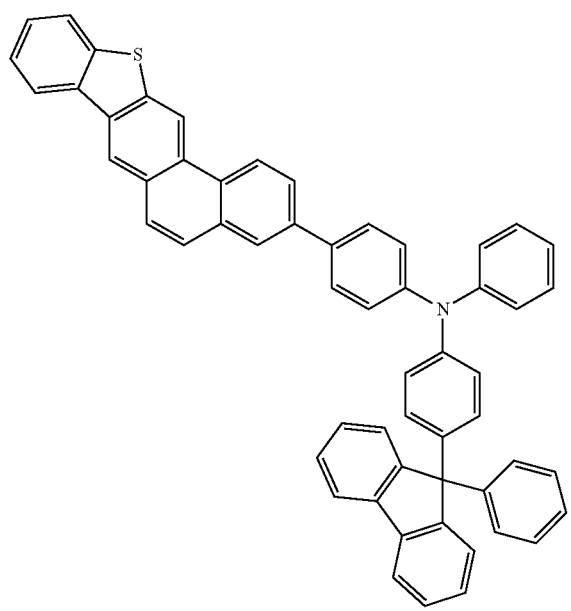
H-42
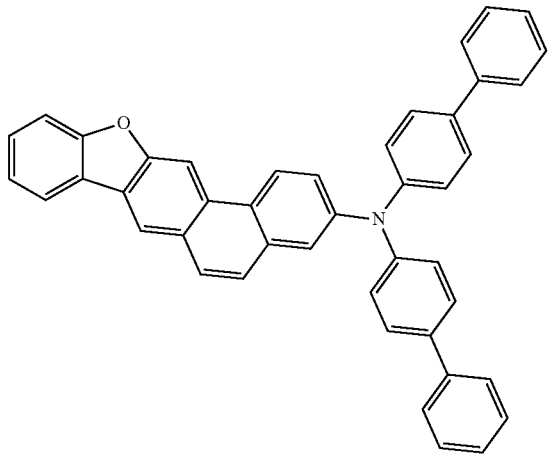
H-43
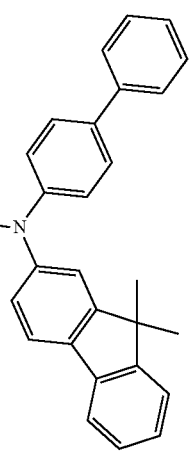
H-44
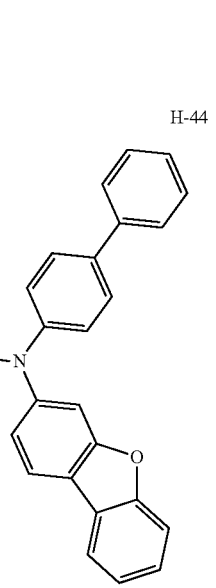

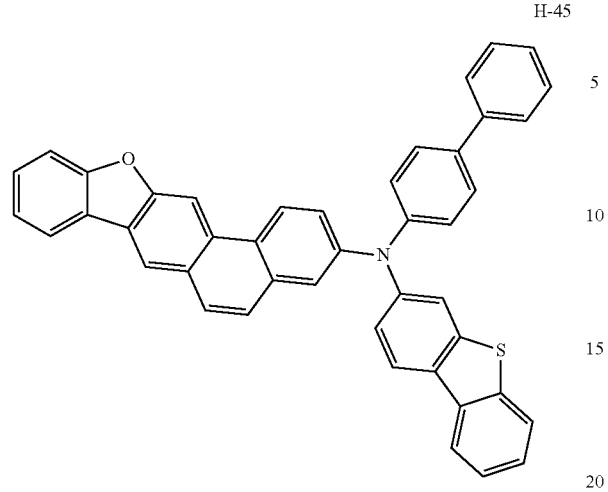
H-45
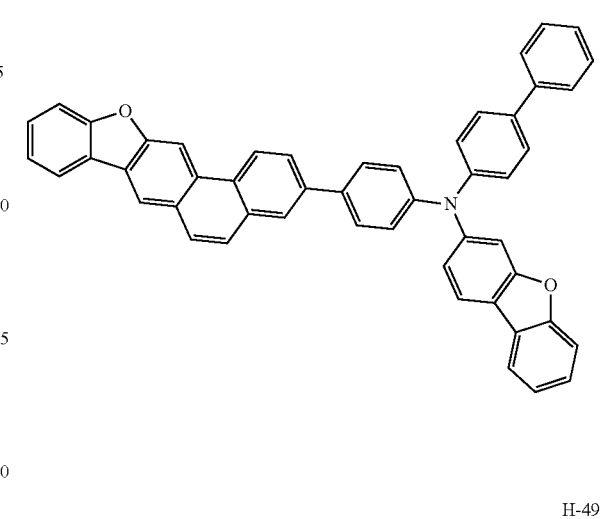
H-48
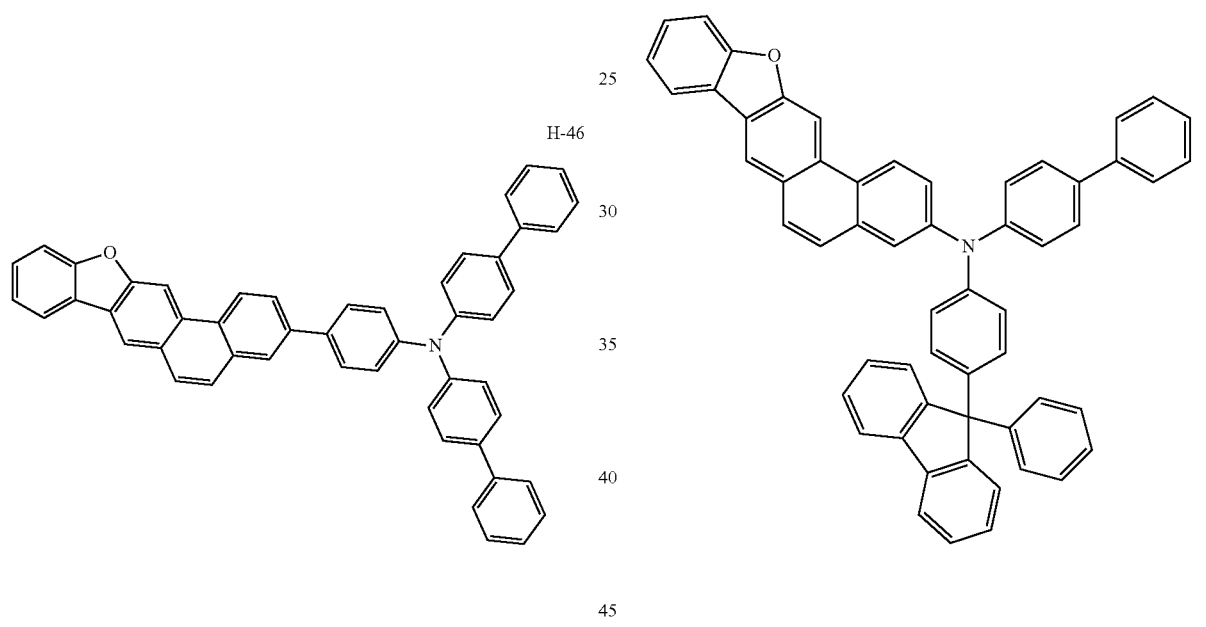
H-46
H-47
H-49
H-50

-continued
H-51
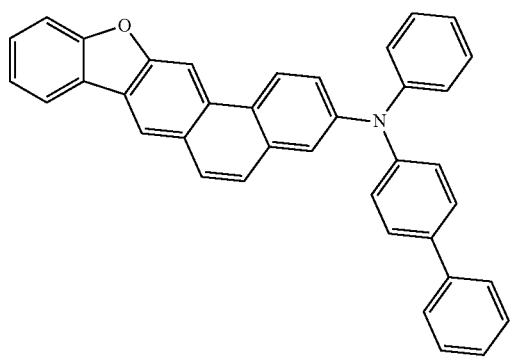
H-52
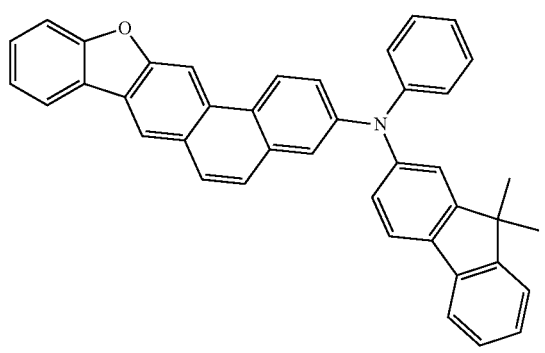
H-53
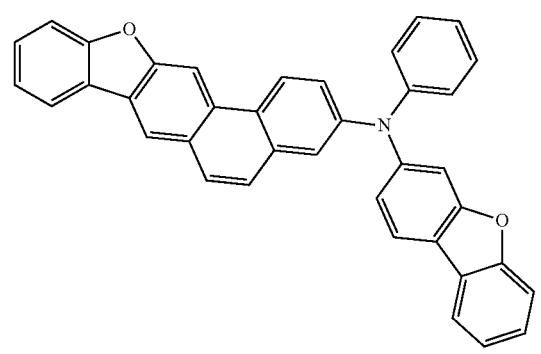
H-54
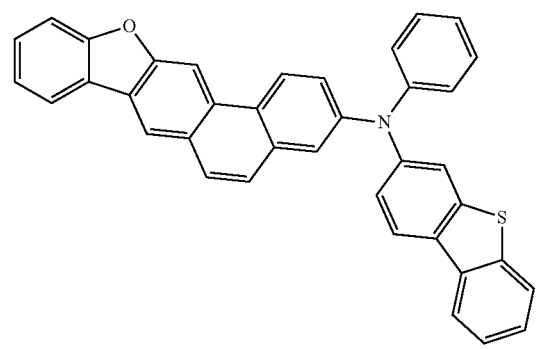
-continued
H-55
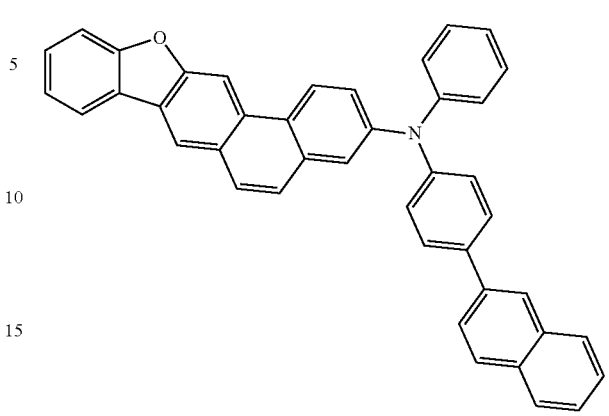
H-56
H-57
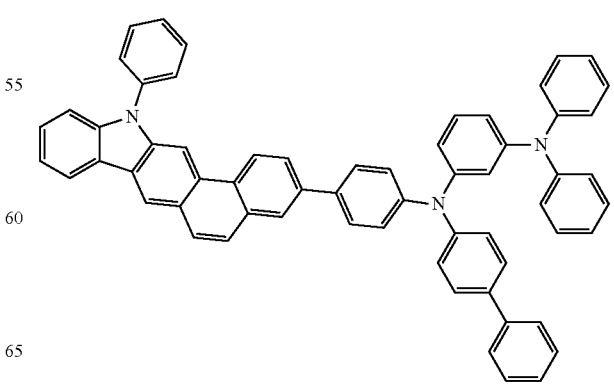

H-58
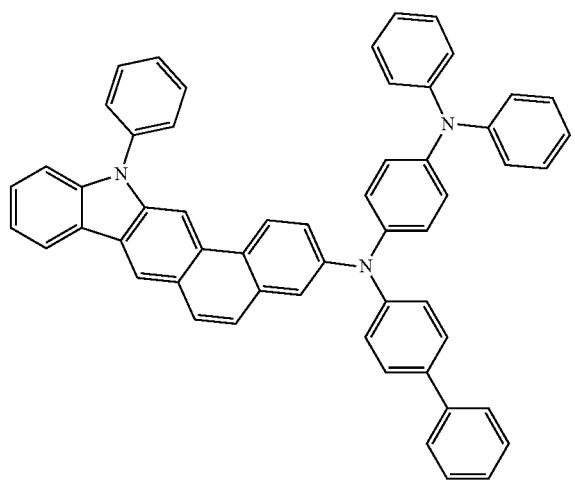
H-59
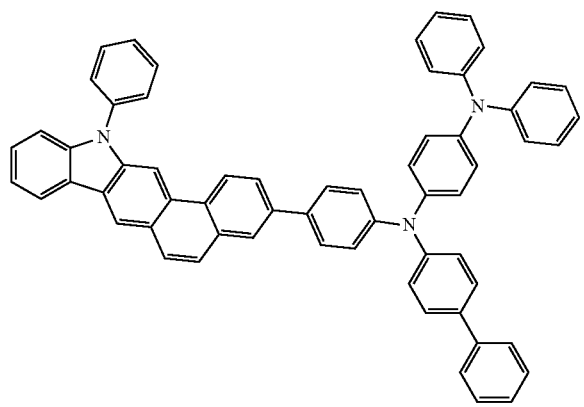
H-60
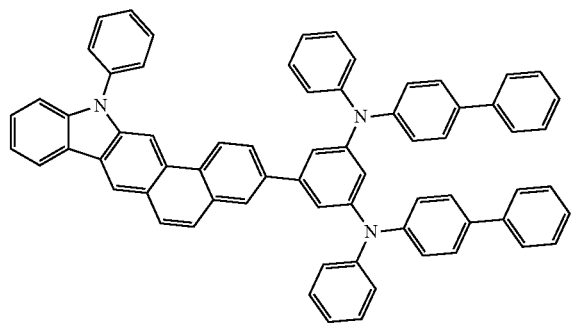
H-61
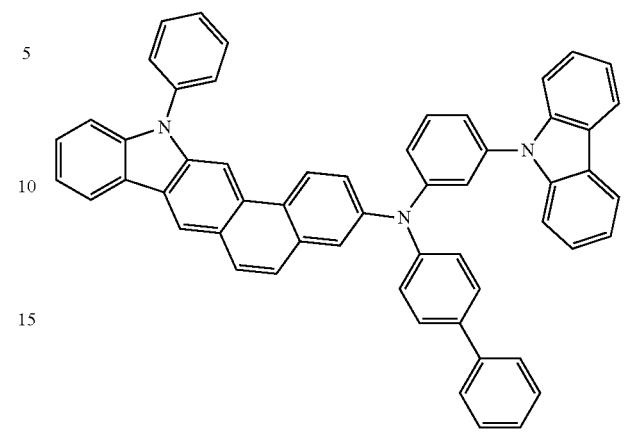
H-62
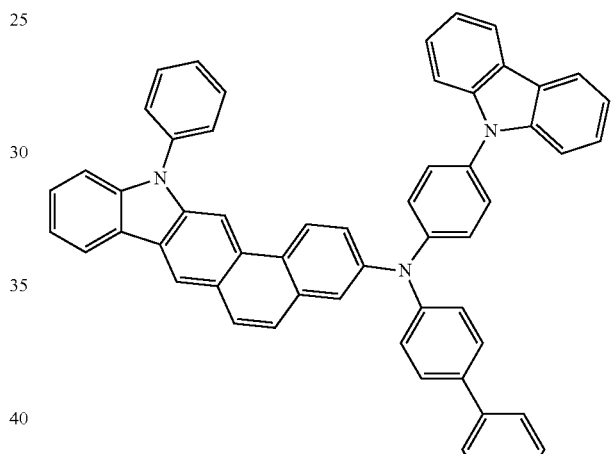
H-63
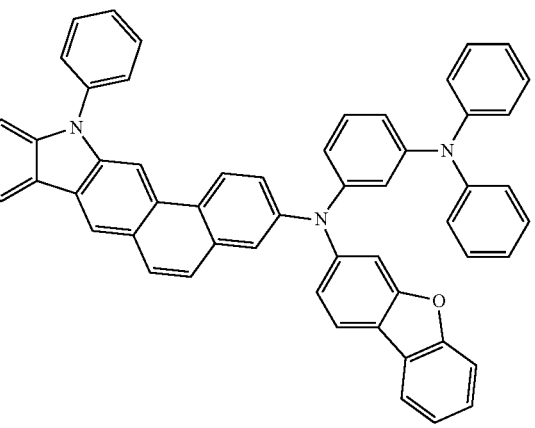

H-64
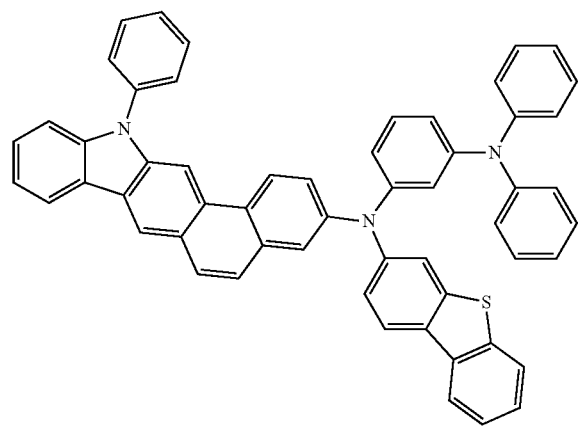
H-65
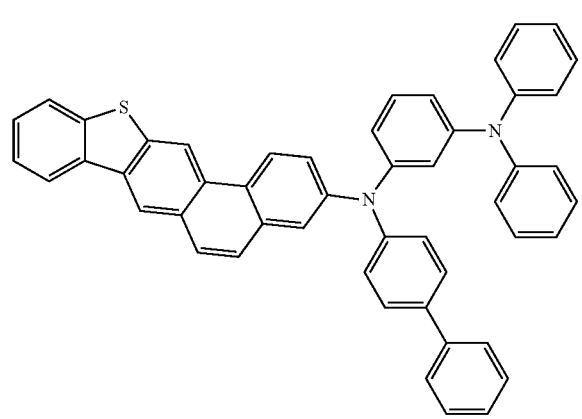
H-66
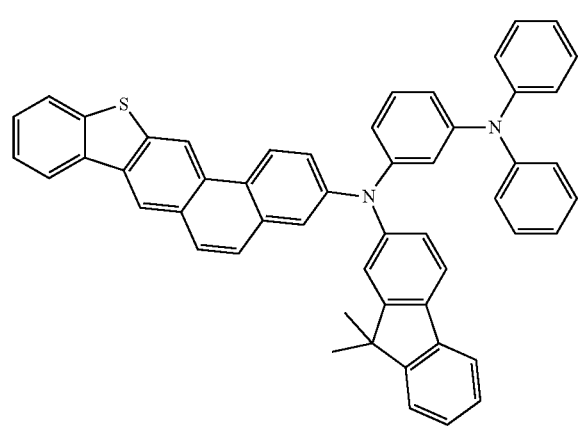
H-67
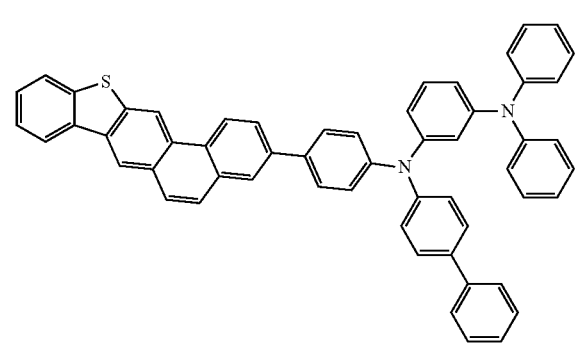
H-68
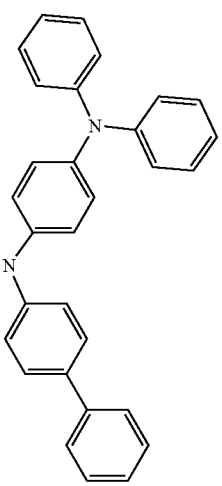
H-69
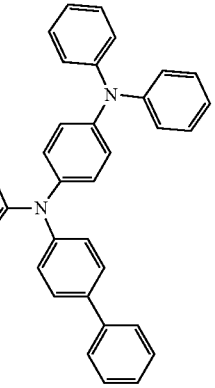
H-70
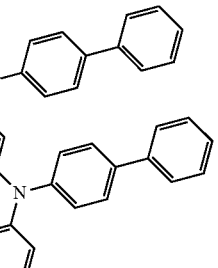
H-71
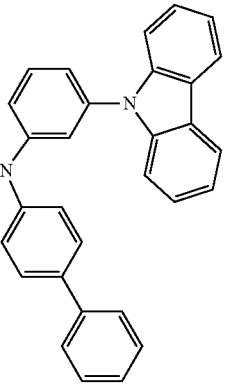

-continued
H-72
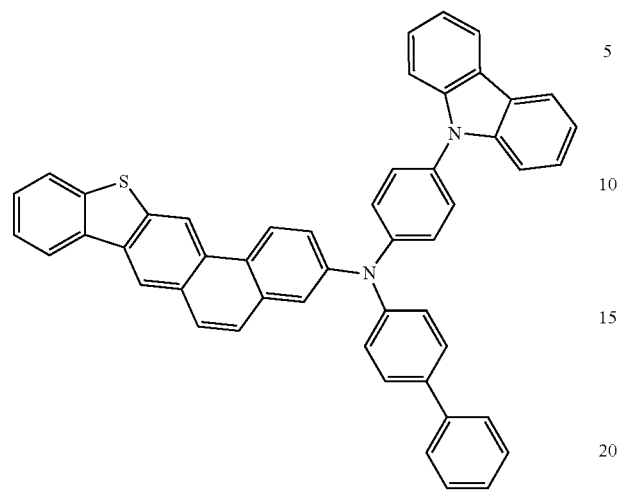
H-73
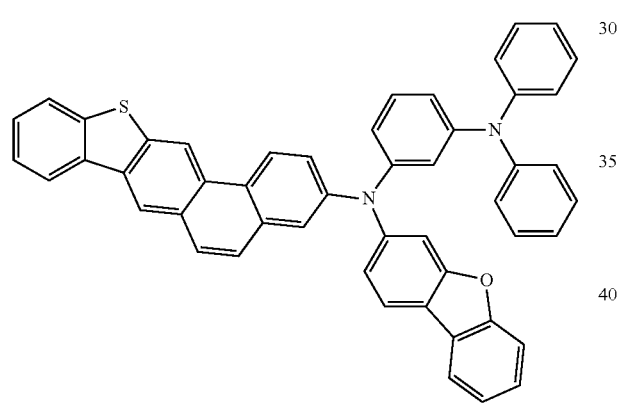
H-74
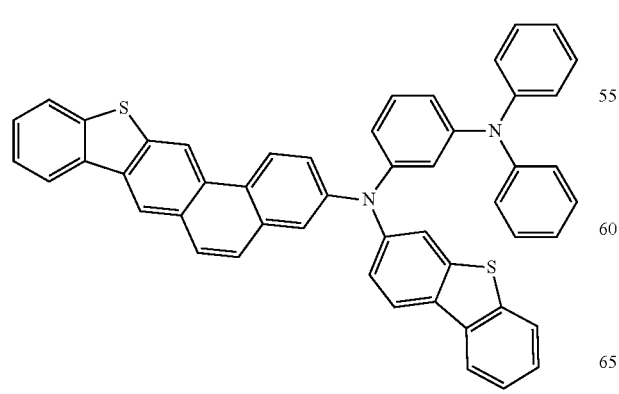
H-75
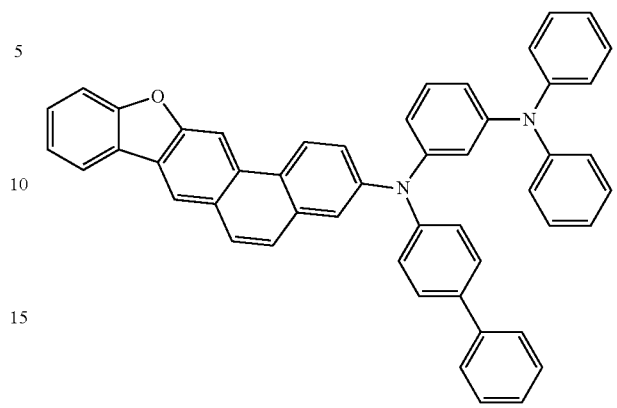
H-76
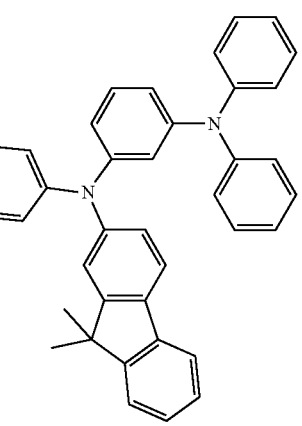
H-77
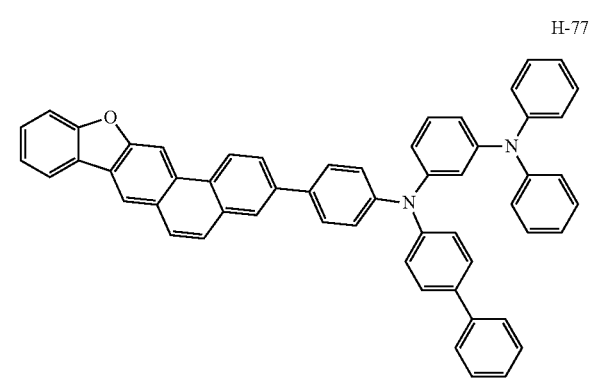

H-78
H-79
H-80
H-81
H-82
H-83
H-84
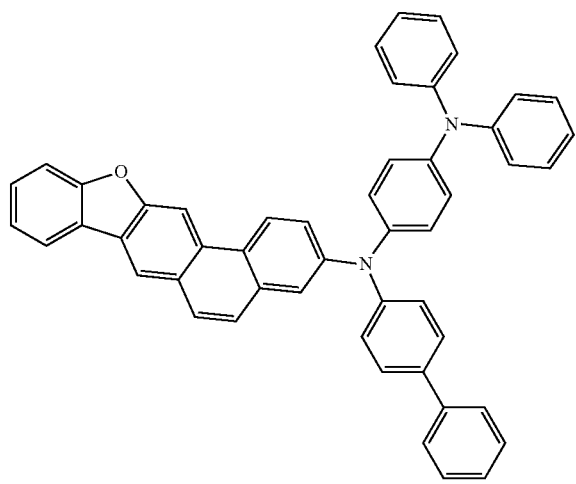
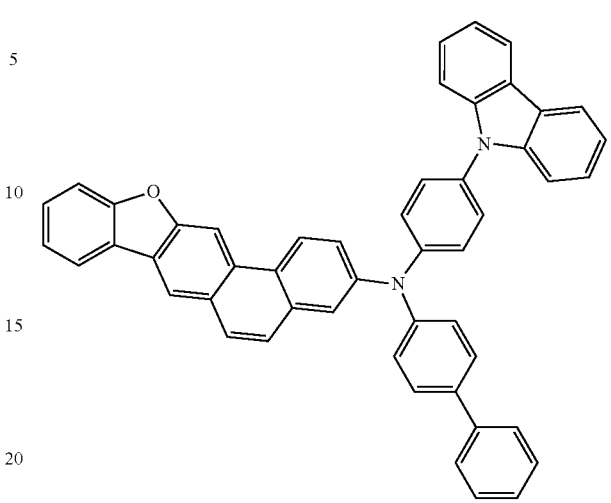
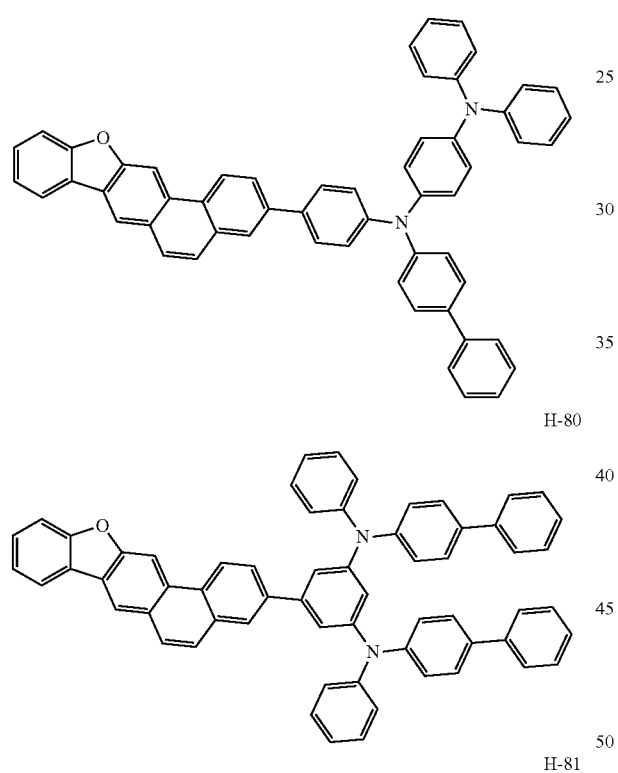
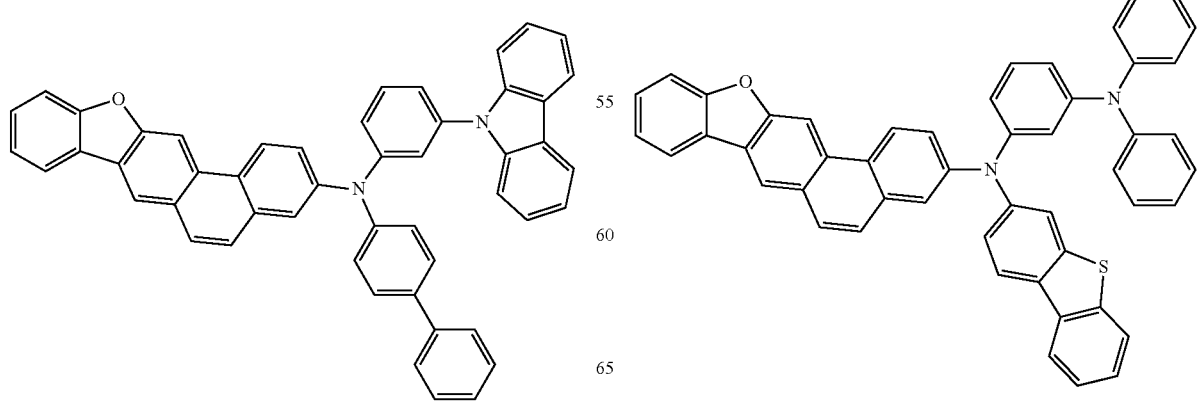

H-85
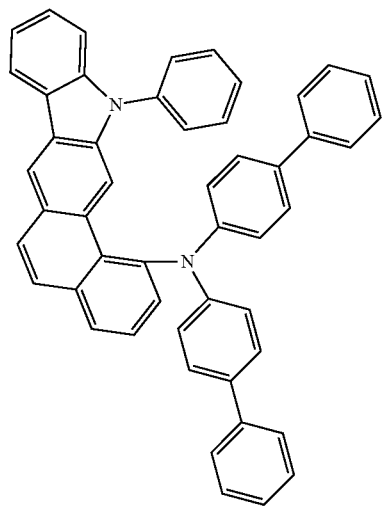
H-88
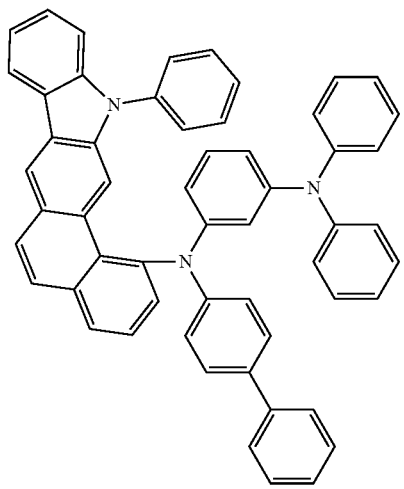
H-86
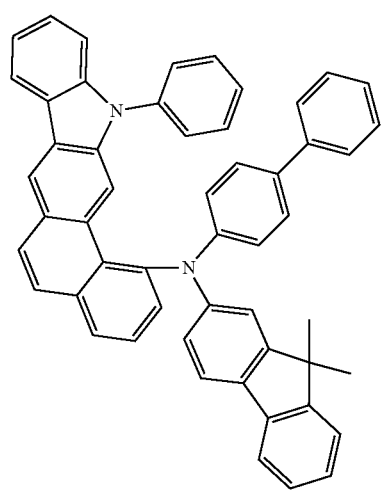
H-89
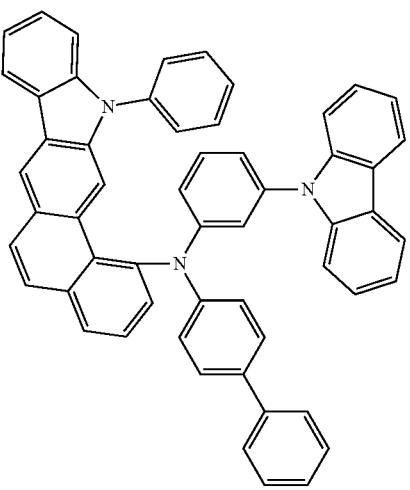
H-87
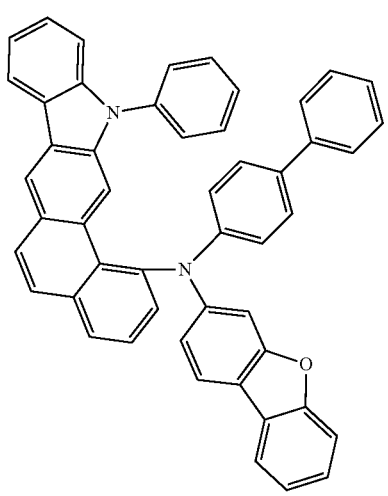
H-90
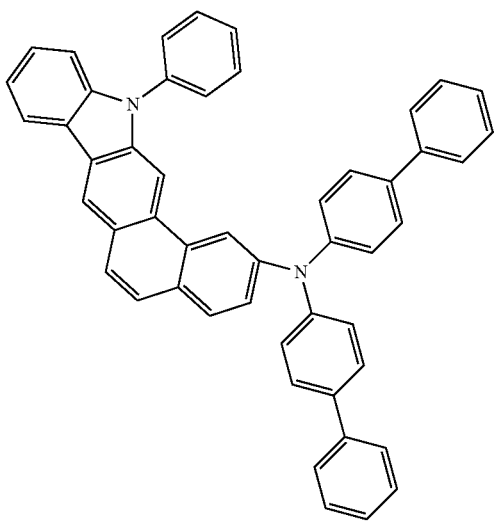

H-91
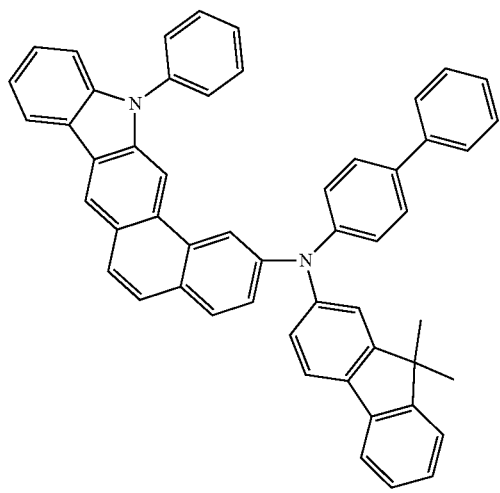
H-92
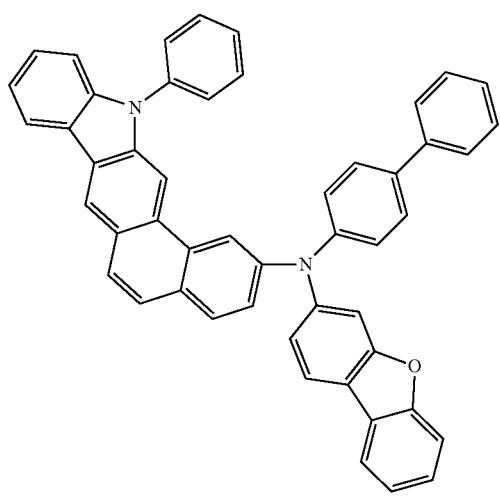
H-93
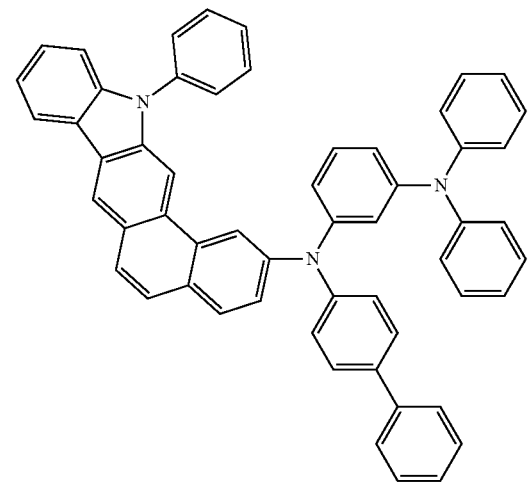
H-94
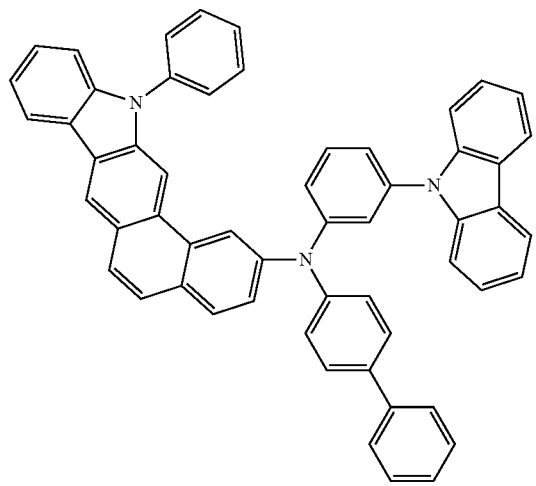
H-95
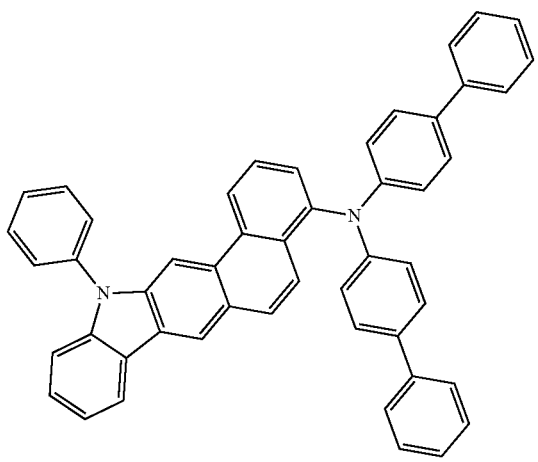
H-96
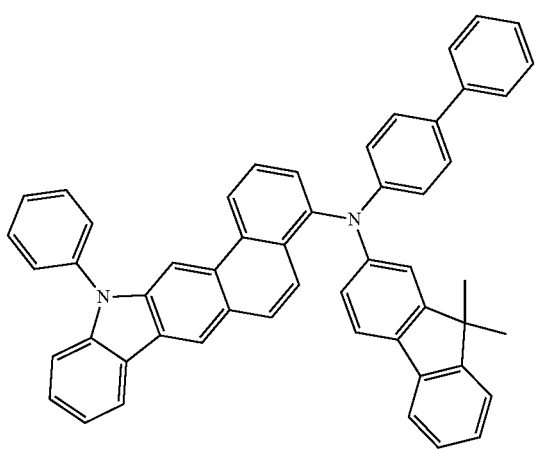

H-97
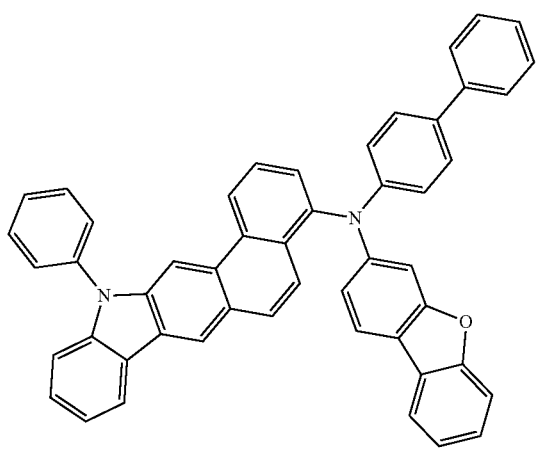
H-98
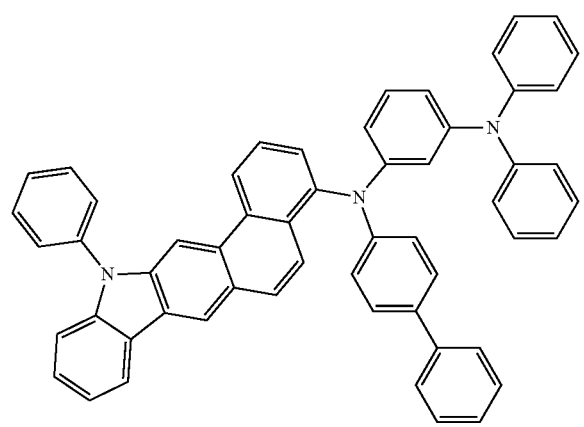
H-99
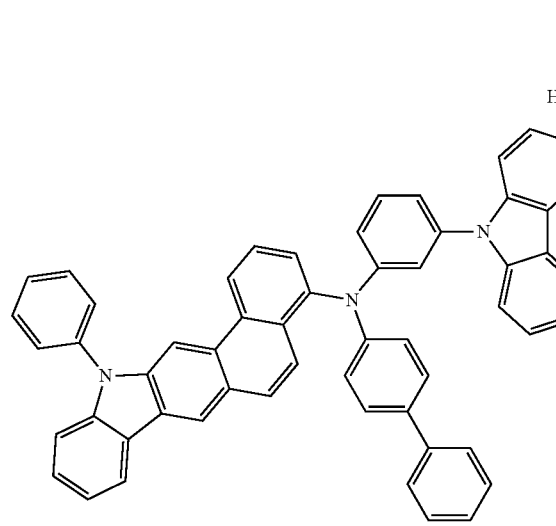
H-100
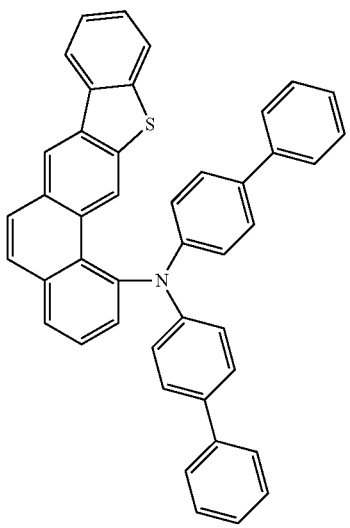
H-101
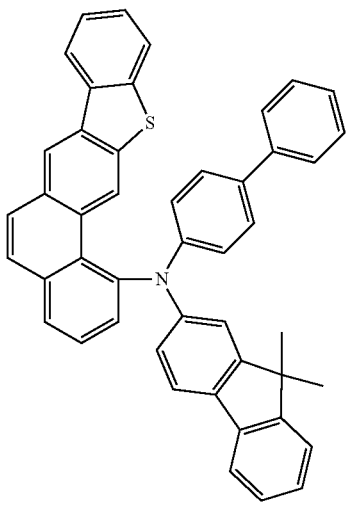
H-102
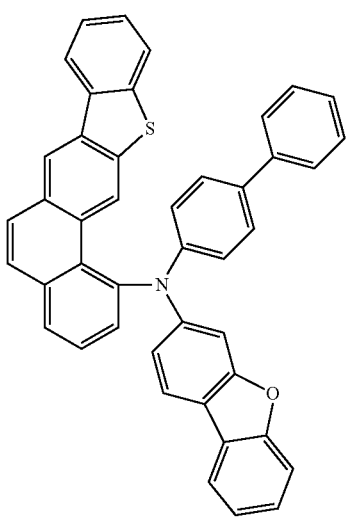

H-103
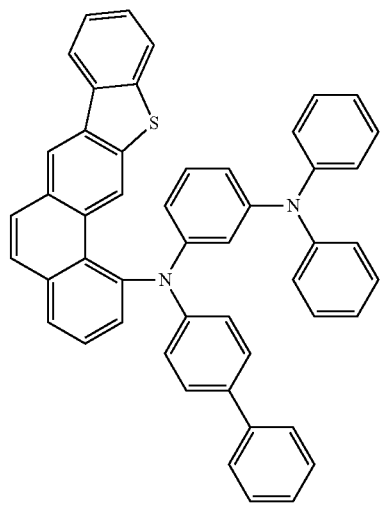
H-104
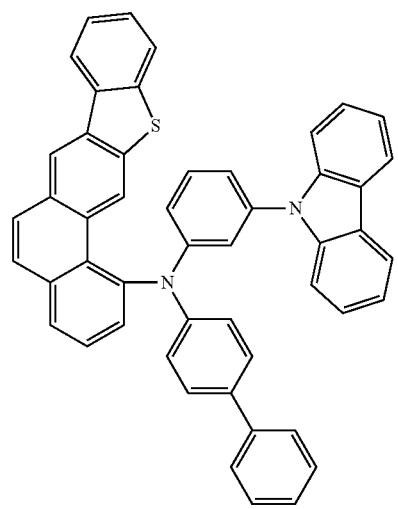
H-105
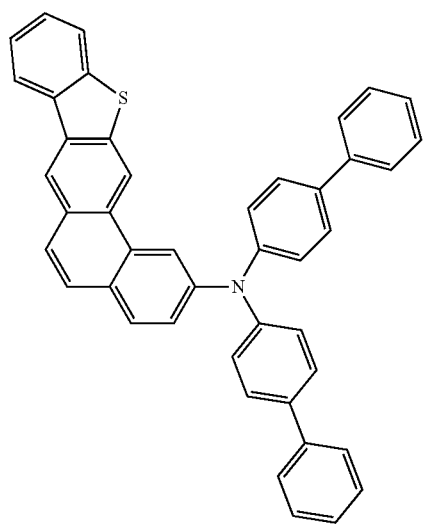
H-106
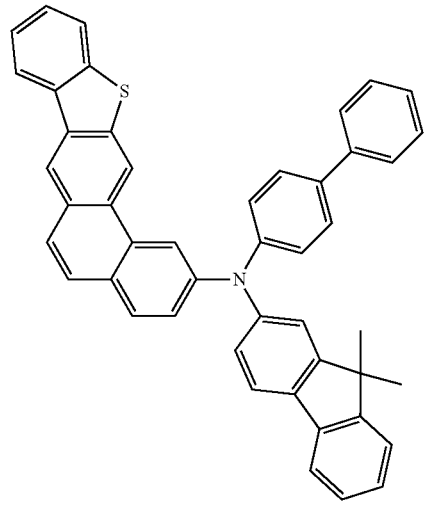
H-107
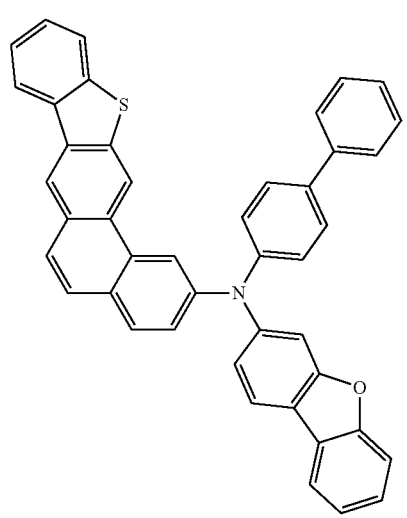
H-108
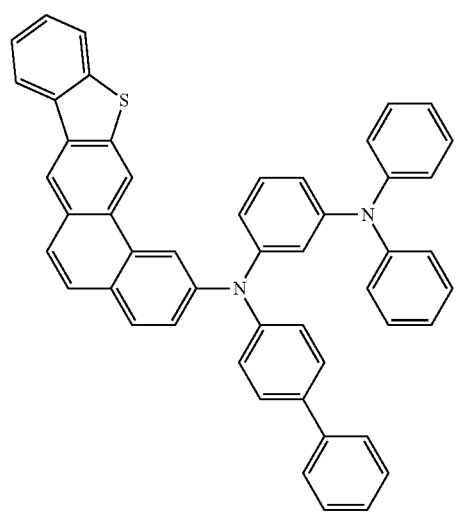

H-109
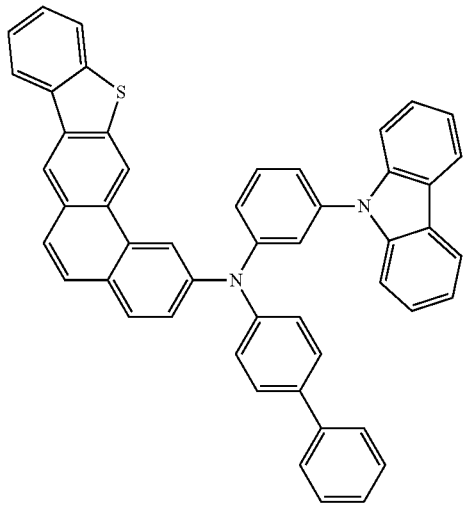
H-110
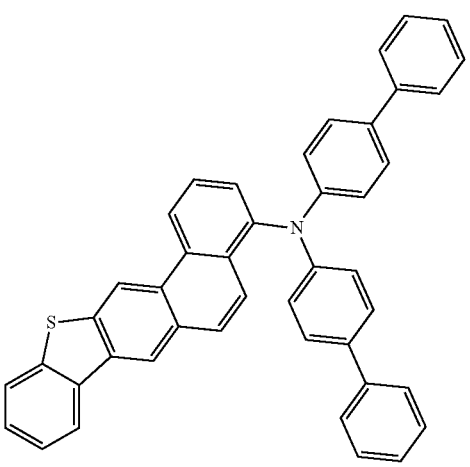
H-111
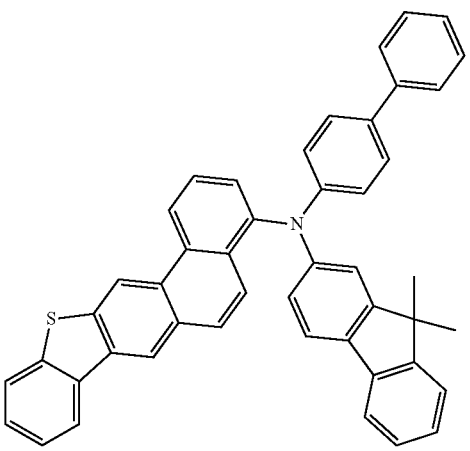
H-112
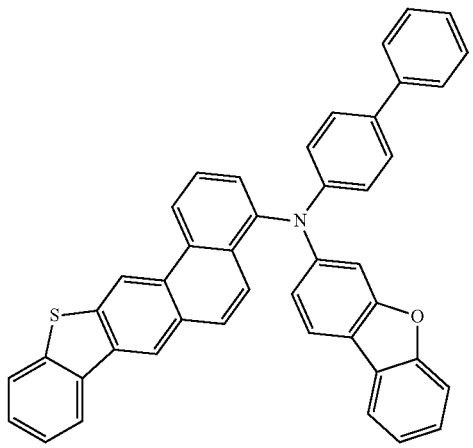
H-113
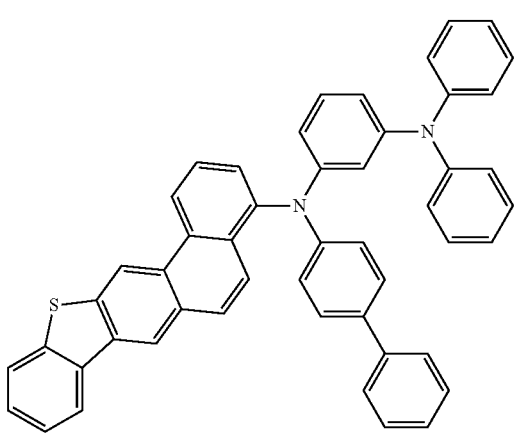
H-114
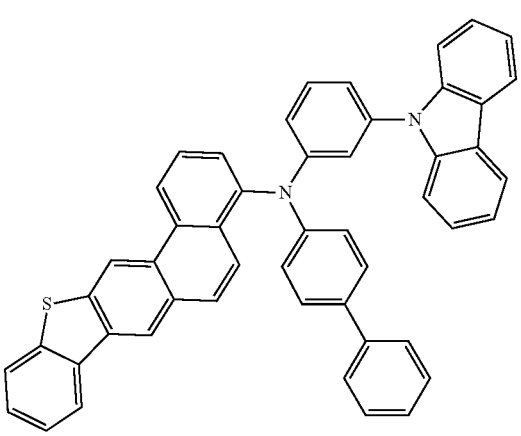

H-115
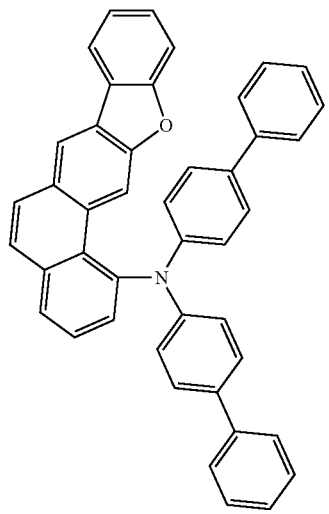
H-116
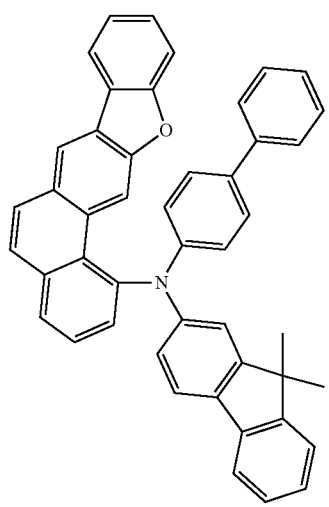
H-117
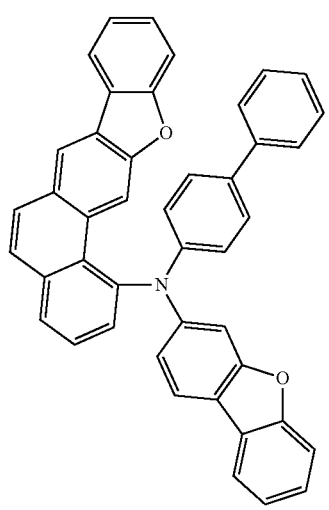
H-118
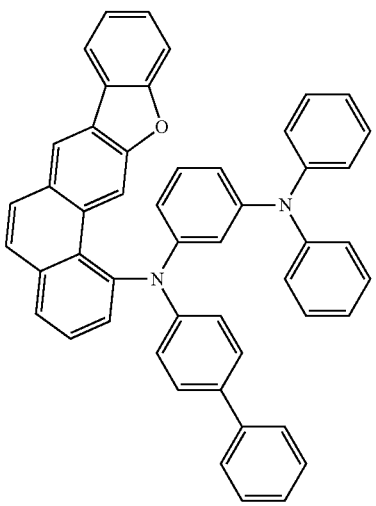
H-119
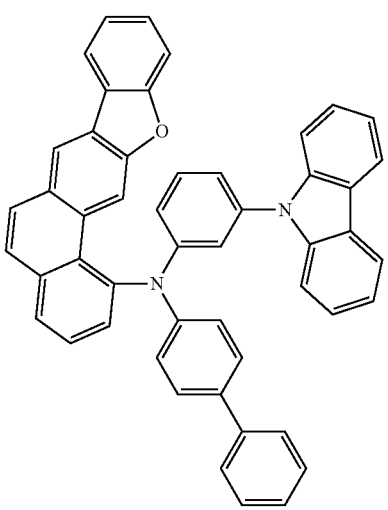
H-120
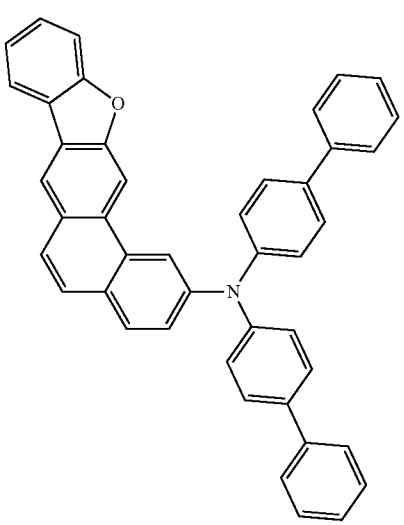

-continued
H-121
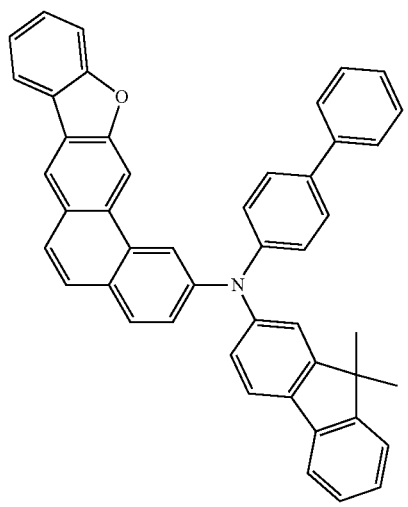
H-122
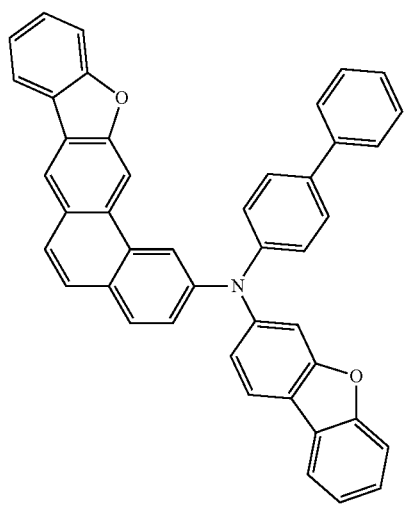
H-123
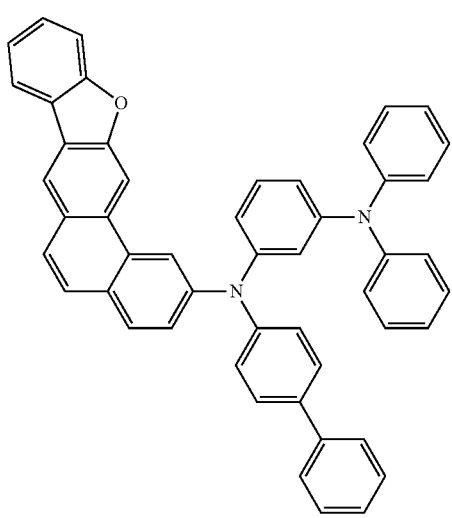
-continued
H-124
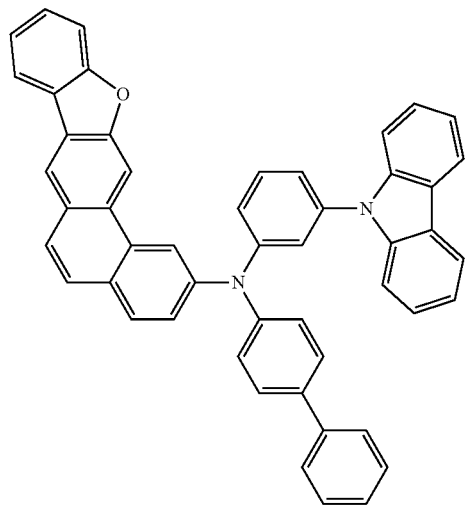
H-125
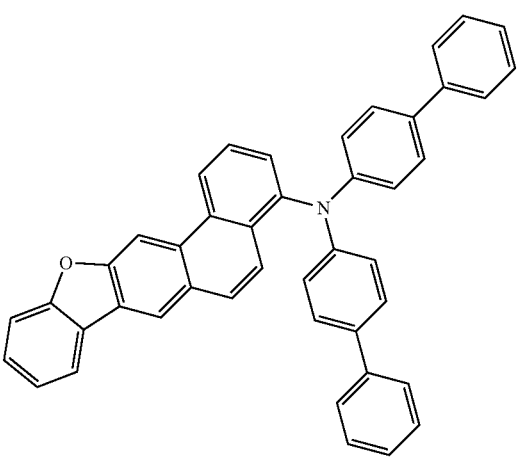
H-126
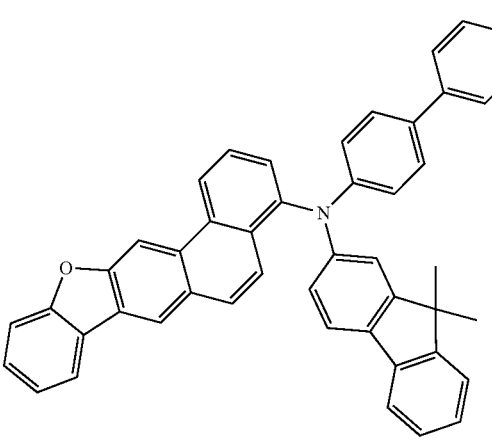

-continued

H-127

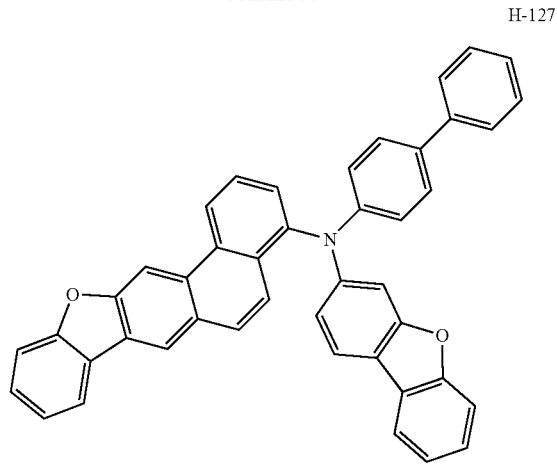

H-128

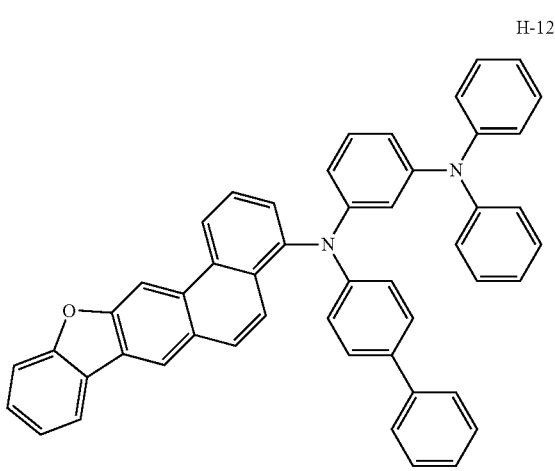

H-129

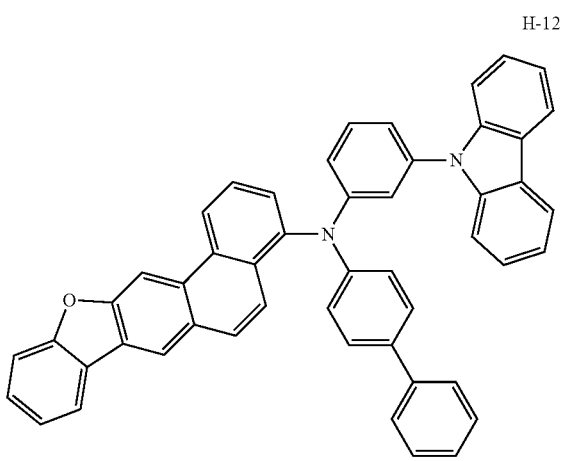

The composition for an organic optoelectronic device according to another embodiment includes the compound for an organic optoelectronic device (hereinafter referred to as "a first compound for an organic optoelectronic device") and a second compound for an organic optoelectronic device represented by Chemical Formula 2.

[Chemical Formula 2]

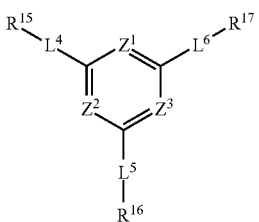

In Chemical Formula 2,
$Z^1$ to $Z^3$ are independently N or C-$L^a$-$R^e$,
at least two of $Z^1$ to $Z^3$ are N,
$L^a$ and $L^4$ to $L^6$ are independently a single bond, a substituted or unsubstituted C6 to C30 arylene group, a substituted or unsubstituted C2 to C30 heterocyclic group, or a combination thereof,
$R^e$ and $R^{15}$ to $R^{17}$ are independently hydrogen, deuterium, a cyano group, a substituted or unsubstituted C1 to C30 alkyl group, a substituted or unsubstituted C6 to C30 aryl group, a substituted or unsubstituted C2 to C30 heterocyclic group, or a combination thereof, and
at least one of $R^{15}$ to $R^{17}$ is a substituted or unsubstituted carbazolyl group, a substituted or unsubstituted dibenzofuranyl group, a substituted or unsubstituted dibenzothiophenyl group, or a substituted or unsubstituted triphenylene group.

The second compound for an organic optoelectronic device is a compound having characteristics capable of receiving electrons when an electric field is applied, that is, electron characteristics, may have a structure capable of easily receiving electrons when an electric field is applied due to a nitrogen-containing ring, such as pyrimidine, triazine, etc. Accordingly, a driving voltage of the organic optoelectronic device including the second organic optoelectronic device compound may be lowered.

In addition, it may be included together with the first compound for an organic optoelectronic device having hole characteristics to exhibit bipolar characteristics.

For example, two of $Z^1$ to $Z^3$ may be nitrogen (N) and the other may be $CR^e$.

For example, $Z^1$ and $Z^2$ may be nitrogen and $Z^3$ may be $CR^e$.

For example, $Z^2$ and $Z^3$ may be nitrogen and $Z^1$ may be $CR^e$.

For example, $Z^1$ and $Z^3$ may be nitrogen and $Z^2$ may be $CR^e$.

As an example, each of $Z^1$ to $Z^3$ may be nitrogen (N).

For example, $L^4$ to $L^6$ may independently be a single bond or a substituted or unsubstituted C6 to C20 arylene group.

Specifically, $L^4$ to $L^6$ may independently be a single bond, a substituted or unsubstituted phenylene group, a substituted or unsubstituted biphenylene group, a substituted or unsubstituted terphenylene group, or a substituted or unsubstituted naphthylene group.

According to an embodiment of the present invention, $L^4$ to $L^6$ may independently be a single bond, a substituted or unsubstituted m-phenylene group, or a substituted or unsubstituted p-phenylene group.

For example, $R^{15}$ may be a substituted or unsubstituted carbazolyl group, a substituted or unsubstituted dibenzofuranyl group, a substituted or unsubstituted dibenzothiophenyl group, or a substituted or unsubstituted triphenylenyl group, and $R^{16}$ and $R^{17}$ may independently be a substituted or unsubstituted phenyl group, a substituted or unsubstituted biphenyl group, a substituted or unsubstituted naphthyl group, a substituted or unsubstituted terphenyl group, a substituted or unsubstituted anthracenyl group, a substituted or unsubstituted phenanthrenyl group, a substituted or unsubstituted quaterphenyl group, a substituted or unsubstituted triphenylenyl group, a substituted or unsubstituted fluorenyl group, a substituted or unsubstituted pyridinyl group, a substituted or unsubstituted pyrimidinyl group, a substituted or unsubstituted triazinyl group, a substituted or unsubstituted carbazolyl group, a substituted or unsubstituted dibenzofuranyl group, a substituted or unsubstituted dibenzothiophenyl group, or a combination thereof.

According to an example embodiment of the present invention, $R^{15}$ may be a substituted or unsubstituted carbazolyl group, a substituted or unsubstituted dibenzofuranyl group, or a substituted or unsubstituted dibenzothiophenyl group, $R^{16}$ and $R^{17}$ are independently a substituted or unsubstituted phenyl group, a substituted or unsubstituted biphenyl group, a substituted or unsubstituted naphthyl group, a substituted or unsubstituted terphenyl group, a substituted or unsubstituted carbazolyl group, a substituted or unsubstituted dibenzofuranyl group, a substituted or unsubstituted dibenzothiophenyl group, or a combination thereof.

For example, Chemical Formula 2 may be represented by any one of Chemical Formula 2-1 to Chemical Formula 2-3.

[Chemical Formula 2-1]

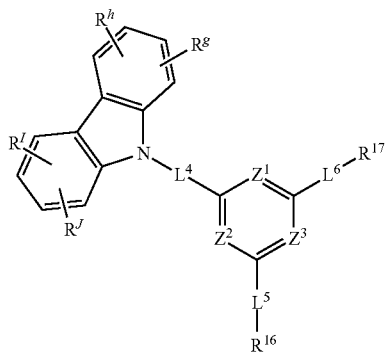

[Chemical Formula 2-2]

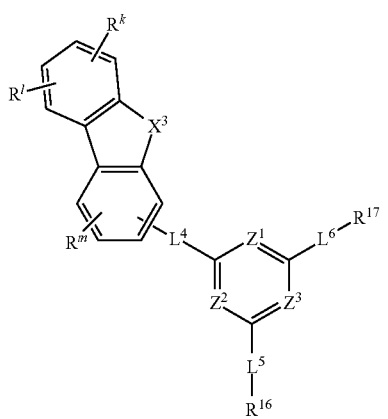

[Chemical Formula 2-3]

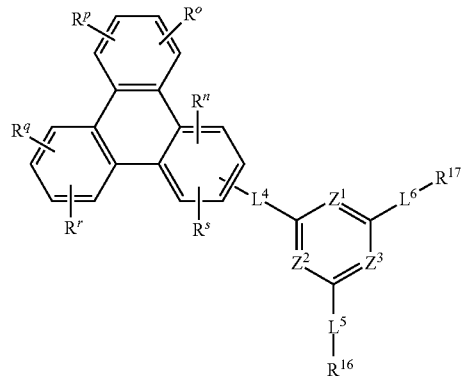

In Chemical Formulas 2-1 to 2-3, $Z^1$ to $Z^3$, $L^4$ to $L^6$, $R^{16}$, and $R^{17}$ are the same as described above, $X^3$ is O, S, or $NR^f$, $R^f$, $R^g$, $R^h$, $R^i$, $R^j$, $R^k$, $R^l$, $R^m$, $R^n$, $R^o$, $R^p$, $R^q$, $R^r$, and $R^s$ are independently hydrogen, deuterium, a cyano group, a substituted or unsubstituted C1 to C30 alkyl group, a substituted or unsubstituted C6 to C30 aryl group, a substituted or unsubstituted C2 to C30 heterocyclic group, or a combination thereof.

For example, $R^g$, $R^h$, $R^i$, $R^j$, $R^n$, $R^o$, $R^p$, $R^q$, $R^r$, and $R^s$ may independently be hydrogen, a cyano group, a substituted or unsubstituted C1 to C10 alkyl group, or a substituted or unsubstituted C6 to C12 aryl group.

For example, $R^k$, $R^l$, and $R^m$ may independently be hydrogen, a cyano group, a substituted or unsubstituted C6 to C12 aryl group, a substituted or unsubstituted pyridinyl group, a substituted or unsubstituted pyrimidinyl group, a substituted or unsubstituted triazinyl group, a substituted or unsubstituted dibenzofuranyl group, a substituted or unsubstituted dibenzothiophenyl group, or a substituted or unsubstituted carbazolyl group.

According to an embodiment of the present invention, Chemical Formula 2 may be represented by Chemical Formula 2-1 or Chemical Formula 2-2.

The second compound for organic optoelectronic device may be, for example, one of compounds of Group 2, but is not limited thereto.

[Group 2]
A-1
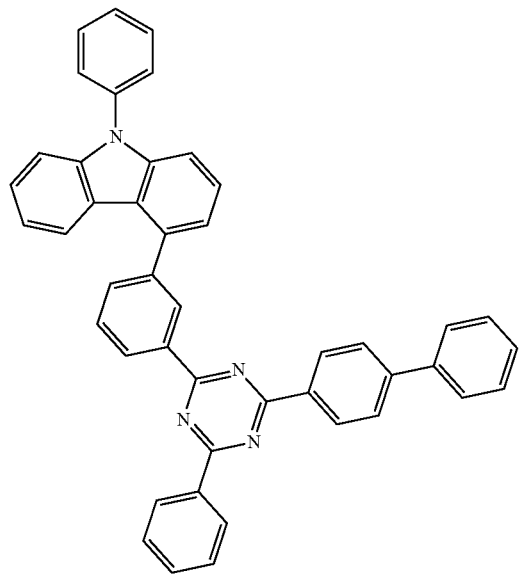
A-3
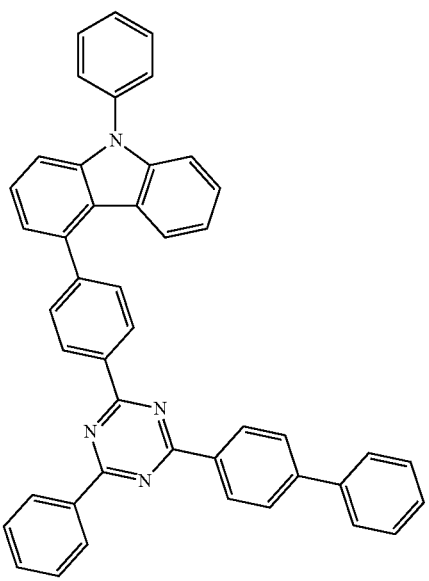
-continued
A-2
A-4
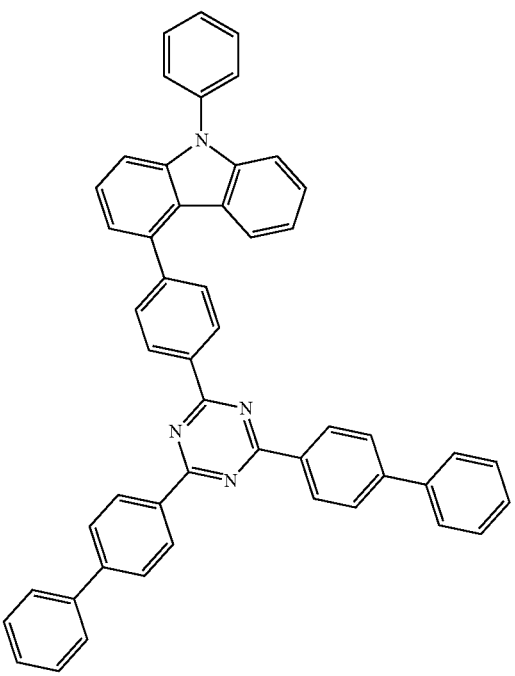

A-5
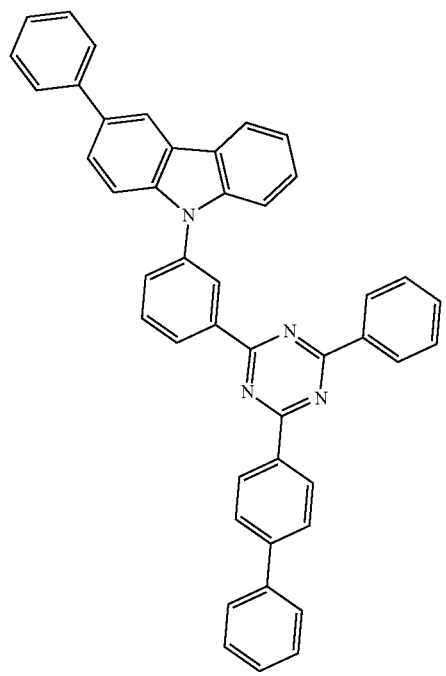
A-6
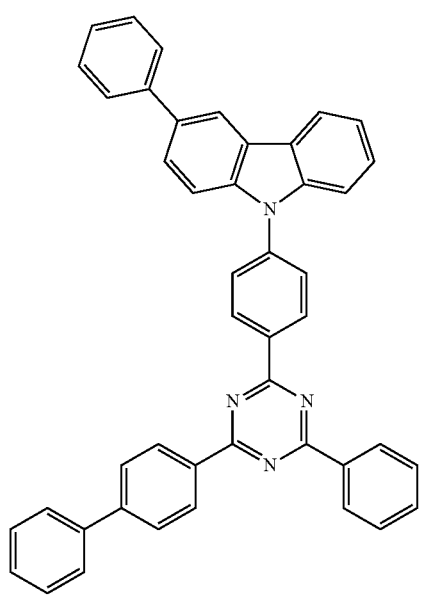
A-7
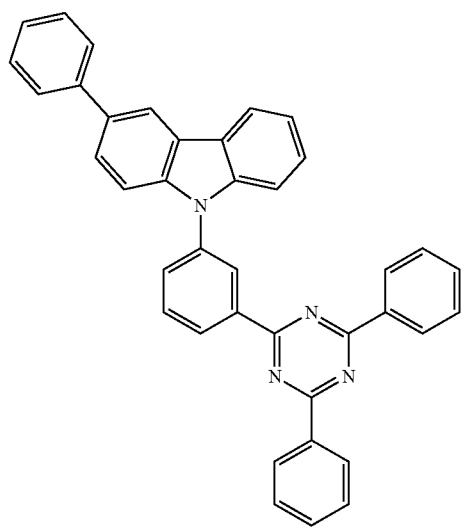
A-8
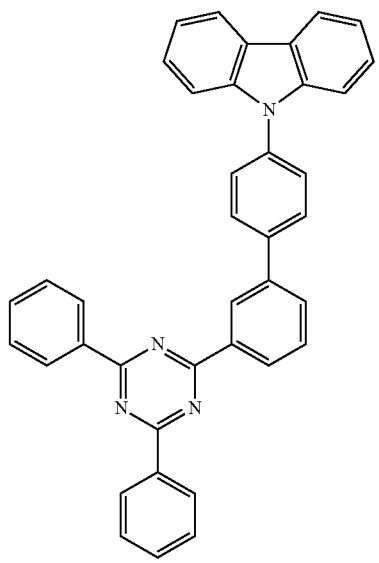
A-9

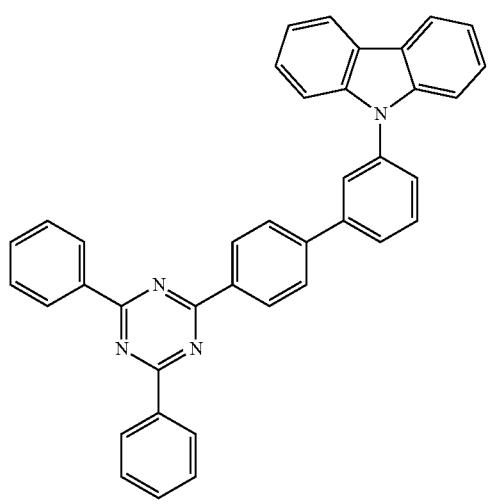
A-10
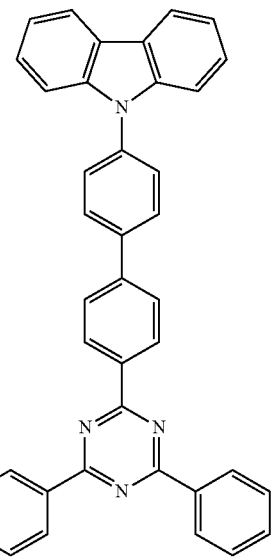
A-12
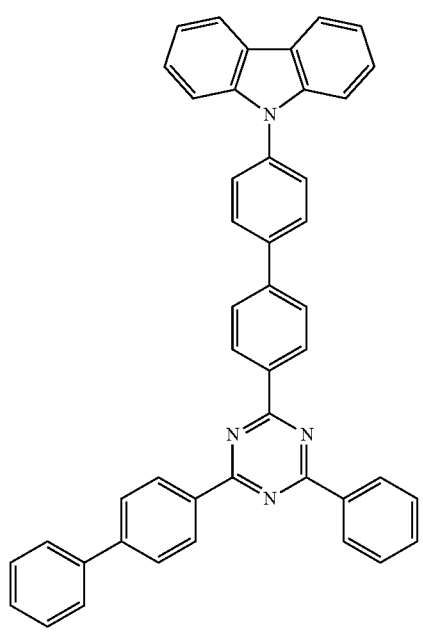
A-11
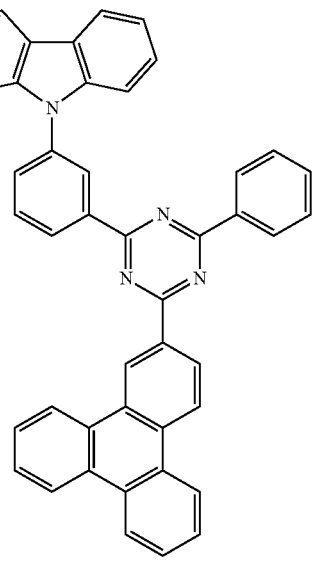
A-13

A-14
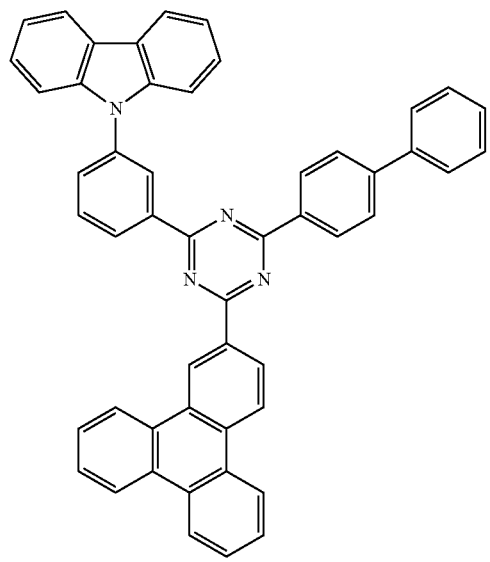
A-15
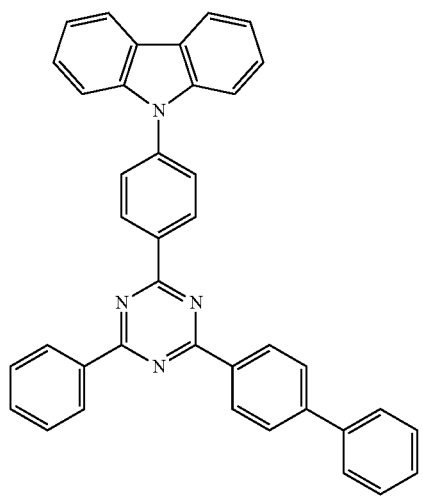
A-16
A-17
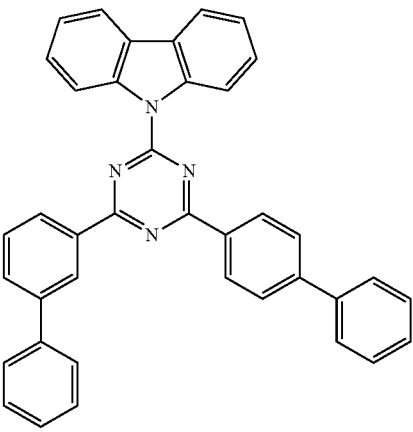
A-18
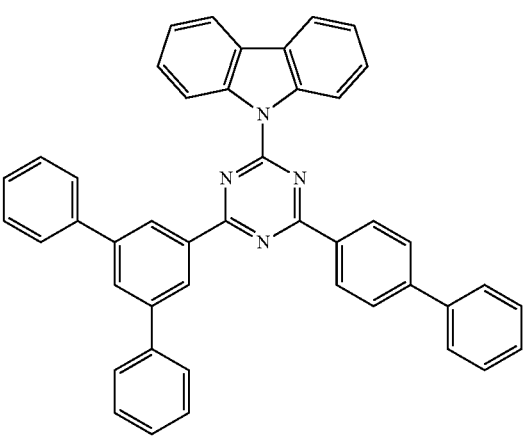
A-19
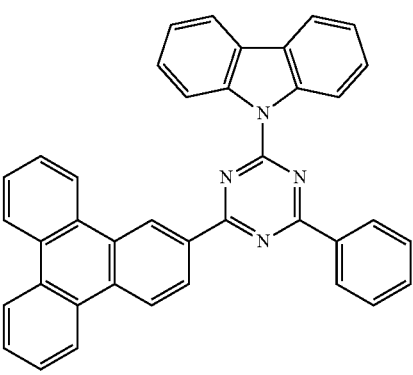
A-20
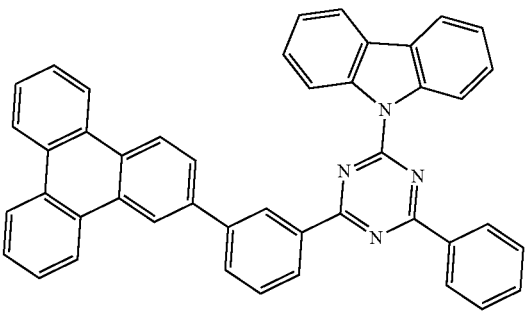

A-21
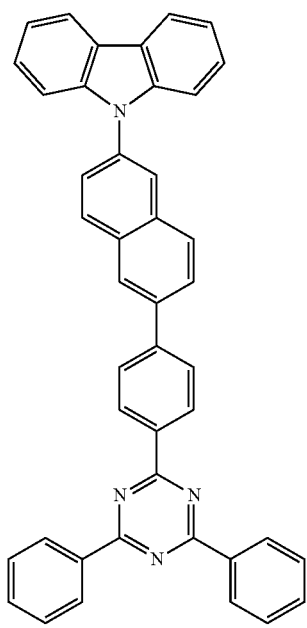
A-22
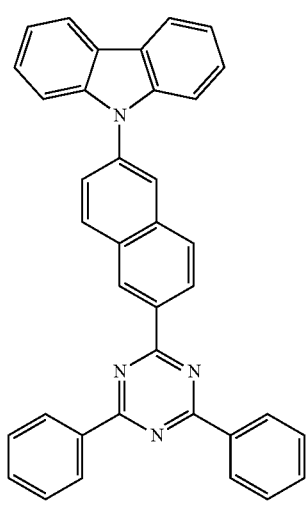
A-23
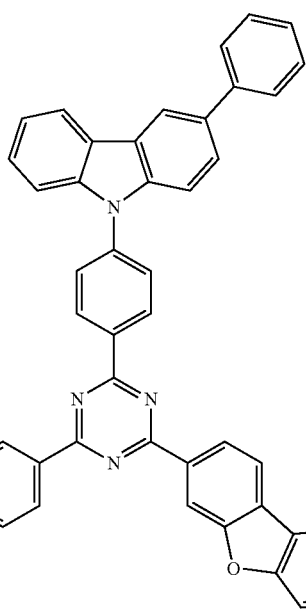
A-24
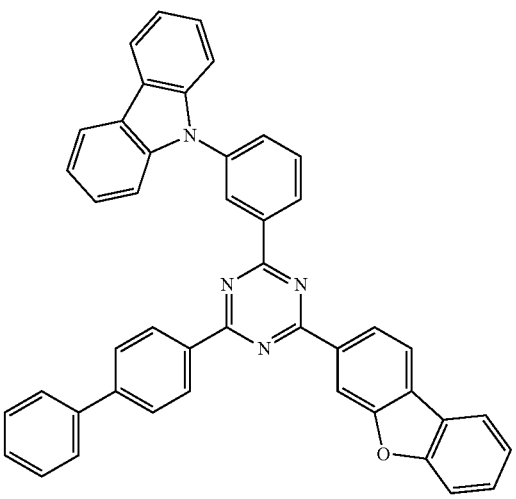
A-25

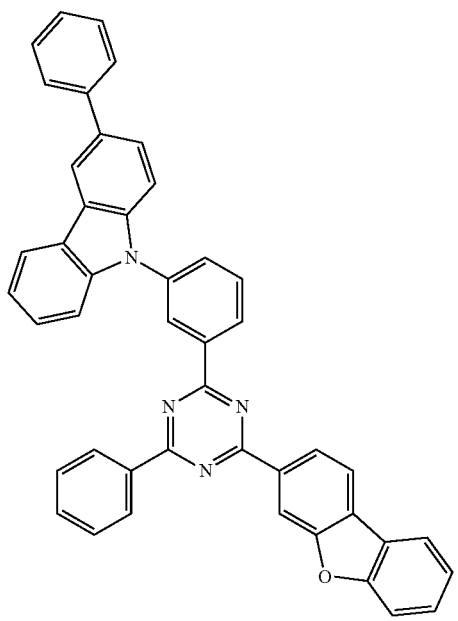
A-26
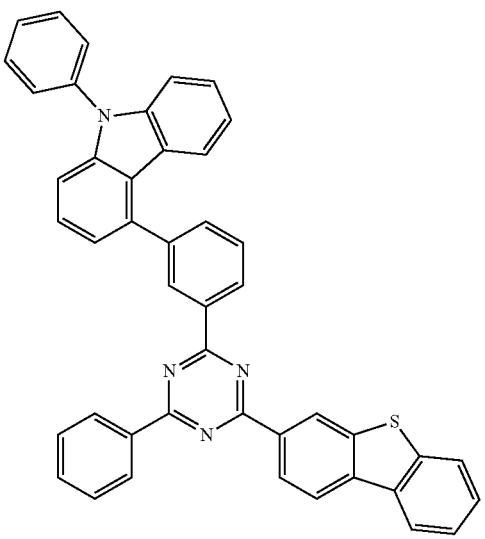
A-28
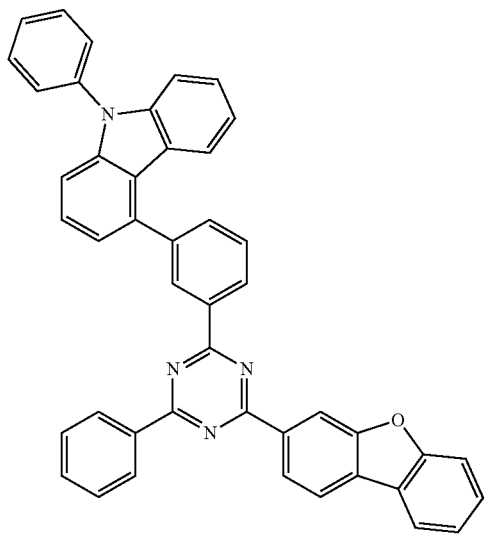
A-27
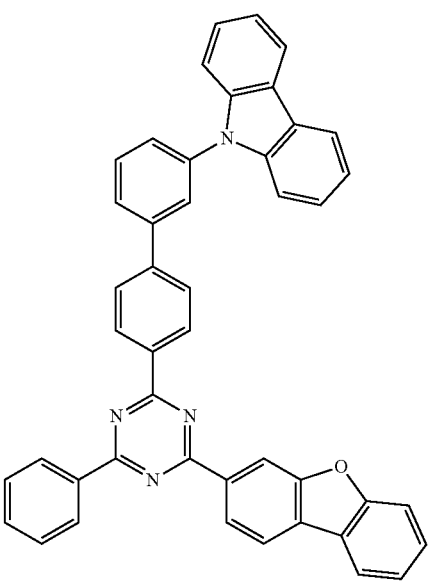
A-29

A-30
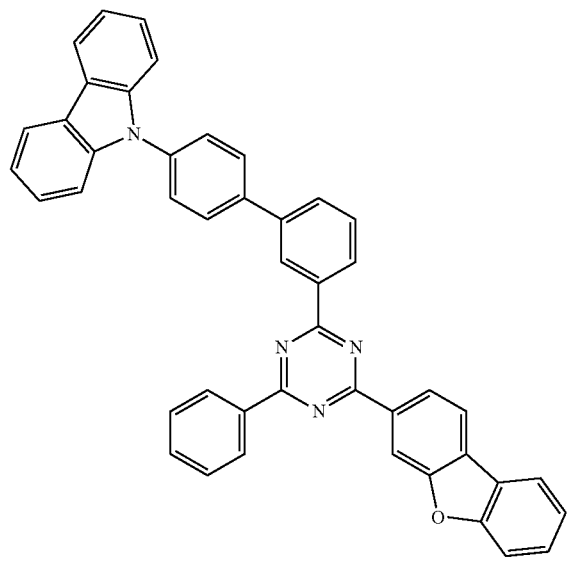
A-31
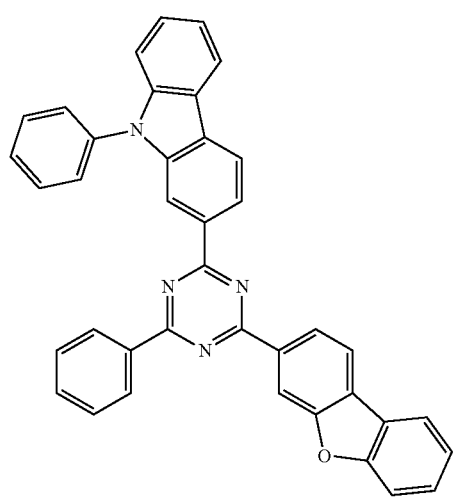
A-32
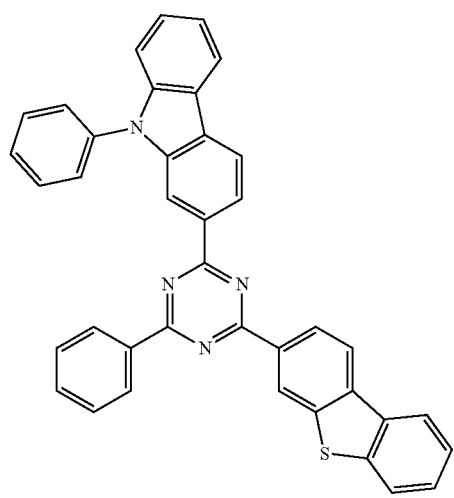
A-33
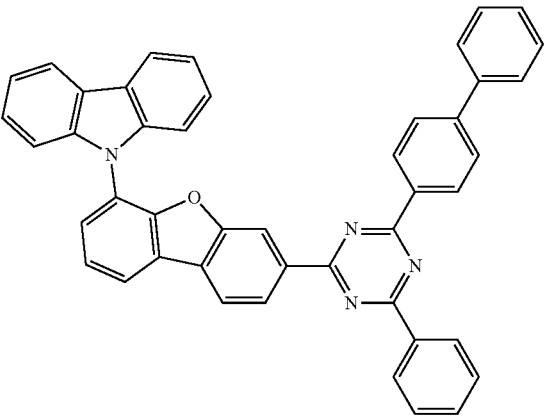
A-34
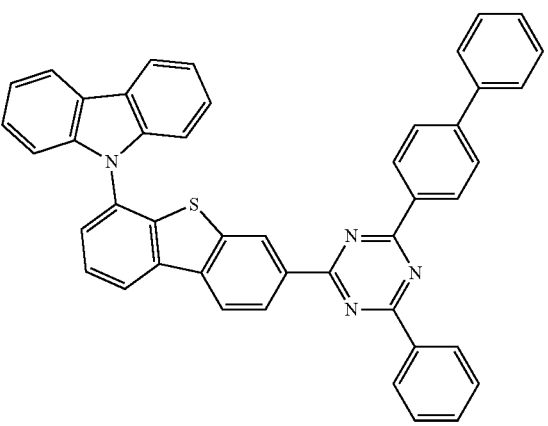
A-35
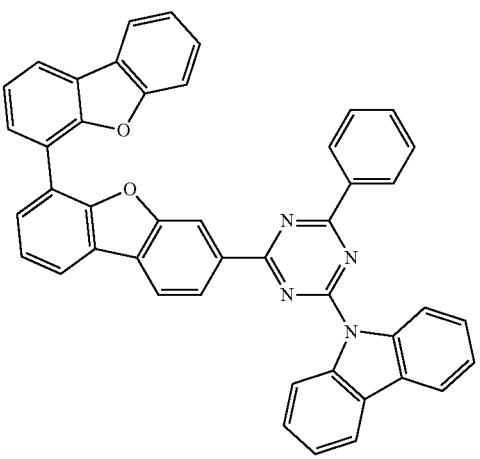

A-36
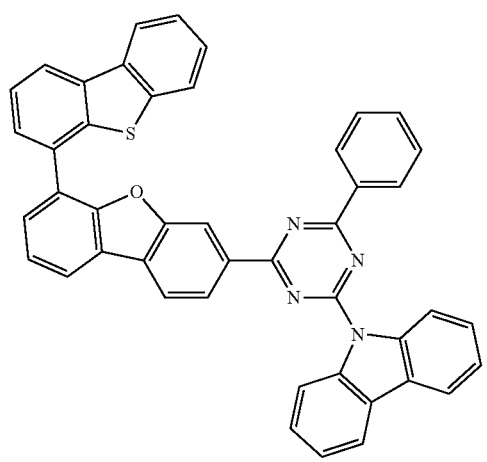
A-37
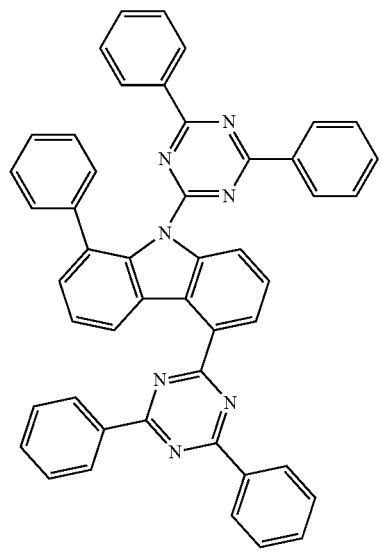
A-38
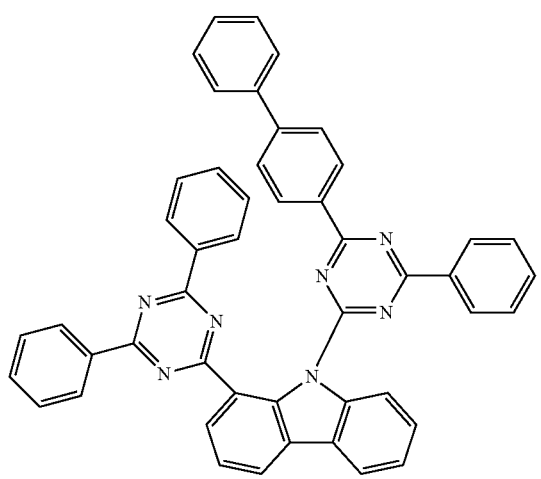
A-39
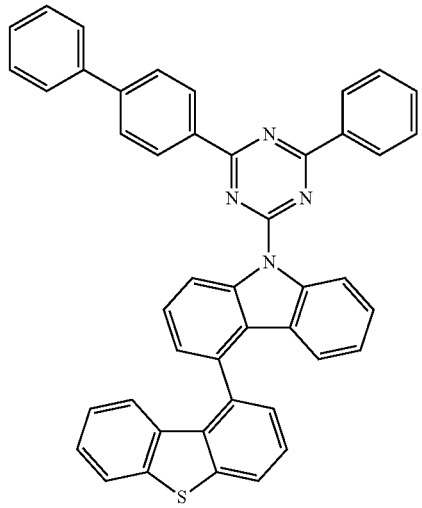
A-40
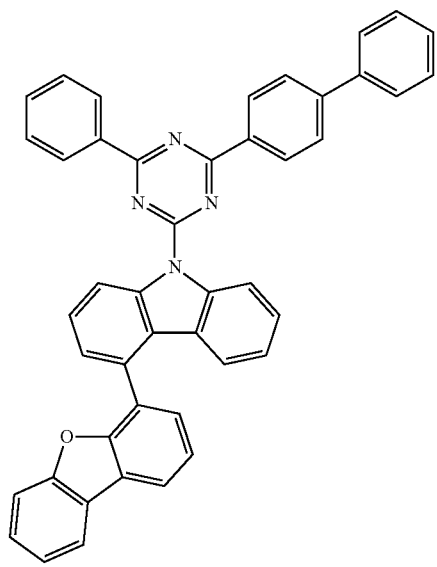
A-41
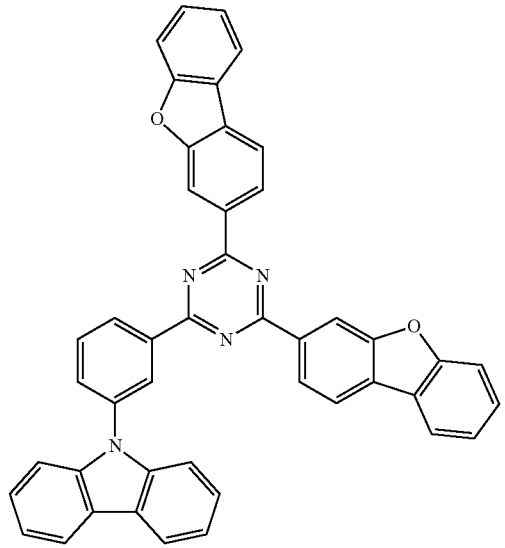

A-42
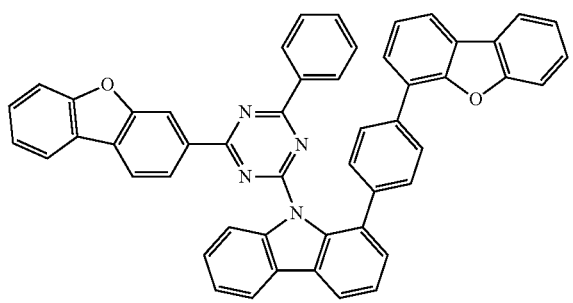
A-43
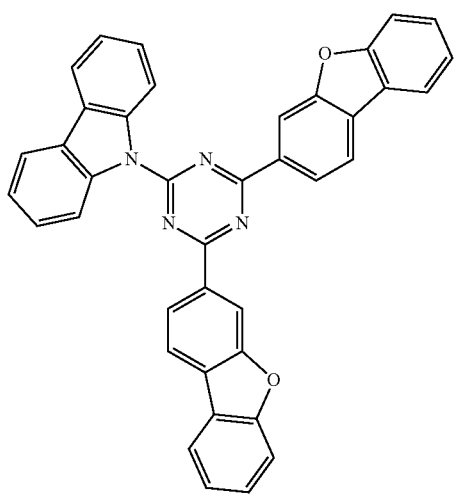
A-44
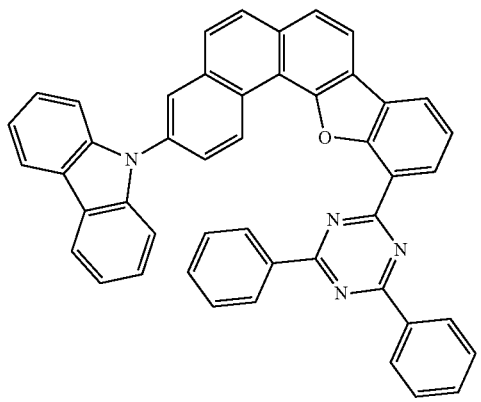
B-1
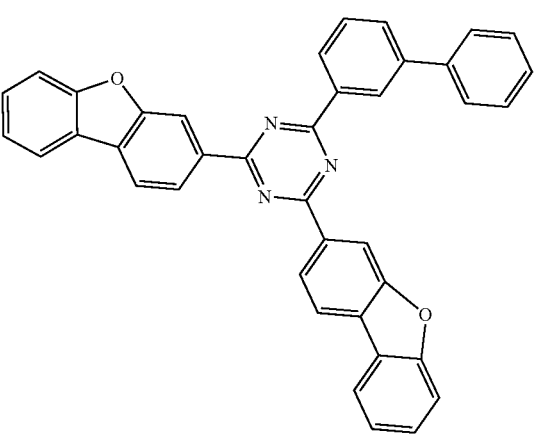
B-2
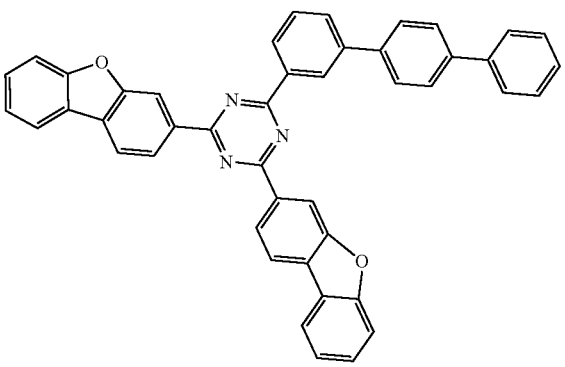
B-3
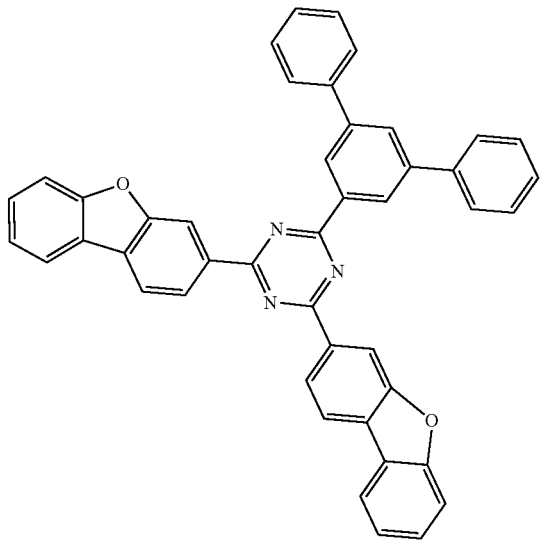
B-4
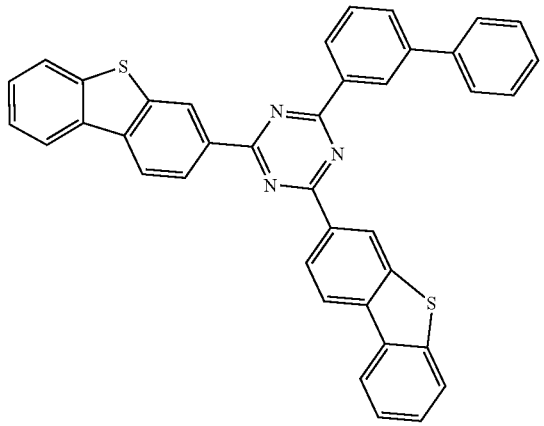

B-5
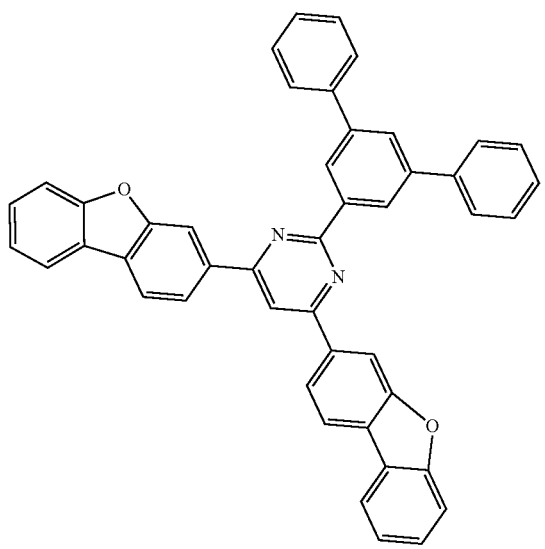
B-8
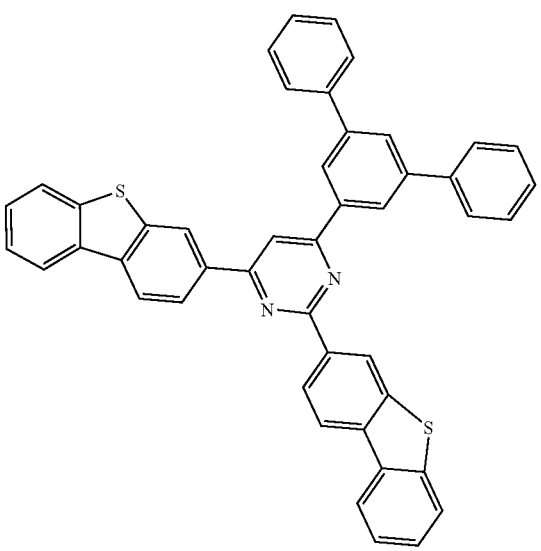
B-6
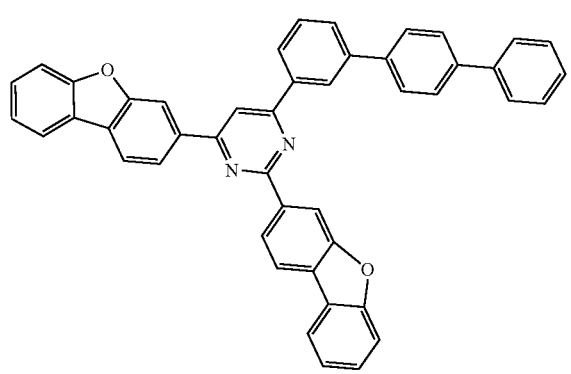
B-9
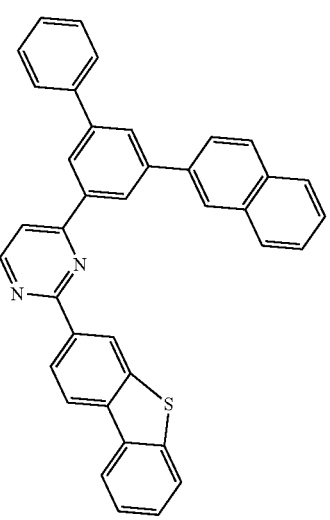
B-7
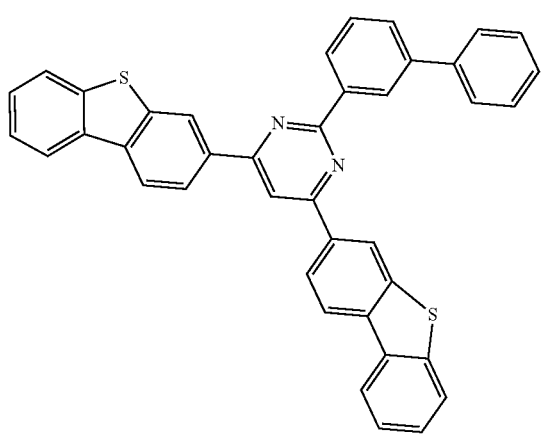
B-10
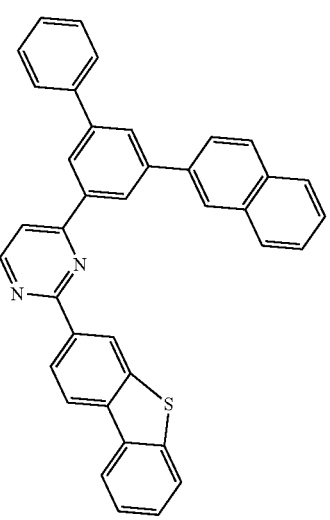

-continued
B-11
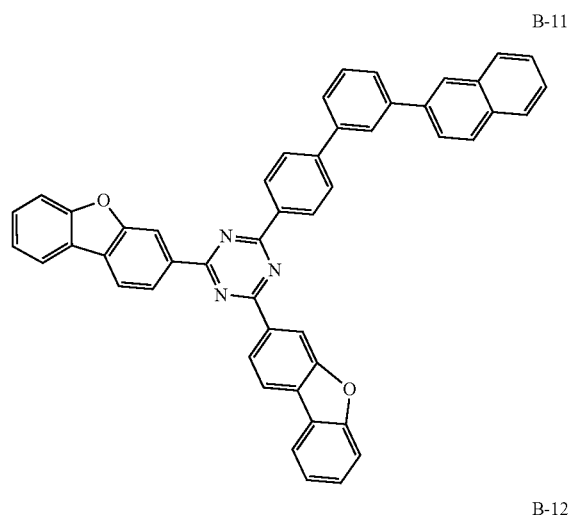
B-12
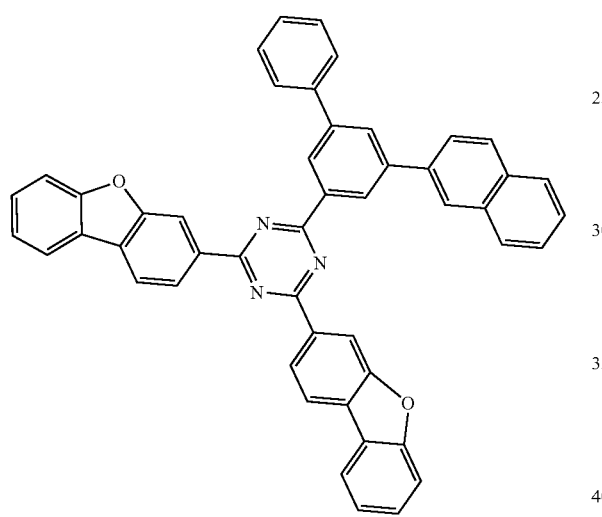
B-13
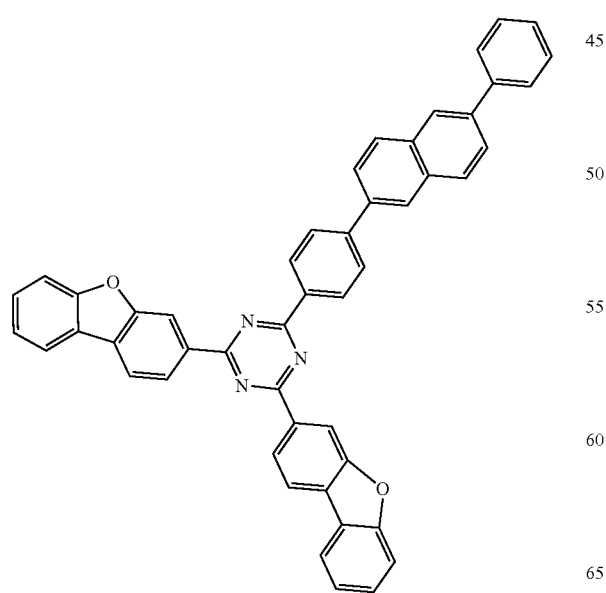
-continued
B-14
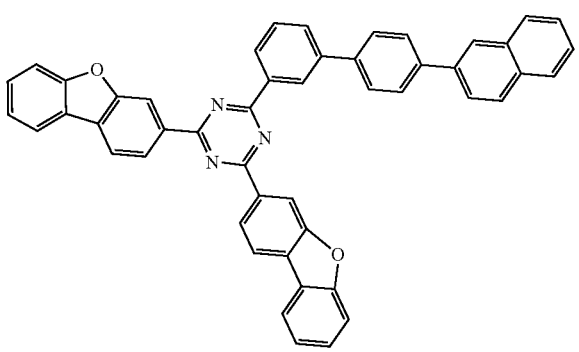
B-15
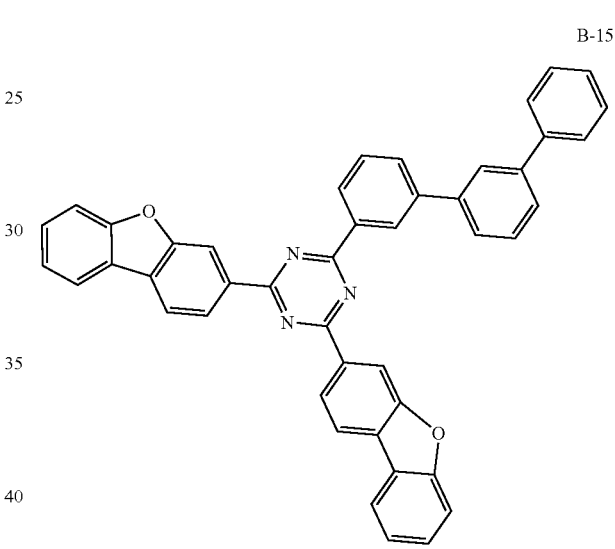
B-16
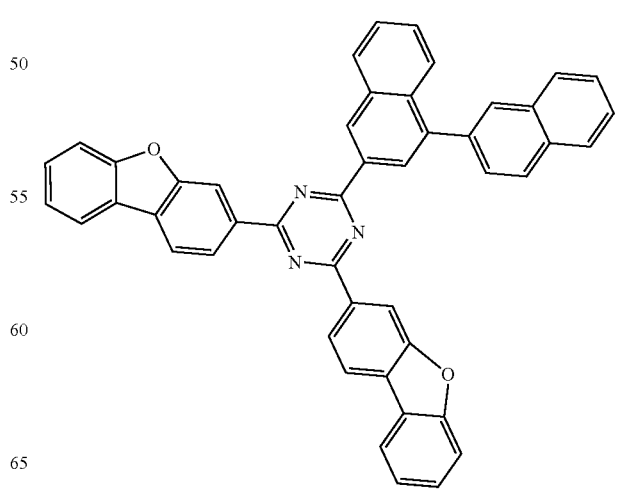

B-17
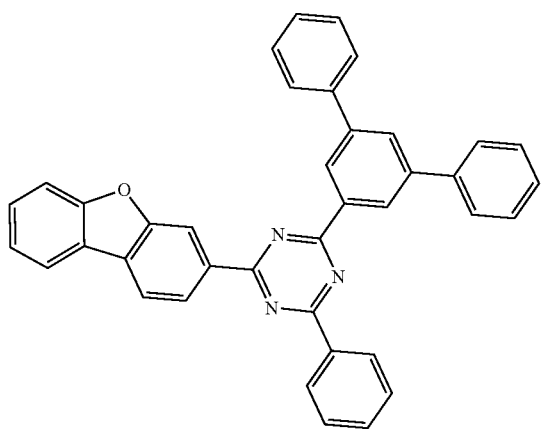
B-18
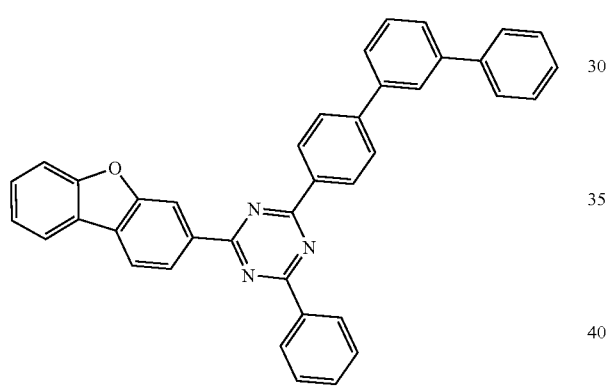
B-19
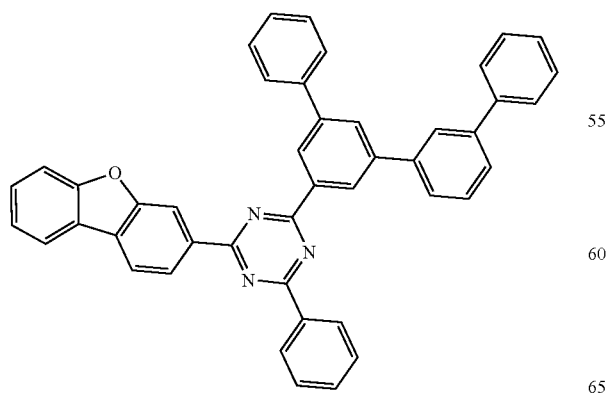
B-20
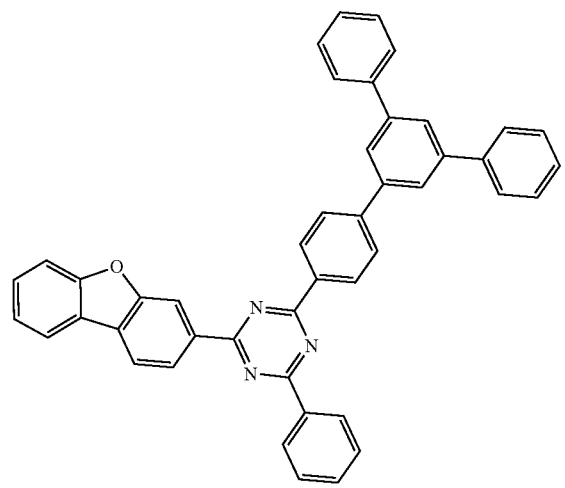
B-21
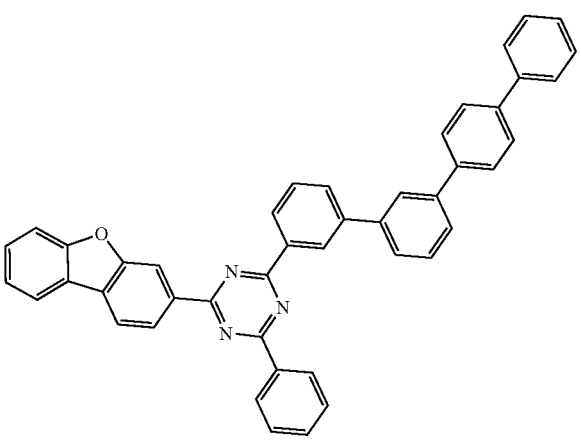
B-22
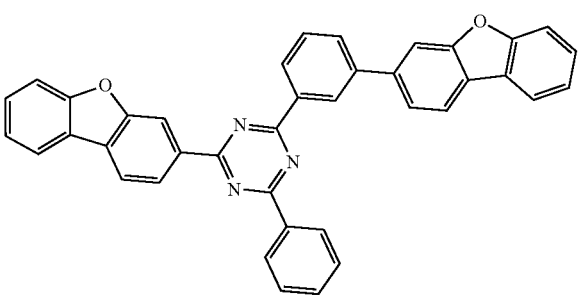

B-23
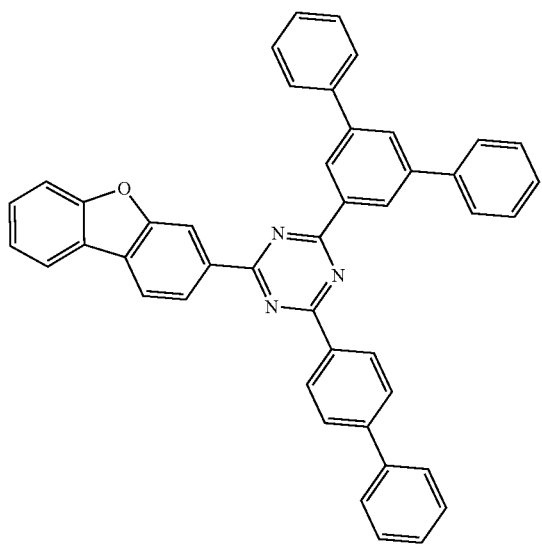
B-24
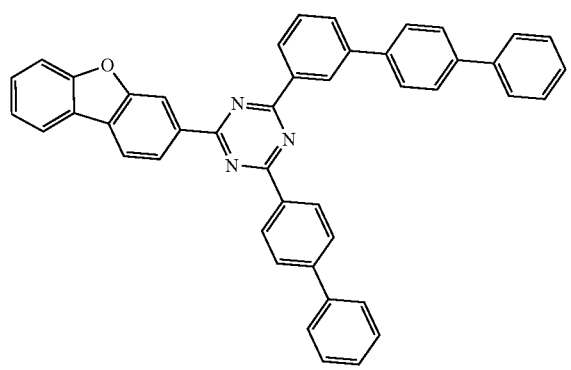
B-25
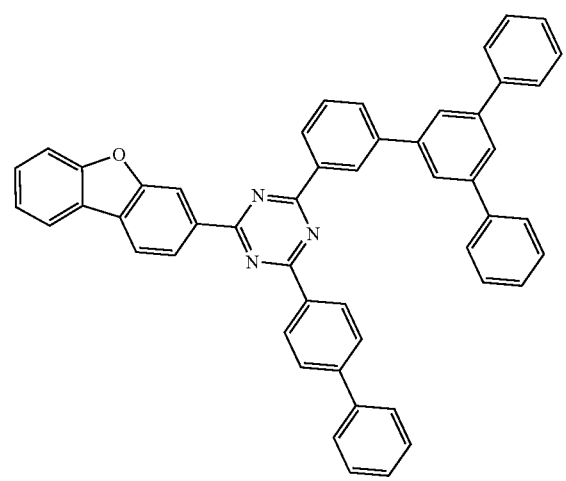
B-26
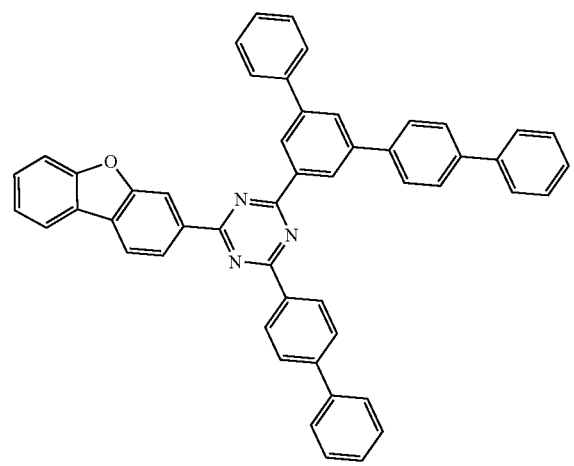
B-27
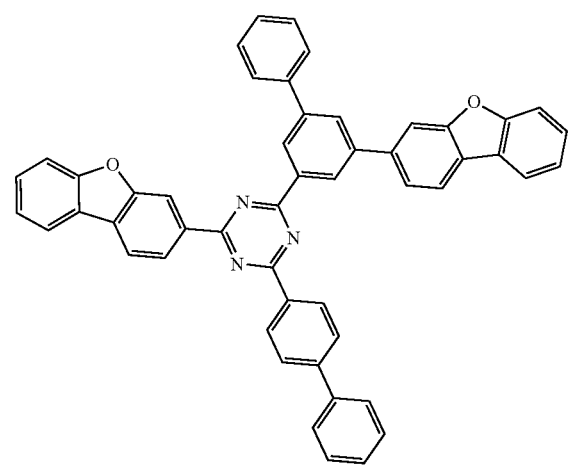
B-28
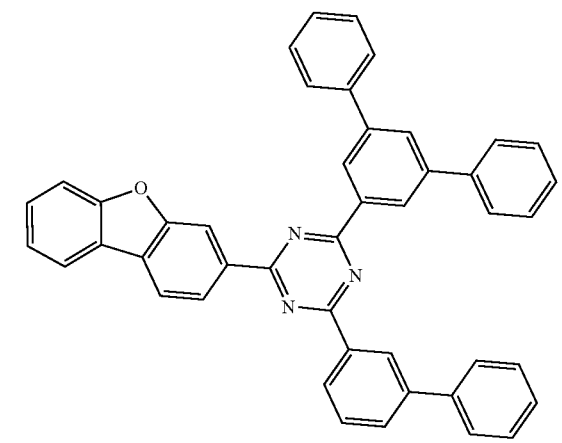

B-29

B-30

B-31

B-32

B-33

B-34

B-35

B-36
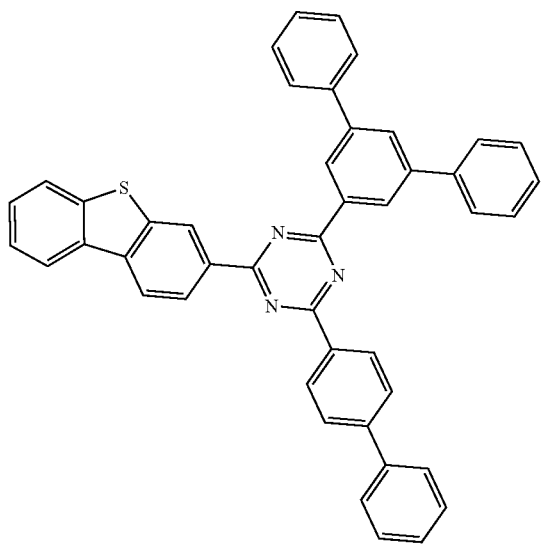
B-37
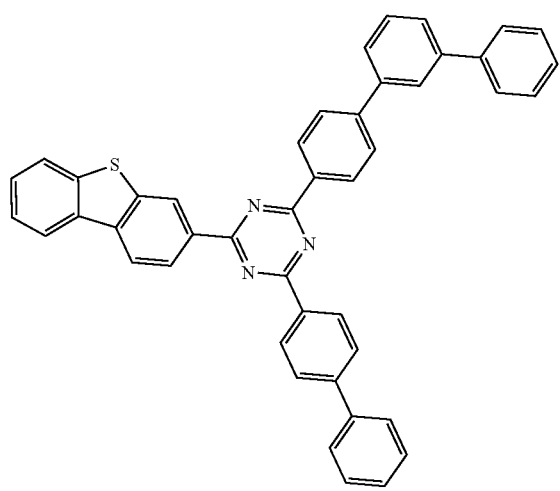
B-38
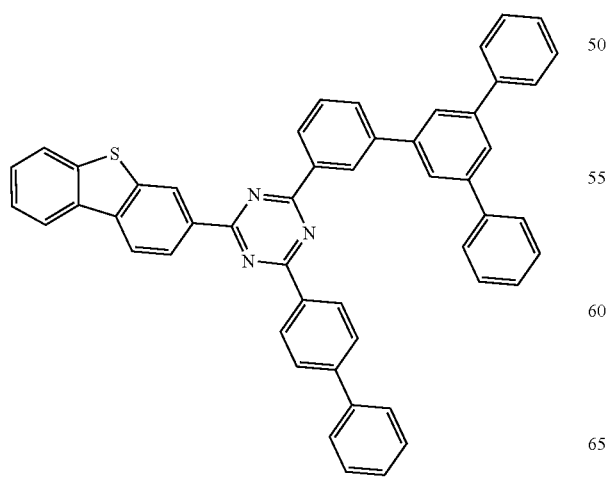
B-39
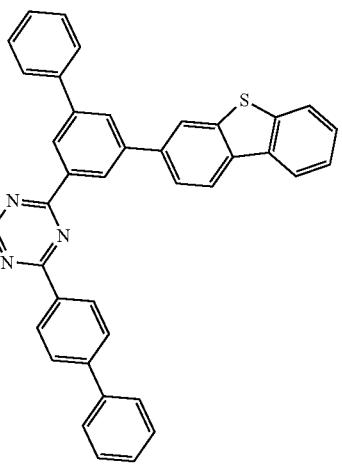
B-40
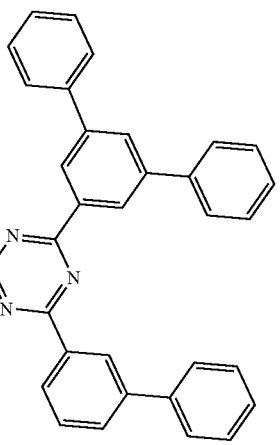
B-41
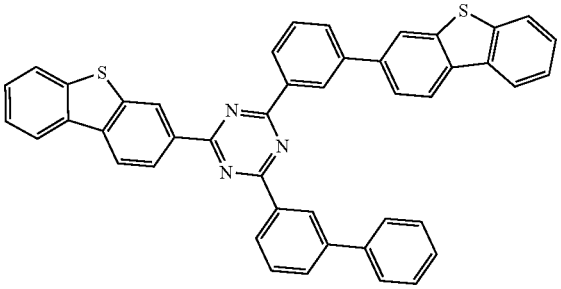

B-42
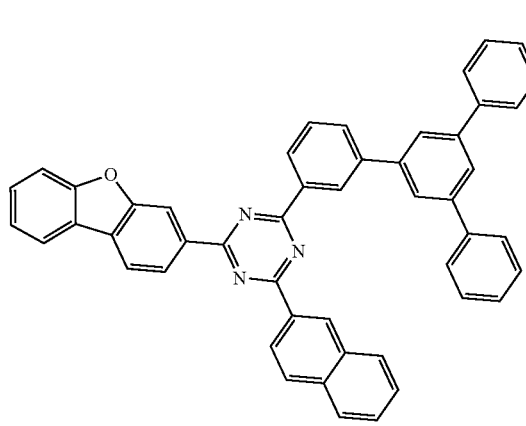
B-43
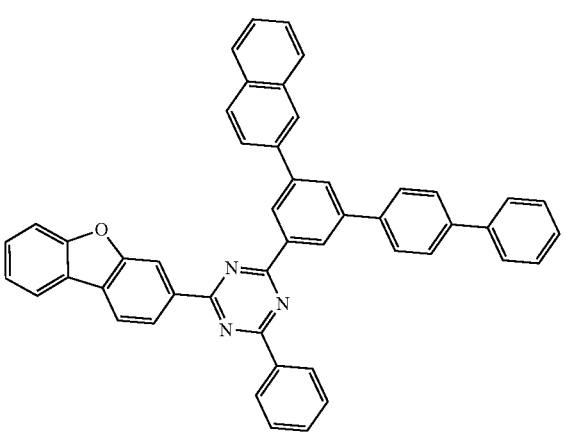
B-44
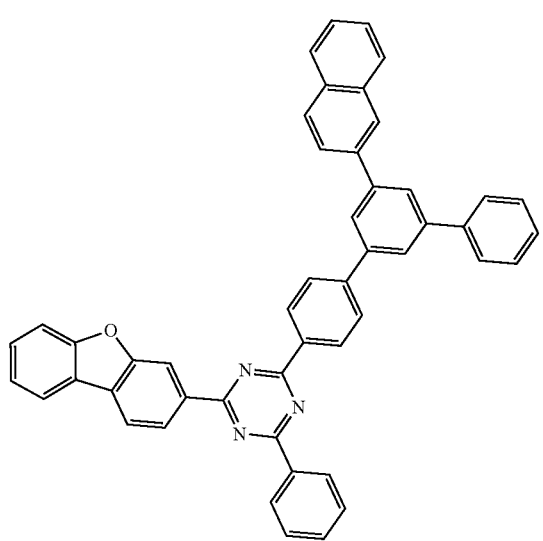
B-45
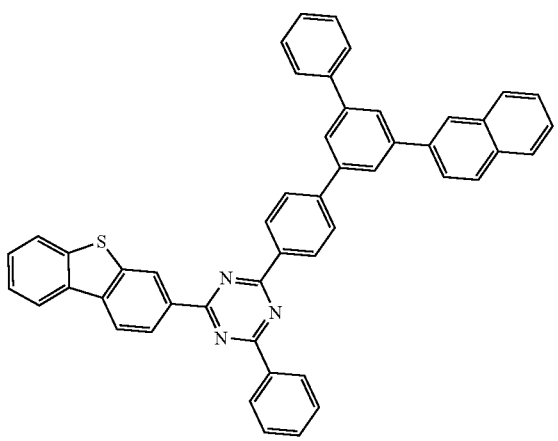
B-46
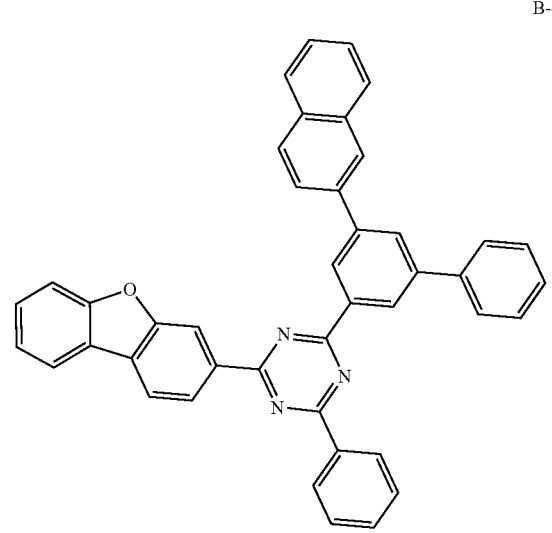
B-47
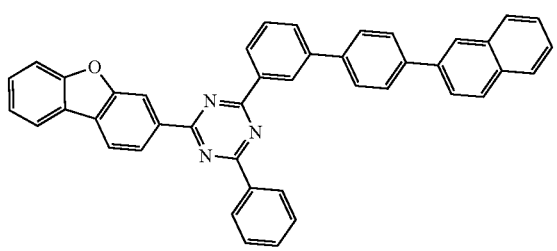
B-48
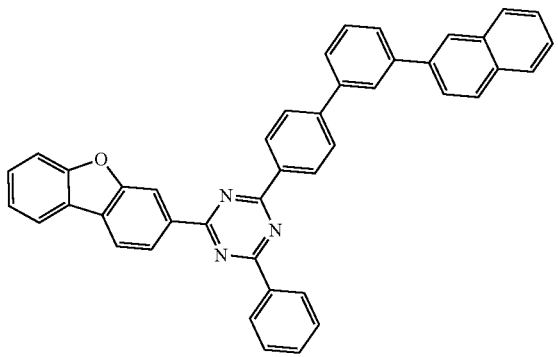

B-49
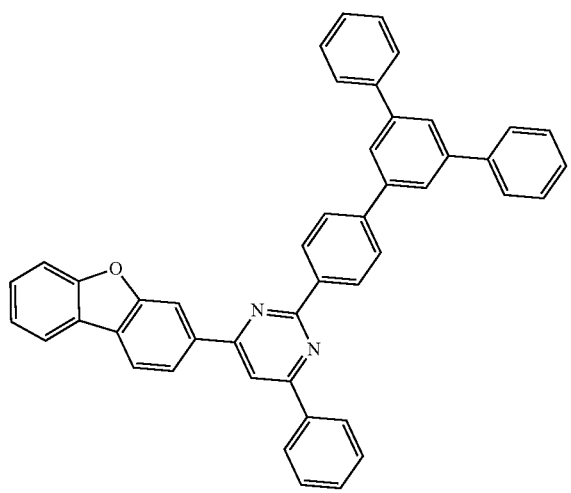
B-50
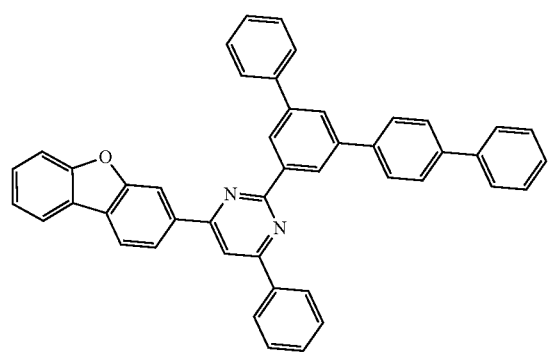
B-51
B-52
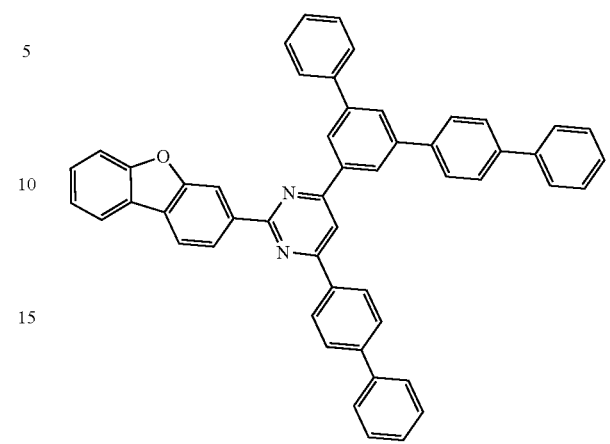
B-53
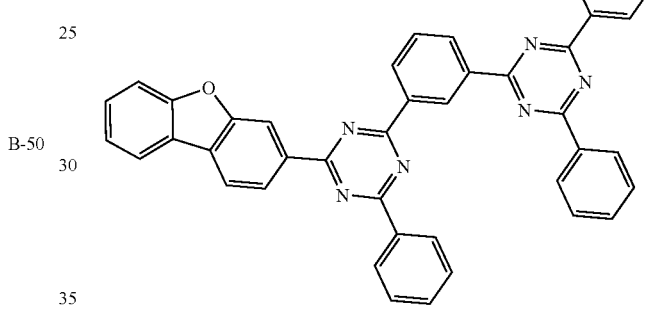
B-54
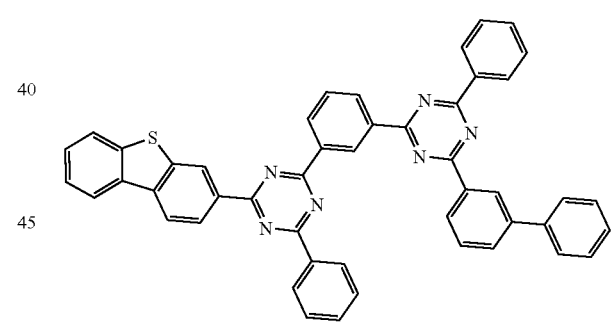
B-55
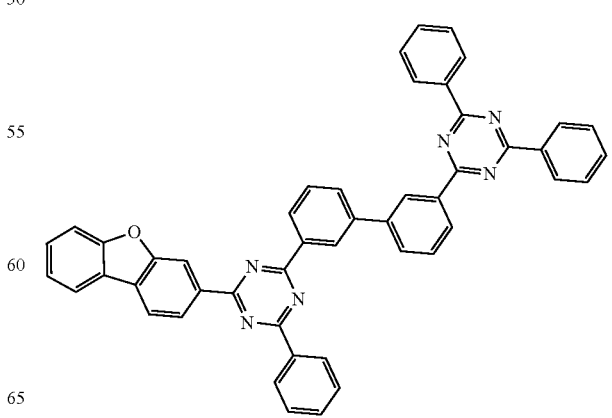

B-56
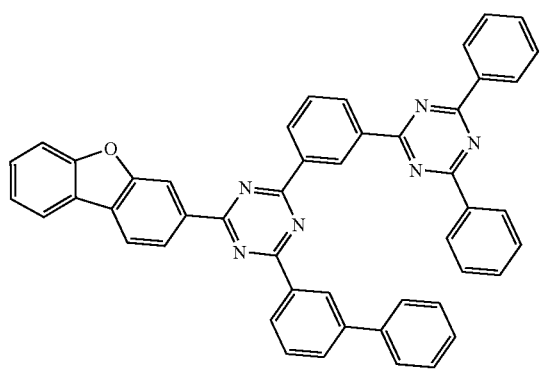
B-57
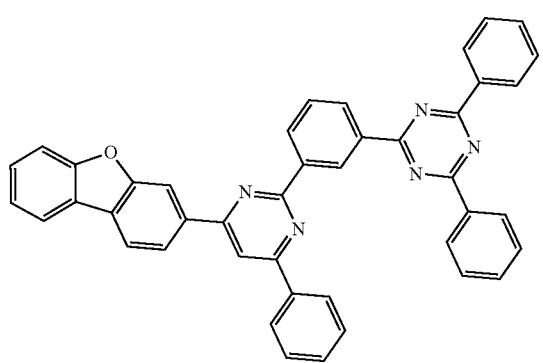
B-58
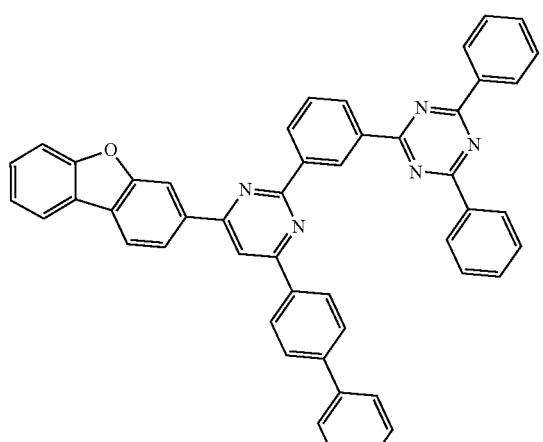
B-59
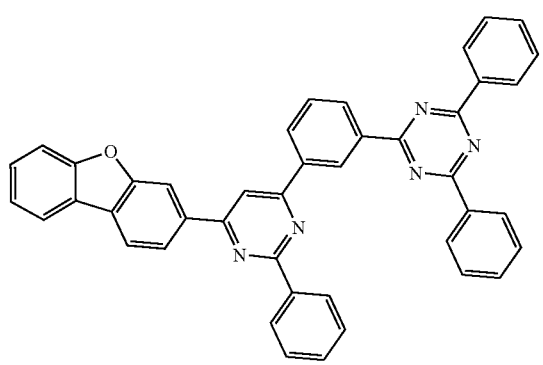
B-60
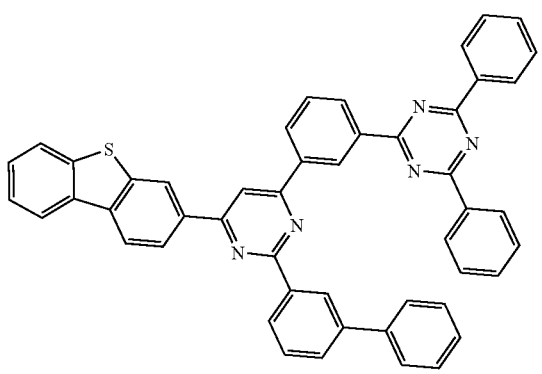
B-61
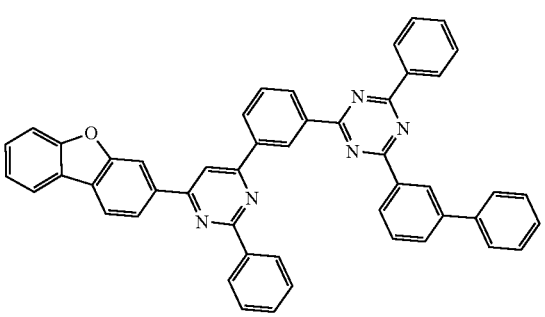
B-62
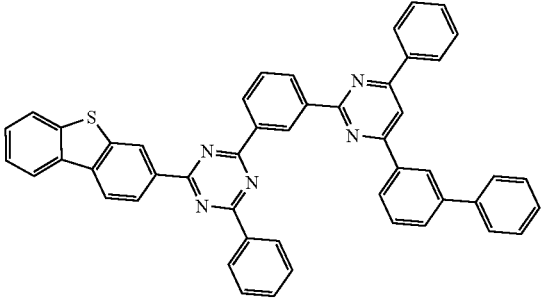
B-63
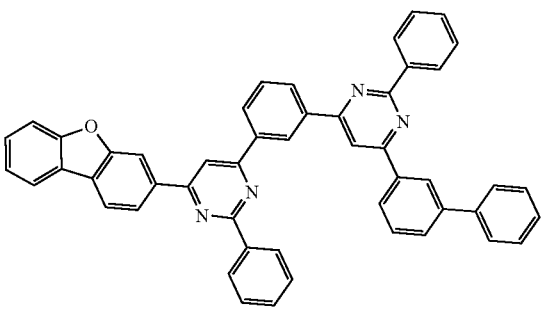

B-64
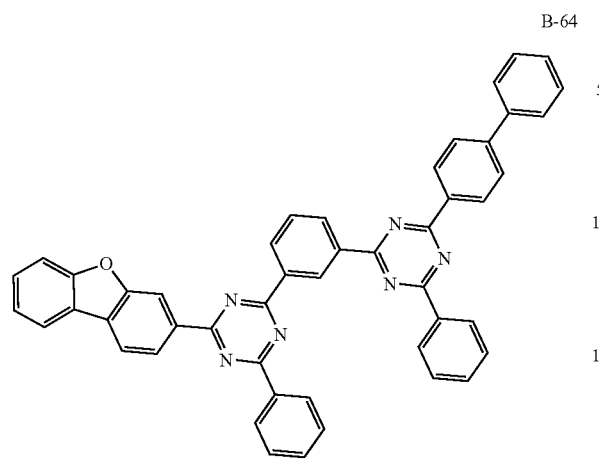
B-65
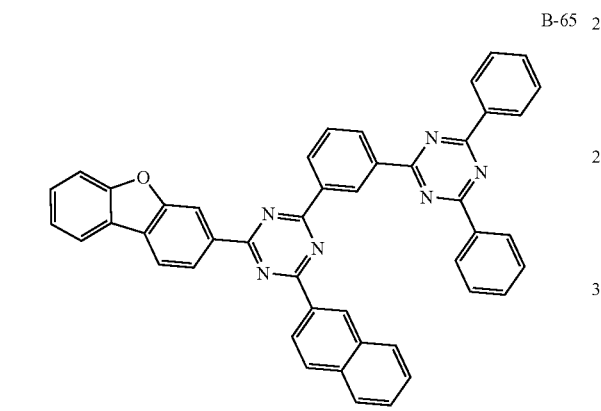
B-66
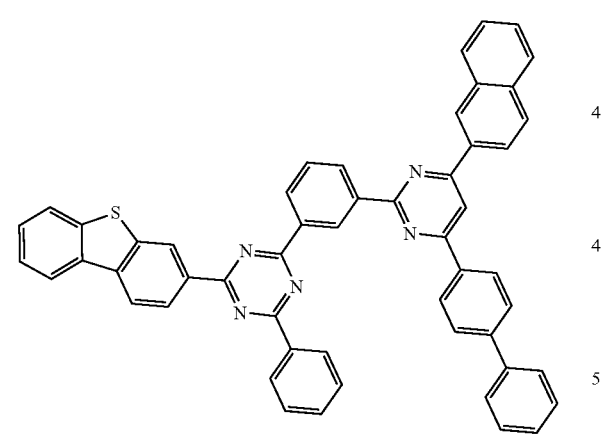
B-67
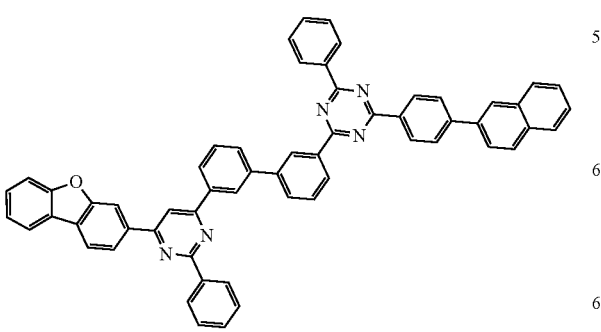
B-68
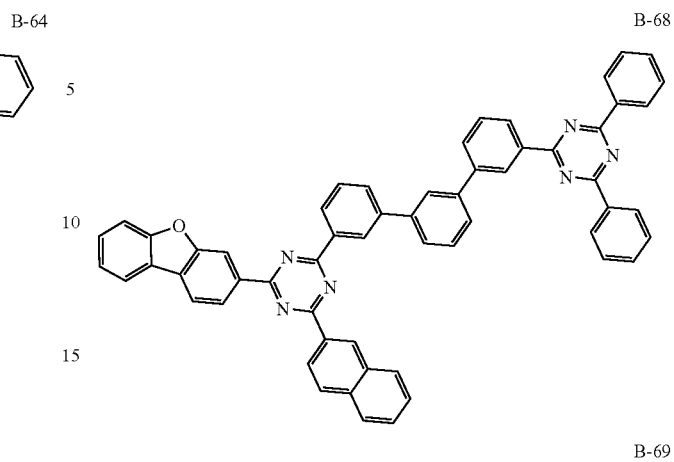
B-69
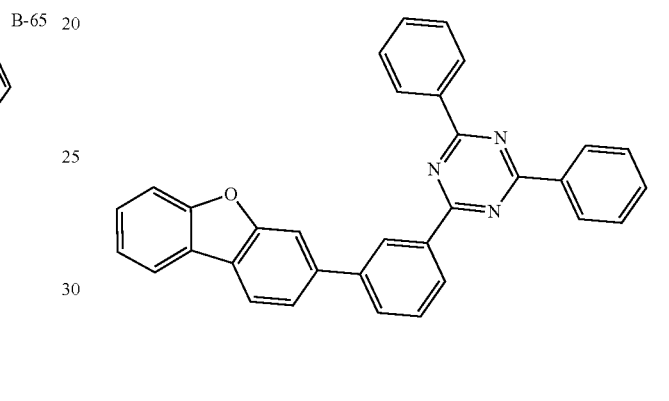
B-70
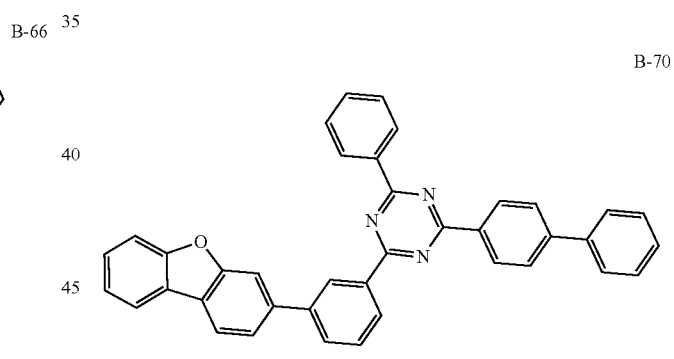
B-71
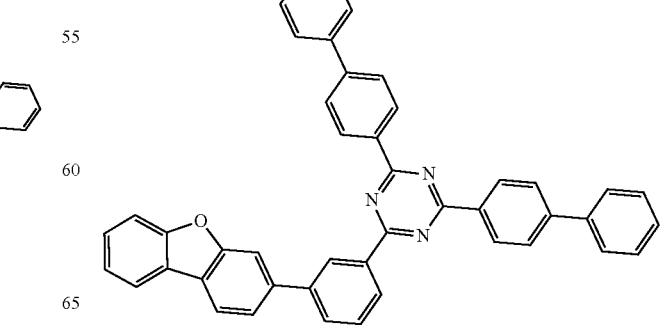

B-72
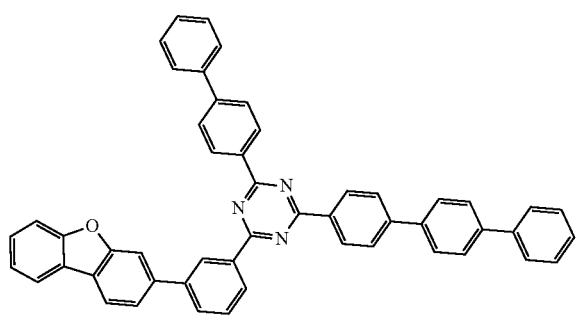
B-73
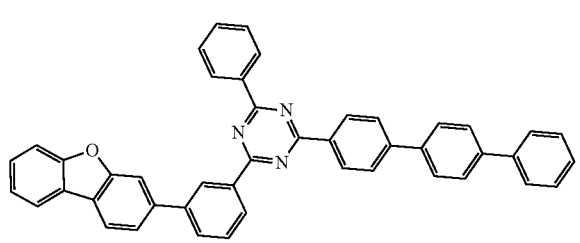
B-74
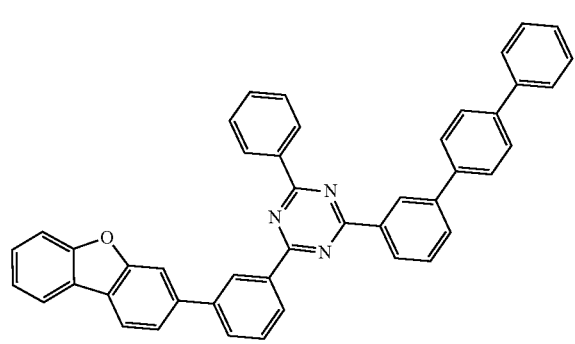
B-75
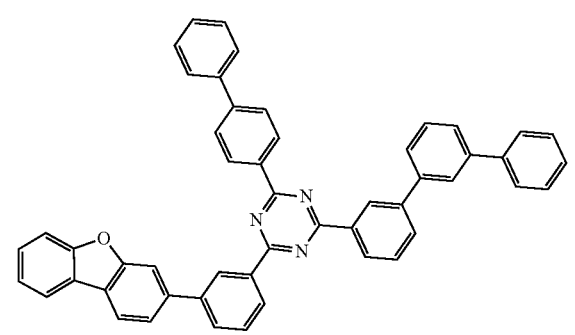
B-76
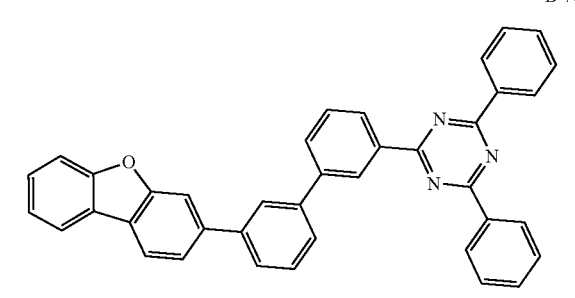
B-77
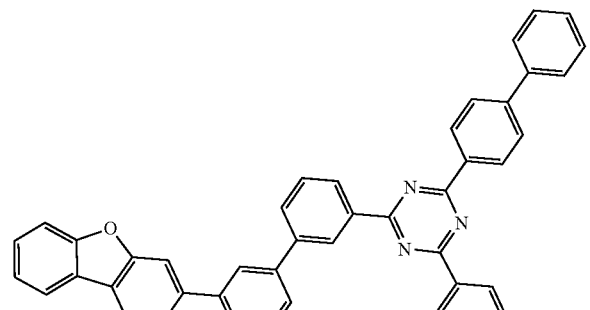
B-78
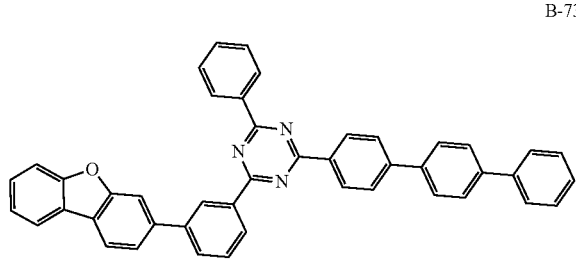
B-79
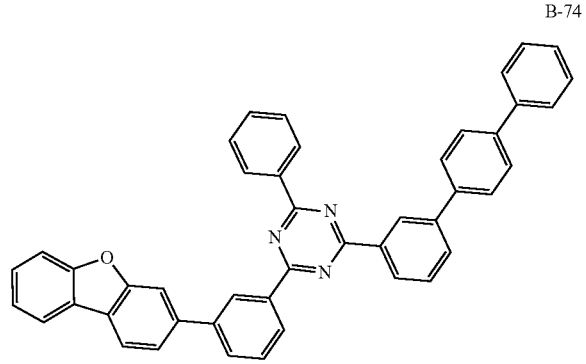
B-80
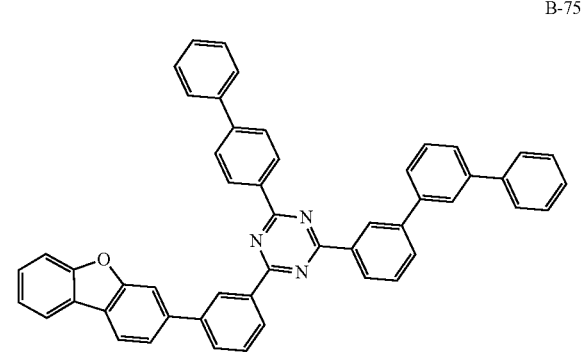
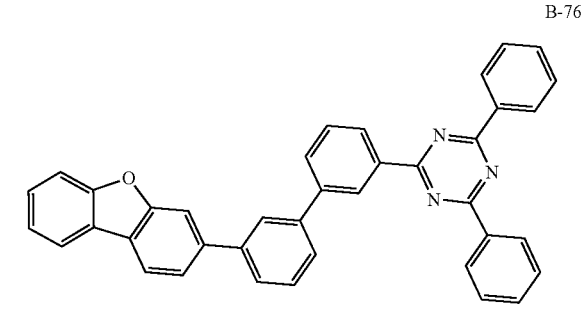

-continued
B-81
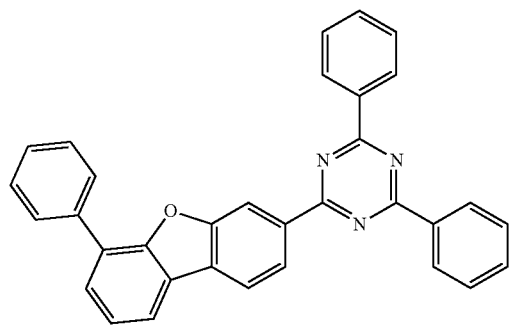
B-82
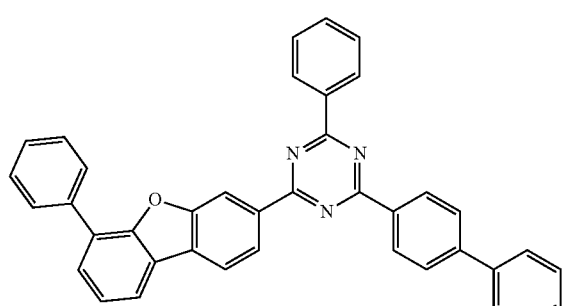
B-83
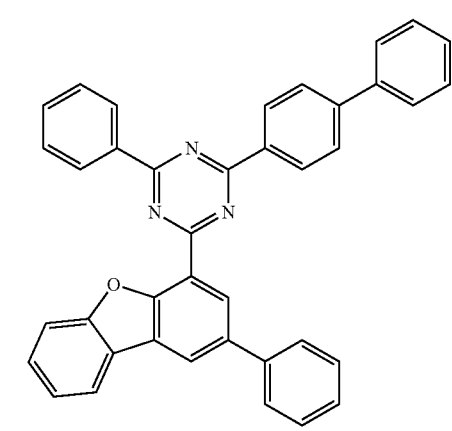
B-84
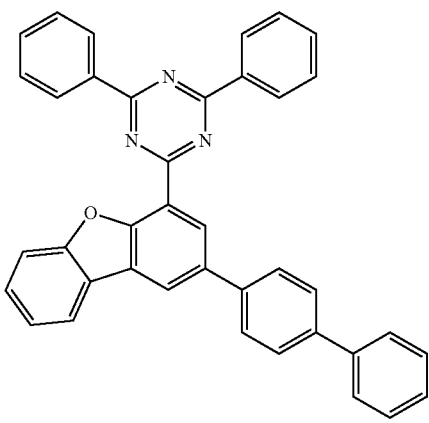
-continued
B-85
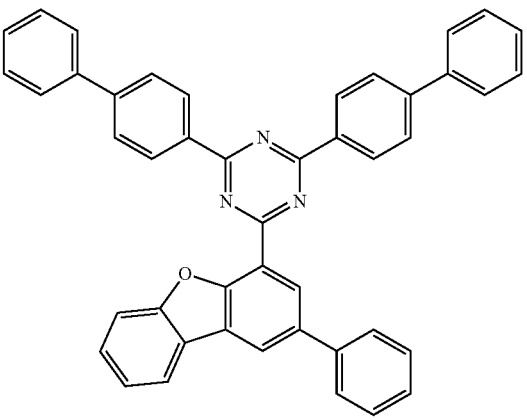
B-86
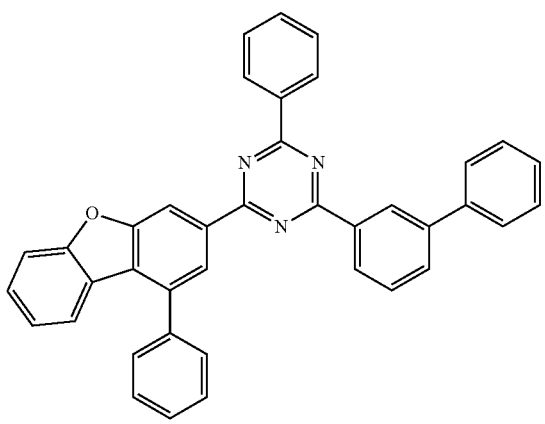
B-87
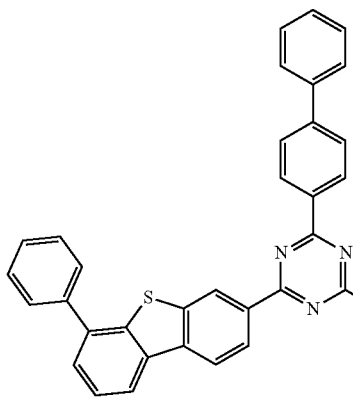
B-88
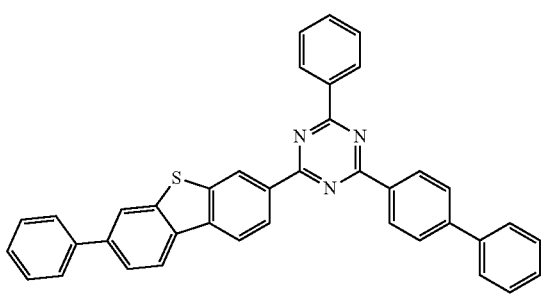

B-89
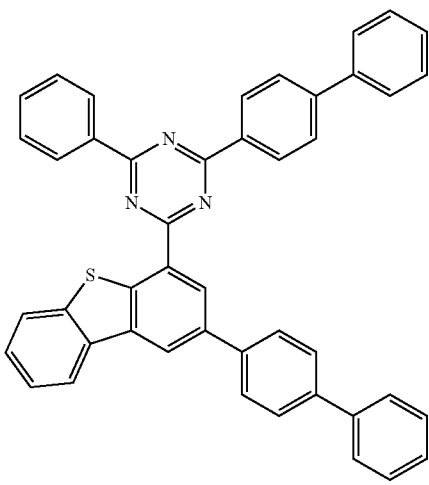
B-92
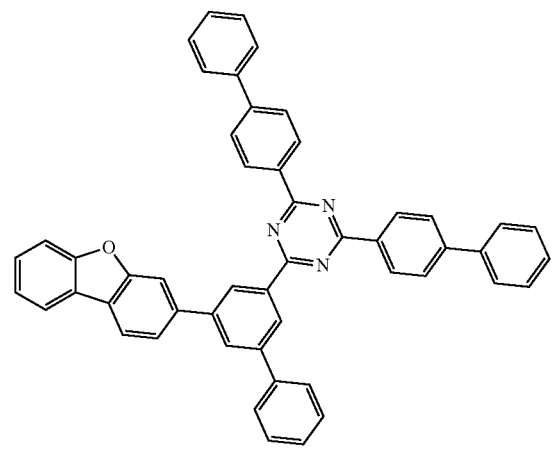
B-90
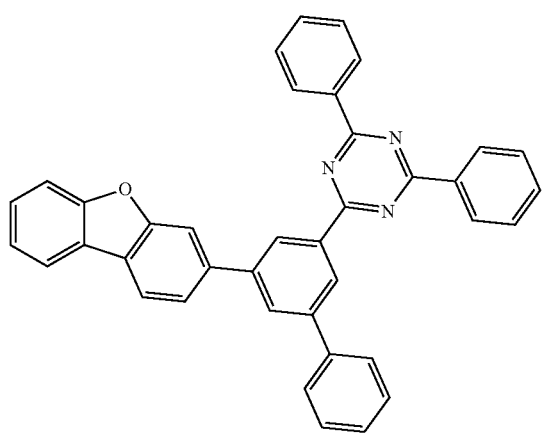
B-93
B-91
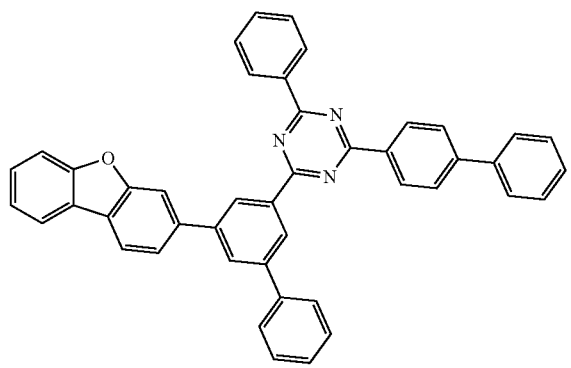
B-94
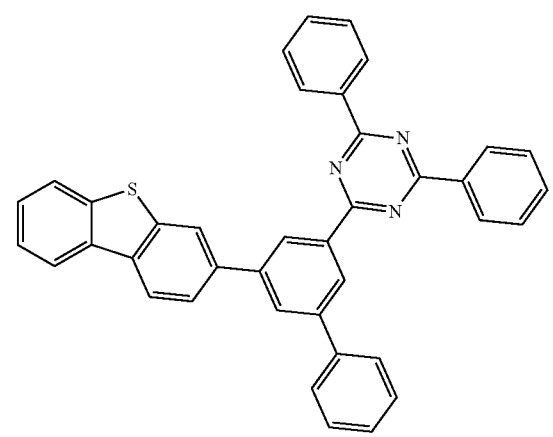

B-95
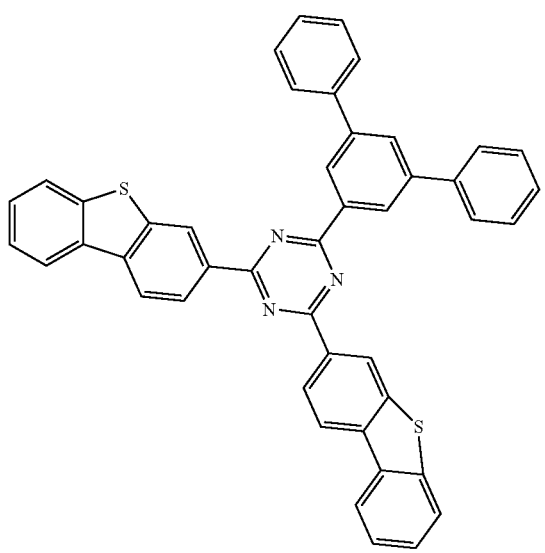
B-98
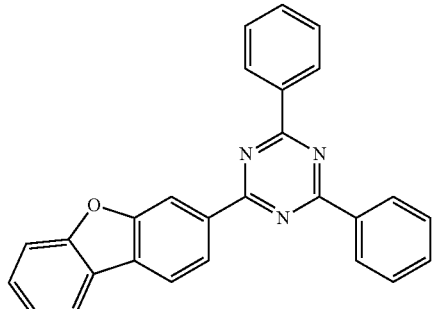
B-96
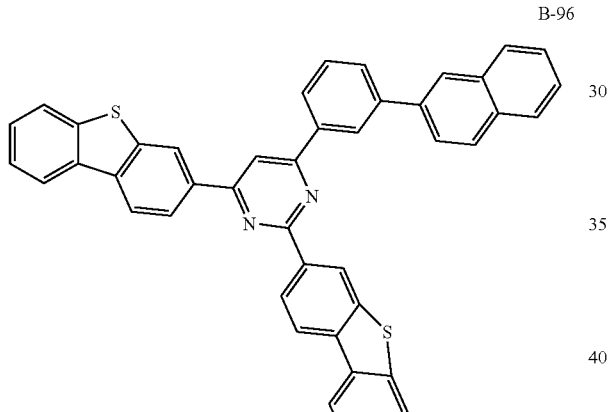
B-99
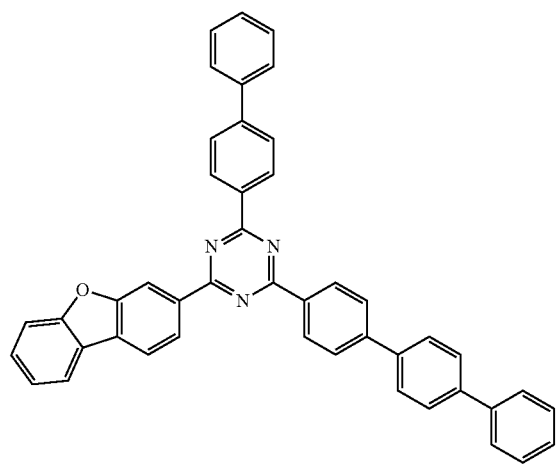
B-97
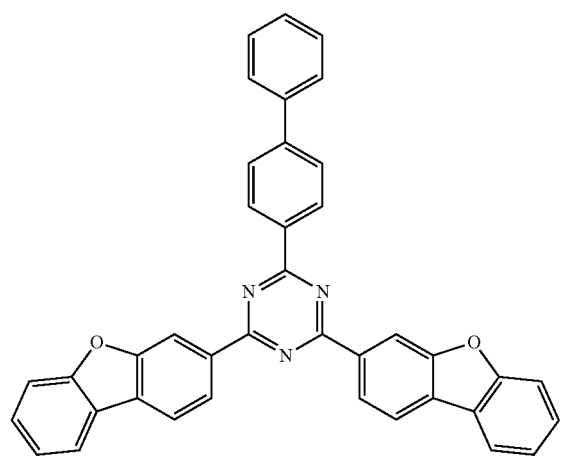
B-100
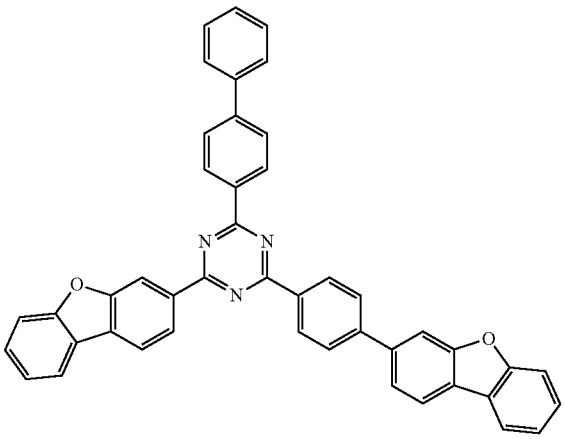

-continued
B-101
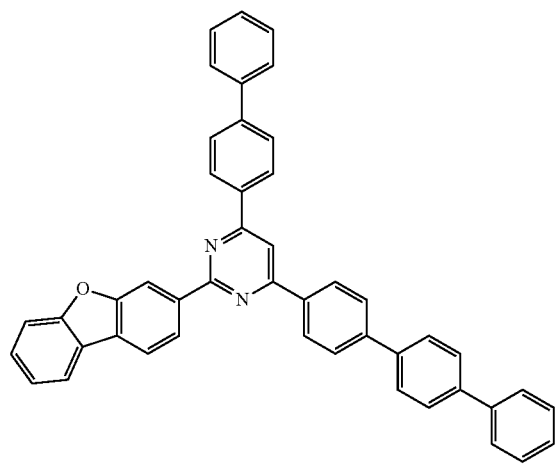
B-102
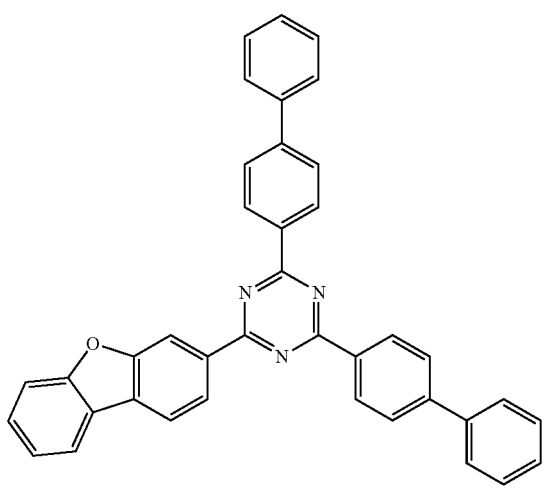
B-103
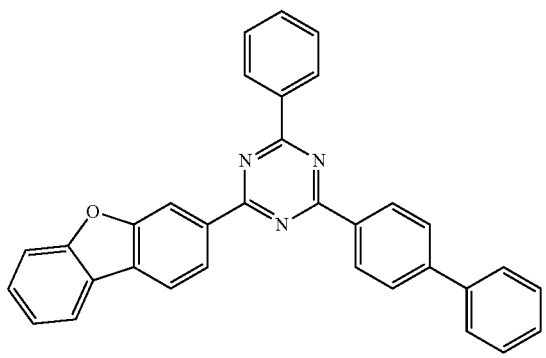
-continued
B-104
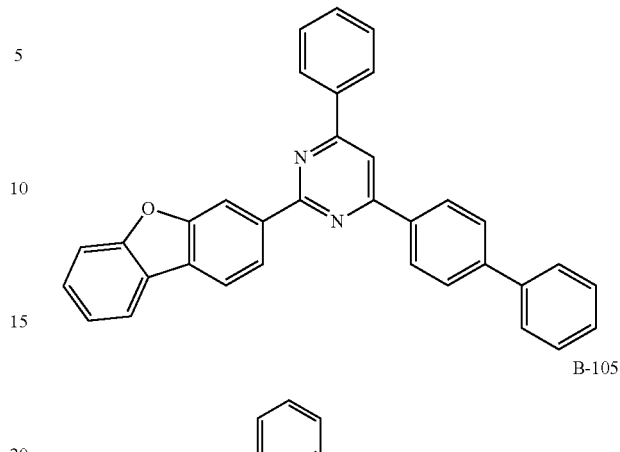
B-105
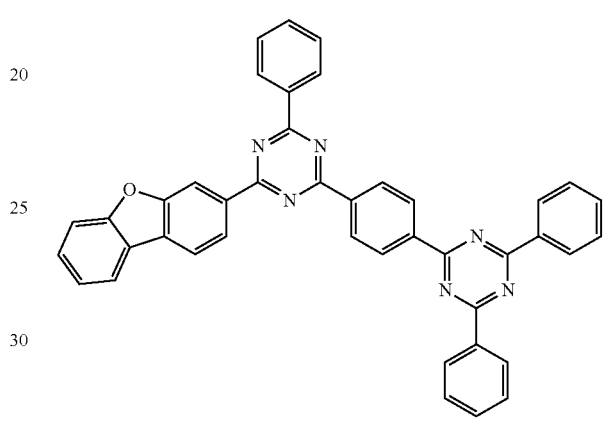
B-106
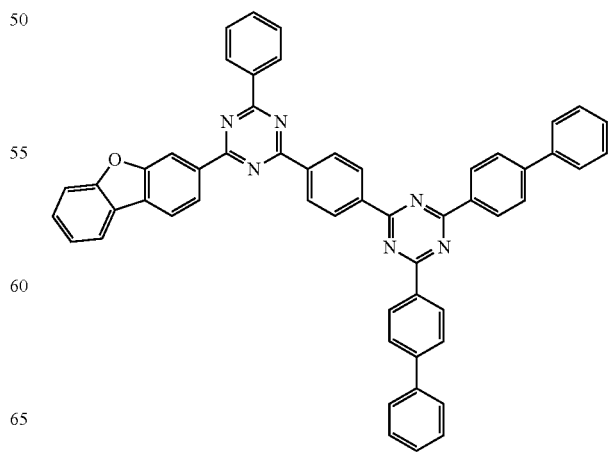
B-107

B-108
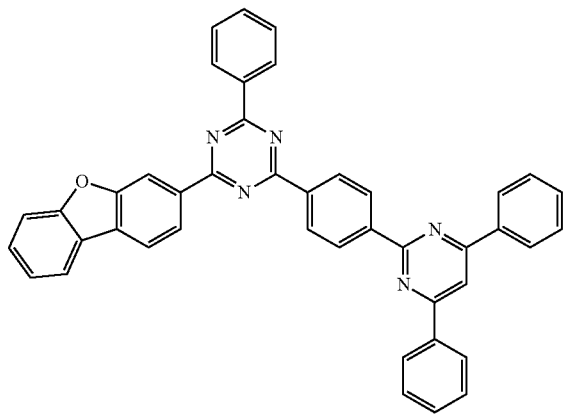
B-109
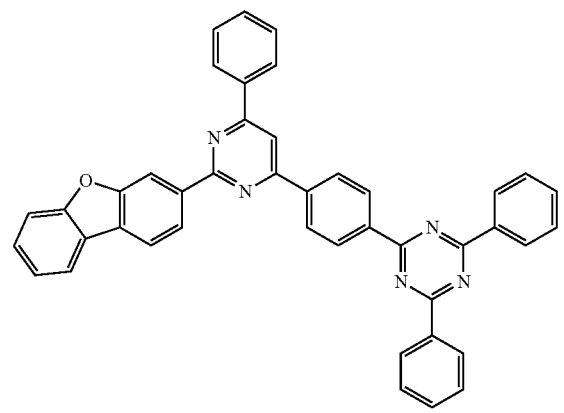
B-110
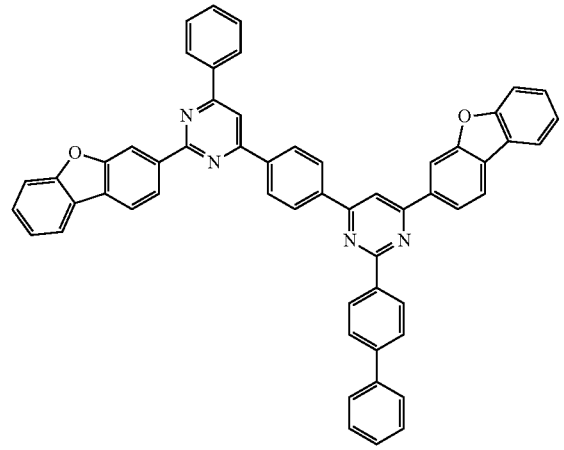
B-111
B-112
B-113
B-114
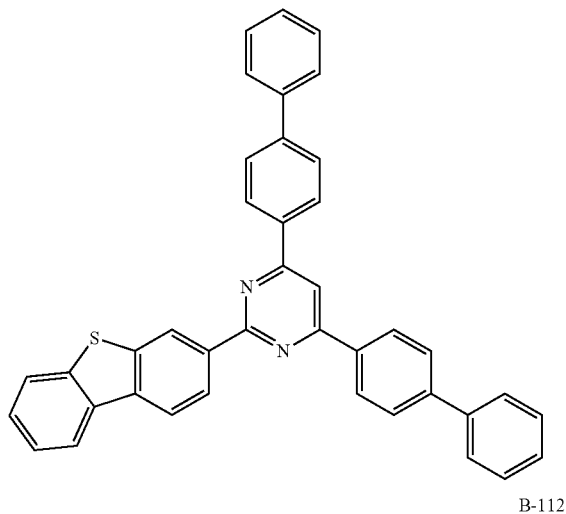
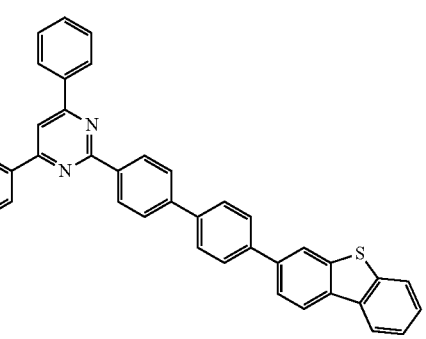

B-115
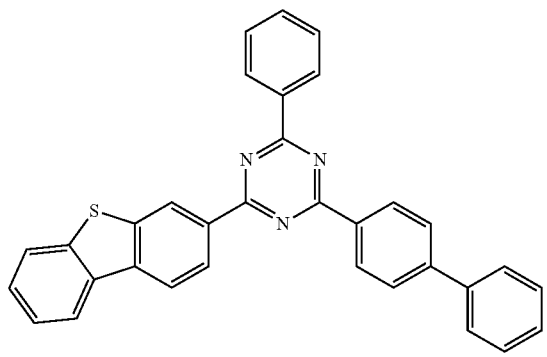
B-118
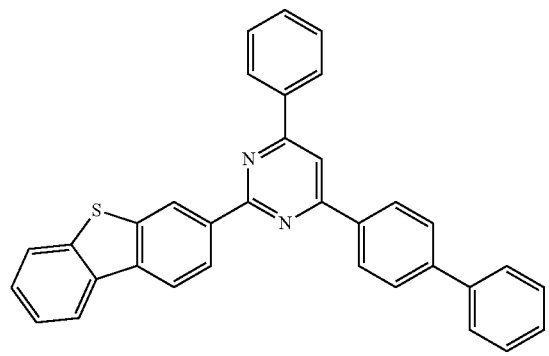
B-116
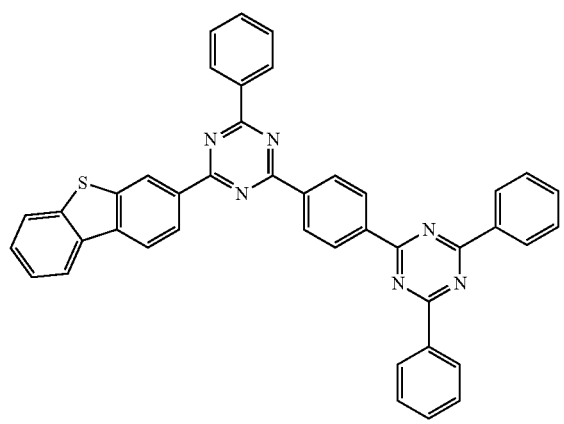
B-119
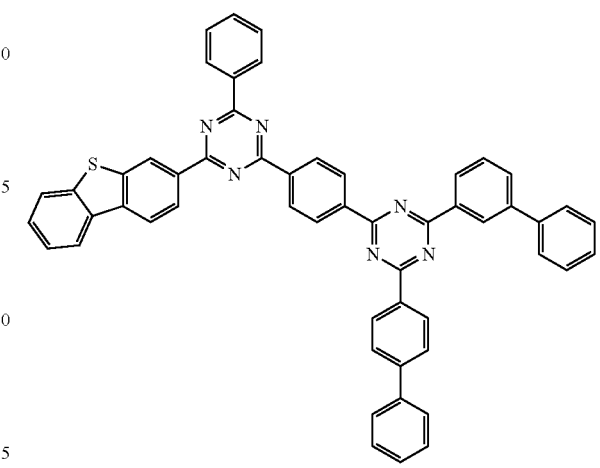
B-117
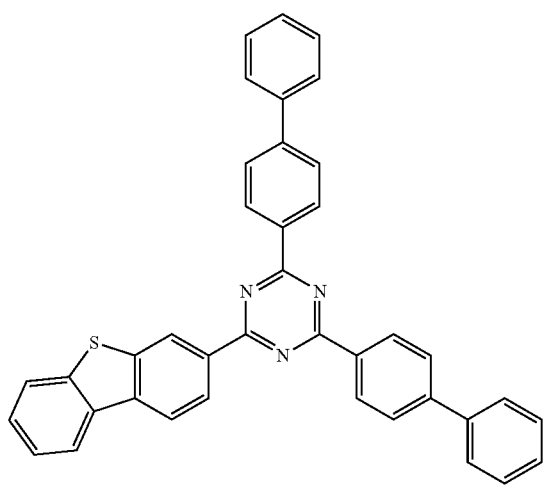
B-120

B-121
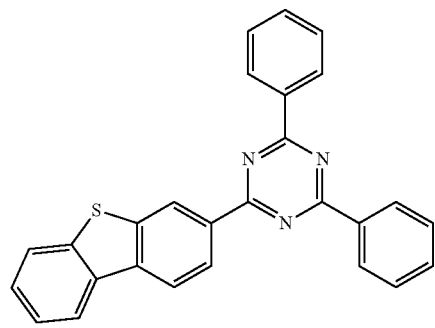
B-122
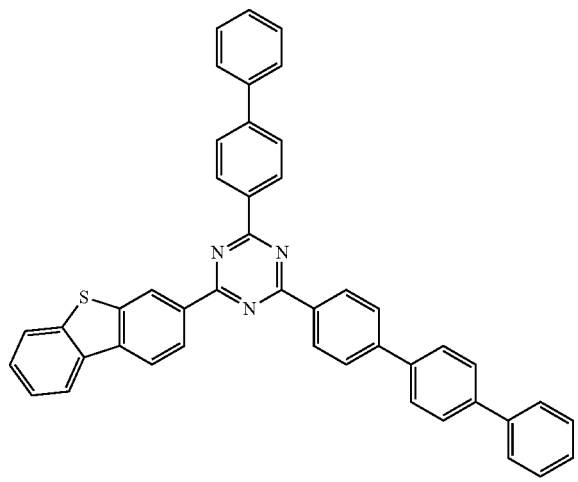
B-123
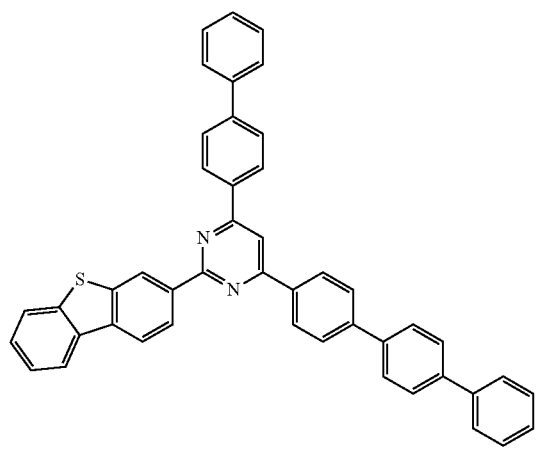
B-124
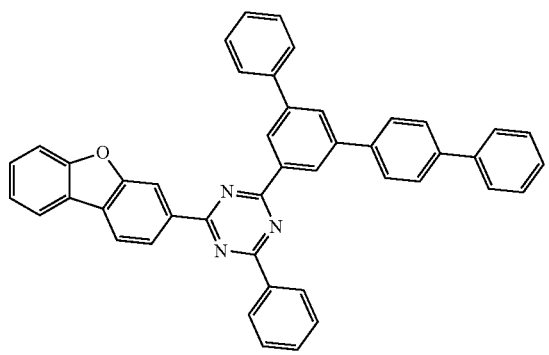
B-125
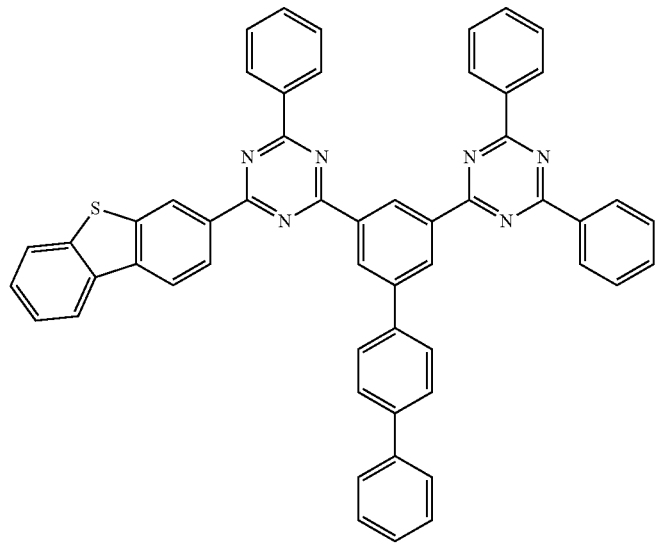

-continued
B-126
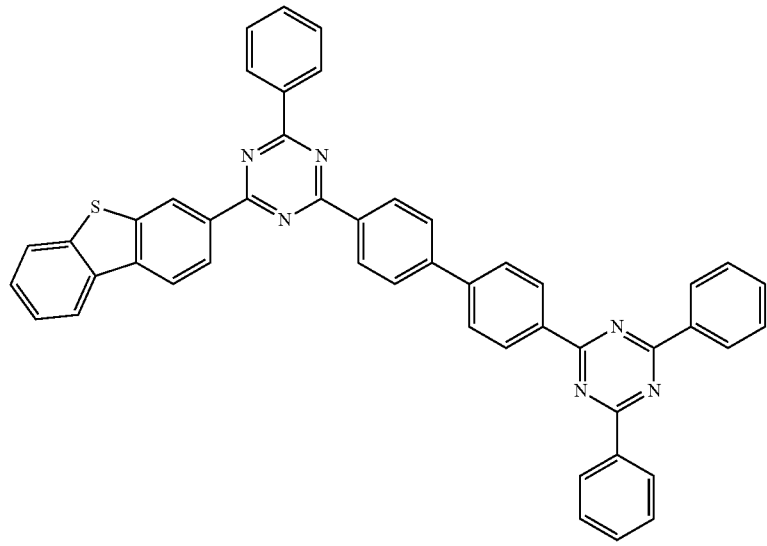
B-127
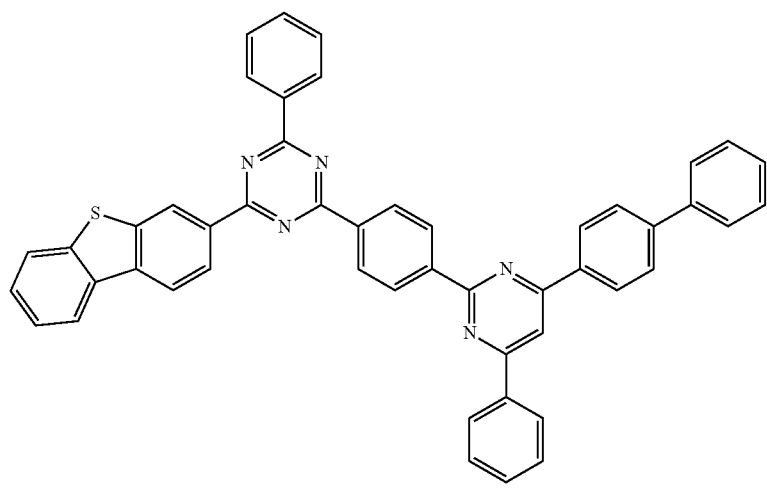
B-128
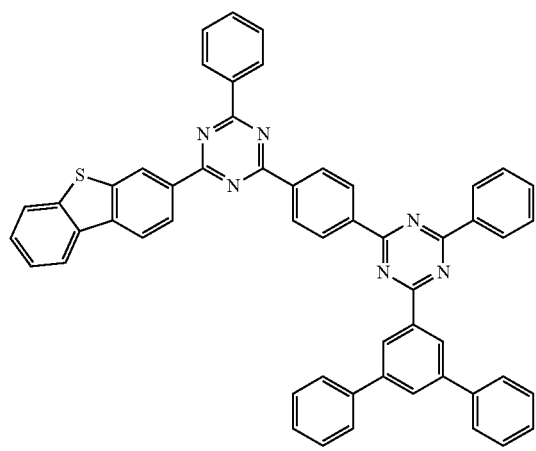
B-129
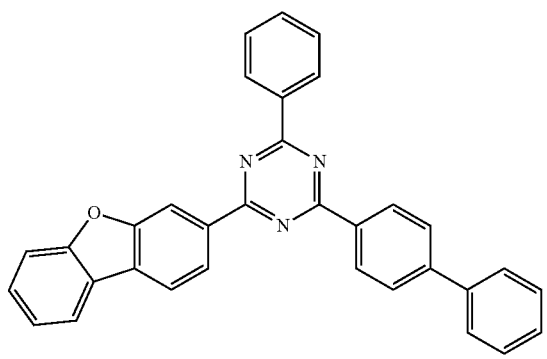

-continued
B-130
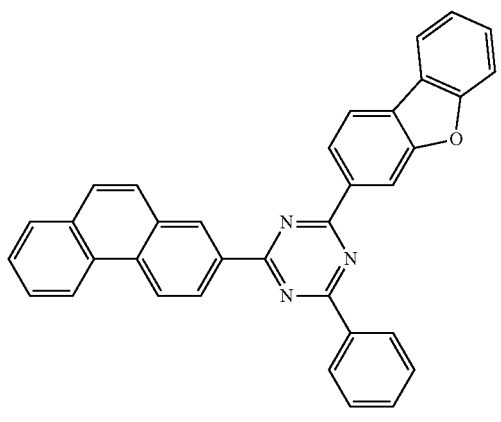
B-131
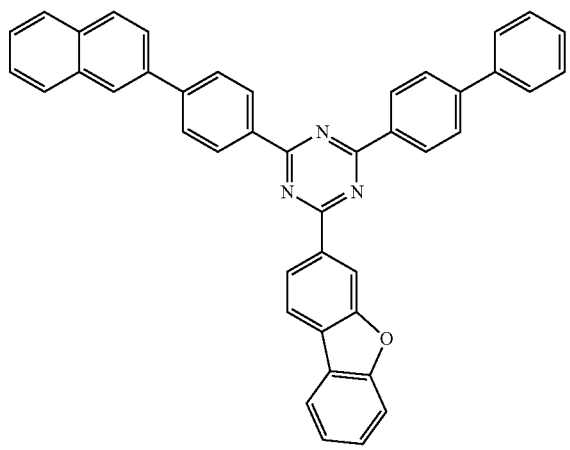
B-132
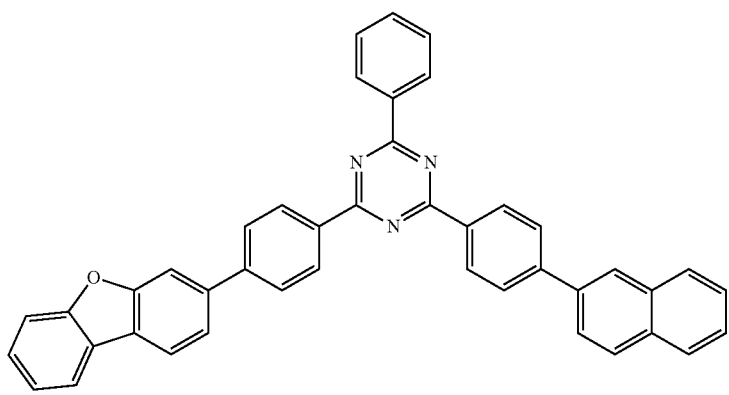
B-133
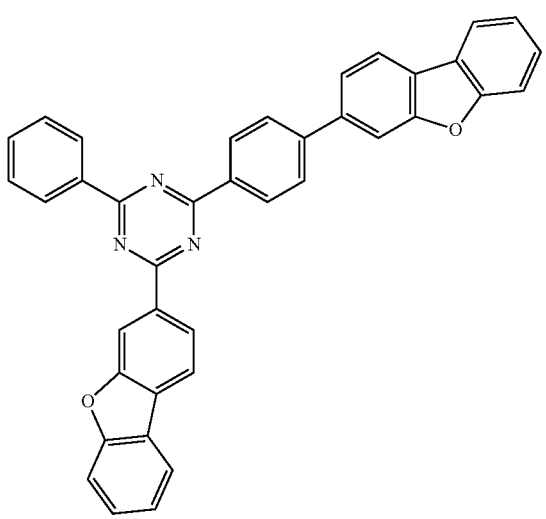
B-134
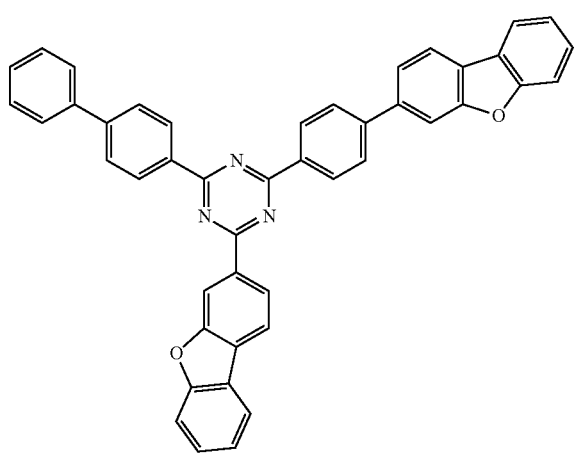

-continued
B-135
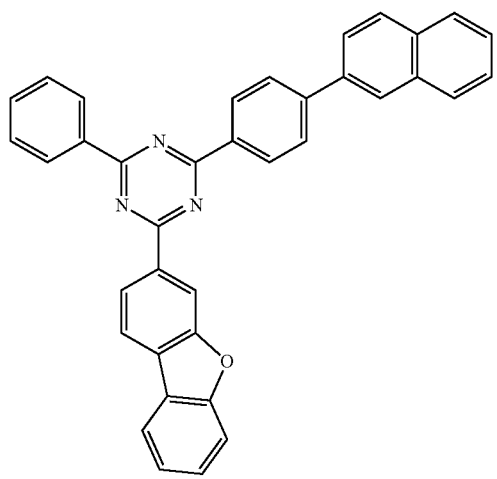
B-136
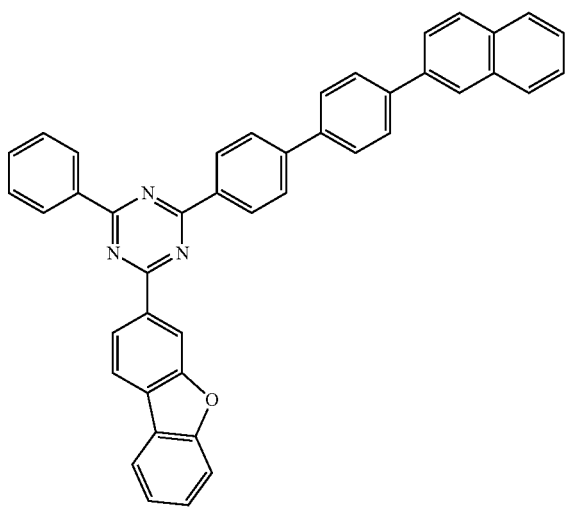
B-137
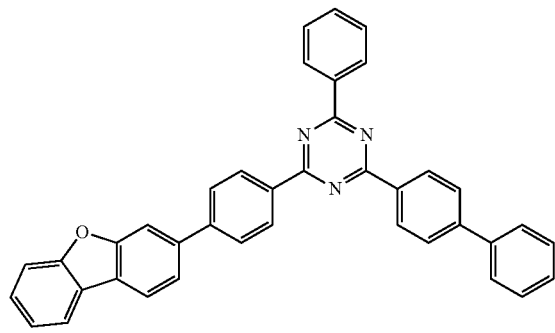
B-138
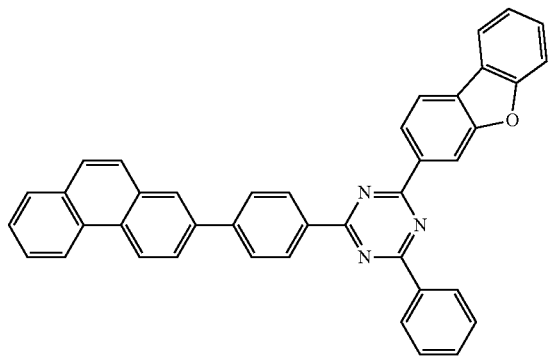
B-139
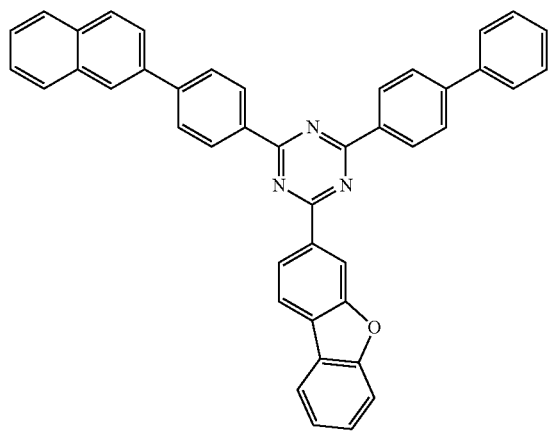
B-140
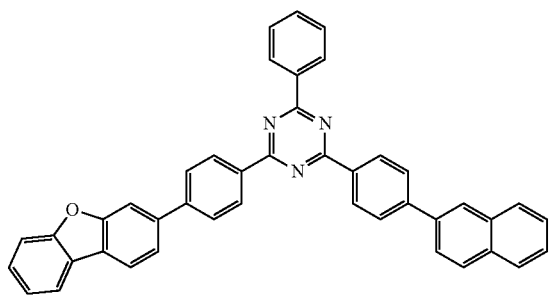

-continued
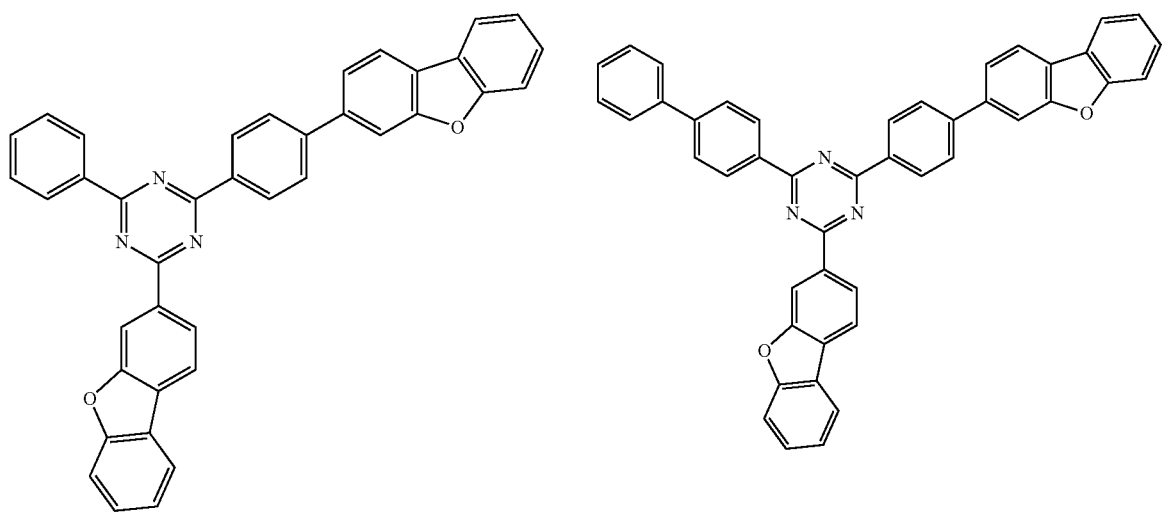
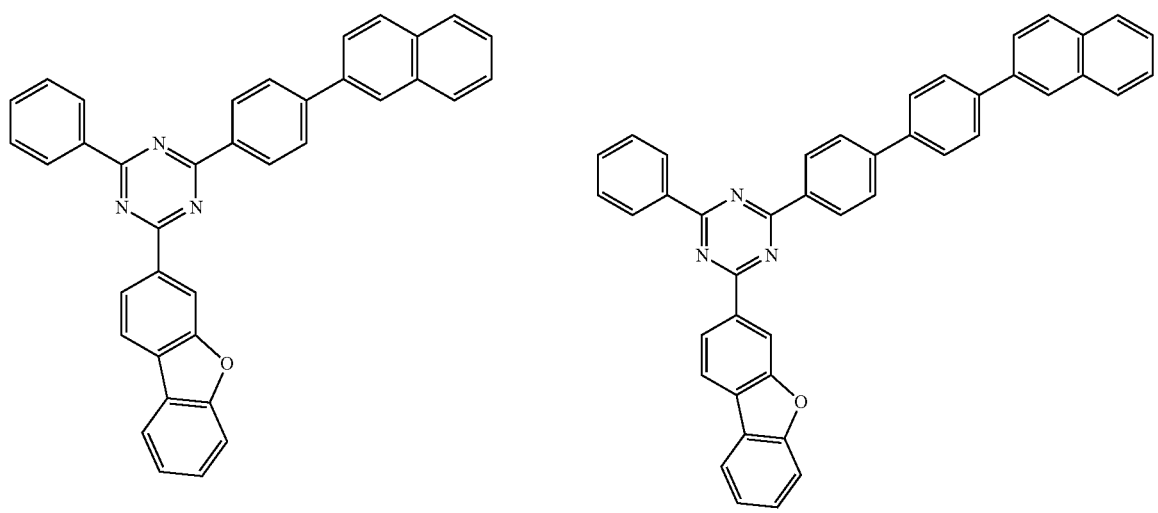
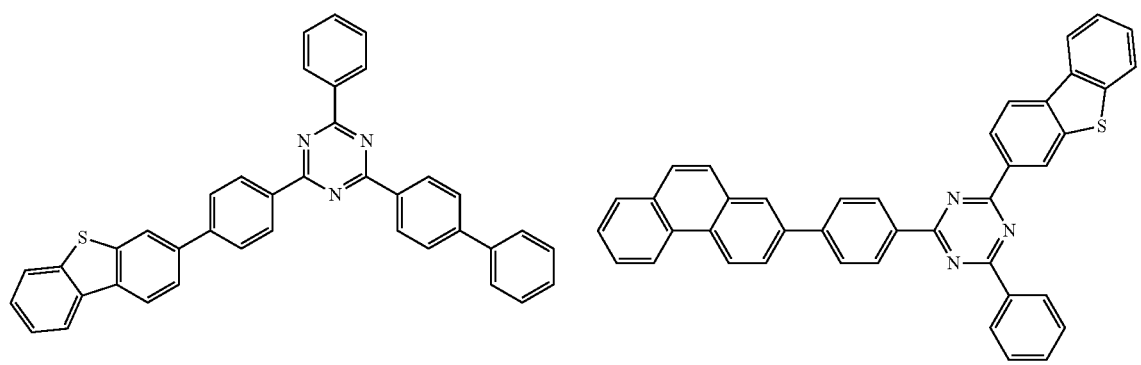

-continued
B-147
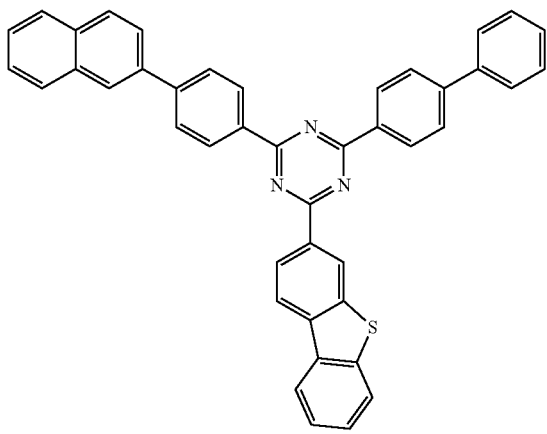
B-148
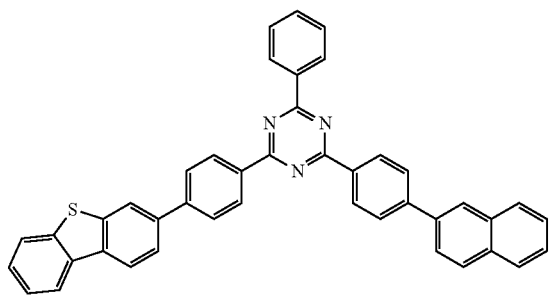
B-149
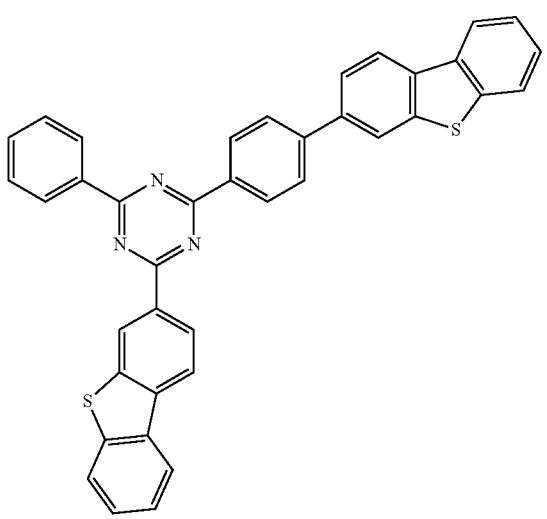
B-150
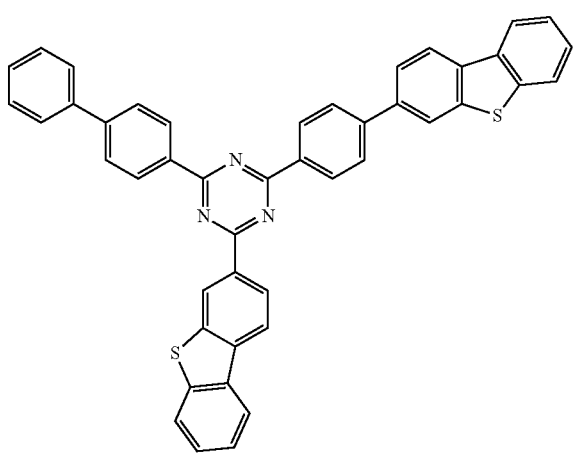
B-151
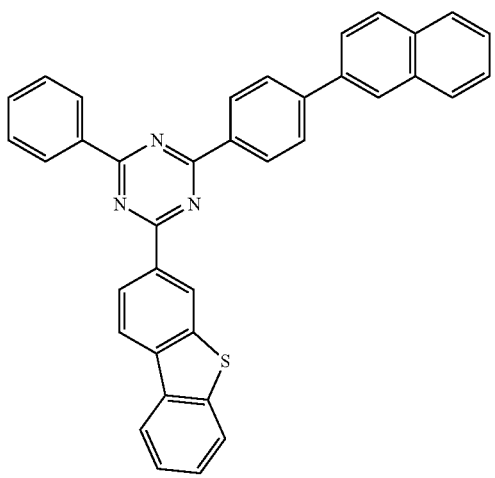
B-152
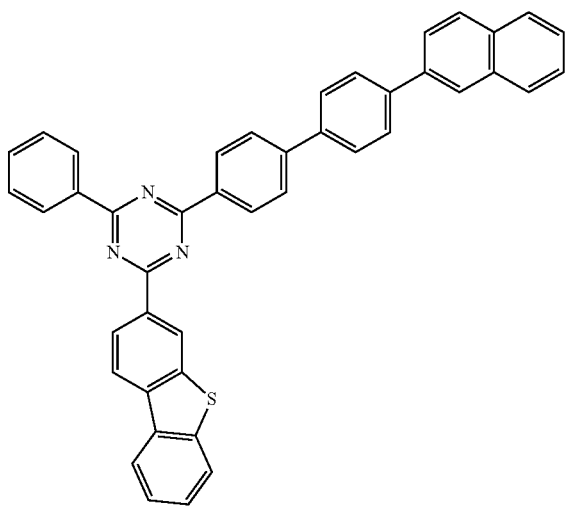

-continued
B-153
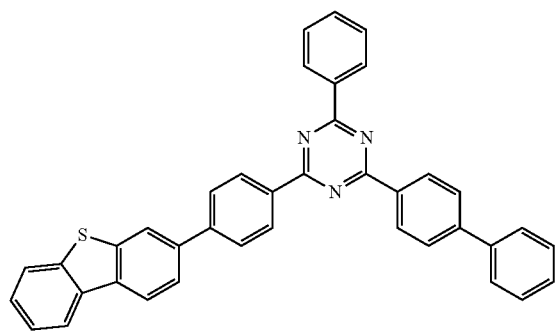
B-154
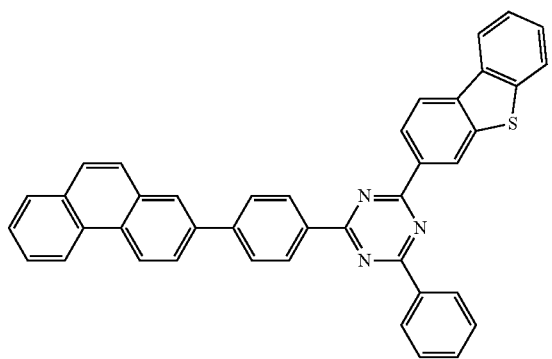
B-155
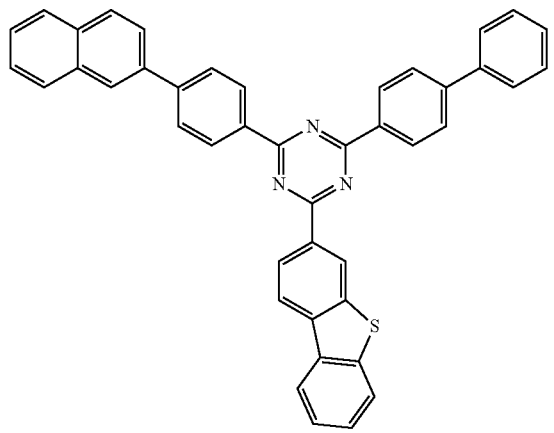
B-156
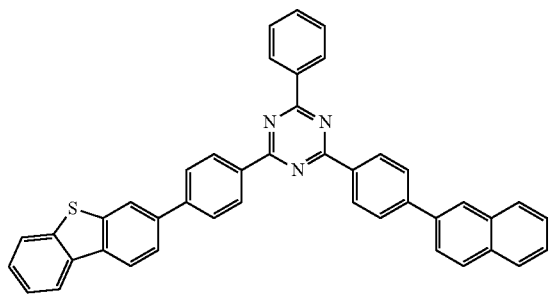
B-157
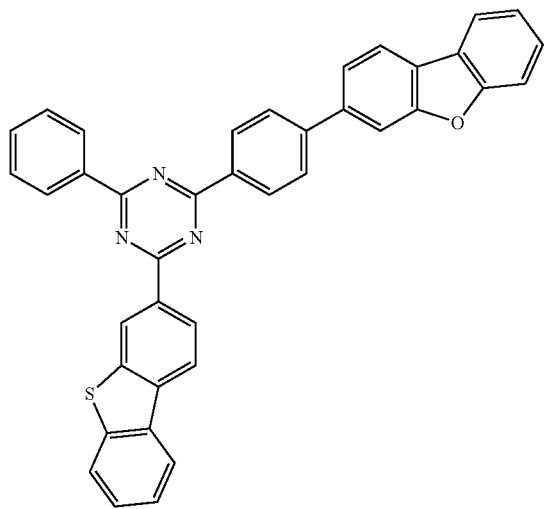
B-158
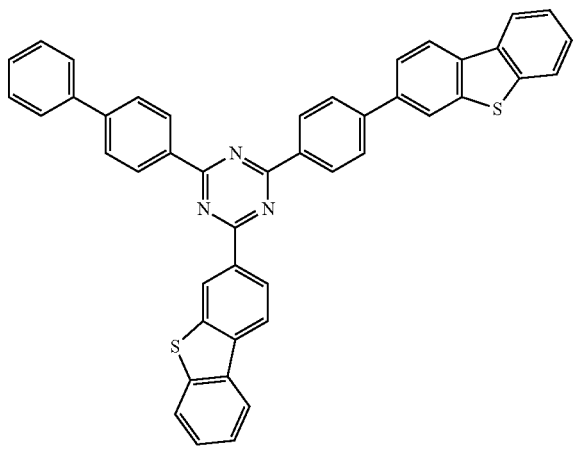

-continued
B-159
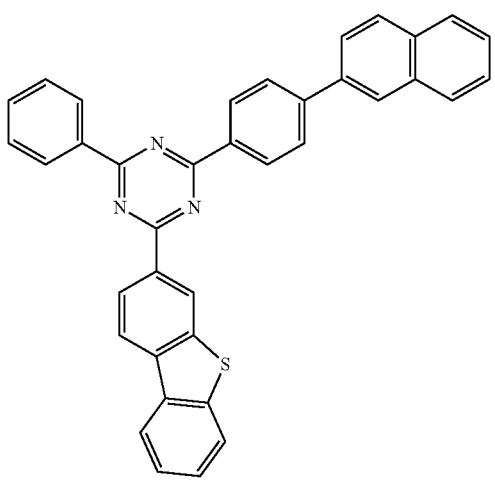
B-160
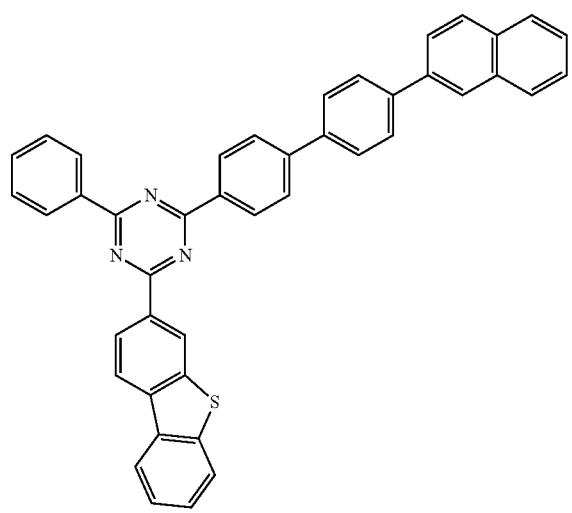
C-1
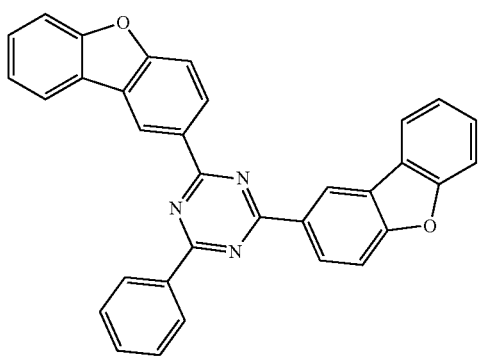
C-2
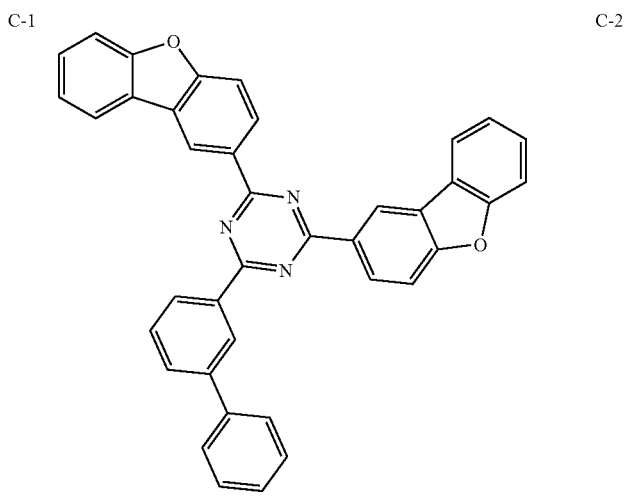
C-3
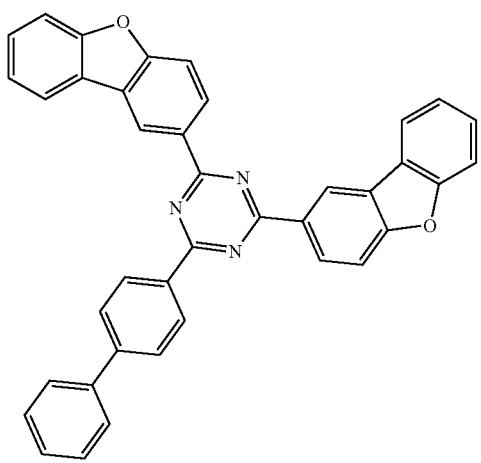
C-4
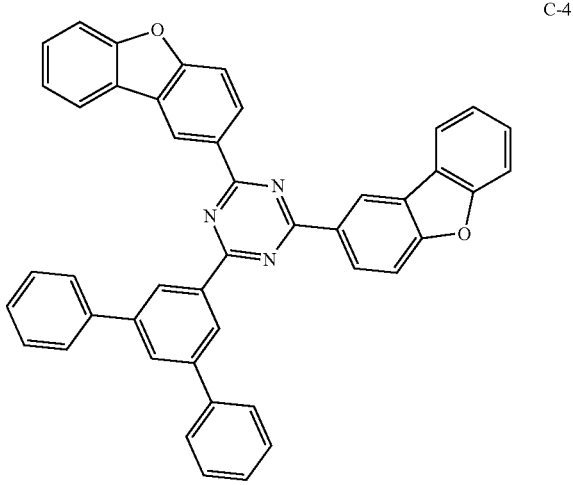

-continued
C-5
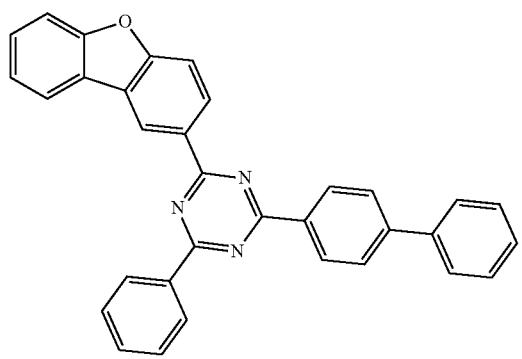
C-6
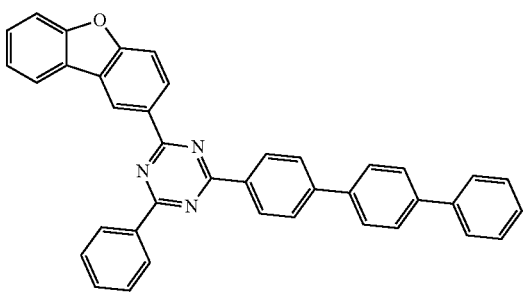
C-7
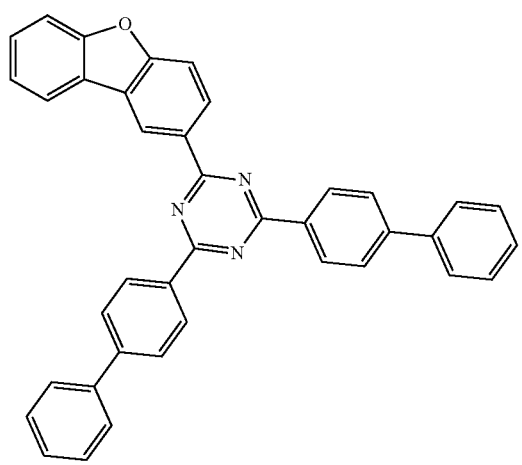
C-8
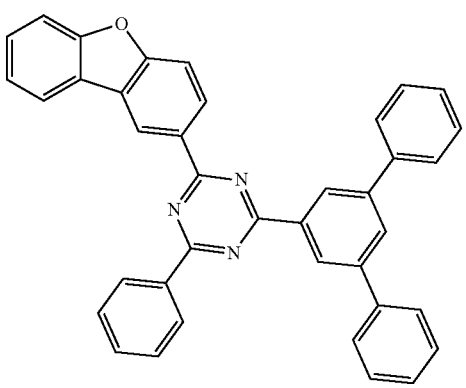
C-9
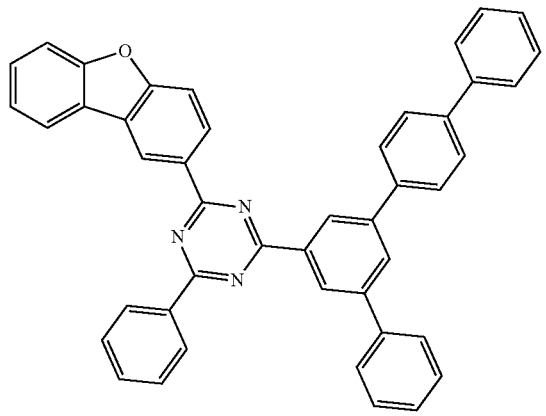
C-10
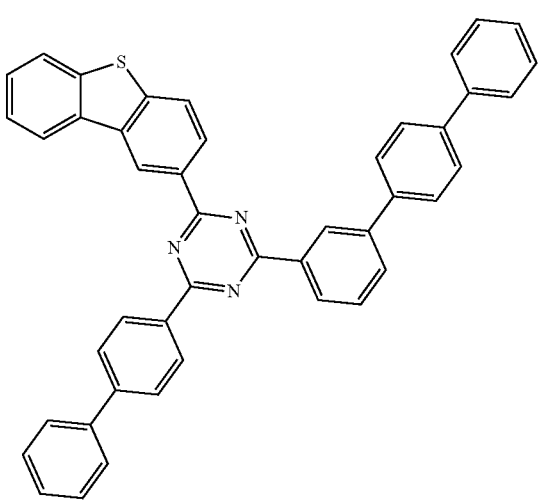

-continued
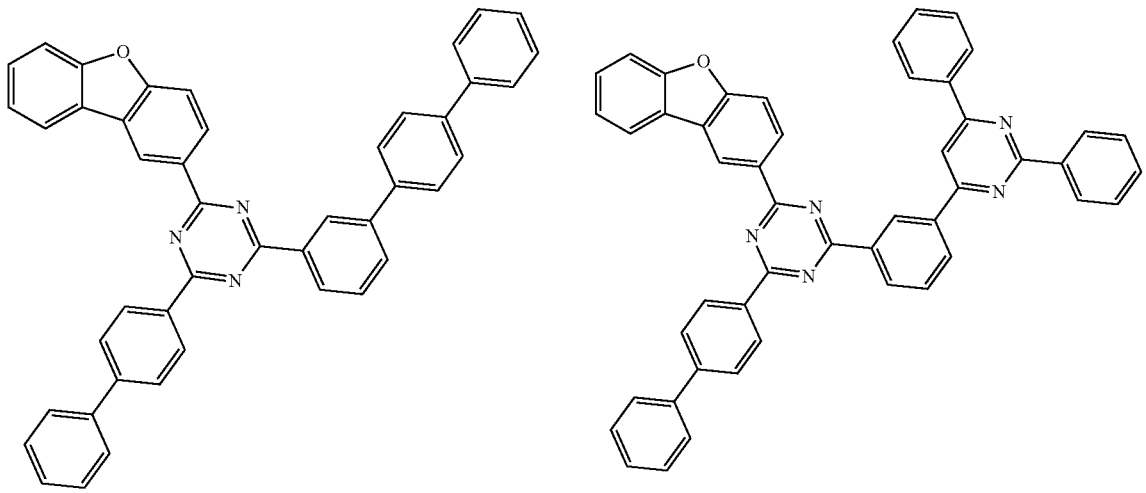
C-11
C-12
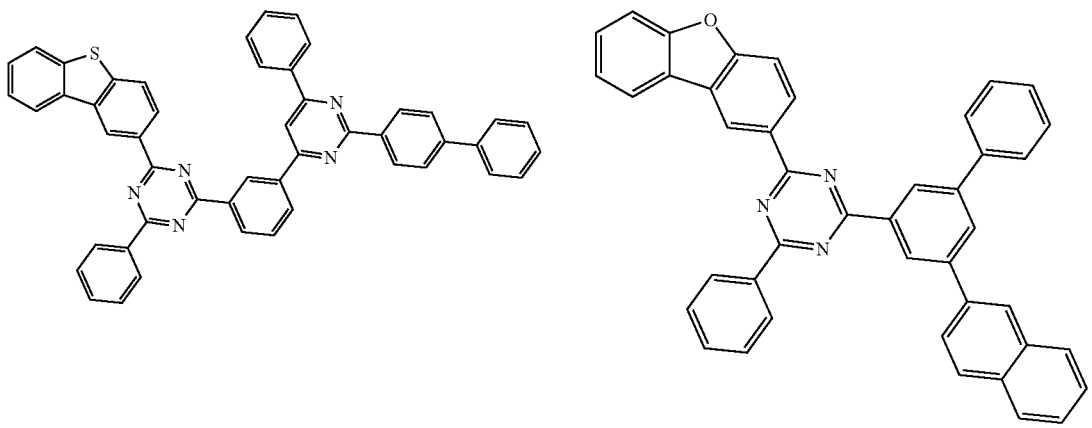
C-13
C-14
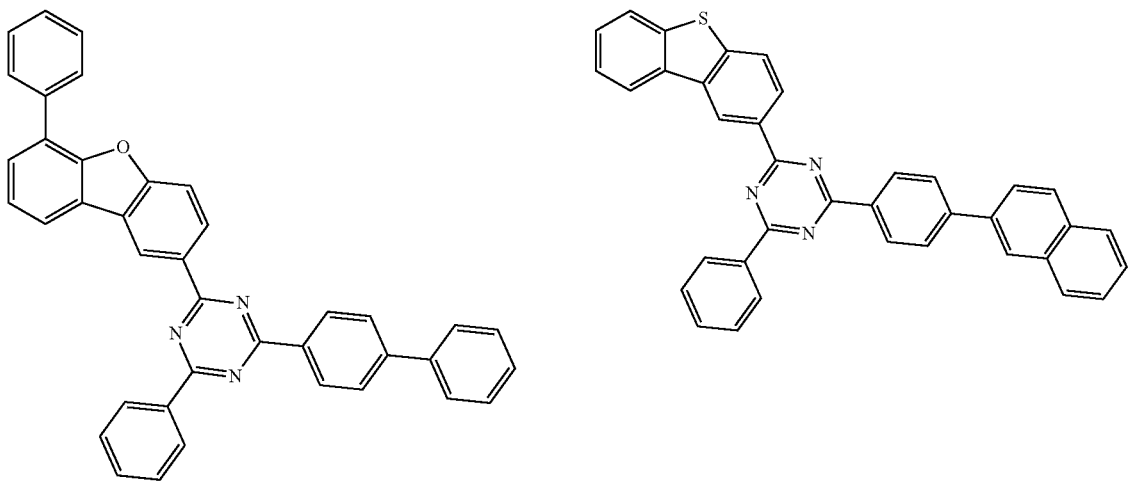
C-15
C-16

-continued
C-17
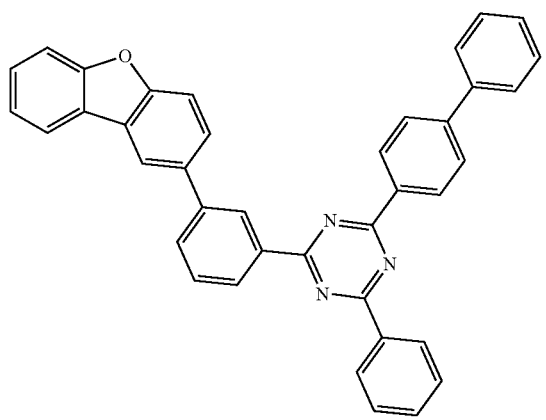
C-18
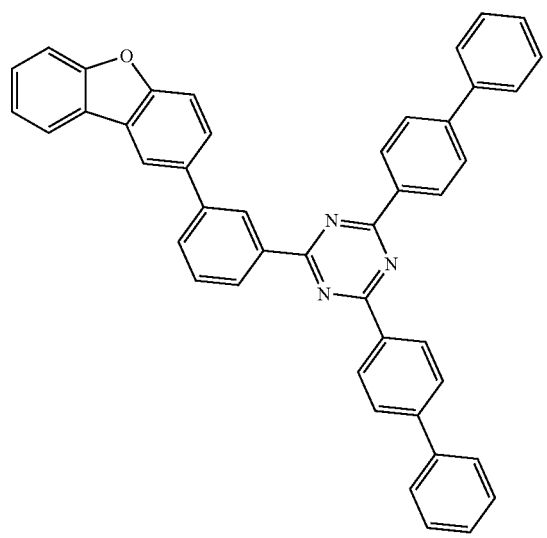
C-19
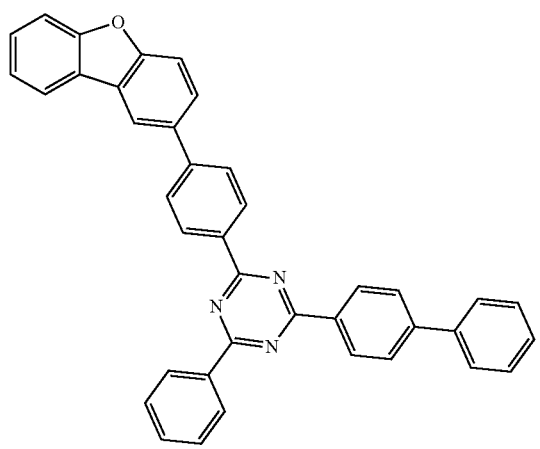
C-20
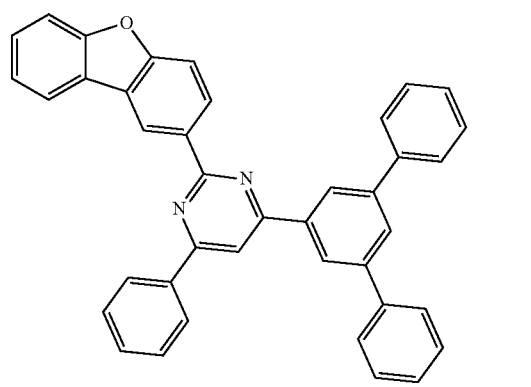
D-1
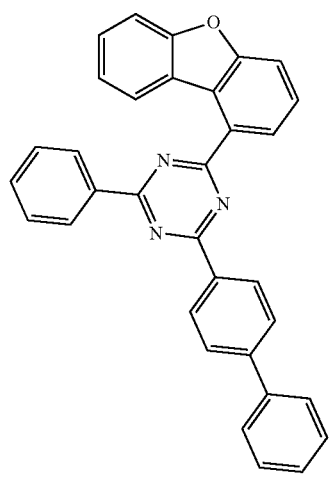
D-2
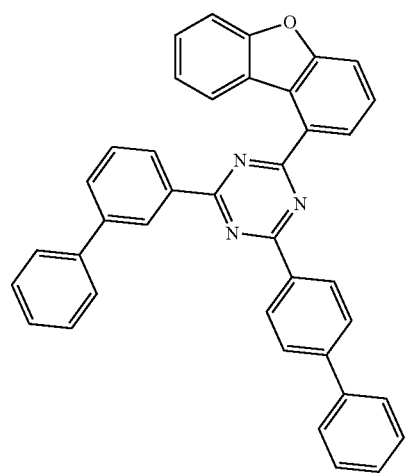

-continued
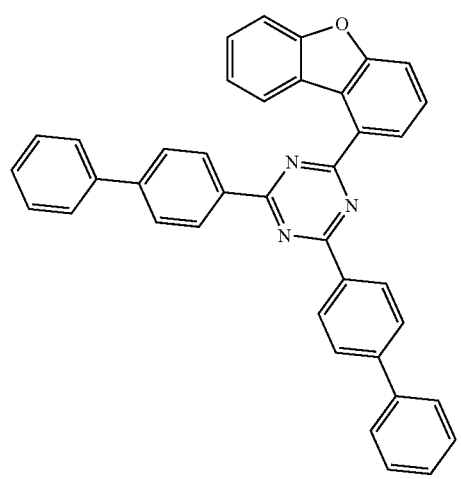
D-3
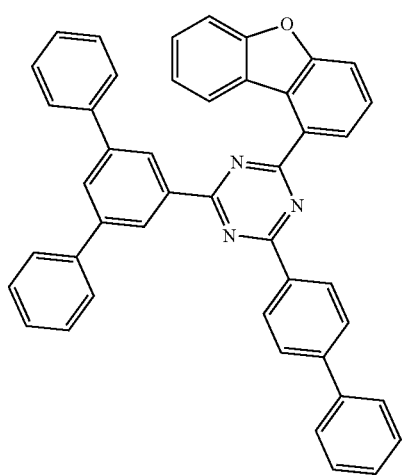
D-4
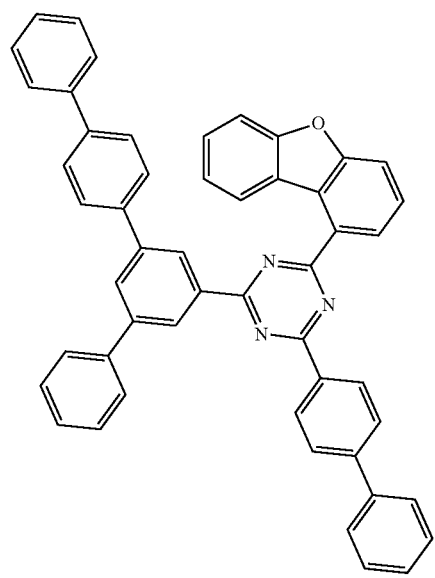
D-5
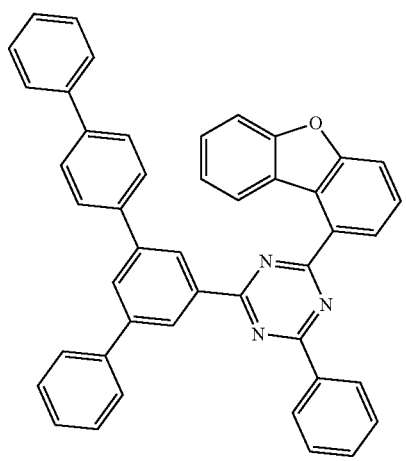
D-6
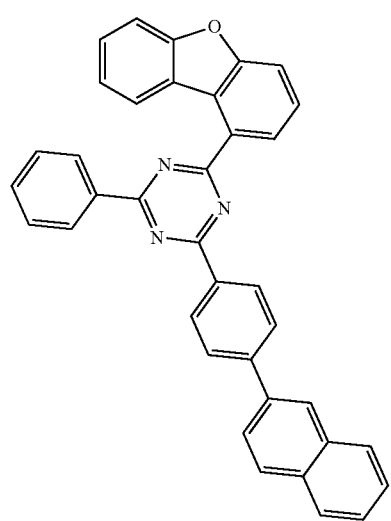
D-7
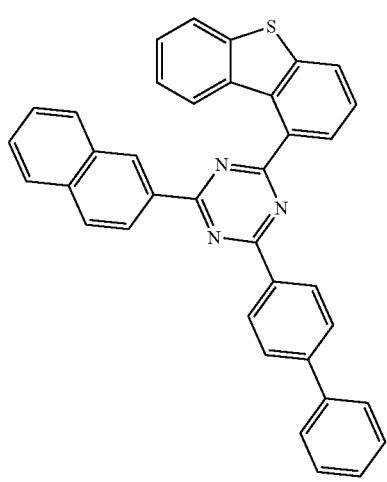
D-8

-continued
D-9
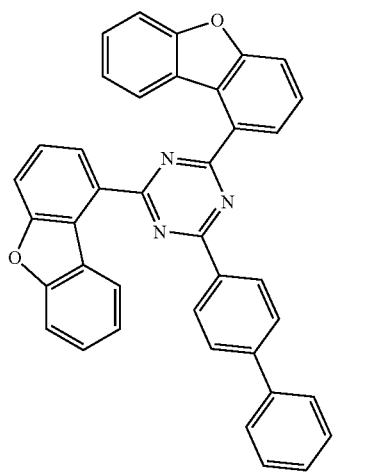
D-10
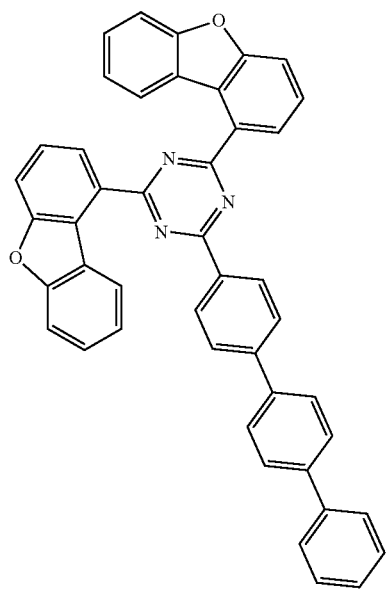
D-11
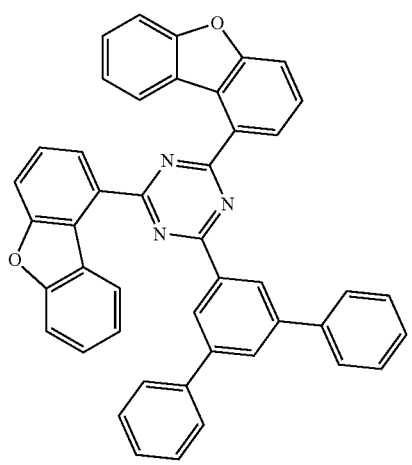
D-12
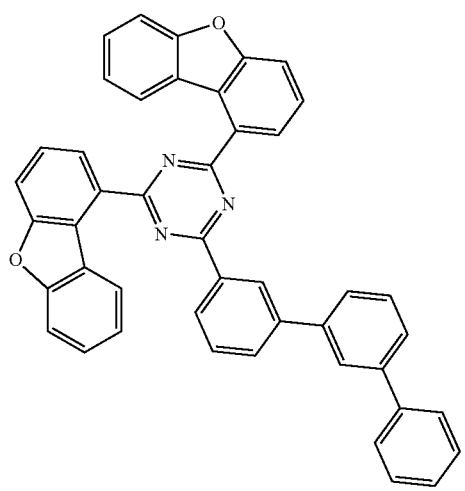
D-13
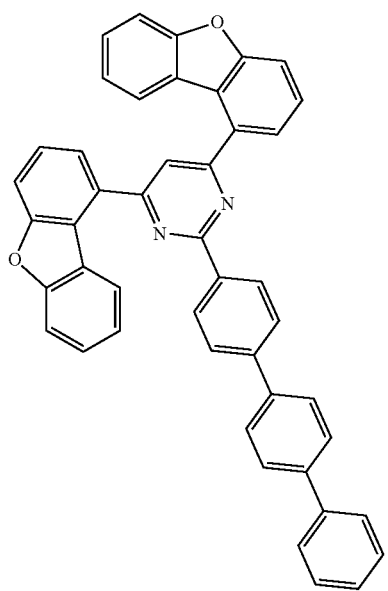
D-14
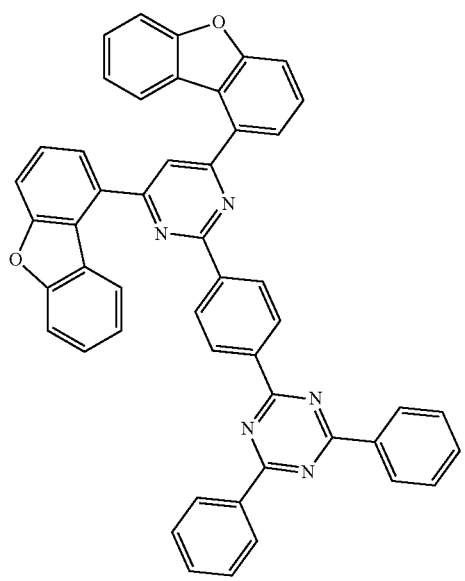

-continued
D-15
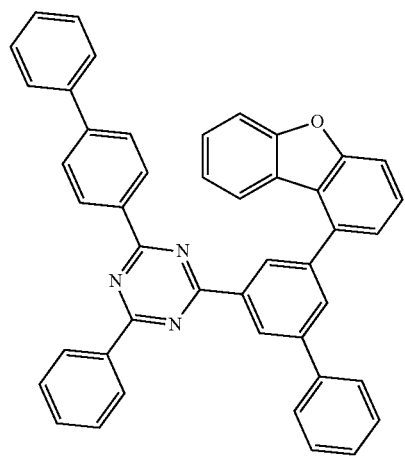
D-16
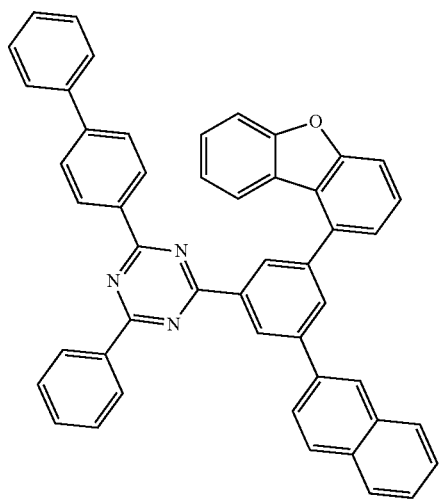
D-17
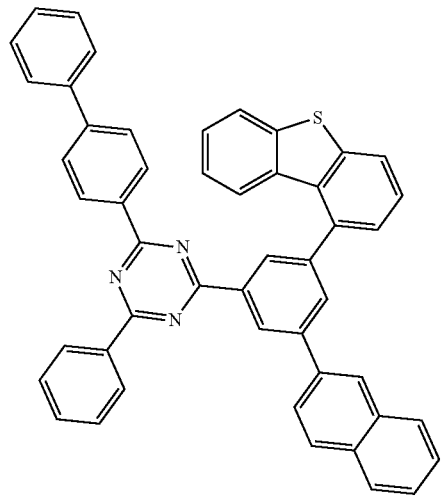
D-18
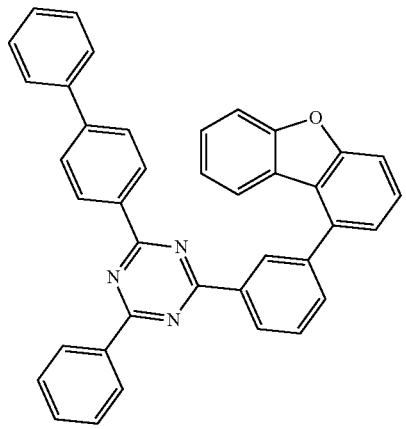
D-19
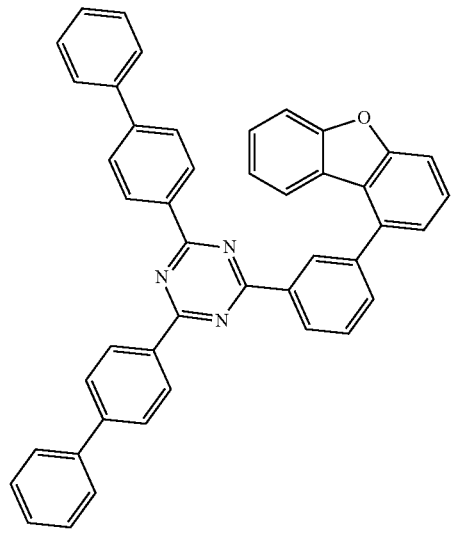
D-20
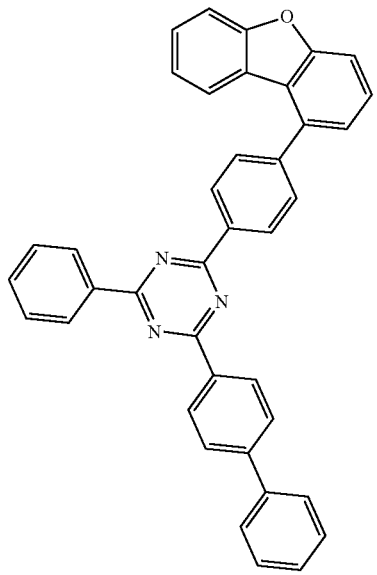

-continued
D-21
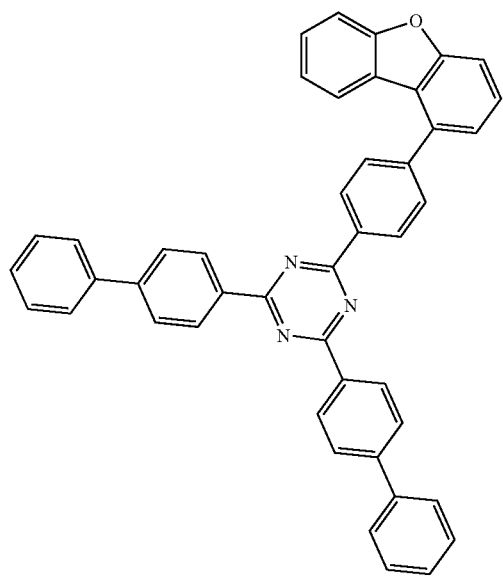
D-22
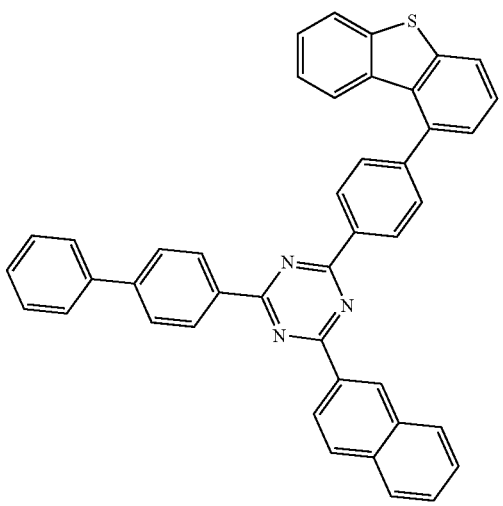
D-23
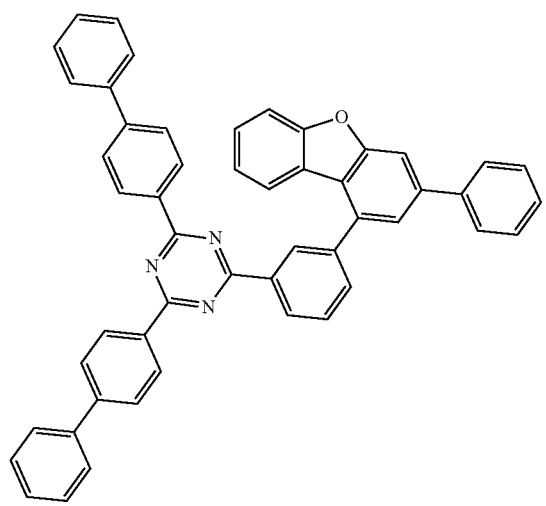
D-24
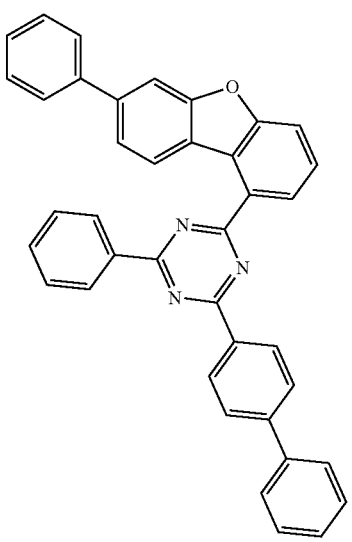
D-25
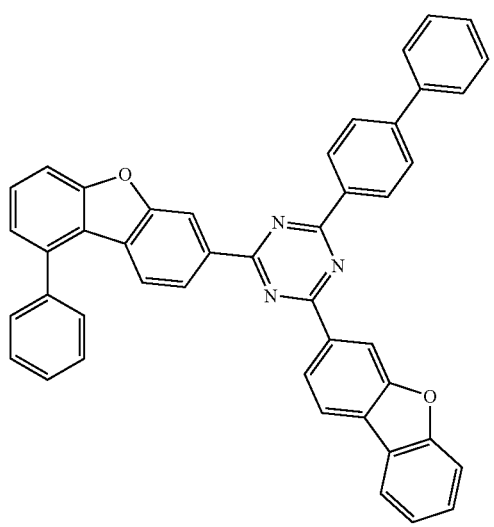
D-26
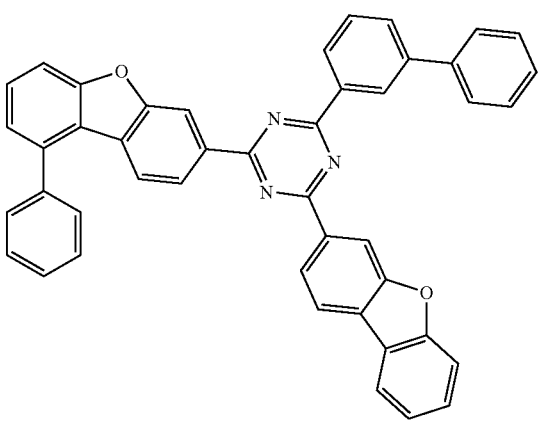

-continued
D-27
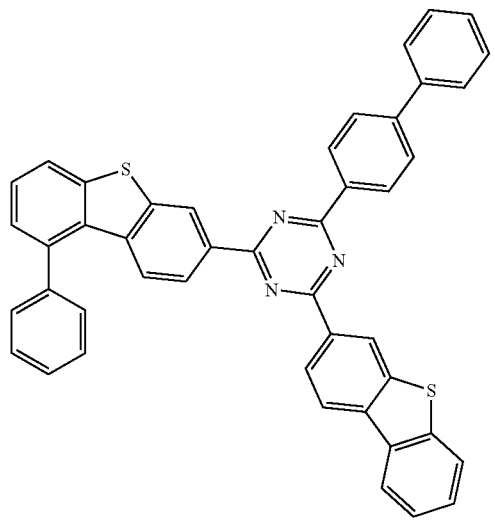
D-28
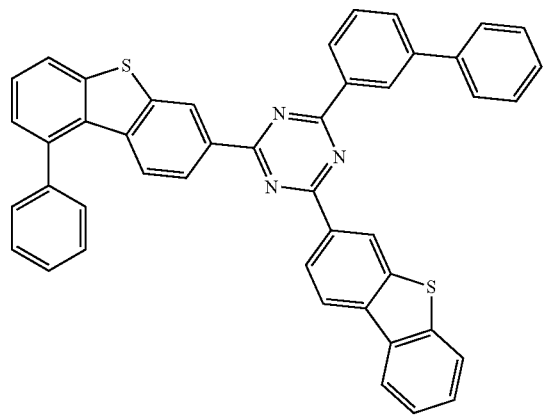
E-1
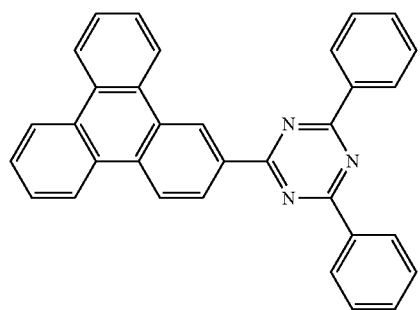
E-2
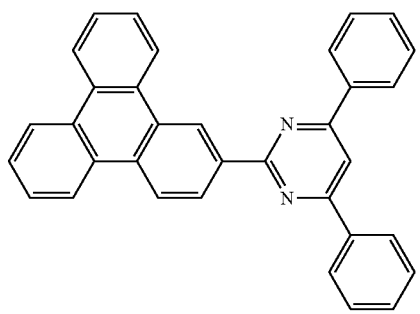
E-3
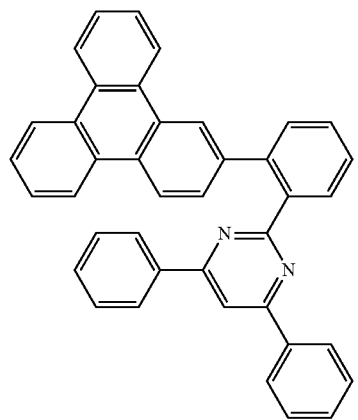
E-4
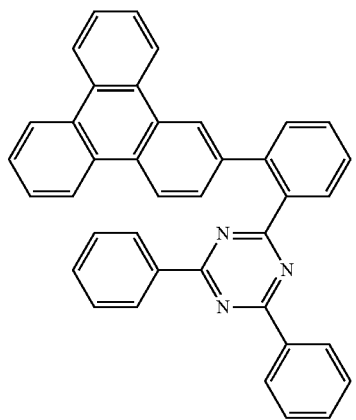
E-5
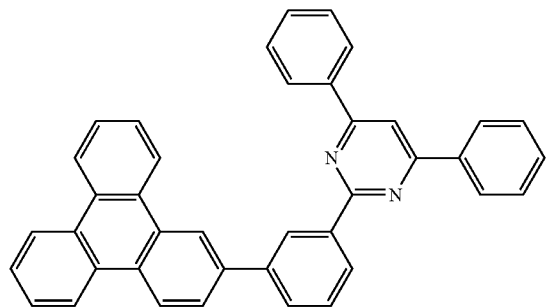
E-6
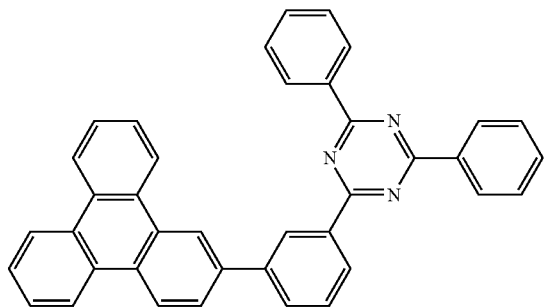

-continued
E-7
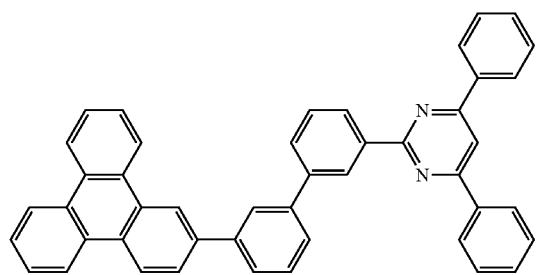
E-8
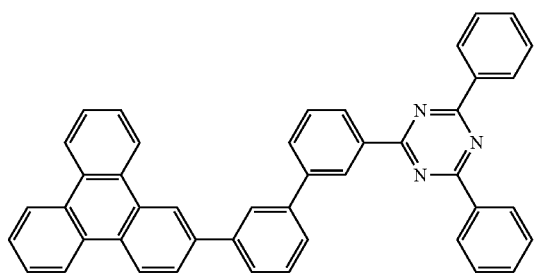
E-9
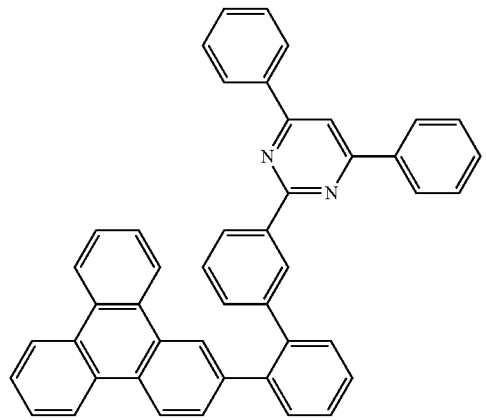
E-10
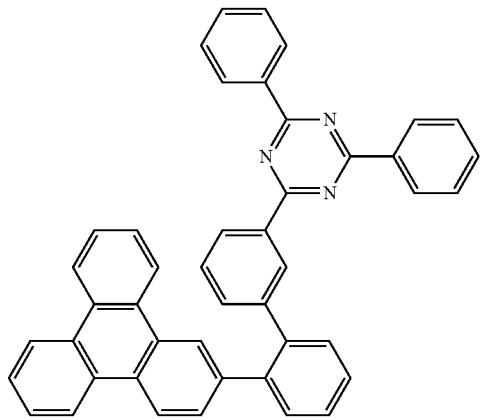
E-11
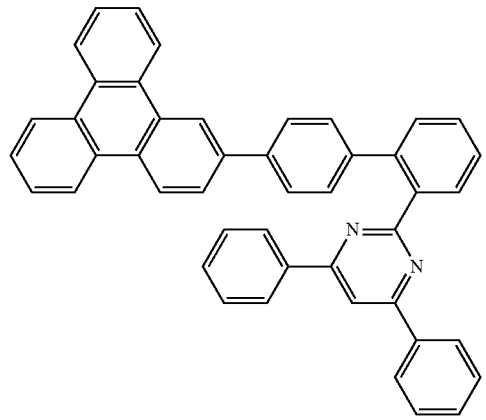
E-12
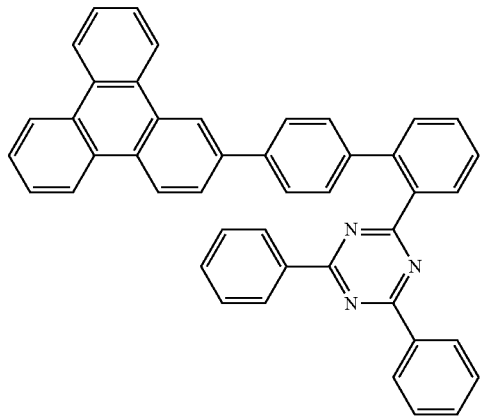
E-13
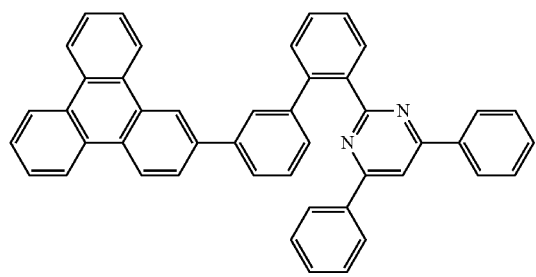
E-14
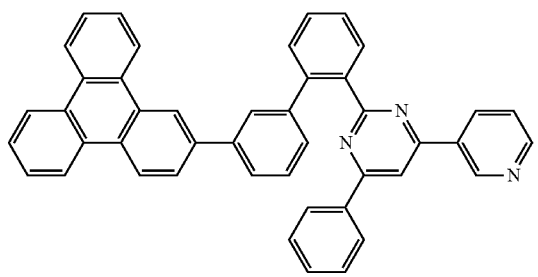

-continued
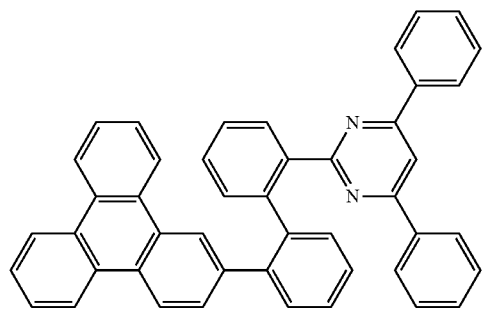
E-15
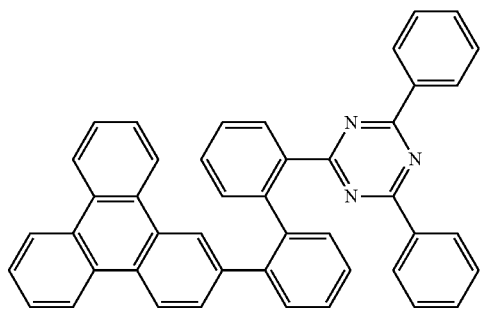
E-16
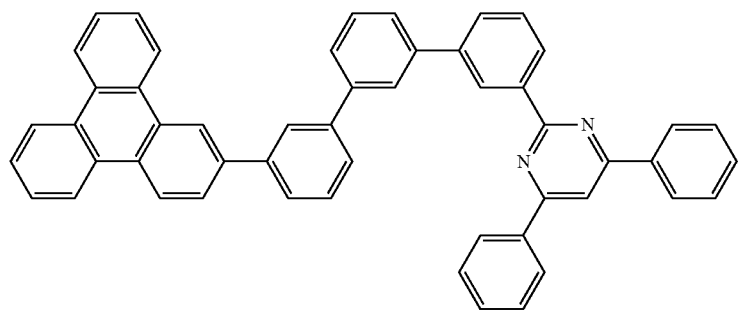
E-17
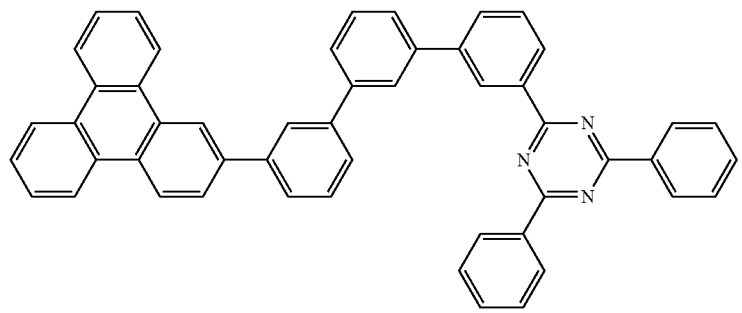
E-18
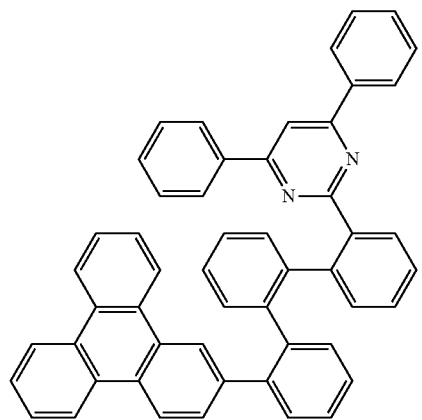
E-19
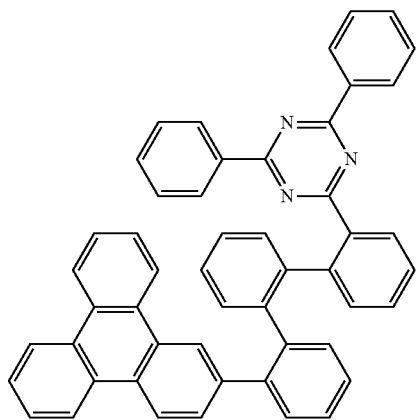
E-20

-continued
E-21
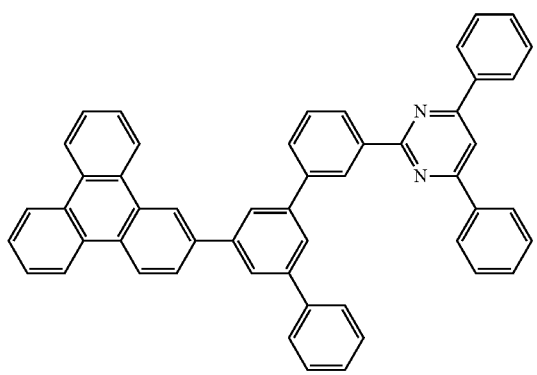
E-22
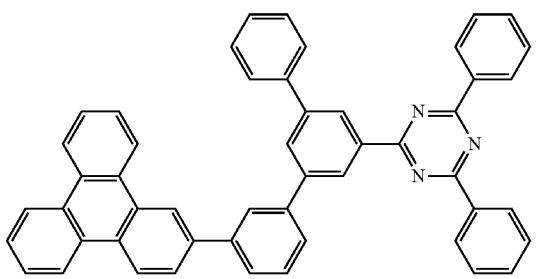
E-23
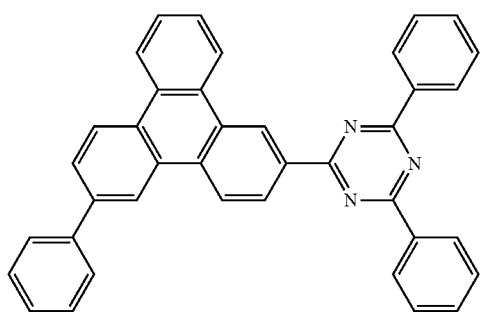
E-24
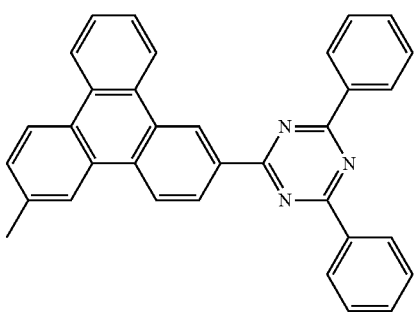
E-25
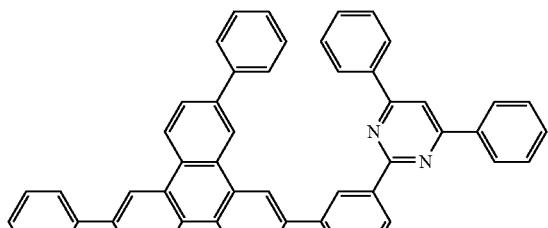
E-26
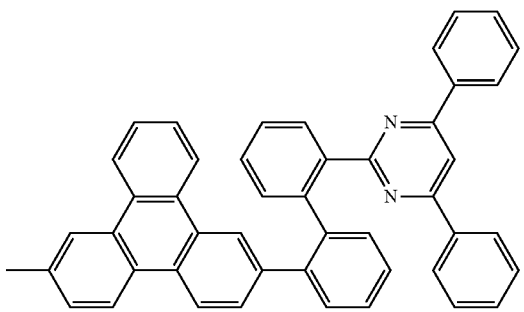
E-27
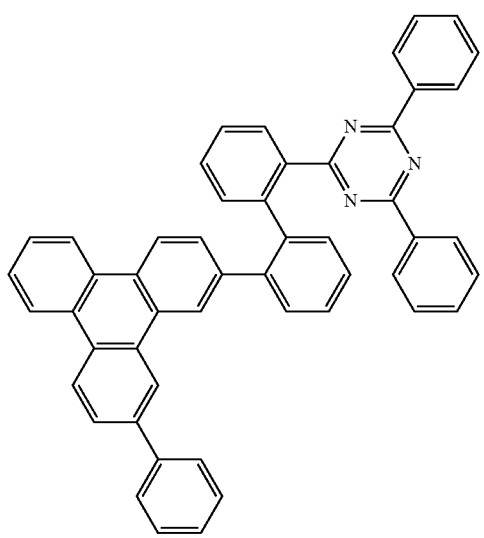

E-28
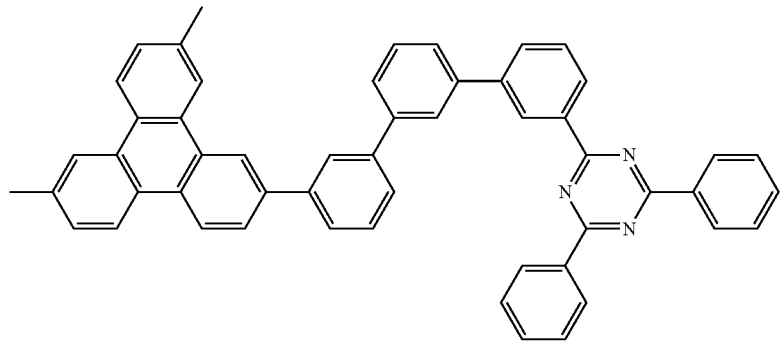
E-29 E-30
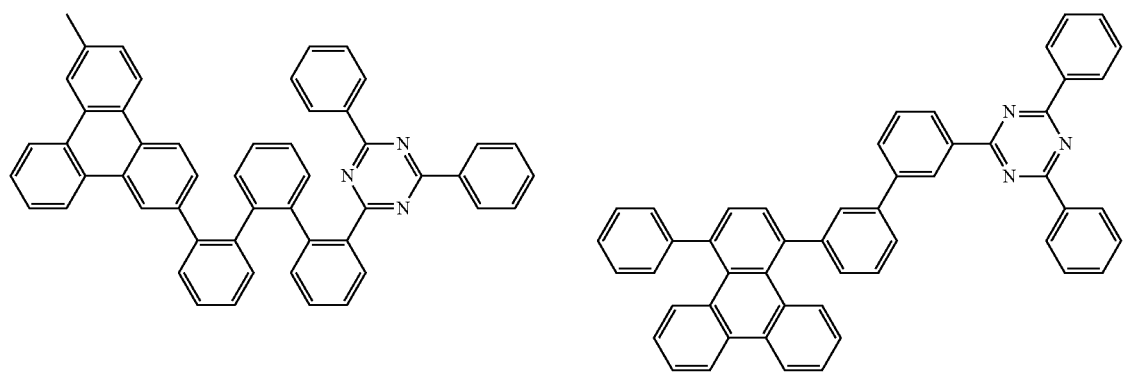
E-31 E-32
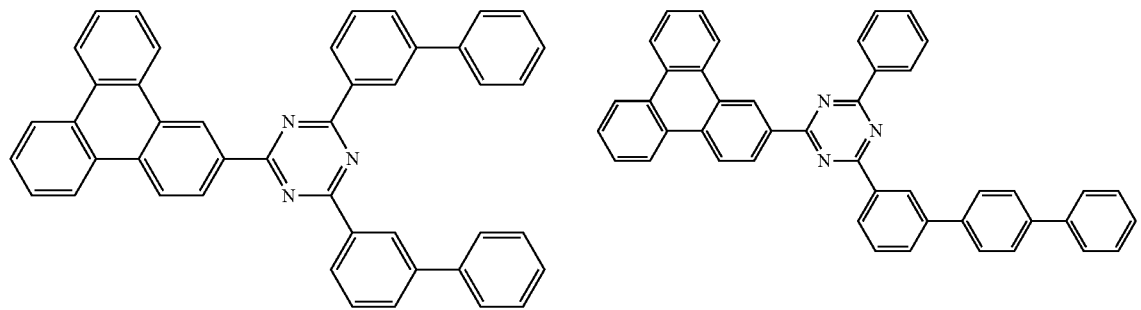
E-33 E-34
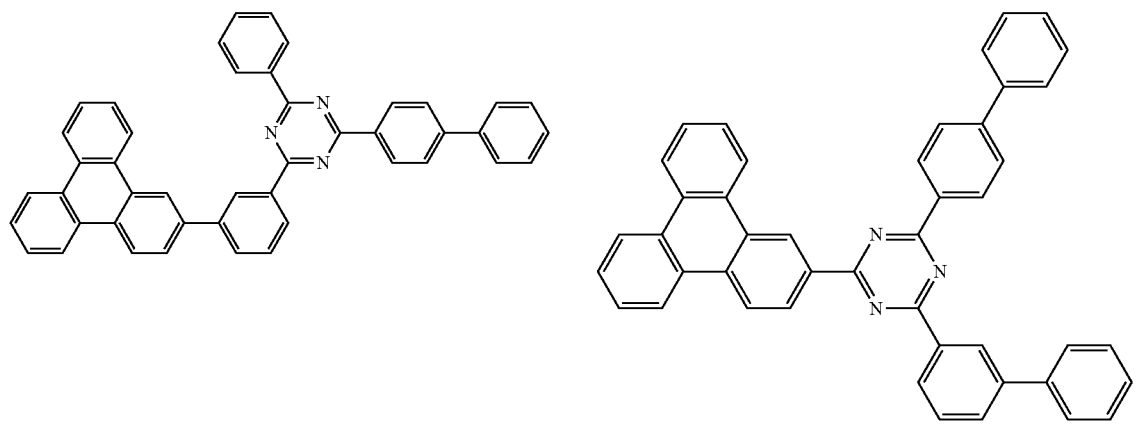

-continued
E-35
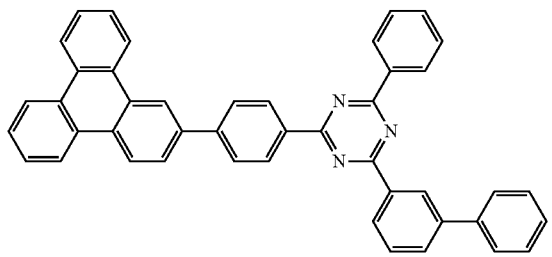
E-36
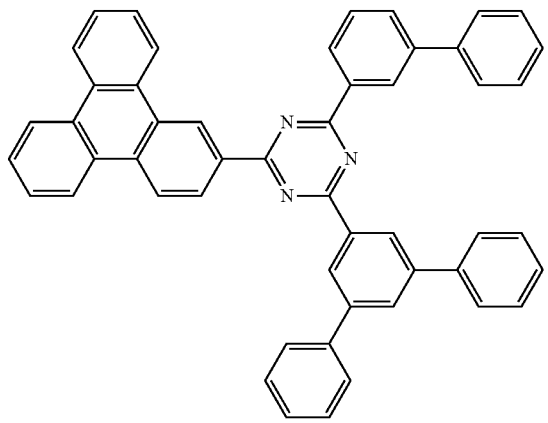
E-37
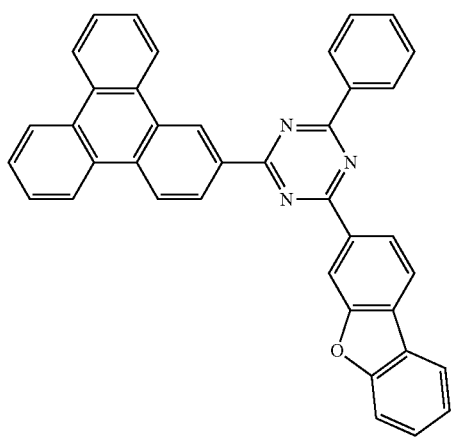
E-38
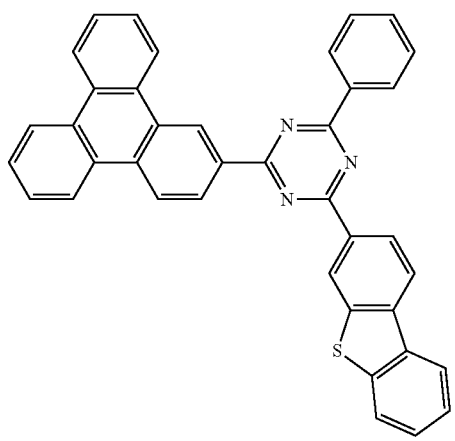
E-39
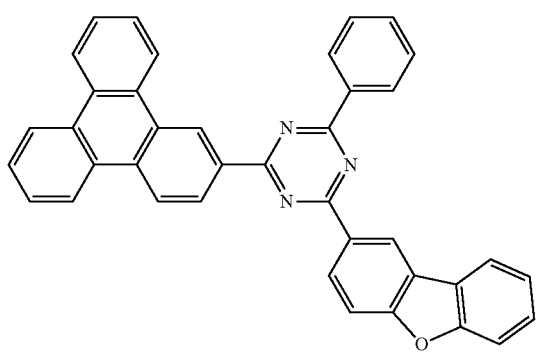
E-40
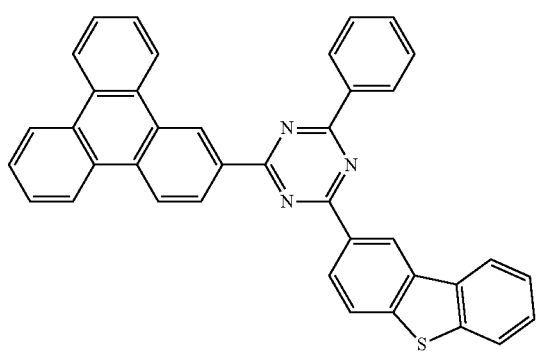
E-41
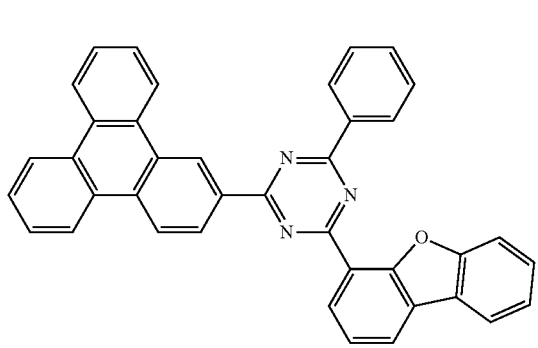
E-42
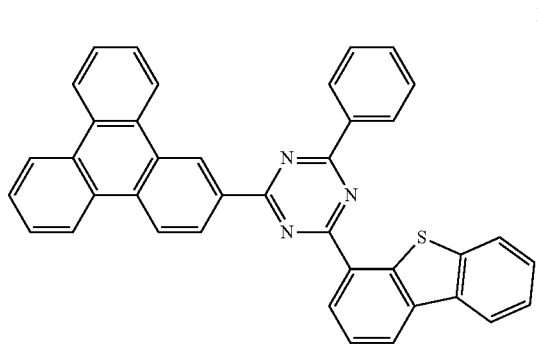

-continued
E-43
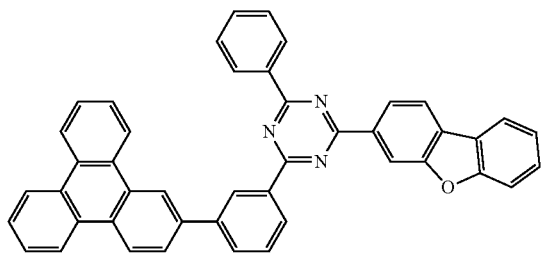
E-44
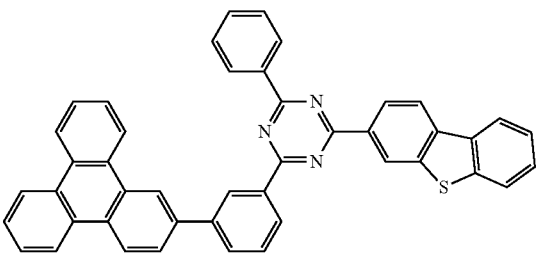
E-45
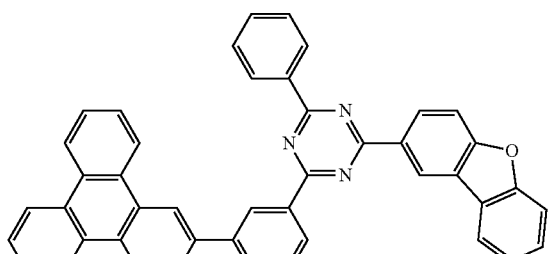
E-46
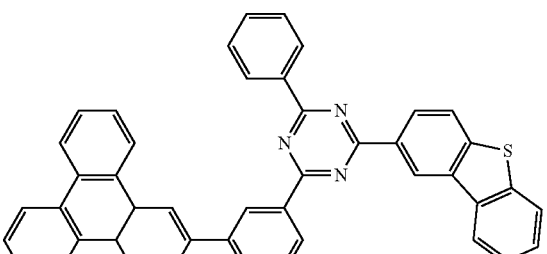
E-47
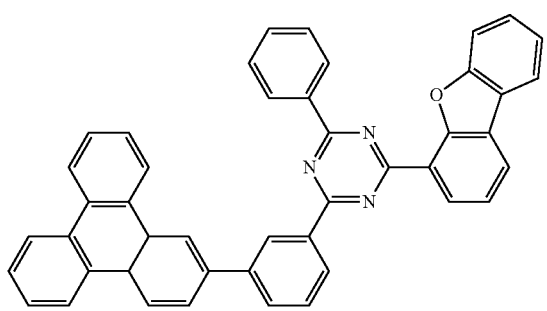
E-48
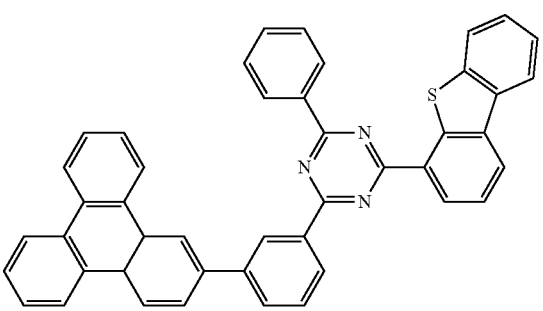
E-49
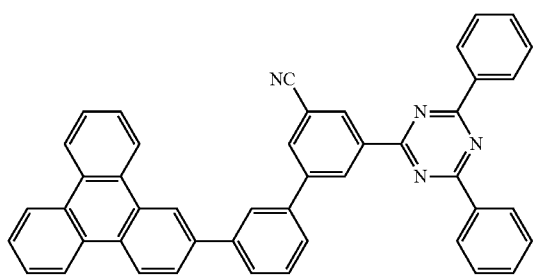
E-50
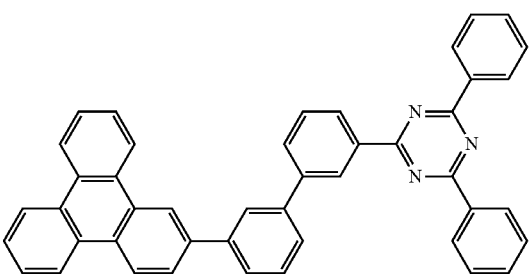
E-51
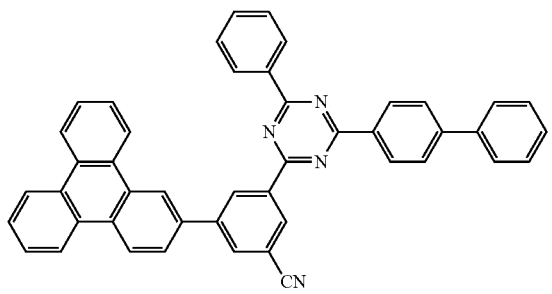
E-52
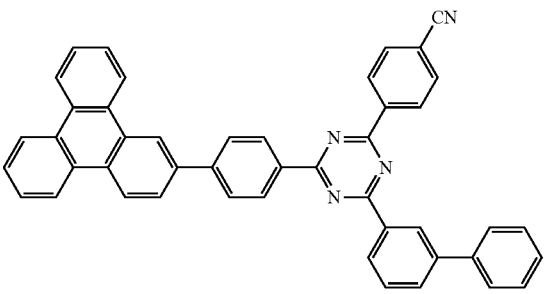

-continued

E-53

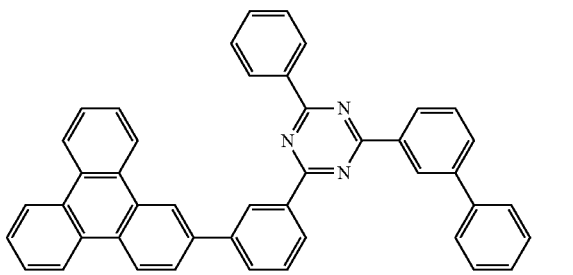

E-54

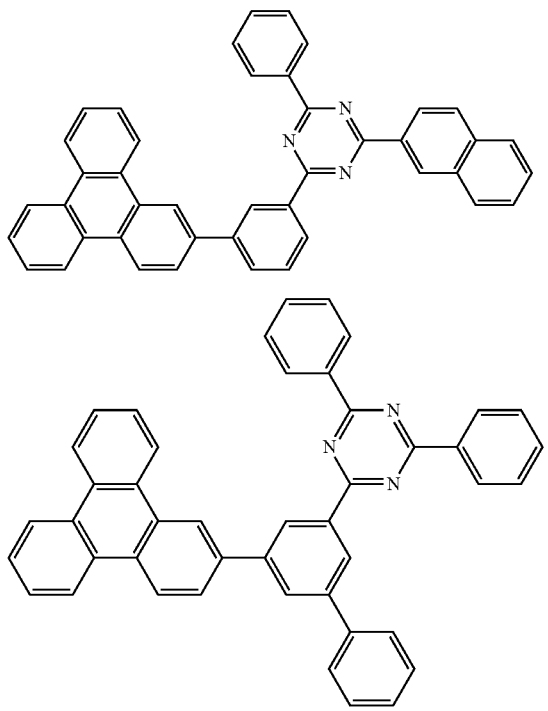

E-55

The first compound and the second compound may be, for example, included in a weight ratio of 1:99 to 99:1. Within the above range, bipolar characteristics may be implemented by adjusting an appropriate weight ratio using the hole transport capability of the first compound and the electron transport capability of the second compound to improve efficiency and life-span. Within the above range, they may be, for example, included in a weight ratio of about 10:90 to 90:10, about 20:80 to 80:20, about 30:70 to 70:30, about 40:60 to 60:40, or about 50:50. For example, they may be included in a weight ratio of 70:30 to 50:50, for example, a weight ratio of 70:30 or 60:40.

For example, the composition for an organic optoelectronic device may include a first compound for an organic optoelectronic device represented by any one of Chemical Formulas 1-1 to 1-4 and a second organic optoelectronic device represented by any one of Chemical Formulas 2-1 to 2-3.

As an example, the composition for an organic optoelectronic device may include a first compound for an organic optoelectronic device represented by any one of Chemical Formulas 1a to 1d and a second compound for an organic optoelectronic device represented by any one of Chemical Formulas 2-1 to 2-3.

As a specific example, the first compound for an organic optoelectronic device may be represented by Chemical Formula 1-3, and the second compound for an organic optoelectronic device may be represented by Chemical Formula 2-1 or Chemical Formula 2-2.

As a specific example, the first compound for an organic optoelectronic device may be represented by Chemical Formula 1a or 1d, and the second compound for an organic optoelectronic device may be represented by Chemical Formula 2-1 or 2-2.

For example, the composition for an organic optoelectronic device may include a first compound for an organic optoelectronic device that is one of the compounds H-1 to H-129 and a second compound for organic optoelectronic device that is one of the compounds A-1 to A-44, B-1 to B-160, C-1 to C20, D-1 to D-28, and E-1 to E-55.

The composition for an organic optoelectronic device may further include at least one compound in addition to the aforementioned first compound for an organic optoelectronic device and second compound for organic optoelectronic device.

The composition may further include a dopant. The dopant may be, for example, a phosphorescent dopant, such as a red, green or blue phosphorescent dopant, and may be, for example, a red phosphorescent dopant.

The dopant is a material mixed with the first compound for an organic optoelectronic device and second compound for organic optoelectronic device, in small amount to cause light emission and may generally be a material such as a metal complex that emits light by multiple excitation into a triplet or more. The dopant may be, for example, an inorganic, organic, or organic-inorganic compound, and may include one or two or more types.

The dopant may be, for example, a phosphorescent dopant, and examples of the phosphorescent dopant may be an organometallic compound including Ir, Pt, Os, Ti, Zr, Hf, Eu, Tb, Tm, Fe, Co, Ni, Ru, Rh, Pd, or a combination thereof. The phosphorescent dopant may be, for example, a compound represented by Chemical Formula Z, but is not limited thereto.

$L^7MX^a$       [Chemical Formula Z]

In Chemical Formula Z, M is a metal, $L^7$ and $X^a$ are the same as or different from each other, and are a ligand that forms a complex compound with M.

The M may be, for example, Ir, Pt, Os, Ti, Zr, Hf, Eu, Tb, Tm, Fe, Co, Ni, Ru, Rh, Pd, or a combination thereof, and $L^7$ and $X^a$ may be, for example, a bidentate ligand.

The composition may be formed by a dry film formation method such as chemical vapor deposition (CVD).

Hereinafter, an organic optoelectronic device including the aforementioned composition is described.

The organic optoelectronic device may be any device to convert electrical energy into photoenergy and vice versa without particular limitation, and may be, for example an organic photoelectric device, an organic light emitting diode, an organic solar cell, and an organic photo-conductor.

Herein, an organic light emitting diode as one example of an organic optoelectronic device is described referring to drawings.

FIGS. 1 and 2 are cross-sectional views showing organic light emitting diodes according to embodiments.

Referring to FIG. 1, an organic light emitting diode 100 according to an embodiment includes an anode 120 and a cathode 110 facing each other and an organic layer 105 disposed between the anode 120 and cathode 110.

The anode 120 may be made of a conductor having a large work function to help hole injection, and may be for example a metal, a metal oxide and/or a conductive polymer. The anode 120 may be, for example a metal such as nickel, platinum, vanadium, chromium, copper, zinc, gold, and the like or an alloy thereof; a metal oxide such as zinc oxide, indium oxide, indium tin oxide (ITO), indium zinc oxide (IZO), and the like; a combination of a metal and an oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example a metal, a metal oxide and/or a conductive polymer. The cathode 110 may be for example a metal such as magnesium, calcium, sodium, potassium, titanium, indium, yttrium, lithium, gadolinium, aluminum silver, tin, lead, cesium, barium, and the like, or an alloy thereof; a multi-layer structure material such as LiF/Al, $LiO_2$/Al, LiF/Ca, LiF/Al, and $BaF_2$/Ca, but is not limited thereto.

The organic layer 105 may include the aforementioned compound for an organic optoelectronic device or composition for an organic optoelectronic device.

The organic layer 105 may include a light emitting layer 130 that may include the aforementioned composition for an organic optoelectronic device.

The composition for an organic optoelectronic device may be, for example, a red light emitting composition.

The light emitting layer 130 may include, for example, the aforementioned first compound for an organic optoelectronic device and second compound for an organic optoelectronic device as each phosphorescent host.

Referring to FIG. 2, an organic light emitting diode 200 further includes a hole auxiliary layer 140 in addition to the light emitting layer 130. The hole auxiliary layer 140 further increases hole injection and/or hole mobility and blocks electrons between the anode 120 and the light emitting layer 130. The hole auxiliary layer 140 may be, for example, a hole transport layer, a hole injection layer, and/or an electron blocking layer, and may include at least one layer.

The hole auxiliary layer 140 may be at least two layers, for example, a hole transport layer between the anode 120 and the light emitting layer 130, and a hole transport auxiliary layer between the hole transport layer and the light emitting layer 130.

According to an embodiment of the present invention, the hole transport auxiliary layer may include the aforementioned compound for an organic optoelectronic device or composition for an organic optoelectronic device.

According to another example embodiment of the present invention, the light emitting layer may include the aforementioned compound for an organic optoelectronic device or composition for an organic optoelectronic device, and the hole transport layer or the hole transport auxiliary layer may include at least one of Compounds RA-1 to RA-4.

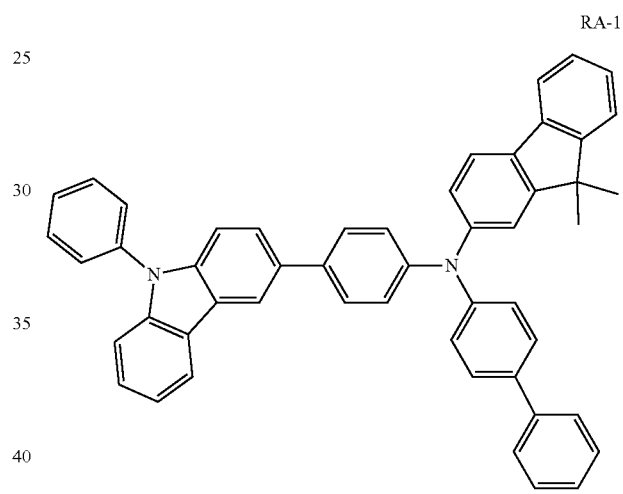

RA-1

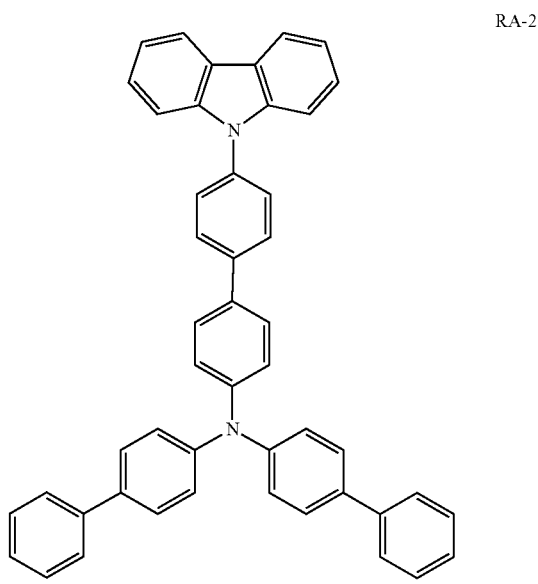

RA-2

-continued

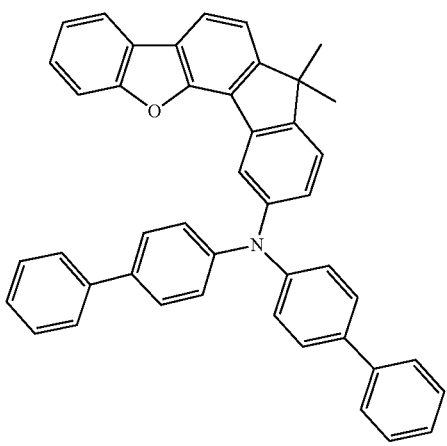
RA-3

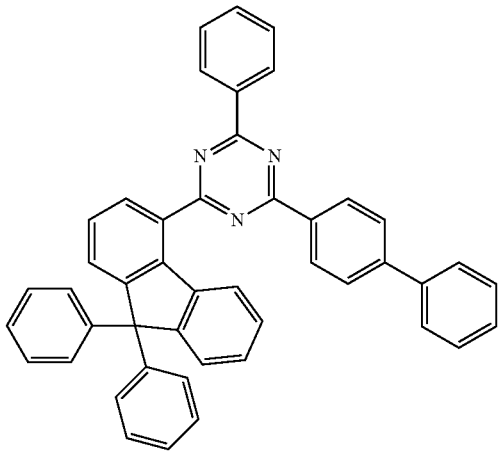
EA-1

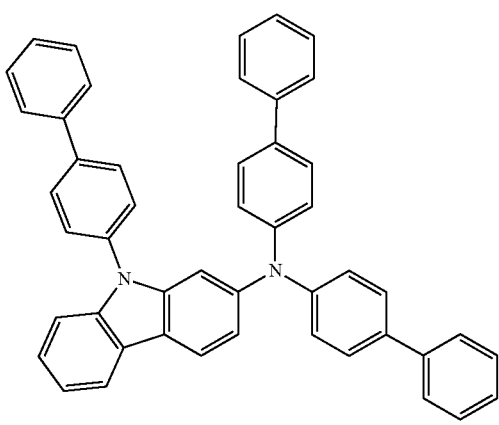
RA-4

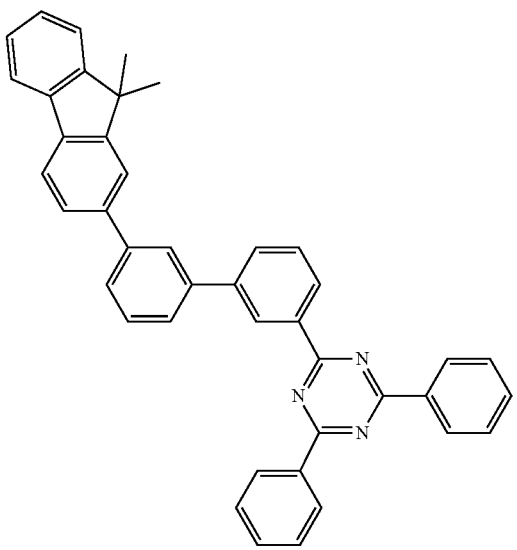
EA-2

In addition, in one embodiment of the present invention, at least one electron auxiliary layer such as an electron transport layer, an electron injection layer, and/or a hole blocking layer, and the like may be further additionally included between the cathode 110 and the light emitting layer 130 in addition to the organic layer 105.

For example, the electron auxiliary layer may be at least two layers and include, for example, an electron transport layer between the cathode 110 and the light emitting layer 130 and an electron transport auxiliary layer between the electron transport layer and the light emitting layer.

According to still another embodiment of the present invention, the electron transport layer or the electron transport auxiliary layer may include at least one of Compounds EA-1 and EA-2.

The organic light emitting diodes 100 and 200 may be manufactured by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

DETAILED DESCRIPTION OF THE EMBODIMENTS

Hereinafter, the embodiments are illustrated in more detail with reference to examples. However, these examples are exemplary, and the present scope is not limited thereto.

Hereinafter, starting materials and reactants used in Examples and Synthesis Examples were purchased from Sigma-Aldrich Co. Ltd., TCI Inc., Tokyo chemical industry or P&H tech as far as there in no particular comment or were synthesized by known methods.

157

Preparation of Compound

First Compound for Organic Optoelectronic Device

Synthesis Example 1: Synthesis of Compound H-1

[Reaction Scheme 1]

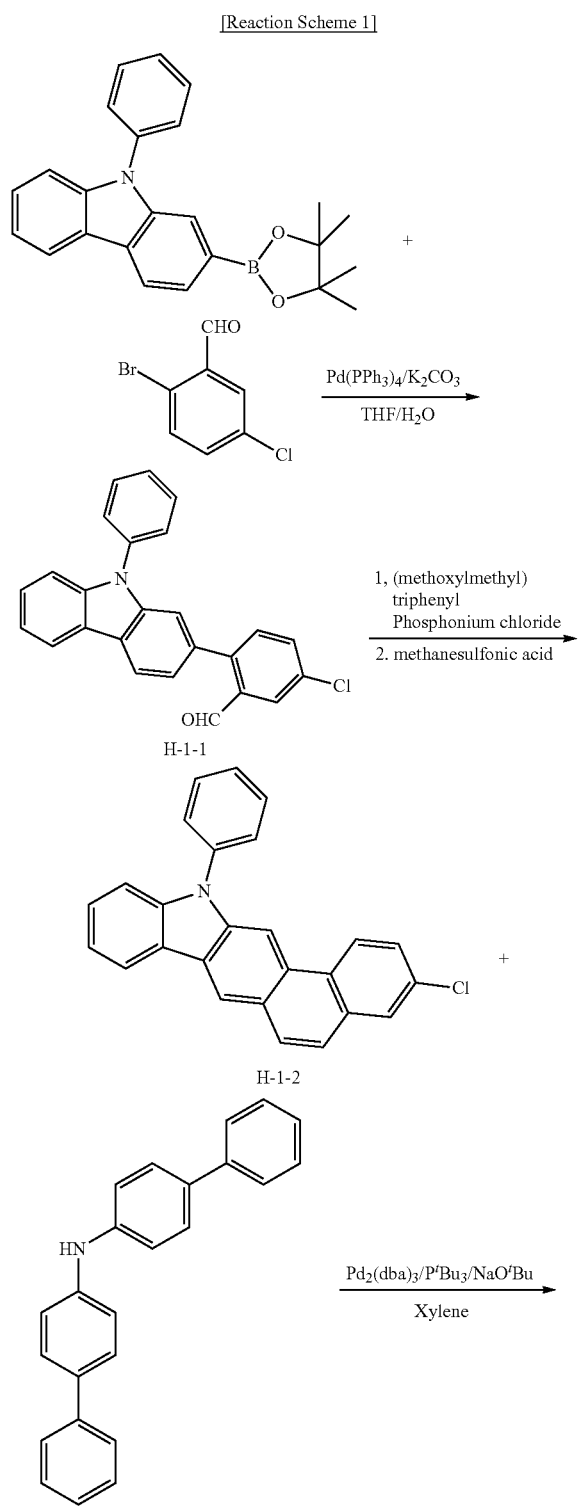

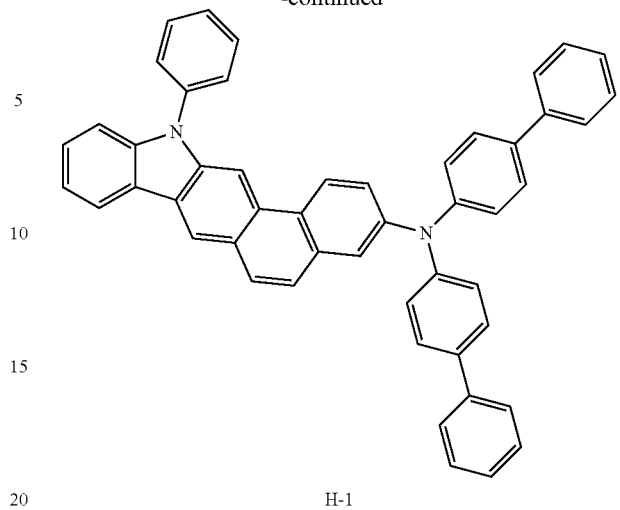

H-1 a) Synthesis of Intermediate H-1-1

In a round-bottomed flask, 50.00 g (135.41 mmol) of 9-phenyl-2-(4,4,5,5-tetramethyl-[1,3,2]dioxaborolan-2-yl)-9H-carbazole, 29.72 g (135.41 mmol) of 2-bromo-5-chlorobenzaldehyde, 4.69 g (4.06 mmol) of Pd(PPh$_3$)$_4$, and 37.43 g (270.81 mmol) of K$_2$CO$_3$ were suspended in a mixed solvent of 400 mL of THF/220 mL of distilled water and then stirred for 12 hours at room temperature. When a reaction was complete, the resultant was concentrated, extracted with methylene chloride, and an organic layer therefrom was silica gel columned to obtain 45.0 g (Yield of 87%) of a target compound, Intermediate H-1-1.

b) Synthesis of Intermediate H-1-2

45.00 g (117.9 mmol) of Intermediate H-1-1 and 45.00 g (117.9 mmol) of (methoxymethyl)triphenyl phosphonium chloride were suspended in 600 ml of THF, and 15.87 g (141.48 mmol) of potassium tert-butoxide was added thereto and then, stirred for 12 hours at room temperature. When a reaction was complete, 400 ml of distilled water was added thereto and then, extracted, then, an organic layer therefrom was concentrated and reextracted with methylene chloride, magnesium sulfate was added thereto and then, stirred for 30 minutes, and a filtrate was concentrated. After adding 100 ml of methylene chloride to the concentrated filtrate, 15 ml of methane sulfonic acid was added thereto and then, stirred for 1 hour.

When a reaction was complete, methyl alcohol was added thereto to produce a solid. The produced solid was filtered and dried to obtain 30.0 g (Yield of 67%) of a target compound, Intermediate H-1-2.

c) Synthesis of Compound H-1

Intermediate H-1-2 (8.85 g, 23.45 mmol), bis-biphenyl-4-yl-amine (7.91 g, 24.62 mmol), sodium t-butoxide (NaOtBu) (3.38 g, 35.17 mmol), Pd$_2$(dba)$_3$ (1.28 g, 1.41 mmol), and tri t-butylphosphine (P(tBu)$_3$) (1.71 g, 50% in toluene) put in xylene (120 mL) and then, heated and refluxed under a nitrogen flow for 12 hours. After removing the xylene, 200 mL of methanol was added to the obtained mixture, and a solid crystallized therein was filtered, dissolved in toluene, and filtered with silica gel/Celite, and an organic solvent in an appropriate amount was concentrated to obtain 12 g (77%) of Compound H-1.

LC/MS calculated for: C50H34N2 Exact Mass: 662.27 found for 662.32 [M+H]

Synthesis Example 2: Synthesis of Compound H-7

[Reaction Scheme 2]

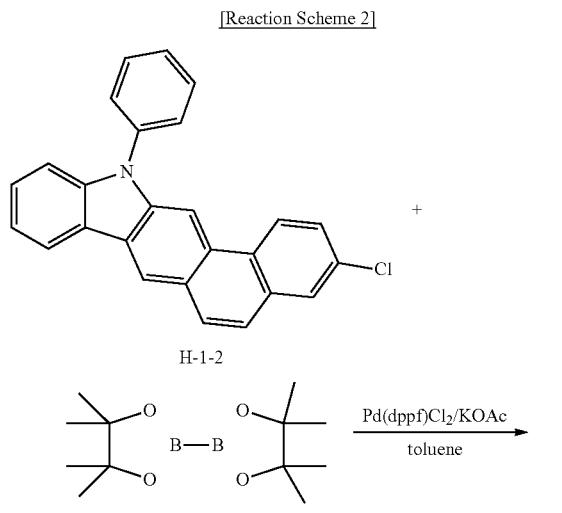

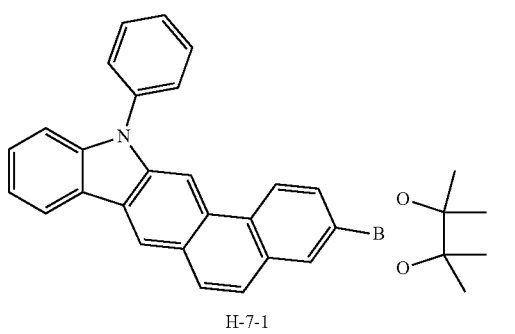

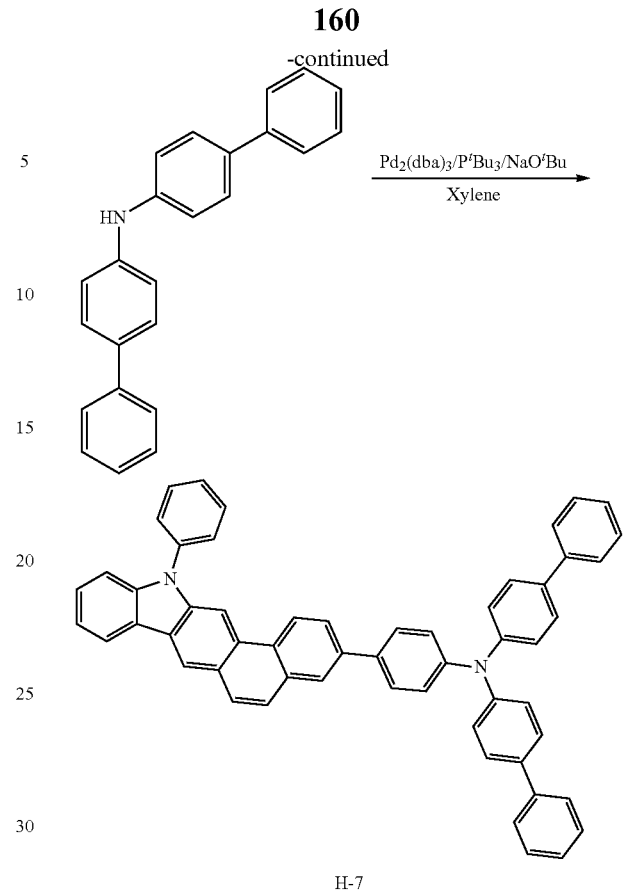

a) Synthesis of Intermediate H-7-1

15.00 g (39.71 mmol) of Intermediate H-1-2, 12.1 g (47.64 mmol) of bis(pinacolato)diboron, 1.62 g (1.98 mmol) of Pd(dppf)Cl$_2$, and 11.69 g (119.09 mmol) of KOAc were suspended in 150 ml of toluene and then, refluxed and stirred for 12 hours. After concentrating the reaction solvent, an organic layer was extracted therefrom with methylene chloride and columned with hexane:EA=4:1 (v/v) to obtain 15.0 g (Yield of 81%) of a target compound, Intermediate H-7-1.

b) Synthesis of Intermediate H-7-2

Intermediate H-7-1 (13.30 g, 28.34 mmol), 1-bromo-4-chloro-benzene (6.51 g, 34.00 mmol), K$_2$CO$_3$ (7.83 g, 56.67 mmol), and Pd(PPh$_3$)$_4$ (0.98 g, 0.85 mmol) were put in a round-bottomed flask and then, dissolved in 100 ml of THF and 50 ml of distilled water and then, stirred at 80° C. for 12 hours. When a reaction was complete, an aqueous layer was removed therefrom, and 10.0 g (78%) of Intermediate H-7-2 was obtained through column chromatography.

c) Synthesis of Compound H-7

Intermediate H-7-2 (9.21 g, 20.30 mmol), bis-biphenyl-4-yl-amine (6.85 g, 21.32 mmol), sodium t-butoxide (NaOtBu) (2.97 g, 30.45 mmol), Pd$_2$(dba)$_3$ (1.11 g, 1.22 mmol), and tri t-butylphosphine (P(tBu)$_3$) (1.48 g, 50% in toluene) were put in xylene (120 mL) and then, heated and refluxed under a nitrogen flow for 12 hours. After removing the xylene, 200 mL of methanol was added to the obtained mixture, and a solid crystallized therein was filtered, dissolved in toluene, and filtered through silica gel/Celite, and an organic solvent in an appropriate amount was concentrated to obtain 12 g (80%) of Compound H-7.

LC/MS calculated for: C56H38N2 Exact Mass: 738.30 found for 738.27 [M+H]

Synthesis Example 3: Synthesis of Compound H-14

[Reaction Scheme 3]

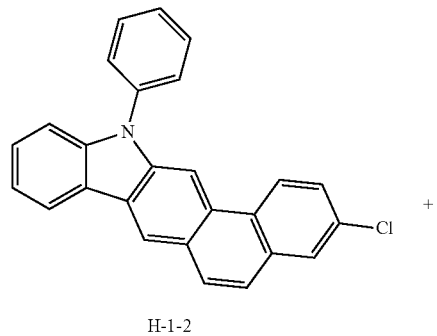

H-1-2

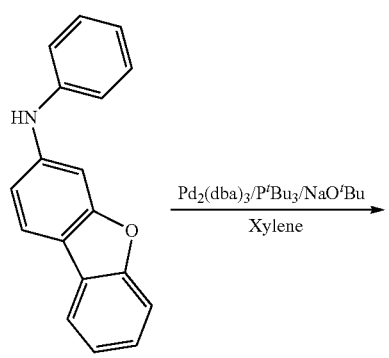

Pd$_2$(dba)$_3$/P$^t$Bu$_3$/NaO$^t$Bu
Xylene

H-14

Compound A-7 was synthesized according to the same method as the c) of Synthesis Example 1 by using Intermediate H-1-2 and dibenzofuran-3-yl-phenyl-amine in an equivalent ratio of 1:1.

LC/MS calculated for: C44H28N2O Exact Mass: 600.22 found for 600.45 [M+H]

Synthesis Example 4: Synthesis of Compound H-23

[Reaction Scheme 4]

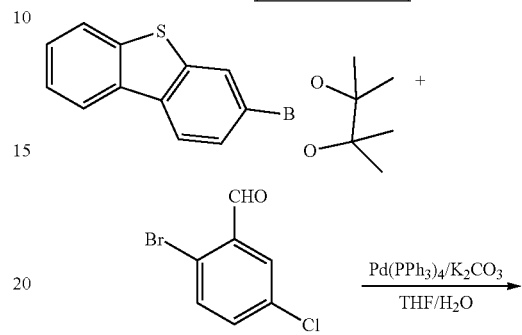

Pd(PPh$_3$)$_4$/K$_2$CO$_3$
THF/H$_2$O

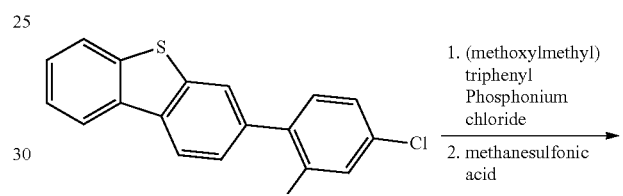

H-23-1

1. (methoxylmethyl) triphenyl Phosphonium chloride
2. methanesulfonic acid

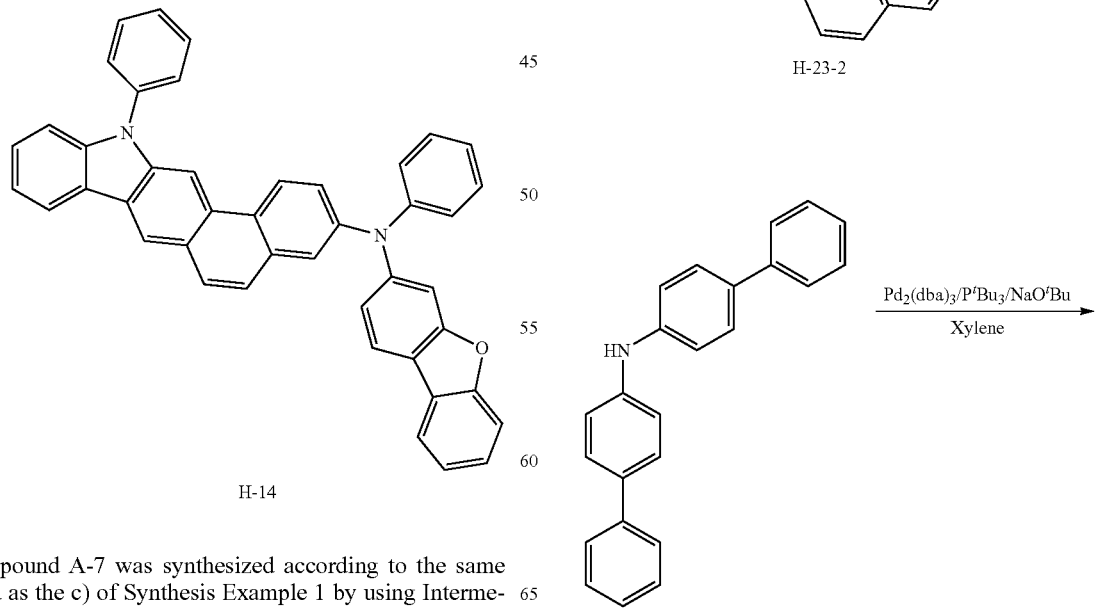

H-23-2

Pd$_2$(dba)$_3$/P$^t$Bu$_3$/NaO$^t$Bu
Xylene

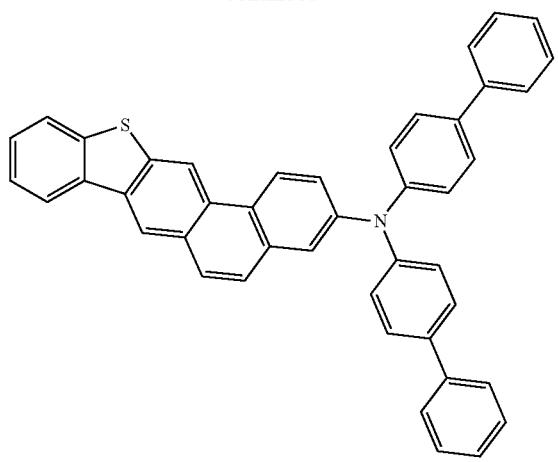

H-23

Compound H-23 was synthesized in the same manner as in Synthesis Example 1 using 2-dibenzothiophen-3-yl-4,4,5,5-tetramethyl-[1,3,2]dioxaborolane instead of the reactant 9-phenyl-2-(4,4,5,5-tetramethyl-[1,3,2]dioxaborolan-2-yl)-9H-carbazole.

LC/MS calculated for: C44H29NS Exact Mass: 603.20 found for 603.77 [M+H]

Synthesis Example 5: Synthesis of Compound H-42

[Reaction Scheme 5]

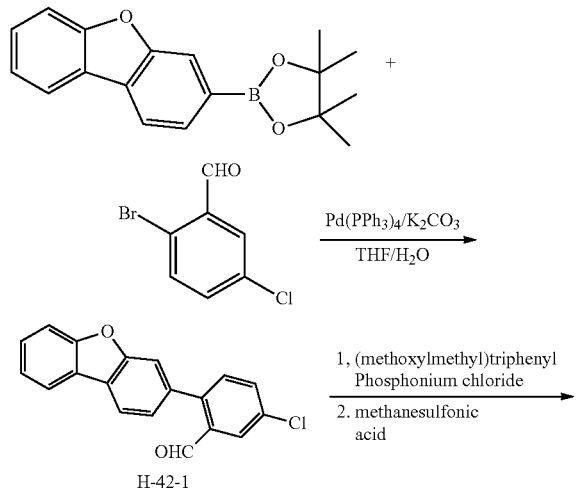

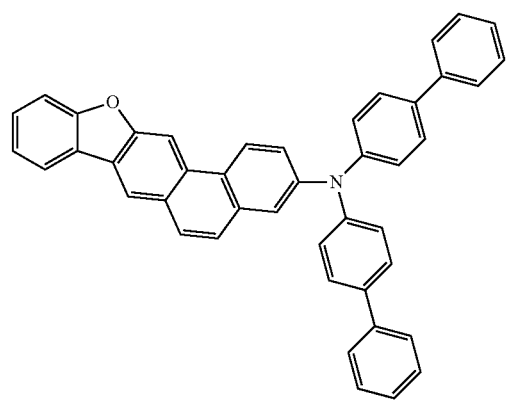

H-42

Compound H-42 was synthesized in the same manner as in Synthesis Example 1 using 2-dibenzofuran-3-yl-4,4,5,5-tetramethyl-[1,3,2]dioxaborolane instead of the reactant 9-phenyl-2-(4,4,5,5-tetramethyl-[1,3,2]dioxaborolan-2-yl)-9H-carbazole.

LC/MS calculated for: C44H29NO Exact Mass: 587.22 found for 587.71 [M+H]

Synthesis Example 6: Synthesis of Compound H-43

[Reaction Scheme 6]

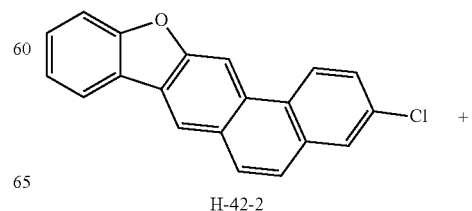

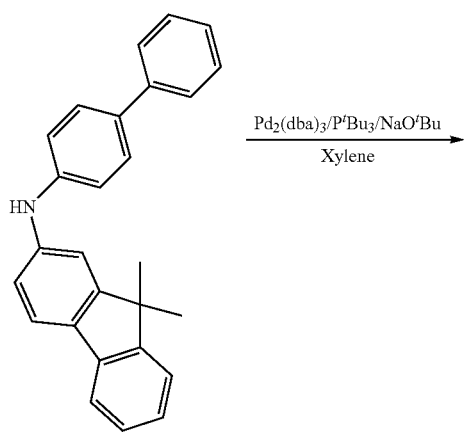

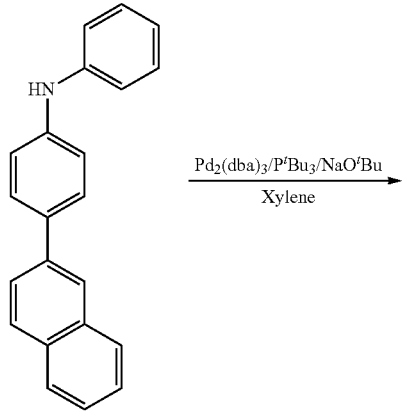

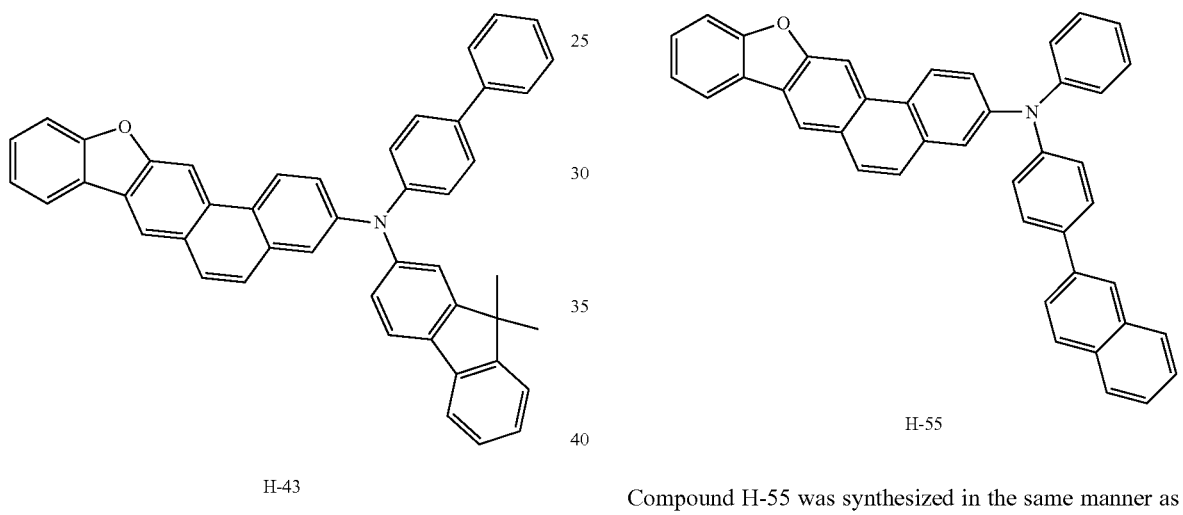

H-43

H-55

Compound H-43 was synthesized in the same manner as c) of Synthesis Example 1 was synthesized using Intermediate H-42-2 and biphenyl-4-yl-(9,9-dimethyl-9H-fluoren-2-yl)-amine in a 1:1 equivalent ratio.

LC/MS calculated for: C47H33NO Exact Mass: 627.26 found for 627.77 [M+H]

Compound H-55 was synthesized in the same manner as c) of Synthesis Example 1 was synthesized using Intermediate H-42-2 and (4-naphthalen-2-yl-phenyl)-phenyl-amine in a 1:1 equivalent ratio.

LC/MS calculated for: C42H27NO Exact Mass: 561.21 found for 561.67 [M+H]

Synthesis Example 7: Synthesis of Compound H-55

Synthesis Example 8: Synthesis of Compound H-49

[Reaction Scheme 7]

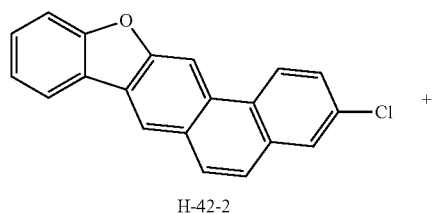

H-42-2

[Reaction Scheme 8]

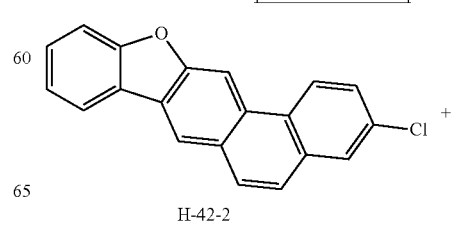

H-42-2

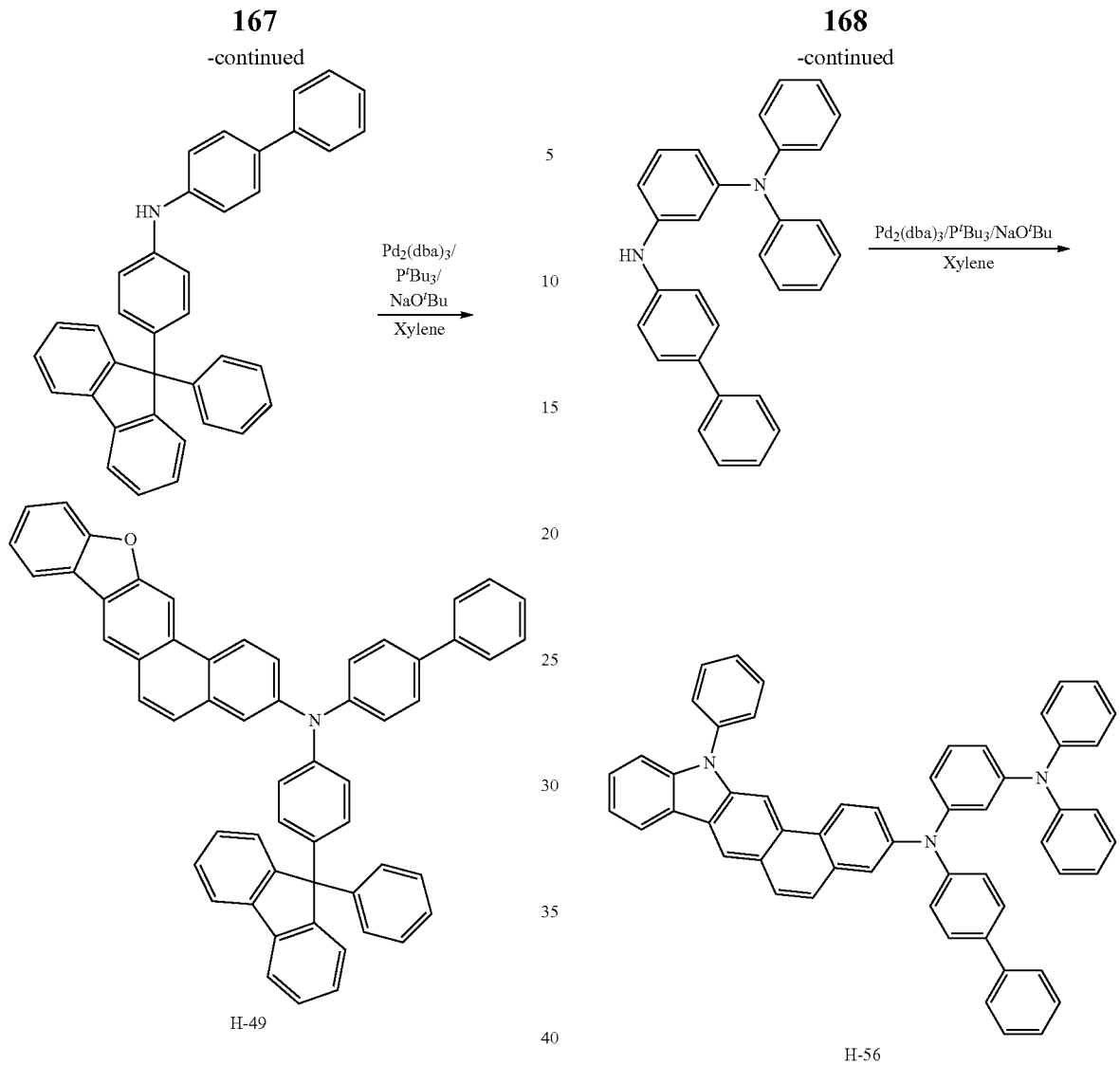

H-49

Compound H-49 was synthesized in the same manner as c) of Synthesis Example 1 was synthesized using Intermediate H-42-2 and biphenyl-4-yl-[4-(9-phenyl-9H-fluoren-9-yl)-phenyl]-amine in a 1:1 equivalent ratio.

LC/MS calculated for: C57H37NO Exact Mass: 751.29 found for 751.91 [M+H]

Synthesis Example 9: Synthesis of Compound H-56

H-56

Compound H-56 was synthesized in the same manner as c) of Synthesis Example 1 was synthesized using Intermediate H-1-2 and N1-([1,1'-biphenyl]-4-yl)-N3,N3-diphenyl-benzene-1,3-diamine in a 1:1 equivalent ratio.

LC/MS calculated for: C56H39N3 Exact Mass: 753.31 found for 753.93 [M+H]

Synthesis Example 10: Synthesis of Compound H-75

[Reaction Scheme 9]

[Reaction Scheme 10]

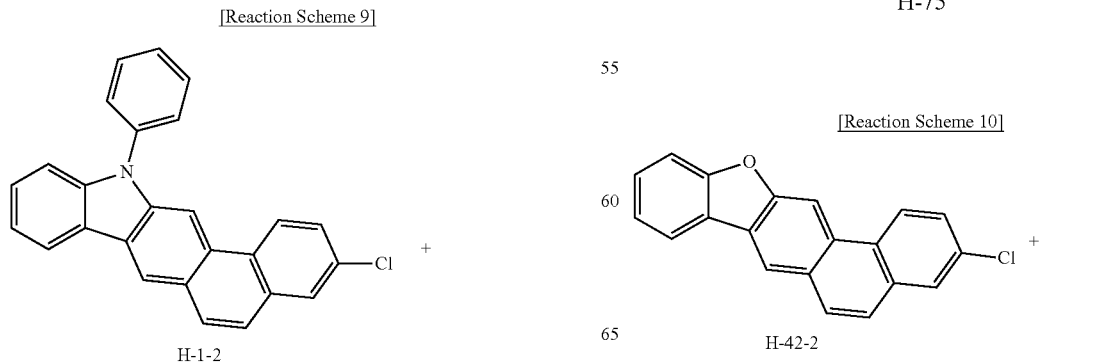

H-1-2

H-42-2

-continued

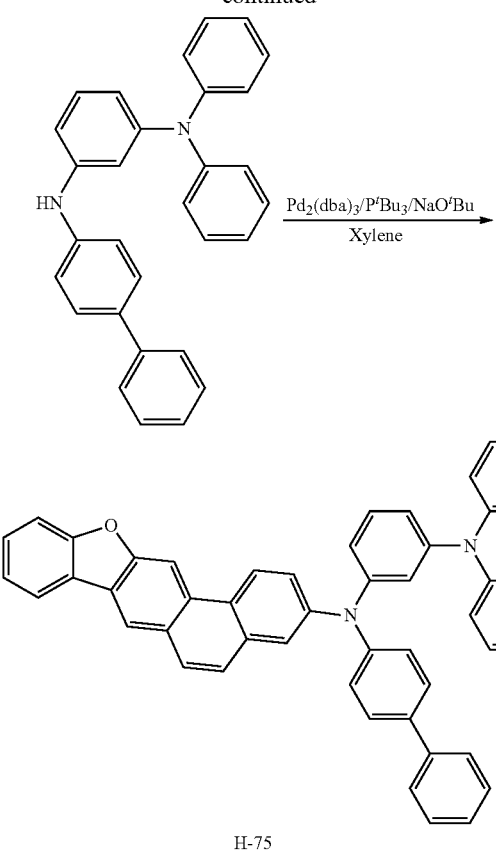

H-75

Compound H-75 was synthesized in the same manner as c) of Synthesis Example 1 was synthesized using Intermediate H-42-2 and N1-([1,1'-biphenyl]-4-yl)-N3,N3-diphenylbenzene-1,3-diamine in a 1:1 equivalent ratio.

LC/MS calculated for: C50H34N2O Exact Mass: 678.27 found for 678.82 [M+H]

Synthesis Example 11: Synthesis of Compound H-85

[Reaction Scheme 11]

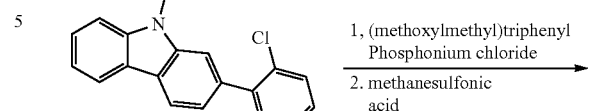

-continued

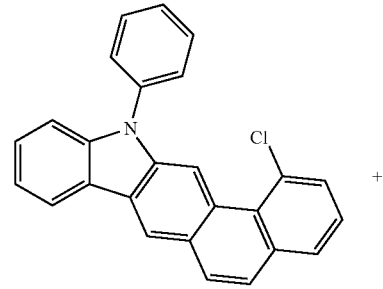

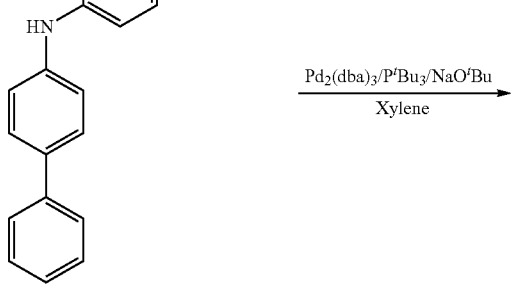

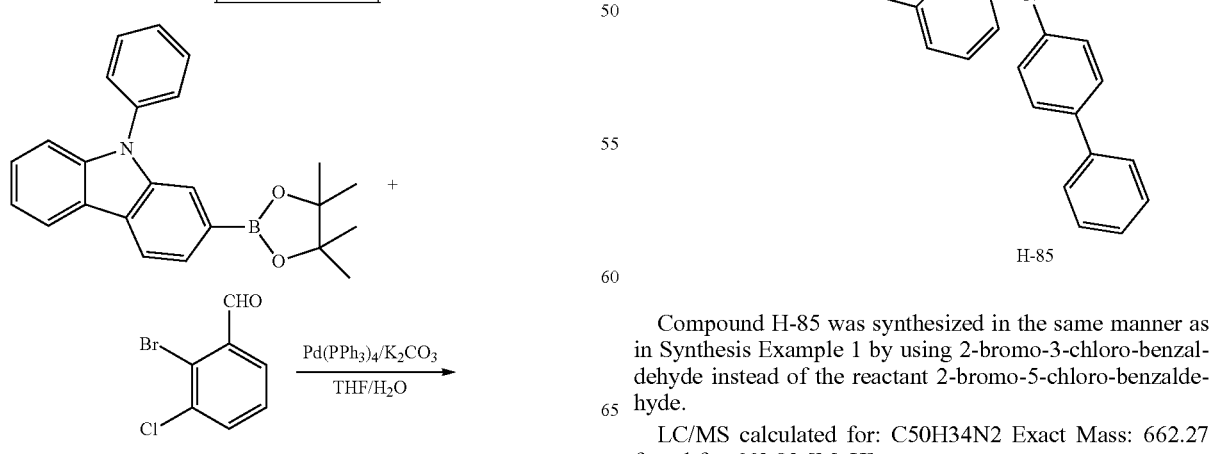

H-85

Compound H-85 was synthesized in the same manner as in Synthesis Example 1 by using 2-bromo-3-chloro-benzaldehyde instead of the reactant 2-bromo-5-chloro-benzaldehyde.

LC/MS calculated for: C50H34N2 Exact Mass: 662.27 found for 662.82 [M+H]

Synthesis Example 12: Synthesis of Compound H-120

[Reaction Scheme 12]

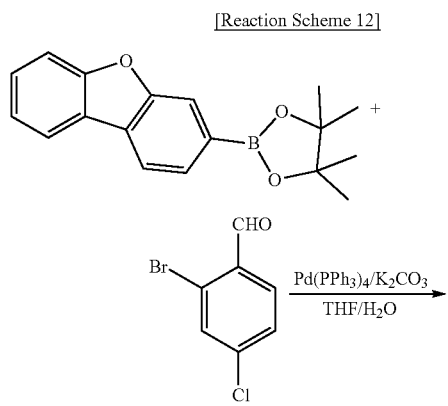

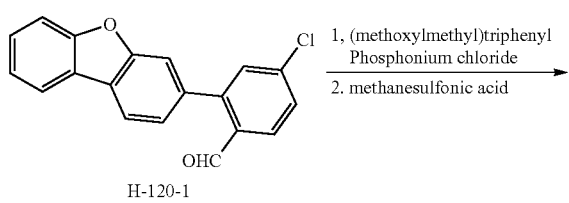

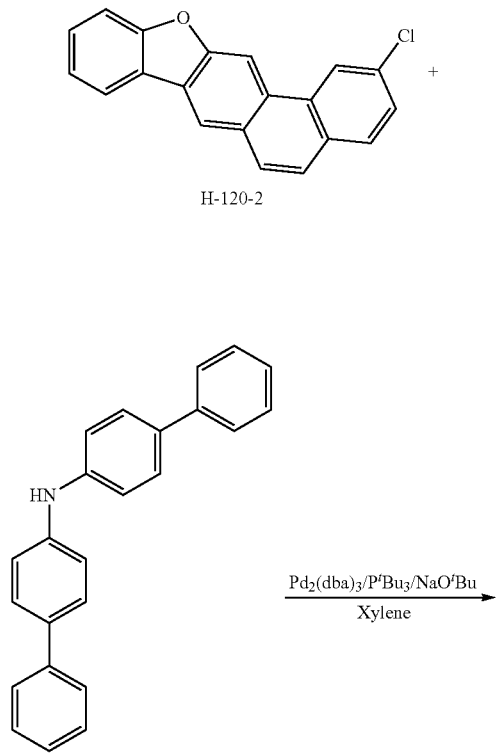

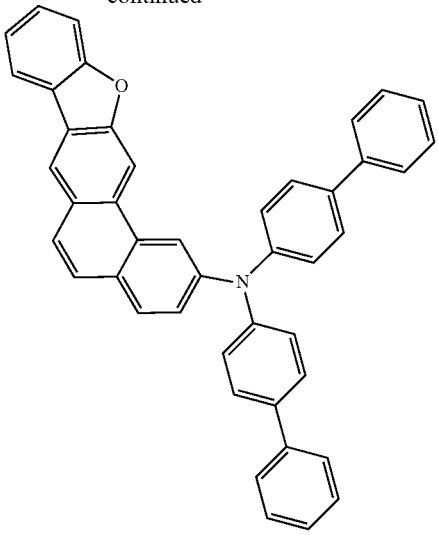

H-120

Compound H-120 was synthesized in the same manner as in Synthesis Example 1 by using 2-dibenzothiophen-3-yl-4,4,5,5-tetramethyl-[1,3,2]dioxaborolane and 2-bromo-4-chloro-benzaldehyde instead of the reactants 9-phenyl-2-(4,4,5,5-tetramethyl-[1,3,2]dioxaborolan-2-yl)-9H-carbazole and 2-bromo-5-chloro-benzaldehyde.

LC/MS calculated for: C44H29NO Exact Mass: 587.22 found for 587.71 [M+H]

Synthesis Example 13: Synthesis of Compound H-125

[Reaction Scheme 13]

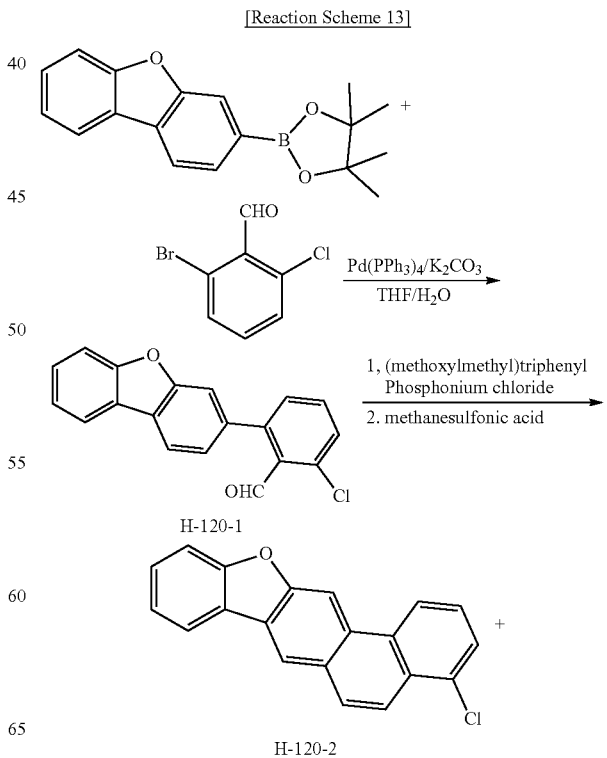

-continued

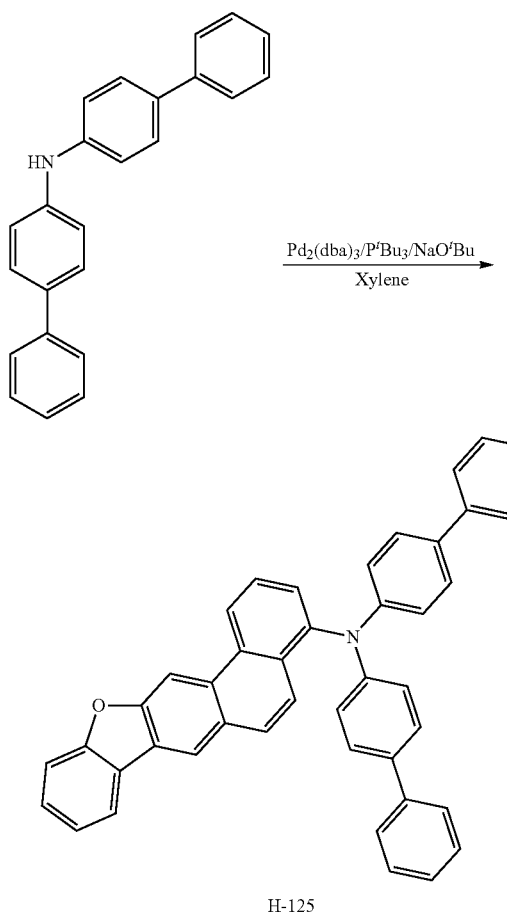

H-125

Compound H-125 was synthesized in the same manner as in Synthesis Example 1 by using 2-dibenzothiophen-3-yl-4,4,5,5-tetramethyl-[1,3,2]dioxaborolane and 2-bromo-6-chloro-benzaldehyde instead of the reactants 9-phenyl-2-(4,4,5,5-tetramethyl-[1,3,2]dioxaborolan-2-yl)-9H-carbazole and 2-bromo-5-chloro-benzaldehyde.

LC/MS calculated for: C44H29NO Exact Mass: 587.22 found for 587.78 [M+H]

Comparative Synthesis Example 1: Synthesis of Compound V-1

[Reaction Scheme 14]

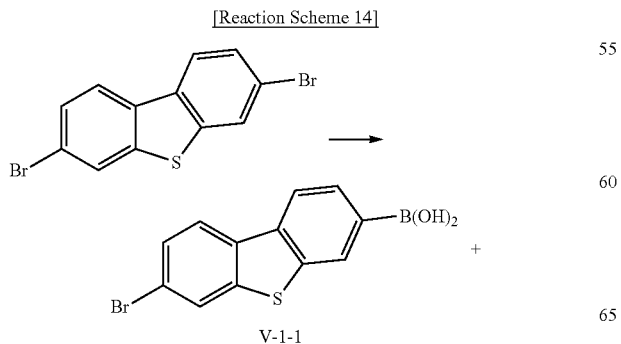

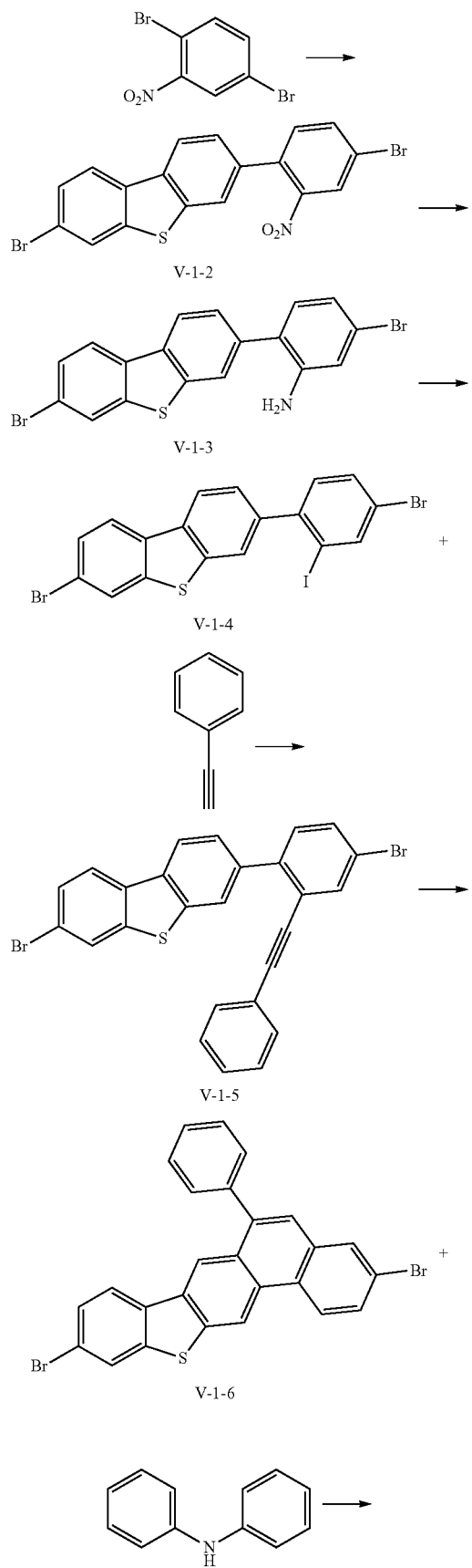

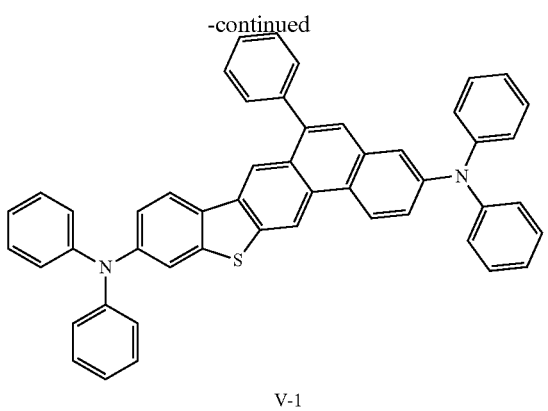

V-1 a) Synthesis of Intermediate V-1-1

50 g (146 mmol) of 3,7-dibromobenzo[b,d]thiophene and 400 mL of tetrahydrofuran were put in a round-bottomed flask and then, cooled down to −78° C. with dry ice and acetone under a nitrogen atmosphere. Subsequently, 100.5 mL of 1.6 M butyllithium was slowly dripped thereinto, while the temperature was maintained, and then, stirred for 2 hours, while the temperature was still maintained. At the same temperature, 103 mL of trimethylborate was slowly dripped thereinto and then, heated up to room temperature and stirred for 24 hours. When a reaction was complete, 2 N hydrochloric acid was added thereto and then, stirred. Then, EA was added to the reaction solution and then, stirred and extracted with EA/H$_2$O, and the obtained EA layer was neutralized into PH 6 to 7. The organic layer was concentrated and recrystallized with hexane, and crystals obtained therefrom were dried to obtain Intermediate V-1-1 (29.4 g, 65.5%).

b) Synthesis of Intermediate V-1-2

29.4 g (96 mmol) of Intermediate V-1-1, 32.3 g (115 mmol) of 2,5-dibromonite benzene, 2.2 g (1.9 mmol) of tetrakis(triphenylphosphine) palladium (0), 26.5 g (192 mmol) of potassium carbonate, 176.4 mL of tetrahydrofuran, 58.8 mL of dioxane, and 176.4 mL of water were put in a round-bottomed flask and then, refluxed. When a reaction was complete, the resultant was cooled down to room temperature and extracted with EA, and an organic layer therefrom was concentrated and column-separated. The separated solution was concentrated and recrystallized with MeOH, and crystals produced therein were dried to obtain Intermediate V-1-2 (28 g, 63.1%).

c) Synthesis of Intermediate V-1-3

28 g (60 mmol) of Intermediate V-1-2, 170 mL of hydrochloric acid, and 560 mL of ethanol were put in a round-bottomed flask and then, cooled down to less than or equal to 0° C., and 17.9 g (151 mmol) of tin powder was added thereto and then, heated, until it was completely dissolved. When a reaction was complete, the resultant was cooled down to room temperature, and a 40% sodium hydroxide aqueous solution was added thereto to increase PH into 10 or higher. The resultant was extracted with EA, an organic layer therefrom was taken and concentrated and then, recrystallized with MeOH, and crystals produced therein were dried to obtain Intermediate V-1-3 (23 g, 87.8%).

d) Synthesis of Intermediate V-1-4

23 g (53 mmol) of Intermediate V-1-3, sodium nitrite 9.2 g (133 mmol), 22 g (132.7 mmol) of potassium iodide, and 228 mL of acetonitrile were put in a round-bottomed flask and then, cooled down to less than or equal to 0° C., while stirred, and then, hydrochloric acid was slowly dripped thereinto. When a reaction was complete, the temperature was increased up to room temperature, and water was added thereto and then, stirred, and after additionally adding MC thereto, also stirred. Subsequently, sodium thiosulfate was added thereto, until the reaction solution became yellow. The resultant was extracted with MC and then, concentrated and column-separated, the separated solution was concentrated and then, recrystallized with hexane, and crystals produced therein were dried to obtain Intermediate V-1-4 (25 g, 86.6%).

e) Synthesis of Intermediate V-1-5

25 g (46 mmol) of Intermediate V-1-4, 1.1 g (1 mmol) of tetrakis(triphenyl phosphine)palladium (0), 0.4 g (2 mmol) of copper iodide, and 200 mL of triethylamine were put in a round-bottomed flask and then, stirred at room temperature. While the resultant was stirred, 4.7 mL (46 mmol) of phenylacetylene was slowly dripped thereinto. The obtained mixture was stirred for 1 hour, and hexane was poured into to complete a reaction. The reaction solution was concentrated and then, column-separated to obtain Intermediate V-1-5 (19 g, 79.7%).

f) Synthesis of Intermediate V-1-6

19 g (37 mmol) of Intermediate V-1-5, 1.8 g (4 mmol) of iron (III) trifluoromethanesulfonate, and 300 mL of 1,2-dichloroethane were put in a round-bottomed flask and then, refluxed for 24 hours. When a reaction was complete, the resultant was cooled down to room temperature and then, concentrated and column-separated, the separated solution was concentrated and recrystallized with MeOH, and the produced crystals were dried to obtain Intermediate V-1-6 (17 g, 89.5%).

g) Synthesis of Compound V-1

17 g (33 mmol) of Intermediate V-1-6, 13.3 g (79 mmol) of diphenylamine, 0.29 g (1.3 mmol) of palladium(II)acetate, 12.6 g (131 mmol) of sodium-t-butoxide, and 200 mL of toluene were put in a round-bottomed flask and then, heated while stirred, and when the temperature reached 60° C., 2.12 g (5.2 mmol) of tri-t-butylphosphine was added thereto and then, refluxed. When a reaction was complete, the reaction solution was cooled down to room temperature and then, concentrated and column-separated, the separated solution was recrystallized, and the produced crystals were filtered and dried to obtain Compound V-1 (8.6 g, 37.7%).

LC/MS calculated for: C50H34N2S Exact Mass: 694.24 found for 694.88 [M+H]

Comparative Synthesis Example 2: Synthesis of Compound V-2

[Reaction Scheme 15]

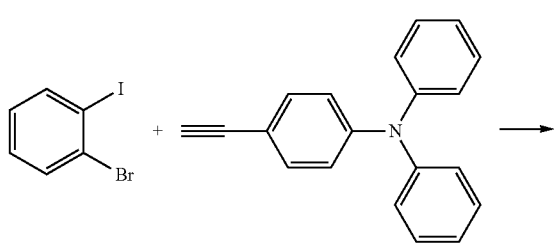

-continued

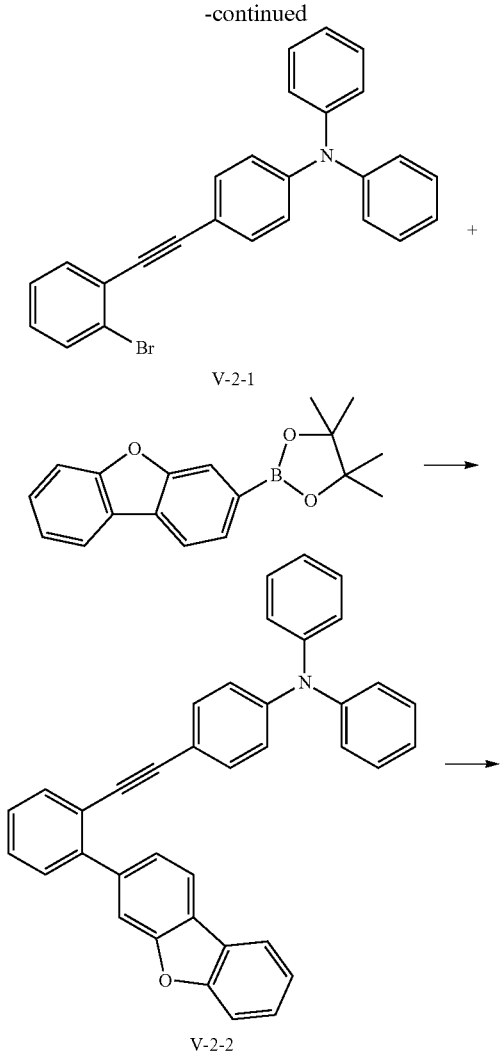

a) Synthesis of Intermediate V-2-1

7.5 g (1.2 eq) of 2-bromoiodobenzene, 780 mg (0.05 eq) of bis(chloro(triphenylphosphine)) palladium(II), and 250 mg (0.06 eq) of CuI were mixed, the mixture was added to 70 mL of THF and then, stirred under a nitrogen flow, and 13 mL (8 eq) of triethylamine and 6 g (1 eq) of (4-ethinyl-phenyl)-diphenyl-amine were slowly added thereto in a dropwise fashion and then, stirred for 2 hours at room temperature condition. After removing the solvent from a resulting material therefrom by using a rotary evaporator, 50 mL of water was added to the reaction solution and then, three times extracted with 50 mL of ethyl ether. An organic layer obtained therefrom was dried by using magnesium sulfate, and a residue by evaporating a solvent therefrom was separated and purified to obtain 5 g (Yield: 55%) of Intermediate V-2-1.

b) Synthesis of Intermediate V-2-2

5.0 g (1.0 eq) of Intermediate V-2-1, 4.2 g (1.2 eq) of 3-(4,4,5,5-tetramethyl-[1,3,2]dioxaborolane-2-yl)-dibenzofuran, 950 mg (0.07 eq) of Pd(PPh$_3$)$_4$, and 2.8 g (1.7 eq) of K$_2$CO$_3$ were mixed with mL of THF 30 and 15 mL of distilled water, heated up to 70° C., and stirred for 24 hours, while refluxed. The obtained mixture was cooled down to room temperature and then, three times extracted with 100 mL of water and 100 mL of diethyl ether. An organic layer obtained therefrom was dried by using magnesium sulfate, and a residue obtained therefrom by evaporating a solvent was separated and purified through column to obtain 3.6 g (Yield of 60%) of Intermediate V-2-2.

c) Synthesis of Compound V-2

3.6 g (1 eq) of Intermediate V-2-2 was mixed with 500 mL of methylene chloride, and 20 mL (40 eq) of trifluoroacetic acid was slowly added thereto in a dropwise fashion and then, stirred for 1 hour at room temperature. When a reaction was complete, 100 mL of water and 100 mL of diethyl ether were added to the reaction solution and then, three times extracted. Subsequently, an organic layer obtained therefrom was dried by using magnesium sulfate, and a residue obtained by evaporating the solvents therefrom was separated and purified through a column to obtain 3.2 g (Yield of 90%) of Compound V-2.

LC/MS calculated for: C38H25NO Exact Mass: 511.19 found for 511.61 [M+H]

Second Compound for Organic Optoelectronic Device

Synthesis Example 14: Synthesis of Compound A-8

[Reaction Scheme 16]

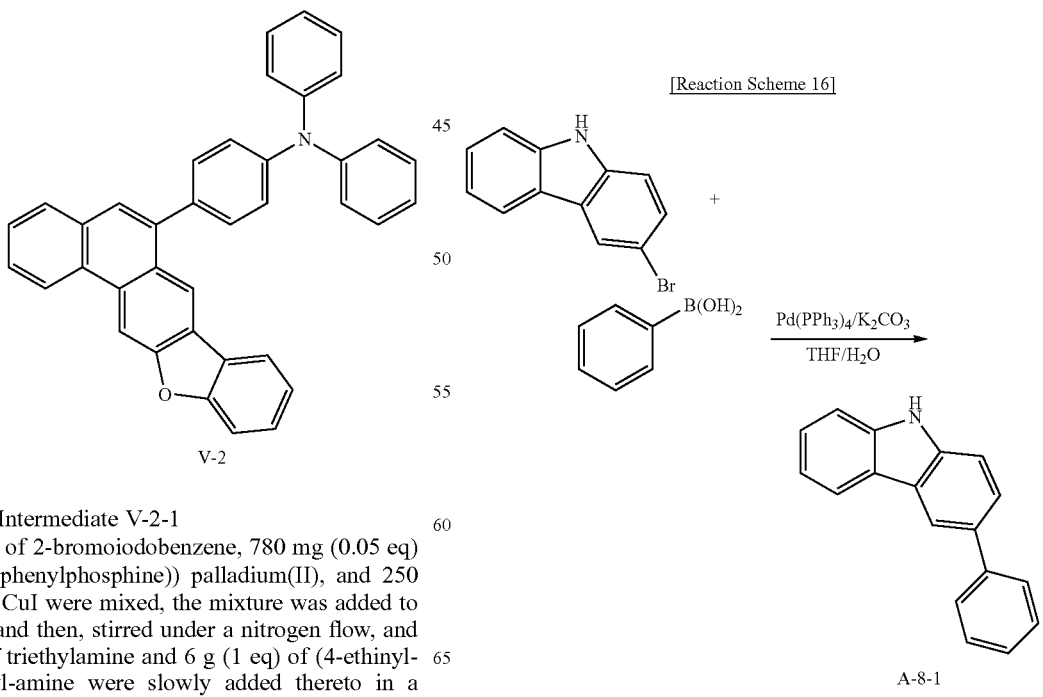

-continued

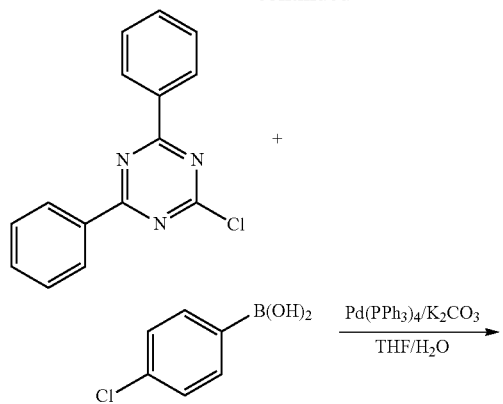

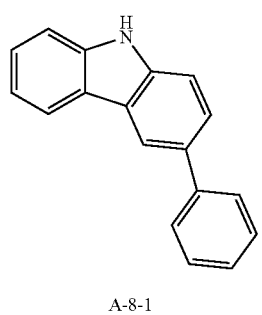

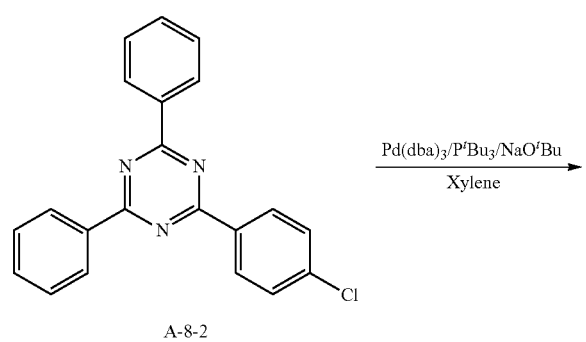

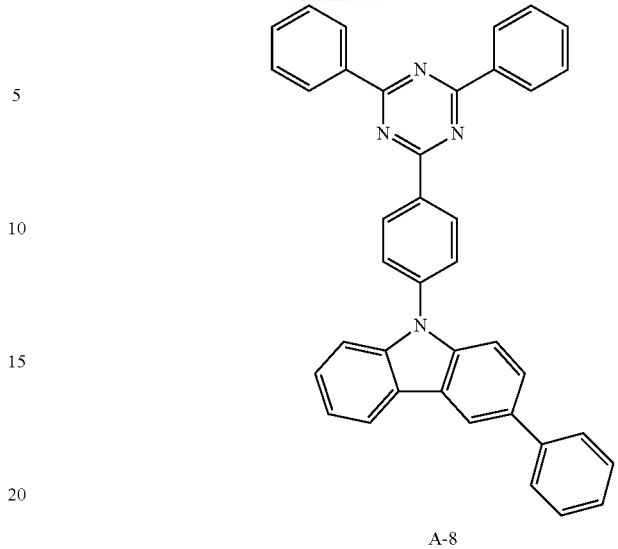

A-8 a) Synthesis of Intermediate A-8-1

3-bromocarbazole (35 g, 142 mmol) was dissolved in 0.5 L of tetrahydrofuran (THF) in a 1 L round-bottomed flask, and then, phenyl boronic acid (17.3 g, 142 mmol) and tetrakis(triphenylphosphine)palladium (8.2 g, 7.1 mmol) were added thereto and then, stirred. Subsequently, potassium carbonate (49.1 g, 356 mmol) saturated in water was added thereto and then, heated and refluxed at 80° C. for 12 hours. When a reaction was complete, water was added to the reaction solution, and the mixture was extracted with dichloromethane (DCM), treated with magnesium sulfate anhydrous to remove moisture therefrom, filtered, and concentrated under a reduced pressure. This obtained residue was separated and purified through flash column chromatography to obtain 22.0 g of Intermediate A-8-1.

b) Synthesis of Intermediate A-8-2

2-chloro-4,6-diphenyl-[1,3,5]triazine (40 g, 149 mmol) was dissolved in 0.5 L of tetrahydrofuran (THF) in a 1 L round-bottomed flask, and 4-chlorophenyl boronic acid (25.7 g, 164 mmol) and tetrakis(triphenylphosphine)palladium (8.63 g, 7.5 mmol) were added thereto and then, stirred. Subsequently, potassium carbonate (51.6 g, 374 mmol) saturated in water was added thereto and then, heated and refluxed at 80° C. for 12 hours. When a reaction was complete, water was added to the reaction solution, and the mixture was extracted with dichloromethane (DCM), treated with magnesium sulfate anhydrous to remove moisture, filtered, and concentrated under a reduced pressure. This obtained residue was separated and purified through flash column chromatography to obtain 32.1 g of Intermediate A-8-2.

c) Synthesis of Compound A-8

Intermediate A-8-1 (22.0 g, 90.4 mmol), Intermediate A-8-2 (31.1 g, 90.4 mmol), sodium t-butoxide (NaOtBu) (13.01 g, 135.6 mmol), Pd$_2$(dba)$_3$ (2.48 g, 2.7 mmol), and tri t-butylphosphine (P(tBu)$_3$) (5.49 g, 50% in toluene) were added to xylene (300 mL) and then, heated and refluxed under a nitrogen flow for 12 hours. After removing the xylene, a solid crystallized by adding 200 mL of methanol to the obtained mixture was filtered, dissolved in monochlorobenzene (MCB), and filtered through silica gel/Celite, and an organic solvent in an appropriate amount was concentrated to obtain Compound A-8 (32 g, 64.3%).

LC/MS calculated for: C39H26N4 Exact Mass: 550.22 found for 550.65 [M+H]

Synthesis Example 15: Synthesis of Compound A-12

[Reaction Scheme 17]

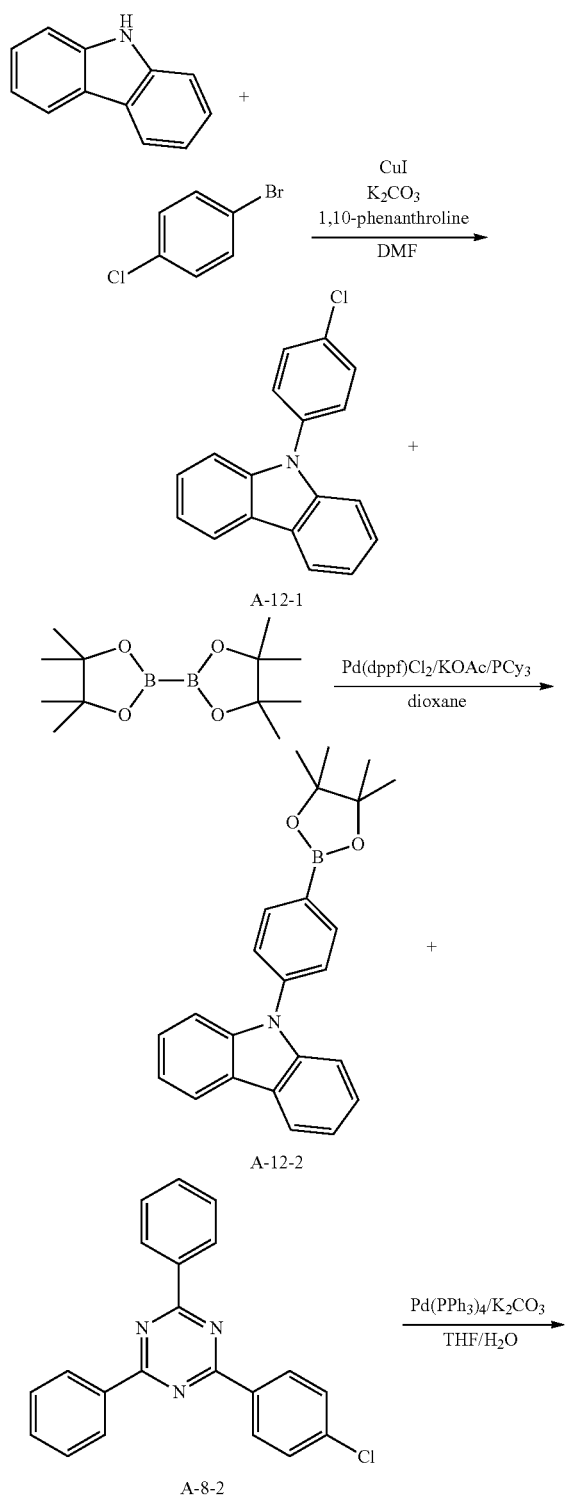

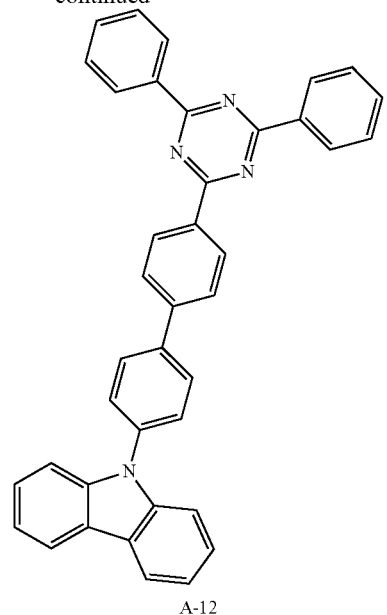

a) Synthesis of Intermediate A-12-1

Carbazole (35 g, 209.3 mmol), 1-bromo-4-chloro-benzene (60.11 g 313.98 mmol), CuI (3.99 g, 20.9 mmol), K₂CO₃ (43.39 g, 313.98 mmol), and 1,10-phenanthroline (3.77 g, 20.9 mmol) were put in a round-bottomed flask and dissolved in 700 ml of DMF. The obtained solution was stirred at 180° C. for 18 hours. When a reaction was complete, the resultant obtained after removing the reaction solvent under a reduced pressure was dissolved in dichloromethane and silica gel-filtered. After concentrating the dichloromethane, a product therefrom was recrystallized with hexane to obtain 40.0 g (68.8%) of Intermediate A-12-1.

b) Synthesis of Intermediate A-12-2

Intermediate A-12-1 (40 g, 144 mmol), bis(pinacolato) diboron (54.86 g, 216 mmol), Pd(dppf)Cl₂ (7.1 g, 8.64 mmol), tricyclohexylphosphine (8.08 g, 28.8 mmol), and potassium acetate (42.4 g, 432.04 mmol) were put in a round-bottomed flask and then, dissolved in 720 ml of dioxane. The mixture was refluxed and stirred at 120° C. for 12 hours. When a reaction was complete, the mixture was poured into an excessive amount of distilled water and then, stirred for 1 hour. A solid therefrom was filtered and dissolved in DCM. After removing moisture with MgSO₄, an organic solvent was filtered by using a silica gel pad and then, removed under a reduced pressure. A solid therefrom was recrystallized with EA and hexane to obtain 31.3 g (58.9%) of Intermediate A-12-2.

c) Synthesis of Compound A-12

Intermediate A-12-2 (31 g, 83.95 mmol) was dissolved in 0.3 L of tetrahydrofuran (THF) in a 1 L round-bottomed flask, and Intermediate A-8-2 (28.86 g, 83.95 mmol) and tetrakis(triphenylphosphine)palladium (4.85 g, 4.2 mmol) were added thereto and then, stirred. Subsequently, potassium carbonate (29.01 g, 209.9 mmol) saturated in water was added thereto at 80° C. for 12 hours and then, heated and refluxed. When a reaction was complete, water was added to the reaction solution and then, stirred for 30 minutes and filtered, and a solid obtained therefrom was dissolved in monochlorobenzene at 133° C., treated with magnesium sulfate anhydrous to remove moisture, and filtered by using silica gel, and a filtrate therefrom was cooled down to room temperature and filtered. The obtained solid was repeatedly purified by using monochlorobenzene to obtain 31.0 g (67.1%) of Compound A-12.

LC/MS calculated for: C39H26N4 Exact Mass: 550.22 found for 550.75 [M+H]

Synthesis Example 16: Synthesis of Compound A-25

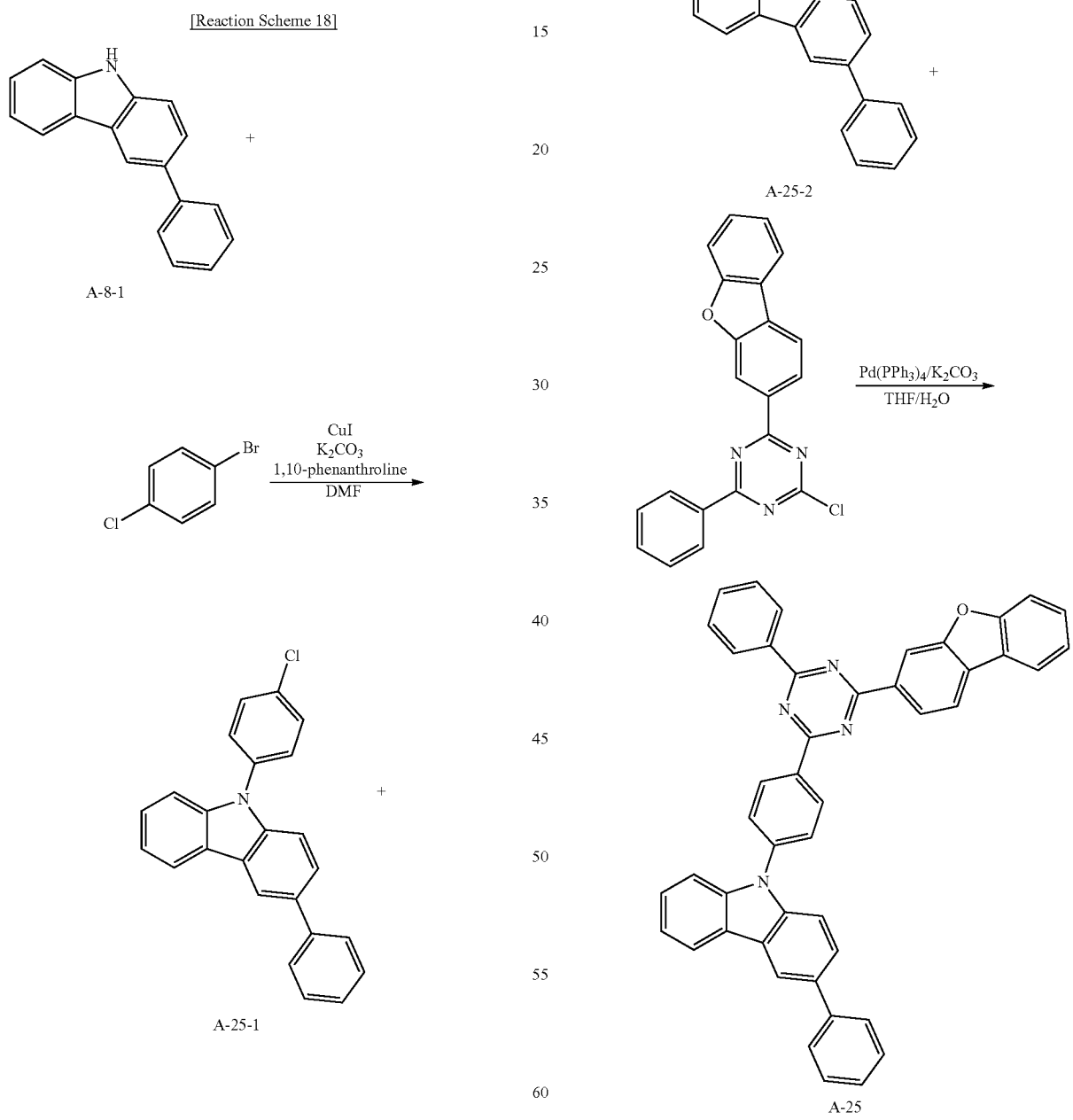

a) Synthesis of Intermediate A-25-1

18 g (56.3%) of Intermediate A-25-1 was synthesized according to the same method as the a) of Synthesis Example 15 by using intermediate A-8-1 (22 g, 90.4 mmol).

b) Synthesis of Intermediate A-25-2

14.8 g (65.3%) of Intermediate A-25-2 was synthesized according to the same method as the b) of Synthesis Example 15 by using intermediate A-25-1 (18 g, 51 mmol).

c) Synthesis of Compound A-25

12.7 g (67.5%) of Compound A-25 was synthesized according to the same method as the c) of Synthesis Example 15 by using Intermediate A-25-2 (10.5 g 29.3 mmol) and 2-chloro-4-dibenzofuran-3-yl-6-phenyl-[1,3,5]triazine (14.38 g, 32.28 mmol).

LC/MS calculated for: C45H28N4O Exact Mass: 640.23 found for 640.73 [M+H]

Synthesis Example 17: Synthesis of Compound B-1

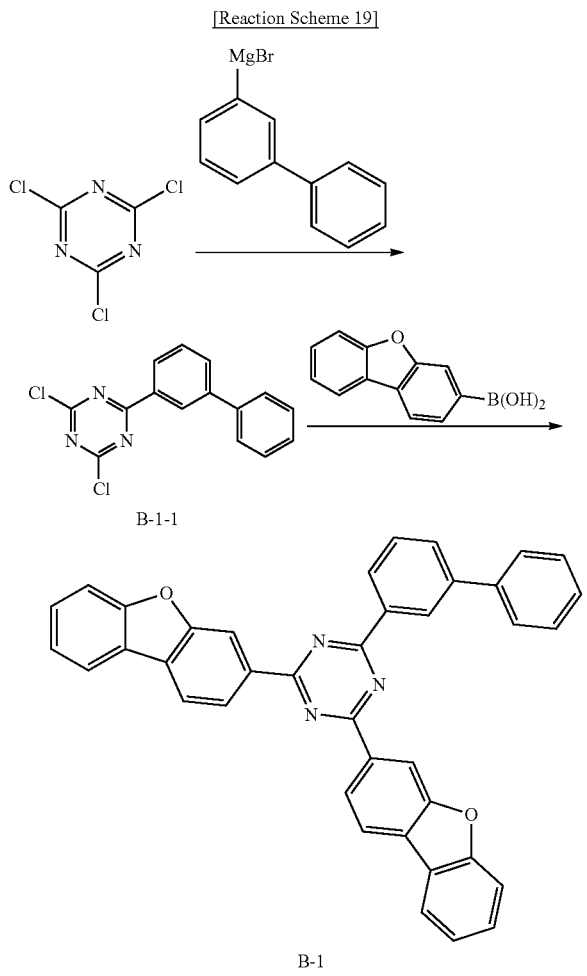

a) Synthesis of Intermediate B-1-1

15 g (81.34 mmol) of cyanuric chloride was dissolved in 200 mL of anhydrous tetrahydrofuran in a 500 mL round-bottomed flask, 1 equivalent of a 3-biphenyl magnesium bromide solution (0.5 M tetrahydrofuran) was added thereto in a dropwise fashion under a nitrogen atmosphere at 0° C. and then, heated up to room temperature. The reaction solution was stirred at room temperature for 1 hour and then, put in 500 mL of ice water to separate layers.

An organic layer was separated therefrom, treated with magnesium sulfate anhydrous, and concentrated. The concentrated residue was recrystallized with tetrahydrofuran and methanol to obtain 17.2 g of Intermediate B-1-1.

b) Synthesis of Compound B-1

17.2 g (56.9 mmol) of Intermediate B-1-1 was added to 200 mL of tetrahydrofuran and 100 mL of distilled water in a 500 mL round-bottomed flask, and 2 equivalent of dibenzofuran-3-boronic acid (cas: 395087-89-5), 0.03 equivalent of tetrakistriphenylphosphine palladium, and 2 equivalent of potassium carbonate were added thereto and then, heated and refluxed under a nitrogen atmosphere. After 18 hours, the reaction solution was cooled down, and a solid precipitated therein was filtered and washed with 500 mL of water. The solid was recrystallized with 500 mL of monochlorobenzene to obtain 12.87 g of Compound B-1.

LC/MS calculated for: C39H23N3O2 Exact Mass: 565.1790 found for: 566.18 [M+H]

Synthesis Example 18: Synthesis of Compound B-3

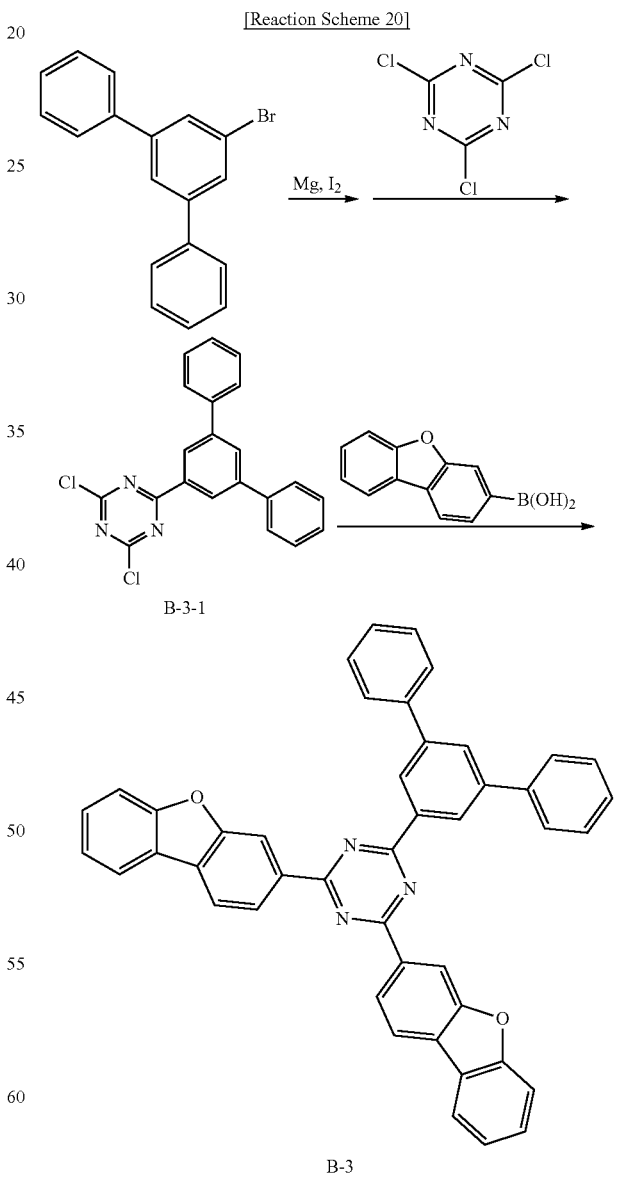

a) Synthesis of Intermediate B-3-1

Magnesium (7.86 g, 323 mmol) and iodine (1.64 g, 6.46 mmol) were added to 0.1 L of tetrahydrofuran (THF) in a nitrogen environment and then, stirred for 30 minutes, and 1-bromo-3,5-diphenylbenzene (100 g, 323 mmol) dissolved in 0.3 L of THF was slowly added thereto in a dropwise fashion at 0° C. for 30 minutes. This obtained mixed solution was slowly added in a dropwise fashion to 64.5 g (350 mmol) of cyanuric chloride dissolved in 0.5 L of THF at 0° C. over 30 minutes. When a reaction was complete, water was added to the reaction solution and then, extracted with dichloromethane (DCM), treated with anhydrous MgSO₄ to remove moisture, filtered, and concentrated under a reduced pressure. This obtained residue was separated and purified through flash column chromatography to obtain Intermediate B-3-1 (79.4 g, 65%).

b) Synthesis of Compound B-3

Compound B-3 was synthesized according to the same method as the b) of Synthesis Example 17 by using Intermediate B-3-1.

LC/MS calculated for: C45H27N3O2 Exact Mass: 641.2103 found for 642.21 [M+H]

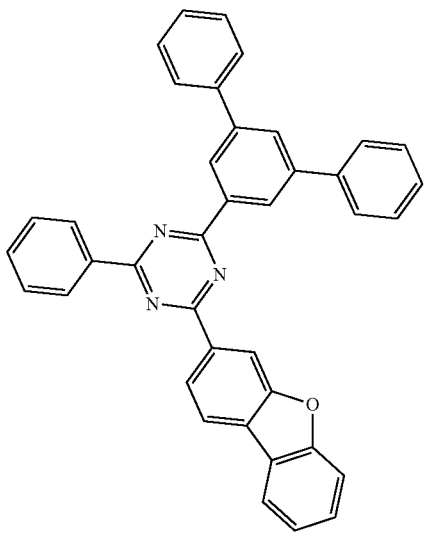

B-17

Synthesis Example 19: Synthesis of Compound B-17

[Reaction Scheme 21]

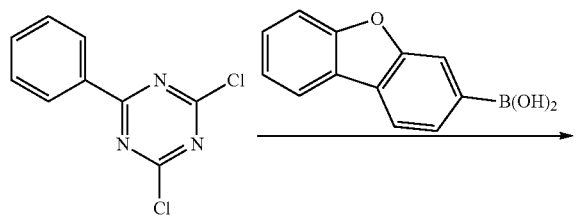

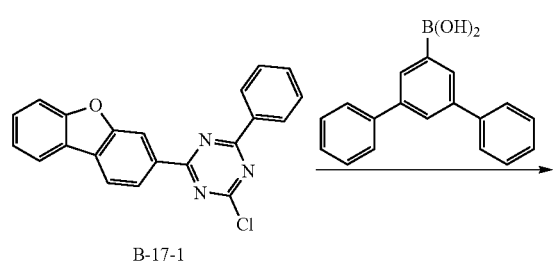

a) Synthesis of Intermediate B-17-1

22.6 g (100 mmol) of 2,4-dichloro-6-phenyltriazine was added to 100 mL of tetrahydrofuran, 100 mL of toluene, and 100 mL of distilled water in a 500 mL round-bottomed flask, and 0.9 equivalent of dibenzofuran-3-boronic acid (CAS No.: 395087-89-5), 0.03 equivalent of tetrakistriphenylphosphine palladium, and 2 equivalent of potassium carbonate were added thereto and then, heated and refluxed under a nitrogen atmosphere. After 6 hours, the reaction solution was cooled down, and after removing an aqueous layer, an organic layer was dried under a reduced pressure. The obtained solid was washed with water and hexane and then, recrystallized with 200 mL of toluene to obtain 21.4 g (Yield of 60%) of Intermediate B-17-1.

b) Synthesis of Compound B-17

Intermediate B-17-1 (56.9 mmol) was added to 200 mL of tetrahydrofuran and 100 mL of distilled water in a 500 mL round-bottomed flask, and 1.1 equivalent of 3,5-diphenylbenzeneboronic acid (CAS No.: 128388-54-5), 0.03 equivalent of tetrakistriphenylphosphine palladium, and 2 equivalent of potassium carbonate were added thereto and then, heated and refluxed under a nitrogen atmosphere. After 18 hours, the reaction solution was cooled down, and a solid precipitated therein was filtered and washed with 500 mL of water. The solid was recrystallized with 500 mL of monochlorobenzene to obtain Compound B-17.

LC/MS calculated for: C39H25N3O Exact Mass: 555.1998 found for 556.21 [M+H]

Synthesis Example 20: Synthesis of Compound B-23

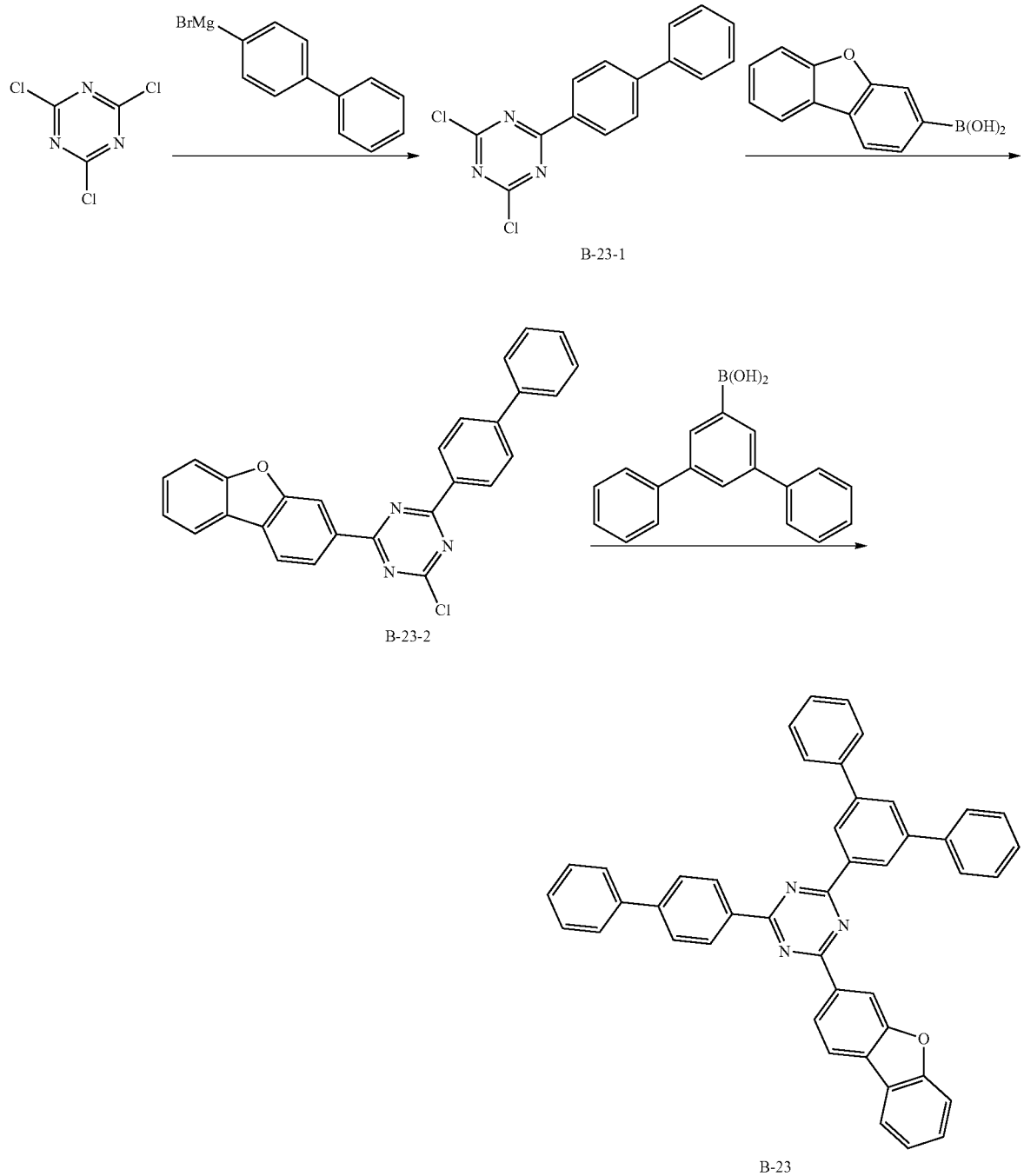

[Reaction Scheme 22]

a) Synthesis of Intermediate B-23-1

15 g (81.34 mmol) of cyanuric chloride was dissolved in 200 mL of anhydrous tetrahydrofuran in a 500 mL round-bottomed flask, 1 equivalent of a 4-biphenyl magnesium bromide solution (0.5 M tetrahydrofuran) was added thereto in a dropwise fashion at 0° C. under a nitrogen atmosphere and then, slowly heated up to room temperature. The reaction solution was stirred at room temperature for 1 hour and put in 500 mL of ice water to separate layers. An organic layer was separated therefrom and then, treated with magnesium sulfate anhydrous and concentrated. The concentrated residue was recrystallized with tetrahydrofuran and methanol to obtain 17.2 g of Intermediate B-23-1.

b) Synthesis of Intermediate B-23-2

Intermediate B-23-2 was synthesized according to the same method as the a) of Synthesis Example 19 by using Intermediate B-23-1.

c) Synthesis of Compound B-23

Compound B-23 was synthesized according to the same method as the b) of Synthesis Example 19 by using Intermediate B-23-2 and 1.1 equivalent of 3,5-diphenylbenzeneboronic acid.

LC/MS calculated for: C45H29N3O Exact Mass: 627.2311 found for 628.24 [M+H]

Synthesis Example 21: Synthesis of Compound B-129

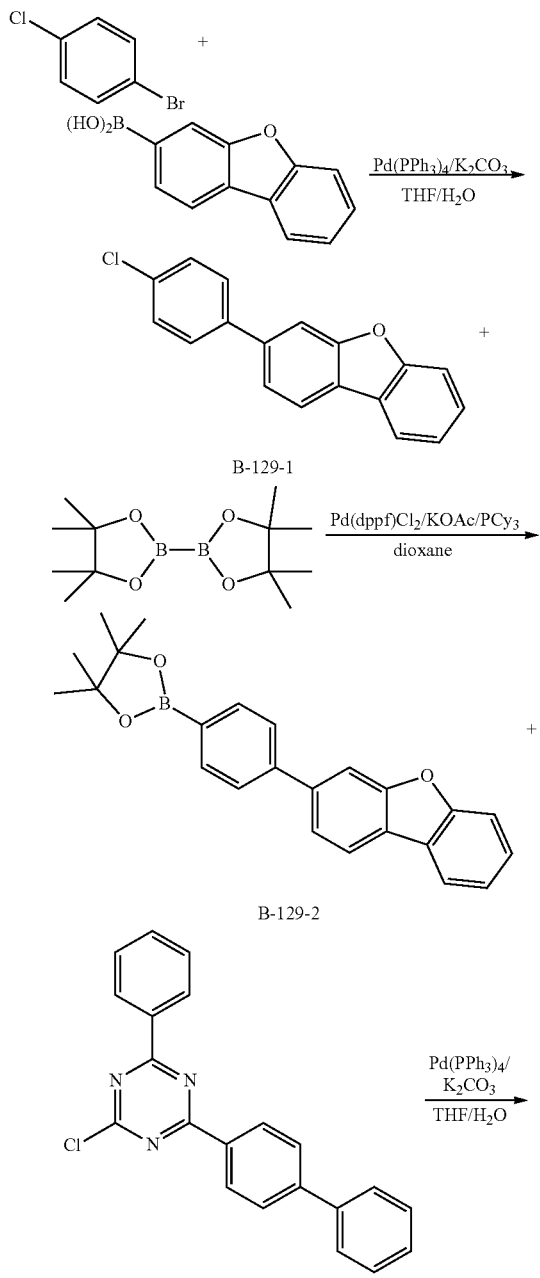

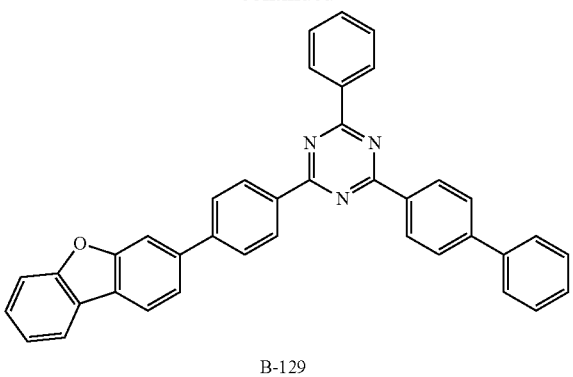

B-129 a) Synthesis of Intermediate B-129-1

Intermediate B-129-1 was synthesized according to the same method as the b) of Synthesis Example 19 by using 1-bromo-4-chloro-benzene and 3-dibenzofuranylboronic acid respectively by 1.0 equivalent.

b) Synthesis of Intermediate B-129-2

Intermediate B-129-2 was synthesized according to the same method as the b) of Synthesis Example 15 by using Intermediate B-129-1 and bispinacolato diboron in an equivalent ratio of 1:1.2.

c) Synthesis of Compound B-129

Compound B-129 was synthesized according to the same method as the b) of Synthesis Example 19 by using intermediate B-129-2 and 2-chloro-4-(biphenyl-4-yl)6-phenyl-1,3,5-triazine respectively by 1.0 equivalent.

LC/MS calculated for: C39H25N3O Exact Mass: 551.20 found for 551.24 [M+H]

Synthesis Example 22: Synthesis of Compound B-133

[Reaction Scheme 24]

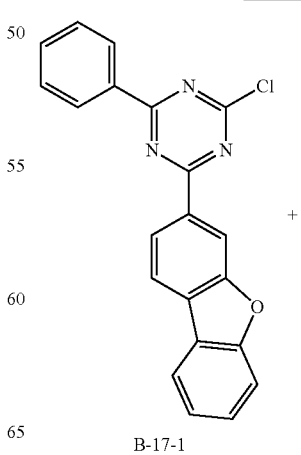

B-17-1

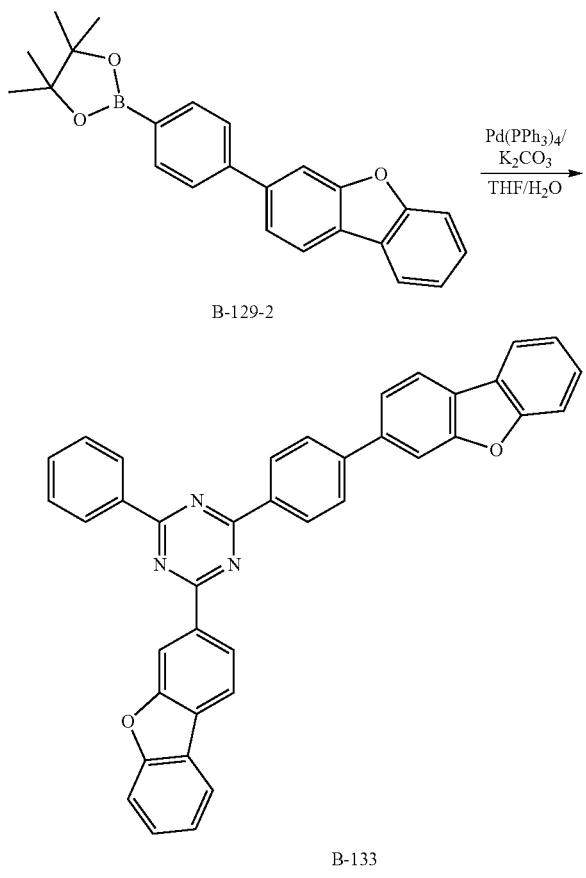

Compound B-133 was synthesized according to the same method as the b) of Synthesis Example 19 by using Intermediate B-17-1 and Intermediate B-129-2.

LC/MS calculated for: C39H23N3O2 Exact Mass: 565.18 found for 565.22 [M+H]

Synthesis Example 23: Synthesis of Compound B-135

[Reaction Scheme 25]

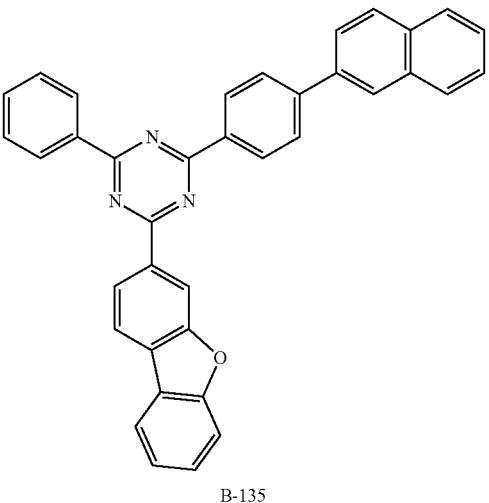

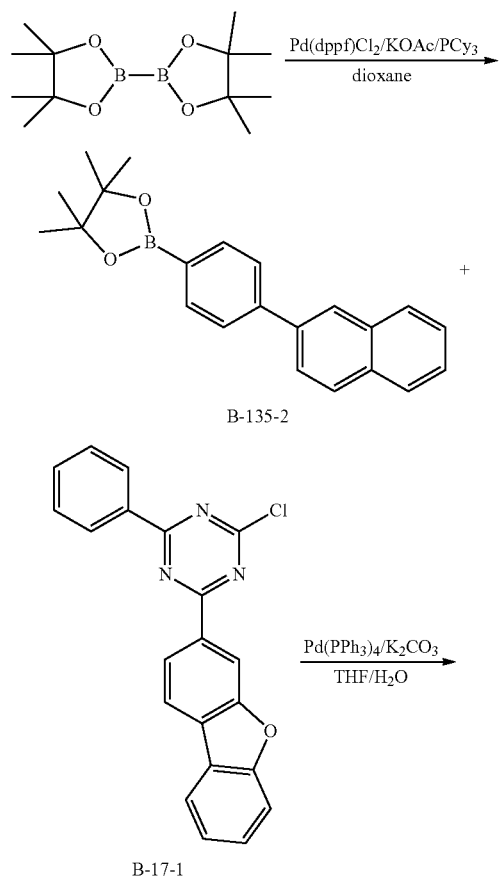

a) Synthesis of Intermediate B-135-1

Intermediate B-135-1 was synthesized according to the same method as the b) of Synthesis Example 19 by using 1-bromo-4-chloro-benzene and 2-naphthalene boronic acid respectively by 1.0 equivalent.

b) Synthesis of Intermediate B-135-2

Intermediate B-135-2 was synthesized according to the same method as the b) of Synthesis Example 19 by using Intermediate B-135-1 and bispinacolato diboron in an equivalent ratio of 1:1.2.

c) Synthesis of Compound B-135

Compound B-135 was synthesized according to the same method as the b) of Synthesis Example 19 by using Intermediate B-135-2 and Intermediate B-17-1 respectively by 1.0 equivalent.

LC/MS calculated for: C37H23N3O Exact Mass: 525.18 found for 525.22 [M+H]

Synthesis Example 24: Synthesis of Compound D-25

[Reaction Scheme 26]

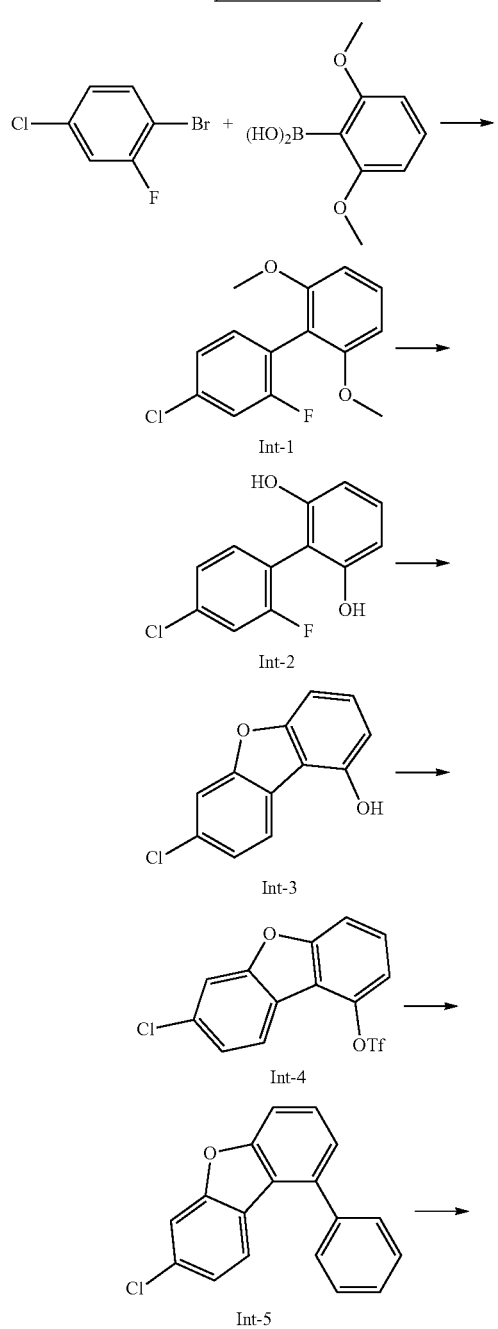

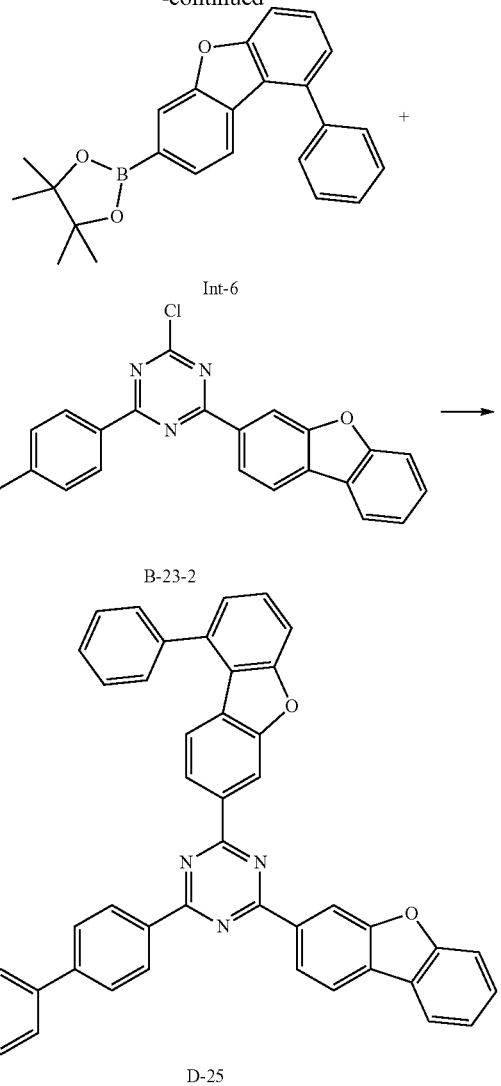

a) Synthesis of Intermediate Int-1

1-bromo-4-chloro-2-fluorobenzene (61 g, 291 mmol), 2,6-dimethoxyphenylboronic acid (50.4 g, 277 mmol), K₂CO₃ (60.4 g, 437 mmol), and Pd(PPh₃)₄ (10.1 g, 8.7 mmol) were put in a round-bottomed flask and dissolved in 500 ml of THF and 200 ml of distilled water and then, refluxed and stirred at 60° C. for 12 hours. When a reaction was complete, an aqueous layer was removed therefrom, and 38 g (51%) of Intermediate Int-1 was obtained through column chromatography (hexane:DCM (20%)).

b) Synthesis of Intermediate Int-2

Intermediate Int-1 (38 g, 142 mmol) and pyridine hydrochloride (165 g, 1425 mmol) were put in a round-bottomed flask and then, refluxed and stirred at 200° C. for 24 hours. When a reaction was complete, the resultant was cooled down to room temperature and slowly poured into distilled water and then, stirred for 1 hour. A solid therein was filtered to obtain 23 g (68%) of Intermediate Int-2.

c) Synthesis of Intermediate Int-3

Intermediate Int-2 (23 g, 96 mmol) and K₂CO₃ (20 g, 144 mmol) were put in a round-bottomed flask and then, dissolved in 100 ml of NMP and then, refluxed and stirred at 180° C. for 12 hours. When a reaction was complete, the mixture was poured into an excessive amount of distilled water. A solid therein was filtered and then, dissolved in ethyl acetate and dried with MgSO4, and an organic layer was removed therefrom under a reduced pressure. 16 g (76%) of Intermediate Int-3 was obtained through column chromatography (hexane:EA (30%)).

d) Synthesis of Intermediate Int-4

Intermediate Int-3 (16 g, 73 mmol) and pyridine (12 ml, 146 mmol) were put in a round-bottomed flask and dissolved in 200 ml of DCM. The temperature was decreased down to 0° C., and trifluoromethanesulfonic anhydride (14.7 ml, 88 mmol) was slowly added thereto in a dropwise fashion. After stirring the mixture for 6 hours, when a reaction was complete, an excessive amount of distilled water was added thereto and then, stirred for 30 minutes and extracted with DCM. After removing an organic solvent under a reduced pressure, 22.5 g (88%) of Intermediate Int-4 was obtained through vacuum-drying.

e) Synthesis of Intermediate Int-5

14.4 g (81%) of Intermediate Int-5 was synthesized according to the same method as the b) of Synthesis Example 19 by using Intermediate Int-4 (22.5 g, 64 mmol), phenylboronic acid (7.8 g, 64 mmol), $K_2CO_3$ (13.3 g, 96 mmol), and $Pd(PPh_3)_4$ (3.7 g, 3.2 mmol).

f) Synthesis of Intermediate Int-6

Intermediate Int-5 (22.5 g, 80 mmol), bis(pinacolato)diboron (24.6 g, 97 mmol), $Pd(dppf)Cl_2$ (2 g, 2.4 mmol), tricyclohexylphosphine (3.9 g, 16 mmol), and potassium acetate (16 g, 161 mmol) were put in a round-bottomed flask and then, dissolved in 320 ml of DMF. The mixture was refluxed and stirred at 120° C. for 10 hours. When a reaction was complete, the mixture was poured into an excessive amount of distilled water and then, stirred for 1 hour. A solid therein was filtered and dissolved in DCM. After removing moisture with $MgSO_4$, an organic solvent was filtered by using a silica gel pad and removed under a reduced pressure. Subsequently, a solid therefrom was recrystallized with EA and hexane to obtain 26.9 g (90%) of Intermediate Int-6.

g) Synthesis of Compound D-25

15.5 g (70%) of Compound D-25 was synthesized according to the same method as the b) of Synthesis Example 19 by using Intermediate B-23-2 (15 g, 35 mmol), Intermediate Int-6 (12.8 g, 35 mmol), $K_2CO_3$ (7.2 g, 52 mmol), and $Pd(PPh_3)_4$ (2 g, 1.7 mmol) in a round-bottomed flask under a nitrogen condition.

LC/MS calculated for: C45H27N3O2 Exact Mass: 641.21 found for 641.25 [M+H]

Synthesis Example 25: Synthesis of Compound D-3

[Reaction Scheme 27]

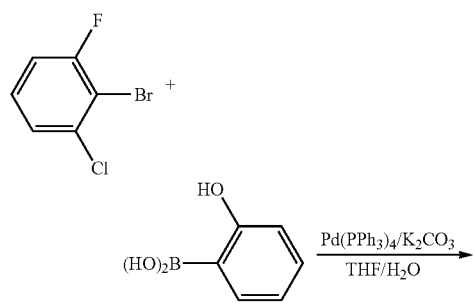

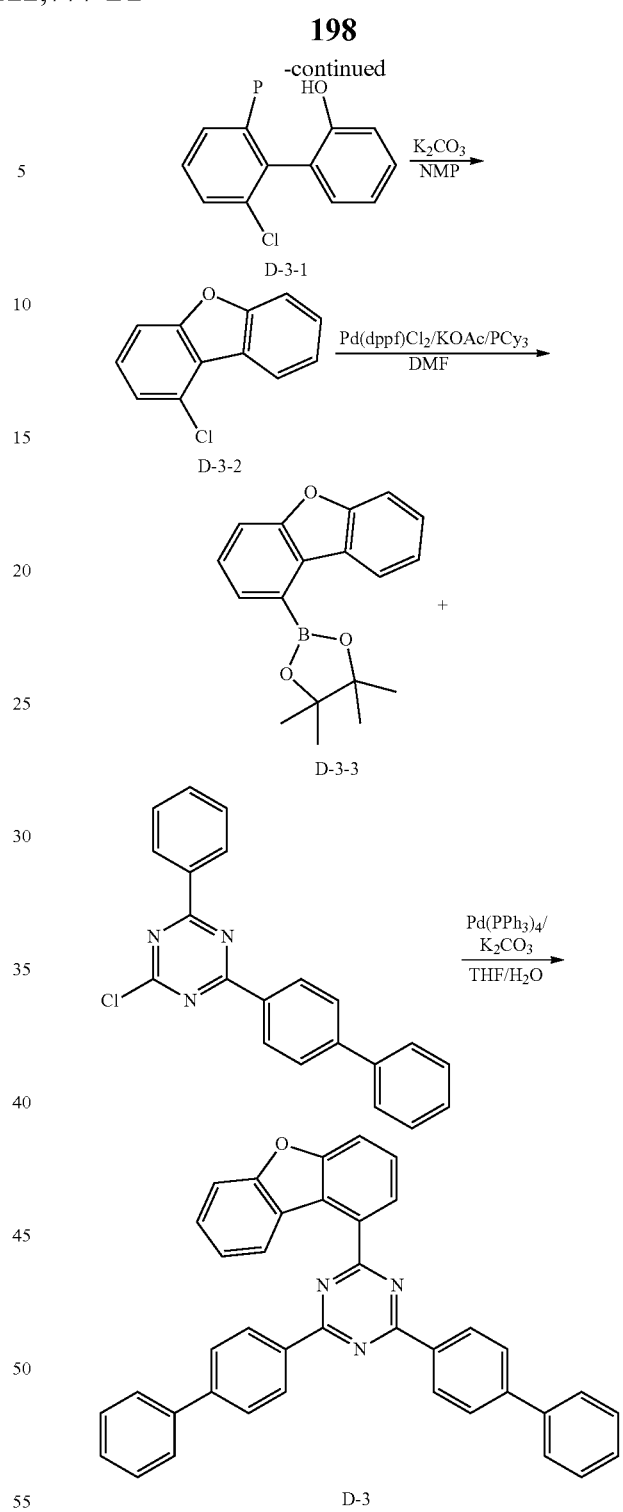

a) Synthesis of Intermediate D-3-1

Intermediate D-3-1 was synthesized according to the same method as the a) of Synthesis Example 24 by using 2-bromo-1-chloro-3-fluoro-benzene and 2-hydroxyphenyl-boronic acid respectively by 1.0 equivalent.

b) Synthesis of Intermediate D-3-2

Intermediate D-3-2 was synthesized according to the same method as the c) of Synthesis Example 24 by using Intermediate D-3-1 and $K_2CO_3$ in an equivalent ratio of 1:1.5.

c) Synthesis of Intermediate D-3-3

Intermediate D-3-3 was synthesized according to the same method as the f) of Synthesis Example 24 by using Intermediate D-3-2 and bis(pinacolato)diboron in an equivalent ratio of 1:1.2.

d) Synthesis of Compound D-3

Compound D-3 was synthesized according to the same method as the b) of Synthesis Example 19 by using Intermediate D-3-3 and 2,4-bis([1,1'-biphenyl]-4-yl)-6-chloro-1,3,5-triazine respectively by 1.0 equivalent.

LC/MS calculated for: C39H25N3O Exact Mass: 551.20 found for 551.24 [M+H]

Synthesis Examples 26 to 29

Compounds E-31, E-33, E-35, and E-37 were synthesized, respectively, using the following starting material 1 and starting material 2 with reference to the synthesis methods disclosed in Korean Patent Application Laid-Open No. 10-2014-0135524.

TABLE 1

| Synthesis Example | Starting material 1 | Starting material 2 | Product | Yield |
|---|---|---|---|---|
| 26 | | | E-31 | 78% |
| 27 | | | E-33 | 79% |
| 28 | | | E-35 | 81% |
| 29 | | | E-37 | 85% |

Manufacture of Organic Light Emitting Diode I

Example 1

The glass substrate coated with ITO (Indium tin oxide) at a thickness of 1500 Å was washed with distilled water and ultrasonic waves. After washing with the distilled water, the glass substrate was washed with a solvent such as isopropyl alcohol, acetone, methanol, and the like ultrasonically and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, and Compound B was deposited to be 50 Å-thick on the injection layer, and then Compound C was deposited to be 700 Å-thick to form a hole transport layer. On the hole transport layer, 400 Å-thick hole transport auxiliary layer was formed by depositing Compound H-1. On the hole transport layer, 400 Å-thick light emitting layer was formed by using Compound E as a host and doping 2 wt % of [Ir(piq)$_2$acac] as a dopant by a vacuum-deposition. Subsequently, on the light emitting layer, a 300 Å-thick electron transport layer was formed by simultaneously vacuum-depositing Compound D and Liq in a ratio of 1:1, and on the electron transport layer, Liq and Al were sequentially vacuum-deposited to be 15 Å-thick and 1,200 Å-thick, manufacturing an organic light emitting diode.

The organic light emitting diode had a five-layered organic thin layer, and specifically the following structure.
ITO/Compound A (700 Å)/Compound B (50 Å)/Compound C (700 Å)/Compound H-1 (400 Å)/EML [Compound E: [Ir(piq)$_2$acac] (2 wt %)] (400 Å)/Compound D: Liq (300 Å)/Liq (15 Å)/Al (1200 Å).
Compound A: N4,N4'-diphenyl-N4,N4'-bis(9-phenyl-9H-carbazol-3-yl)biphenyl-4,4'-diamine
Compound B: 1,4,5,8,9,11-hexaazatriphenylene-hexacarbonitrile (HAT-CN),
Compound C: N-(biphenyl-4-yl)-9,9-dimethyl-N-(4-(9-phenyl-9H-carbazol-3-yl)phenyl)-9H-fluoren-2-amine
Compound D: 8-(4-(4,6-di(naphthalen-2-yl)-1,3,5-triazin-2-yl)phenyl)quinoline
Compound E: 9-phenyl-9'-(4-phenylquinazolin-2-yl)-9H,9'H-3,3'-bicarbazole

Examples 2 to 6 and Comparative Examples 1 and 2

As shown in Table 2, the devices of Examples 2 to 6 and Comparative Examples 1 and 2 were manufactured in the same manner as in Example 1 using the hole transport auxiliary layer of the present invention.

Manufacture of Organic Light Emitting Diode II

Example 7

The glass substrate coated with ITO (Indium tin oxide) at a thickness of 1500 Å was washed with distilled water and ultrasonic waves. After washing with the distilled water, the glass substrate was washed with a solvent such as isopropyl alcohol, acetone, methanol, and the like ultrasonically and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, and Compound B was deposited to be 50 Å-thick on the injection layer, and then Compound C was deposited to be 700 Å-thick to form a hole transport layer. On the hole transport layer, 400 Å-thick hole transport auxiliary layer was formed by depositing Compound C-1. On the hole transport layer, 400 Å-thick light emitting layer was formed by using Compound H-1 and Compound E-35 simultaneously as a host and doping 2 wt % of [Ir(piq)$_2$acac] as a dopant by a vacuum-deposition. Herein, Compound H-1 and Compound E-35 were used in a weight ratio of 7:3, and the ratio was separately described in the case of the following examples. Subsequently, on the light emitting layer, a 300 Å-thick electron transport layer was formed by simultaneously vacuum-depositing Compound D and Liq in a ratio of 1:1, and on the electron transport layer, Liq and Al were sequentially vacuum-deposited to be 15 Å-thick and 1,200 Å-thick, producing an organic light emitting diode.

The organic light emitting diode had a five-layered organic thin layer, and specifically the following structure.
ITO/Compound A (700 Å)/Compound B (50 Å)/Compound (700 Å)/Compound C-1 (400 Å)/EML [Compound H-1: E-35: [Ir(piq)$_2$acac] (2 wt %)] (400 Å)/Compound D: Liq (300 Å)/Liq (15 Å)/Al (1200 Å).
Compound C-1: N,N-di([1,1'-biphenyl]-4-yl)-7,7-dimethyl-7H-fluoreno[4,3-b]benzofuran-10-amine

Example 8 to Example 18, Reference Example 1 and Reference Example 2

Each organic light emitting diode was manufactured in the same manner as in Example 7 except that the composition was changed to the composition shown in Table 3.
Evaluation The power efficiency of the organic light emitting diodes according to Examples 1 to 18, Comparative Examples 1 and 2, and Reference Examples 1 and 2 was evaluated.

Specific measurement methods are as follows, and the results are shown in Tables 2 and 3.
(1) Measurement of Current Density Change Depending on Voltage Change The obtained organic light emitting diodes were measured regarding a current value flowing in the unit device, while increasing the voltage from 0 V to 10 V using a current-voltage meter (Keithley 2400), and the measured current value was divided by area to provide the results.
(2) Measurement of Luminance Change Depending on Voltage Change Luminance was measured by using a luminance meter (Minolta Cs-1000A), while the voltage of the organic light emitting diodes was increased from 0 V to 10 V.
(3) Measurement of Luminous Efficiency Power efficiency (lm/W) at the same current density (10 mA/cm$^2$) were calculated by using the luminance and current density from the items (1) and (2).
(4) Measurement of Life-Span T97 life-spans of the organic light emitting diodes of Example 1 to Example 18, Comparative Example 1, Comparative Example 2, Reference Example 1, and Reference Example 2 were measured as a time when their luminance decreased down to 97% relative to the initial luminance (cd/m$^2$) after emitting light with the initial luminance of 6000 cd/m$^2$ and measuring their luminance decrease depending on time with a Polanonix life-span measurement system.

TABLE 2

| | Hole transport auxiliary layer | Color | Life-span T97(h) |
|---|---|---|---|
| Example 1 | H-1 | red | 80 |
| Example 2 | H-7 | red | 75 |
| Example 3 | H-23 | red | 115 |
| Example 4 | H-42 | red | 125 |
| Example 5 | H-43 | red | 132 |
| Example 6 | H-75 | red | 121 |
| Comparative Example 1 | V-1 | red | 35 |
| Comparative Example 2 | V-2 | red | 15 |

TABLE 3

| | Host | First host+ | | | Life-span |
|---|---|---|---|---|---|
| | First host | Second host | Second host ratio | Color | Efficiency (cd/A) | T97 (h) |
| Example 7 | H-1 | E-35 | 7:3 | red | 19.8 | 75 |
| Example 8 | H-23 | E-35 | 7:3 | red | 19.7 | 70 |
| Example 9 | H-42 | E-35 | 7:3 | red | 21.0 | 105 |
| Example 10 | H-42 | E-35 | 6:4 | red | 19.5 | 95 |
| Example 11 | H-42 | B-133 | 7:3 | red | 21.5 | 120 |
| Example 12 | H-42 | B-135 | 7:3 | red | 22.1 | 125 |
| Example 13 | H-42 | A-25 | 7:3 | red | 21.2 | 85 |
| Example 14 | H-42 | B-23 | 7:3 | red | 21.0 | 88 |
| Example 15 | H-42 | D-3 | 7:3 | red | 21.4 | 104 |
| Example 16 | H-43 | E-35 | 7:3 | red | 22.0 | 107 |
| Example 17 | H-43 | B-135 | 7:3 | red | 22.2 | 110 |
| Example 18 | H-75 | E-35 | 7:3 | red | 21.5 | 110 |
| Reference Example 1 | V-1 | E-35 | 7:3 | red | 18.7 | 25 |
| Reference Example 2 | V-2 | E-35 | 7:3 | red | 17.5 | 12 |

Referring to Table 2, the life-span of the organic light emitting diodes according to Examples 1 to 6 was significantly improved compared with the organic light emitting diodes according to Comparative Examples 1 and 2.

In addition, referring to Table 3, the organic light emitting diodes according to Examples 7 to 18 have greatly improved efficiency and lifetime compared to the organic light emitting diodes according to Reference Examples 1 and 2.

While this invention has been described in connection with what is presently considered to be practical embodiments, it is to be understood that the invention is not limited to the disclosed embodiments, but, on the contrary, is intended to cover various modifications and equivalent arrangements included within the spirit and scope of the appended claims.

The invention claimed is:

1. A composition for an organic optoelectronic device, the composition comprising
a first compound for an organic optoelectronic device represented by Chemical Formula 1, and
a second compound for organic optoelectronic device represented by Chemical Formula 2:

[Chemical Formula 1]

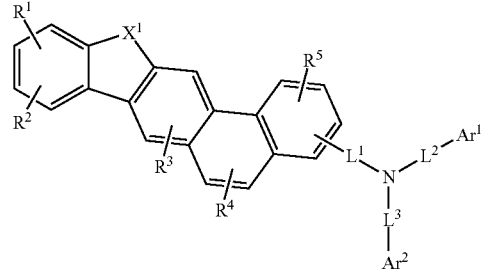

wherein, in Chemical Formula 1, $X^1$ is O or S, $L^1$ to $L^3$ are independently a single bond, a substituted or unsubstituted C6 to C30 arylene group, a substituted or unsubstituted C2 to C20 heterocyclic group, or a combination thereof, $R^1$ to $R^5$ are independently hydrogen, deuterium, a cyano group, a substituted or unsubstituted C1 to C30 alkyl group, a substituted or unsubstituted C6 to C30 aryl group, or a combination thereof, $Ar^1$ and $Ar^2$ are independently a substituted or unsubstituted C6 to C30 aryl group, a substituted or unsubstituted C2 to C30 heterocyclic group, a substituted or unsubstituted C6 to C30 arylamine group, or a combination thereof,

[Chemical Formula 2]

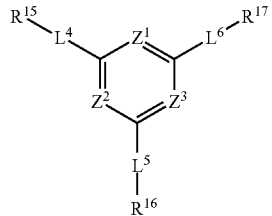

wherein, in Chemical Formula 2, $Z^1$ to $Z^3$ are independently N or $C-L^a-R^c$, at least two of $Z^1$ to $Z^3$ are N, $L^a$ and $L^4$ to $L^6$ are independently a single bond, a substituted or unsubstituted C6 to C30 arylene group, a substituted or unsubstituted C2 to C30 heterocyclic group, or a combination thereof, $R^c$ and $R^{15}$ to $R^{17}$ are independently hydrogen, deuterium, a cyano group, a substituted or unsubstituted C1 to C30 alkyl group, a substituted or unsubstituted C6 to C30 aryl group, a substituted or unsubstituted C2 to C30 heterocyclic group, or a combination thereof, at least one of $R^{15}$ to $R^{17}$ is a substituted or unsubstituted carbazolyl group, a substituted or unsubstituted dibenzofuranyl group, a substituted or unsubstituted dibenzothiophenyl group, or a substituted or unsubstituted triphenylene group.

2. The composition of claim 1, wherein
Chemical Formula 1 is represented by one of Chemical Formulas 1-1 to 1-4:

[Chemical Formula 1-1]

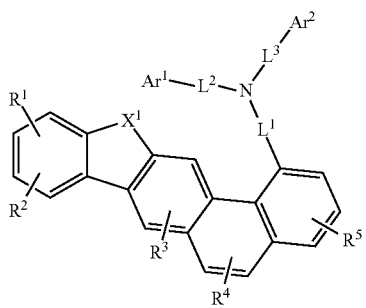

[Chemical Formula 1-2]

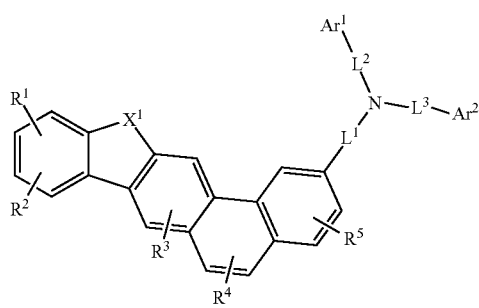

[Chemical Formula 1-3]

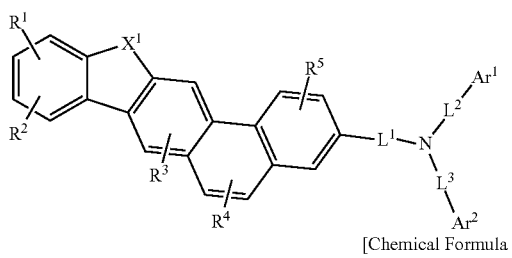

[Chemical Formula 1-4]

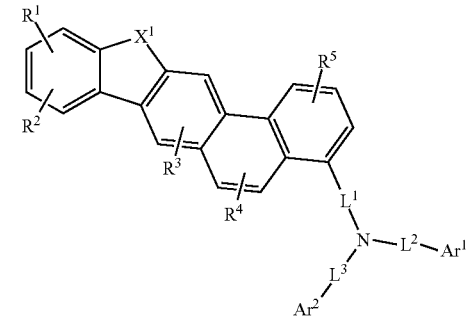

wherein, in Chemical Formulas 1-1 to 1-4,
$X^1$ is O or S,
$L^1$ to $L^3$ are independently a single bond, a substituted or unsubstituted C6 to C30 arylene group, a substituted or unsubstituted C2 to C20 heterocyclic group, or a combination thereof,
$R^1$ to $R^5$ are independently hydrogen, deuterium, a cyano group, a substituted or unsubstituted C1 to C30 alkyl group, a substituted or unsubstituted C6 to C30 aryl group, or a combination thereof, and
$Ar^1$ and $Ar^2$ are independently a substituted or unsubstituted C6 to C30 aryl group, a substituted or unsubstituted C2 to C30 heterocyclic group, a substituted or unsubstituted C6 to C30 arylamine group, or a combination thereof.

3. The composition of claim 1, wherein $Ar^1$ and $Ar^2$ are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted fluorenyl group, a substituted or unsubstituted carbazolyl group, a substituted or unsubstituted dibenzofuranyl group, a substituted or unsubstituted dibenzothiophenyl group, or a substituted or unsubstituted C6 to C30 arylamine group.

4. The composition of claim 1, wherein Chemical Formula 1 is represented by one of Chemical Formulas 1a to 1d:

[Chemical Formula 1a]

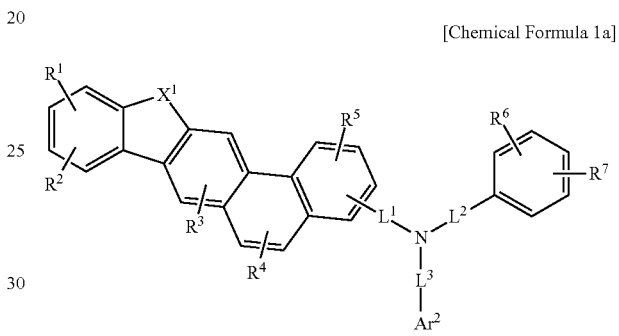

[Chemical Formula 1b]

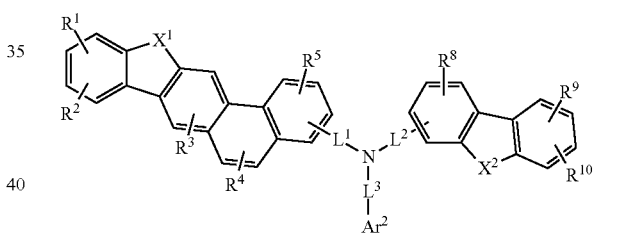

[Chemical Formula 1c]

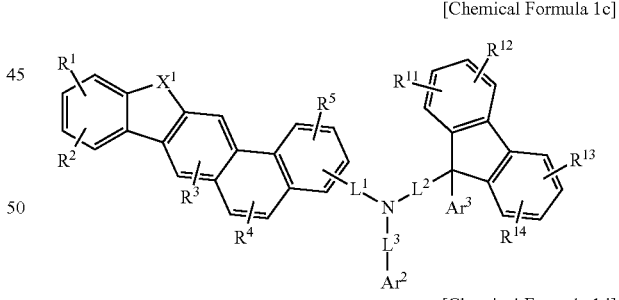

[Chemical Formula 1d]

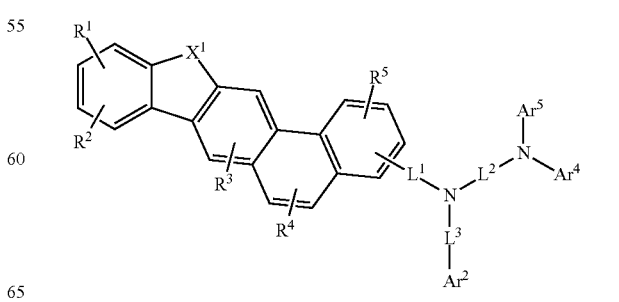

wherein, in Chemical Formulas 1a to 1d,
$X^1$ is O or S,
$X^2$ is O, S, $CR^bR^c$, or $NR^d$,
$L^1$ to $L^3$ are independently a single bond, a substituted or unsubstituted C6 to C30 arylene group, a substituted or unsubstituted C2 to C20 heterocyclic group, or a combination thereof,
$R^b$, $R^c$, $R^d$, and $R^1$ to $R^{14}$ are independently hydrogen, deuterium, a cyano group, a substituted or unsubstituted C1 to C30 alkyl group, a substituted or unsubstituted C6 to C30 aryl group, or a combination thereof,
$Ar^2$ to $Ar^5$ are independently a substituted or unsubstituted C6 to C30 aryl group, a substituted or unsubstituted dibenzofuranyl group, or a substituted or unsubstituted dibenzothiophenyl group, and
$Ar^4$ and $Ar^5$ are independently present or linked to each other to form a substituted or unsubstituted heteroaromatic polycyclic ring.

5. The composition of claim 1, wherein
$Ar^2$ of Chemical Formula 1a to Chemical Formula 1c is a substituted or unsubstituted phenyl group, a substituted or unsubstituted biphenyl group, a substituted or unsubstituted naphthyl group, or a substituted or unsubstituted fluorenyl group,
$Ar^3$ to $Ar^5$ of Chemical Formula 1c and Chemical Formula 1d are independently a substituted or unsubstituted phenyl group, or a substituted or unsubstituted biphenyl group, and
$Ar^2$ of Chemical Formula 1d is a substituted or unsubstituted phenyl group, a substituted or unsubstituted biphenyl group, a substituted or unsubstituted naphthyl group, a substituted or unsubstituted fluorenyl group, a substituted or unsubstituted dibenzofuranyl group, or a substituted or unsubstituted dibenzothiophenyl group.

6. The composition of claim 1, wherein
$Ar^1$ and $Ar^2$ are independently selected from the groups of Group I:

[Group I]

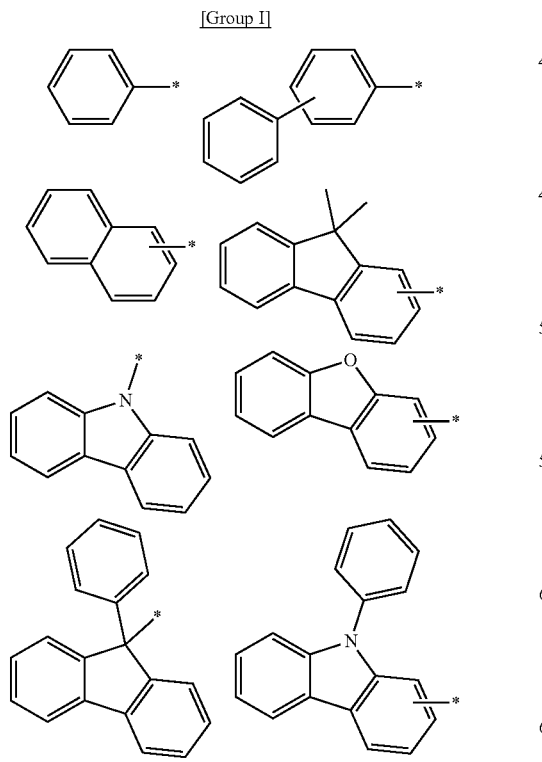

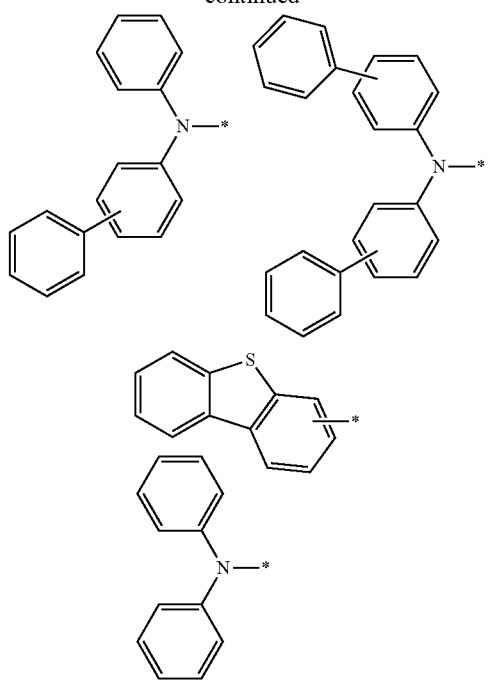

wherein, in Group I, * is a linking point.

7. The composition of claim 1, wherein Chemical Formula 2 is represented by one of Chemical Formula 2-1 to Chemical Formula 2-3:

[Chemical Formula 2-1]

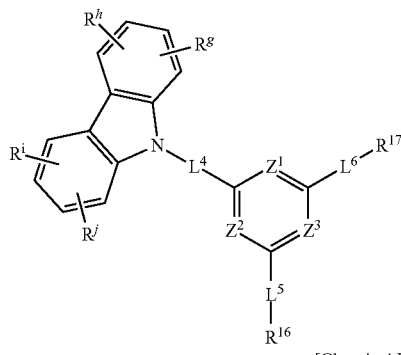

[Chemical Formula 2-2]

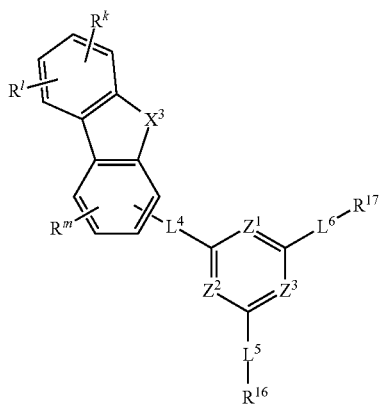

-continued

[Chemical Formula 2-3]

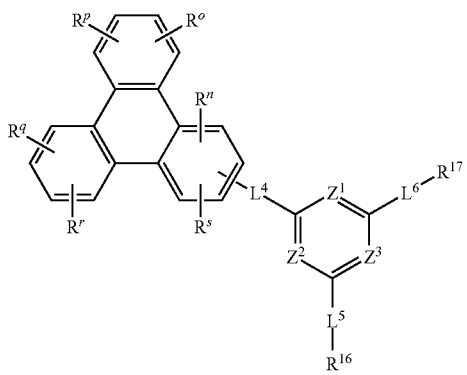

wherein, in Chemical Formula 2-1 to Chemical Formula 2-3,
$Z^1$ to $Z^3$ are independently N or C-$L^a$-$R^e$,
at least two of $Z^1$ to $Z^3$ are N,
$X^3$ is O, S, or NR,
$L^a$ and $L^4$ to $L^6$ are independently a single bond, a substituted or unsubstituted C6 to C30 arylene group, a substituted or unsubstituted C2 to C30 heterocyclic group, or a combination thereof, and
$R^e$, $R^f$, $R^g$, $R^h$, $R^i$, $R^j$, $R^k$, $R^l$, $R^m$, $R^n$, $R^o$, $R^p$, $R^q$, $R^r$, $R^s$, $R^{16}$, and $R^{17}$ are independently hydrogen, deuterium, a cyano group, a substituted or unsubstituted C1 to C30 alkyl group, a substituted or unsubstituted C6 to C30 aryl group, a substituted or unsubstituted C2 to C30 heterocyclic group, or a combination thereof.

8. The composition of claim 7, wherein $R^{16}$ and $R^{17}$ are independently a substituted or unsubstituted phenyl group, a substituted or unsubstituted biphenyl group, a substituted or unsubstituted naphthyl group, a substituted or unsubstituted terphenyl group, a substituted or unsubstituted quaterphenyl group, a substituted or unsubstituted triphenylenyl group, a substituted or unsubstituted fluorenyl group, a substituted or unsubstituted pyridinyl group, a substituted or unsubstituted pyrimidinyl group, a substituted or unsubstituted triazinyl group, a substituted or unsubstituted carbazolyl group, a substituted or unsubstituted dibenzofuranyl group, a substituted or unsubstituted dibenzothiphenyl group, or a combination thereof.

9. The composition of claim 1, wherein
the first compound for an organic optoelectronic device is represented by Chemical Formula 1-3, and
the second compound for organic optoelectronic device is represented by Chemical Formula 2-1 or Chemical Formula 2-2:

[Chemical Formula 1-3]

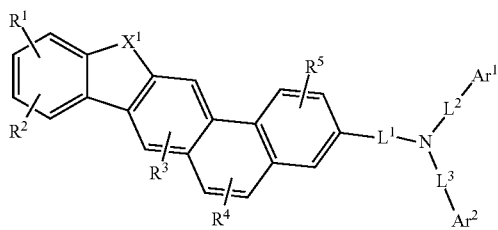

wherein, in Chemical Formula 1-3,
$X^1$ is O or S,
$L^1$ to $L^3$ are independently a single bond or a substituted or unsubstituted C6 to C30 arylene group,
$R^1$ to $R^5$ are independently hydrogen, deuterium, a cyano group, a substituted or unsubstituted C1 to C10 alkyl group, or a substituted or unsubstituted C6 to C20 aryl group, and
$Ar^1$ and $Ar^2$ are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted fluorenyl group, a substituted or unsubstituted carbazolyl group, a substituted or unsubstituted dibenzofuranyl group, a substituted or unsubstituted dibenzothiophenyl group, or a substituted or unsubstituted C6 to C30 arylamine group;

[Chemical Formula 2-1]

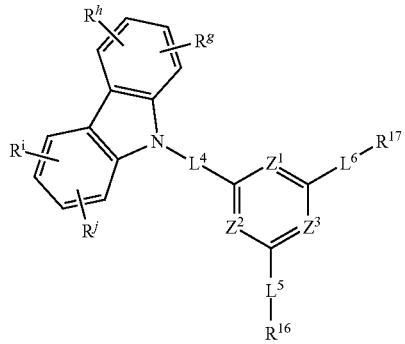

[Chemical Formula 2-2]

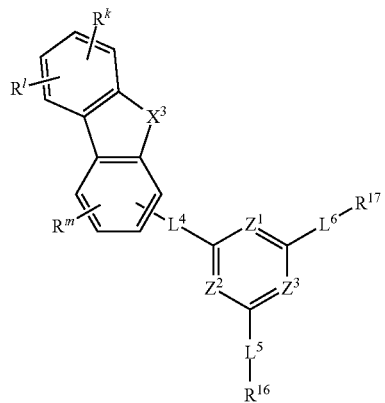

wherein, in Chemical Formula 2-1 and Chemical Formula 2-2,
$Z^1$ to $Z^3$ are each nitrogen (N),
$X^3$ is O, S, or NR,
$L^4$ to $L^6$ are independently a single bond or a substituted or unsubstituted C6 to C20 arylene group,
$R^{16}$ and $R^{17}$ are independently a substituted or unsubstituted phenyl group, a substituted or unsubstituted biphenyl group, a substituted or unsubstituted naphthyl group, a substituted or unsubstituted terphenyl group, a substituted or unsubstituted anthracenyl group, a substituted or unsubstituted phenanthrenyl group, a substituted or unsubstituted quaterphenyl group, a substituted or unsubstituted triphenylenyl group, a substituted or unsubstituted fluorenyl group, a substituted or unsubstituted pyridinyl group, a substituted or unsubstituted pyrimidinyl group, a substituted or unsubstituted triazinyl group, a substituted or unsubstituted carbazolyl group, a substituted or unsubstituted dibenzofuranyl group, a substituted or unsubstituted dibenzothiophenyl group, or a combination thereof, $R^f$, $R^g$, $R^h$, $R^i$, $R^j$, $R^k$, $R^l$, and $R^m$ are independently hydrogen, a cyano group, a substituted or unsubstituted C1 to C10 alkyl group, or a substituted or unsubstituted C6 to C12 aryl group.

10. The composition of claim 1, wherein the first compound for an organic optoelectronic device is represented by Chemical Formula 1a or Chemical Formula 1d, and the second compound for organic optoelectronic device is represented by Chemical Formula 2-1 or Chemical Formula 2-2:

[Chemical Formula 1a]

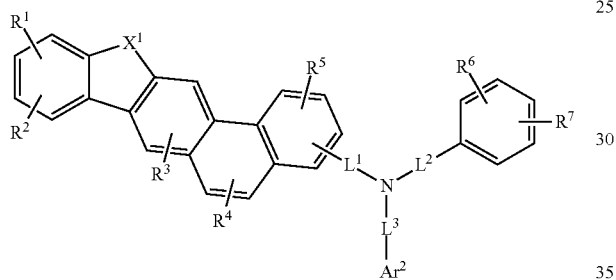

[Chemical Formula 1d]

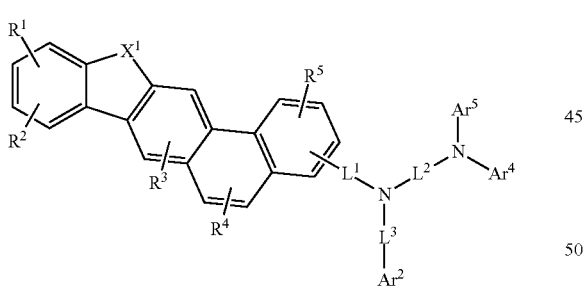

wherein, in Chemical Formula 1a and Chemical Formula 1d, $X^1$ is O or S, $L^1$ to $L^3$ are independently a single bond or a substituted or unsubstituted C6 to C30 arylene group, $R^1$ to $R^7$ are independently hydrogen, deuterium, a cyano group, a substituted or unsubstituted C1 to C10 alkyl group, or a substituted or unsubstituted C6 to C20 aryl group, and $Ar^2$, $Ar^4$ and $Ar^5$ are independently a substituted or unsubstituted C6 to C30 aryl group, a substituted or unsubstituted dibenzofuranyl group, or a substituted or unsubstituted dibenzothiophenyl group;

[Chemical Formula 2-1]

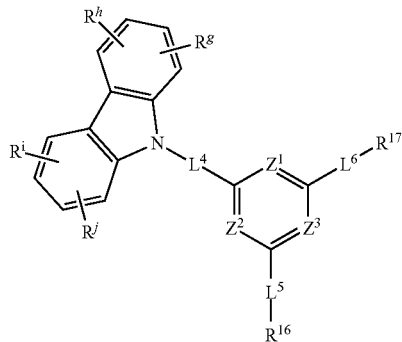

[Chemical Formula 2-2]

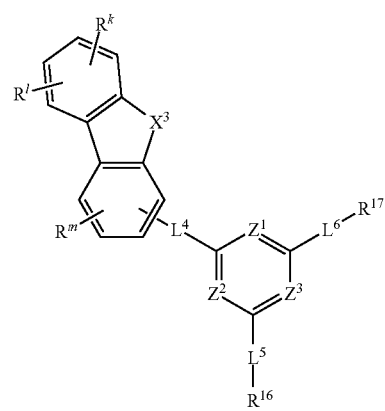

wherein, in Chemical Formula 2-1 and Chemical Formula 2-2, $Z^1$ to $Z^3$ are each nitrogen (N), $X^3$ is O, S, or NR, $L^4$ to $L^6$ are independently a single bond or a substituted or unsubstituted C6 to C20 arylene group, $R^{16}$ and $R^{17}$ are independently a substituted or unsubstituted phenyl group, a substituted or unsubstituted biphenyl group, a substituted or unsubstituted naphthyl group, a substituted or unsubstituted terphenyl group, a substituted or unsubstituted anthracenyl group, a substituted or unsubstituted phenanthrenyl group, a substituted or unsubstituted quaterphenyl group, a substituted or unsubstituted triphenylenyl group, a substituted or unsubstituted fluorenyl group, a substituted or unsubstituted pyridinyl group, a substituted or unsubstituted pyrimidinyl group, a substituted or unsubstituted triazinyl group, a substituted or unsubstituted carbazolyl group, a substituted or unsubstituted dibenzofuranyl group, a substituted or unsubstituted dibenzothiophenyl group, or a combination thereof, $R^f$, $R^g$, $R^h$, $R^i$, $R^j$, $R^k$, $R^l$, and $R^m$ are independently hydrogen, a cyano group, a substituted or unsubstituted C1 to C10 alkyl group, or a substituted or unsubstituted C6 to C12 aryl group.

11. The composition of claim 1, further comprising a dopant.

12. A compound for an organic optoelectronic device, wherein the compound is a compound of Group 1:
[Group 1]
H-1
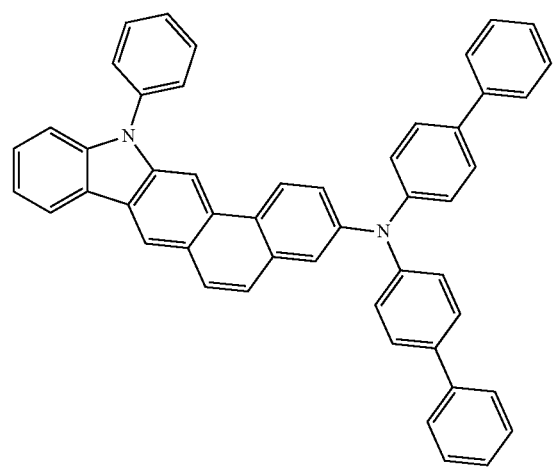
H-2
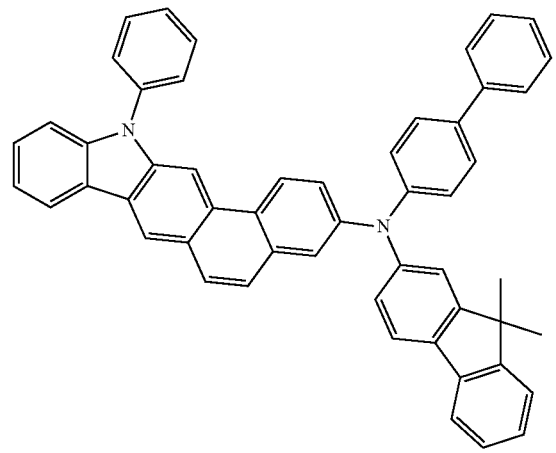
H-3
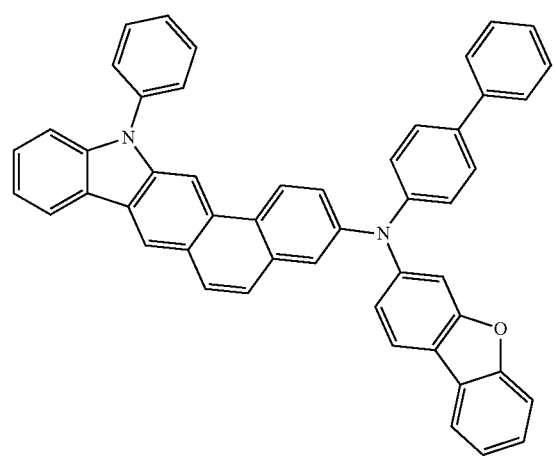
-continued
H-4
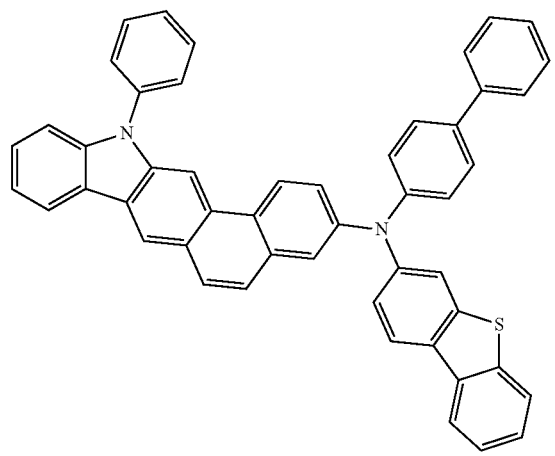
H-5
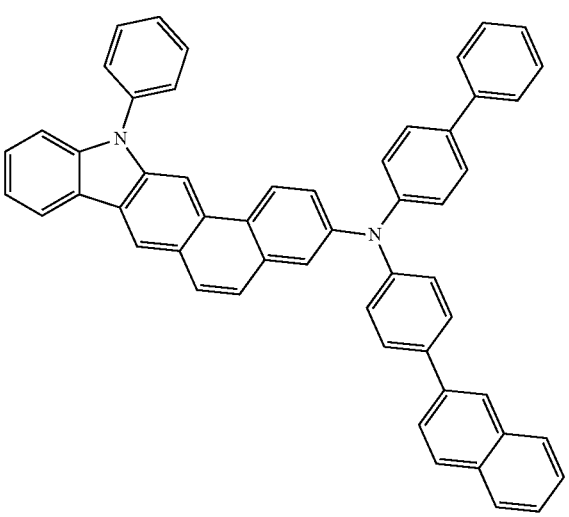
H-6
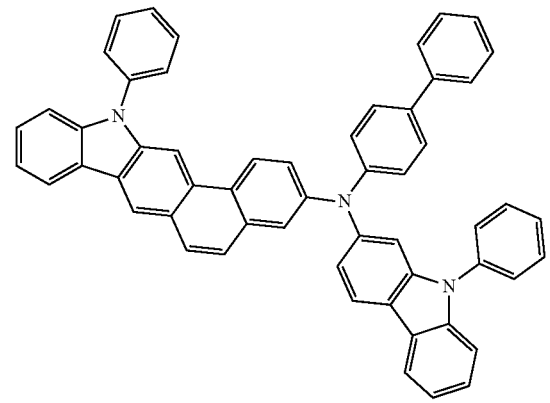

-continued
H-7
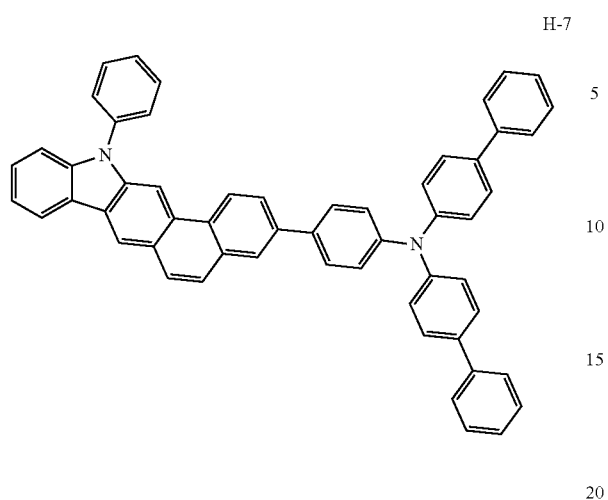
H-8
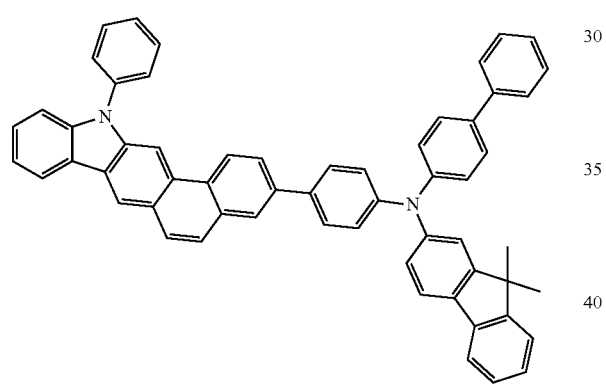
H-9
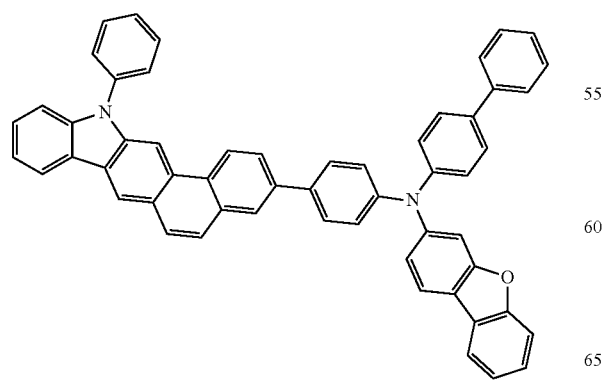
-continued
H-10
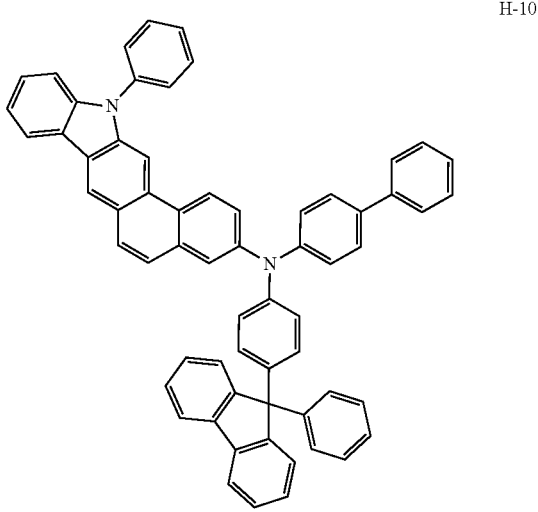
H-11
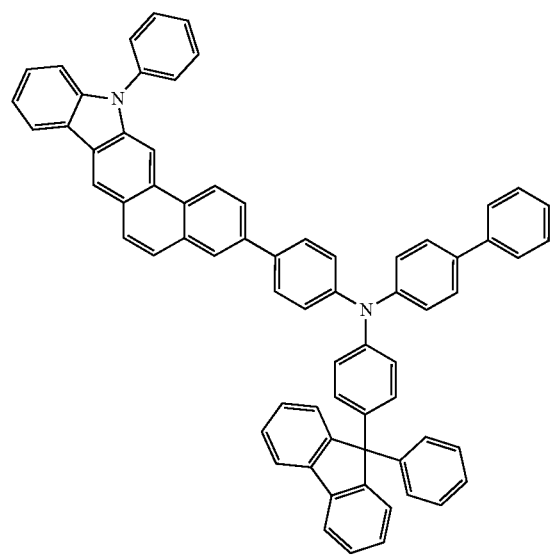
H-12
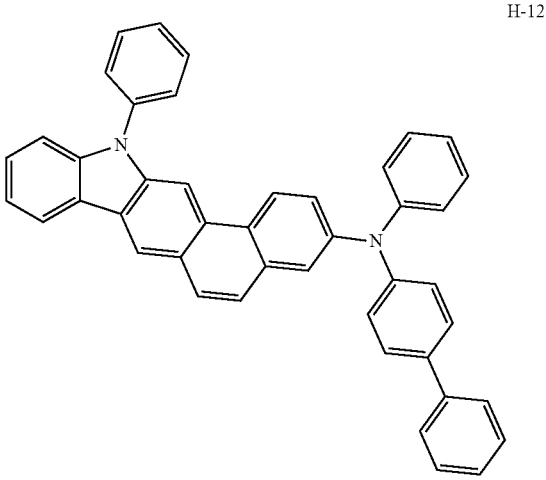

H-13
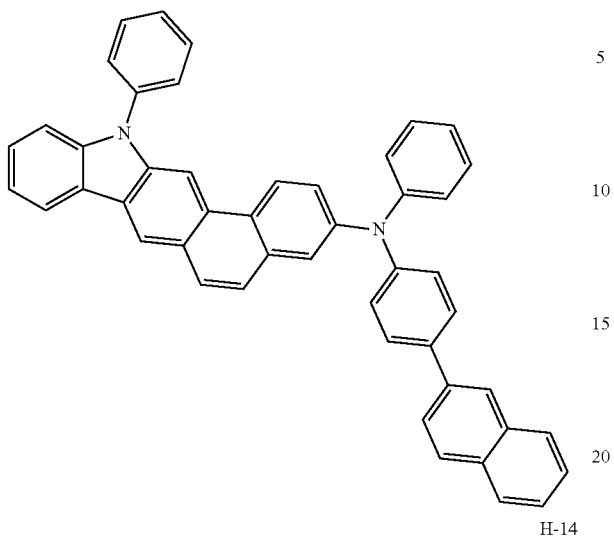
H-14
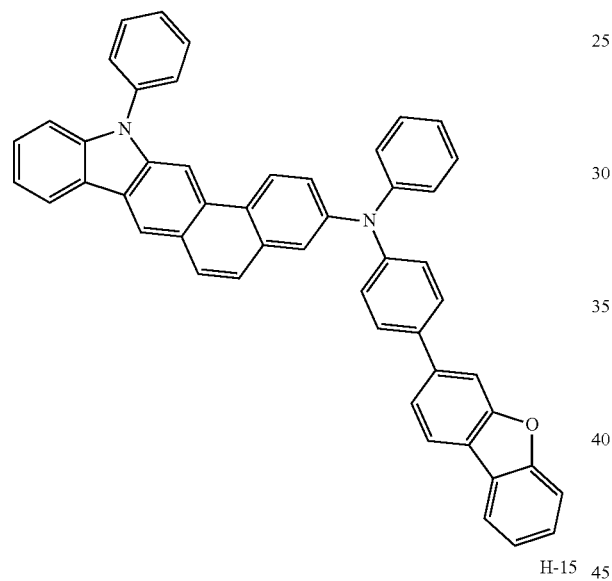
H-15
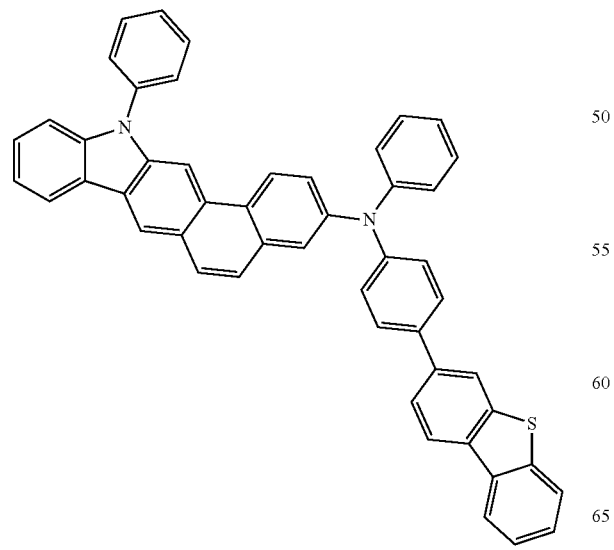
H-16
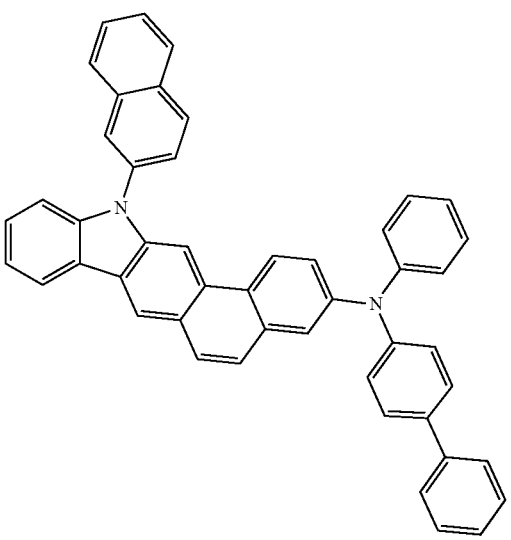
H-17
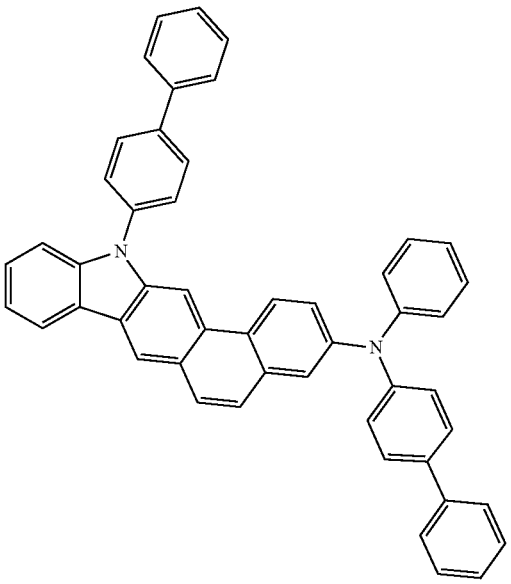
H-18
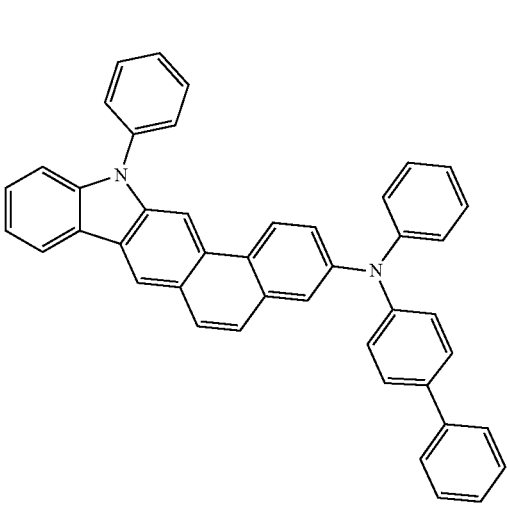

H-19
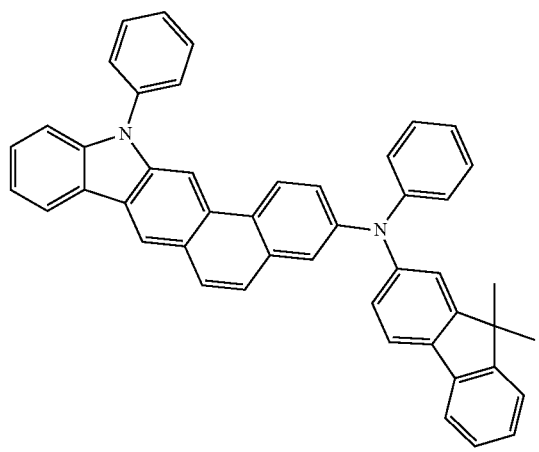
H-22
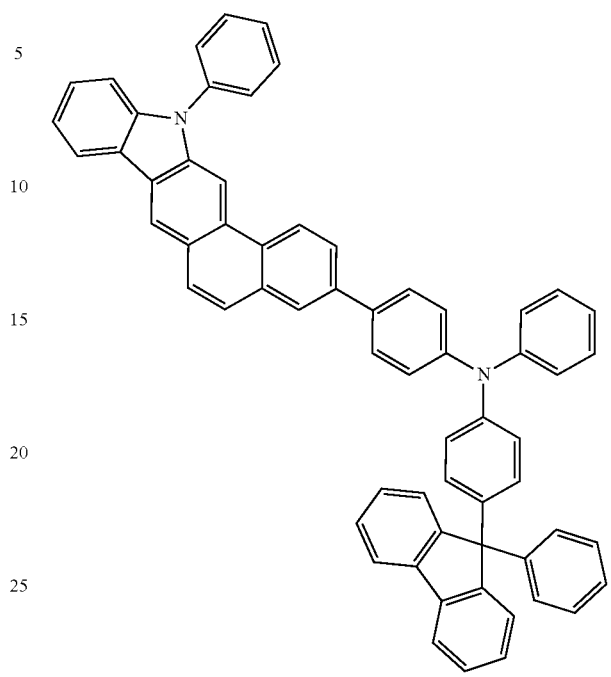
H-20
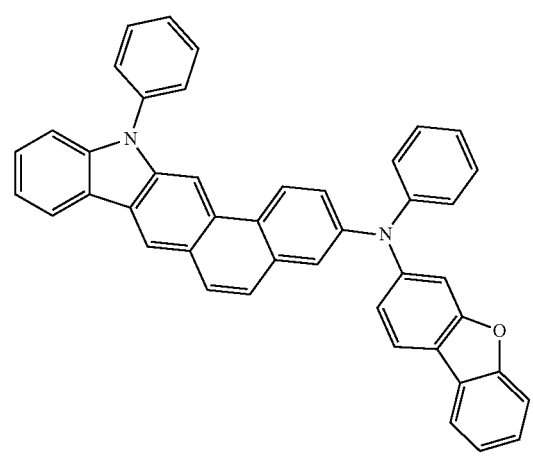
H-23
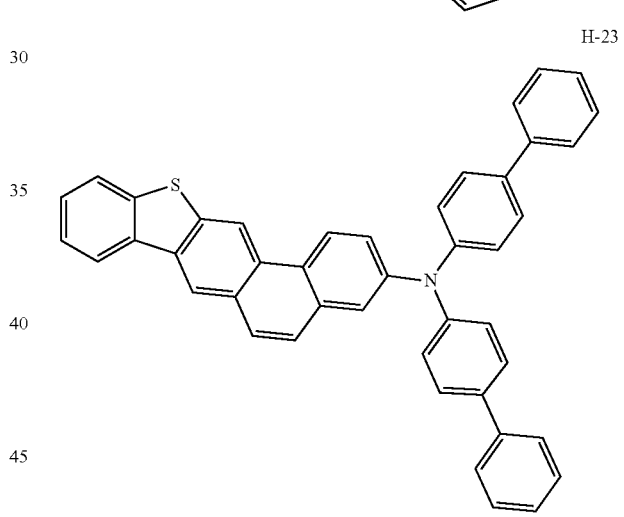
H-21
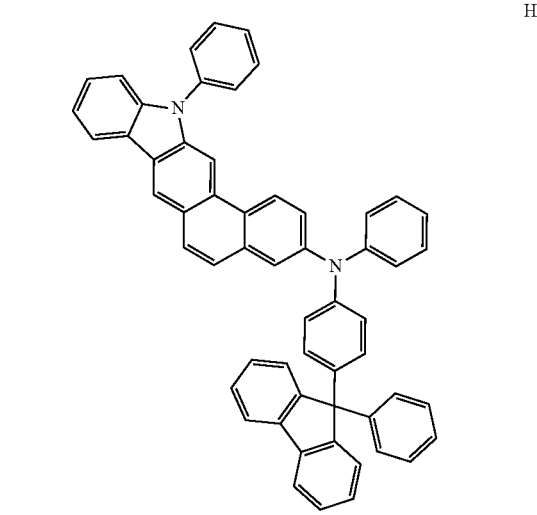
H-24
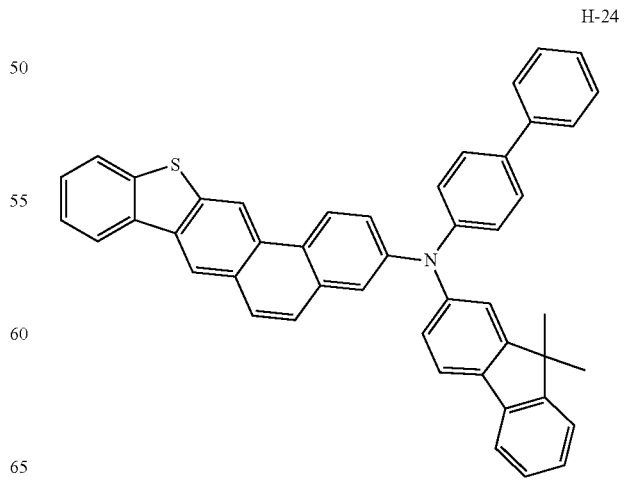

221
-continued
H-25
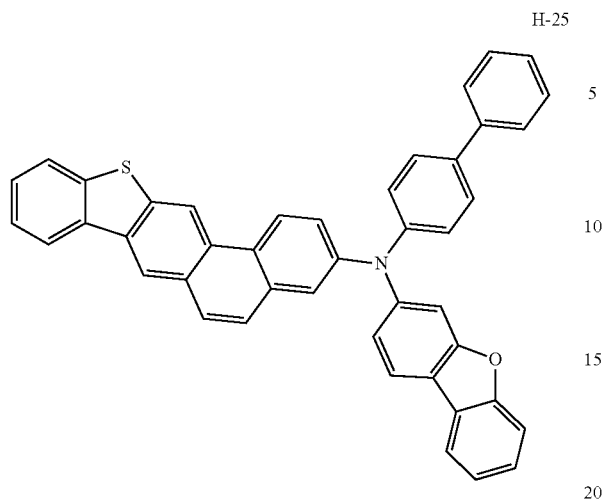
H-26
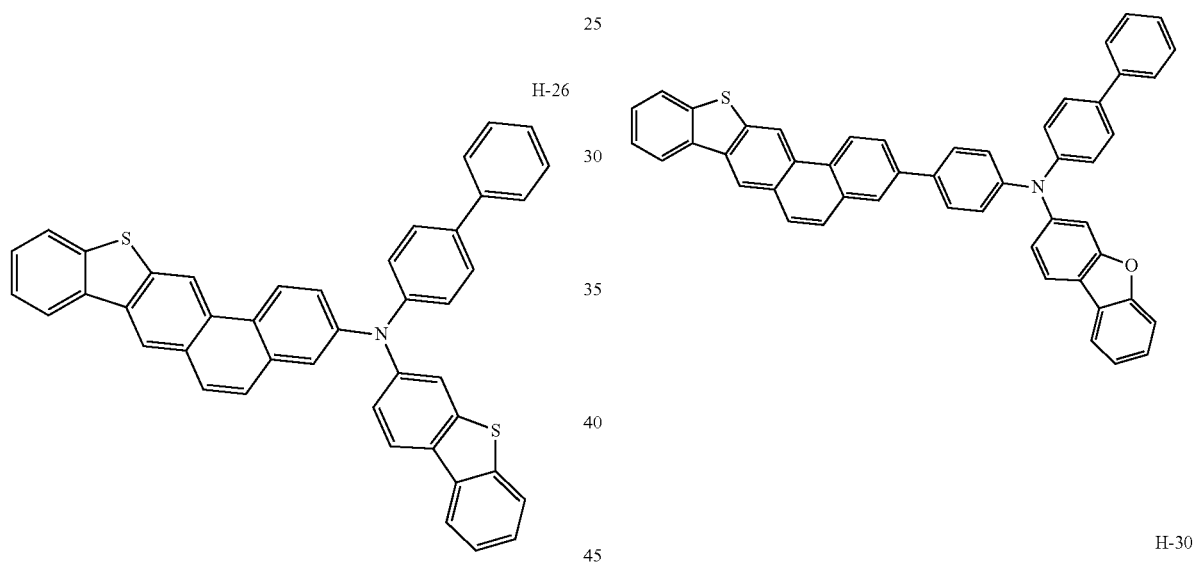
H-27
222
-continued
H-28
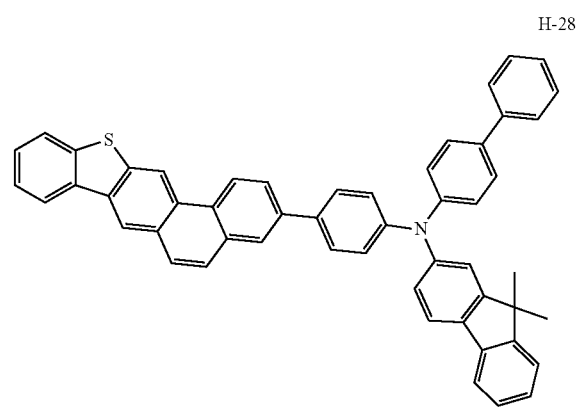
H-29
H-30
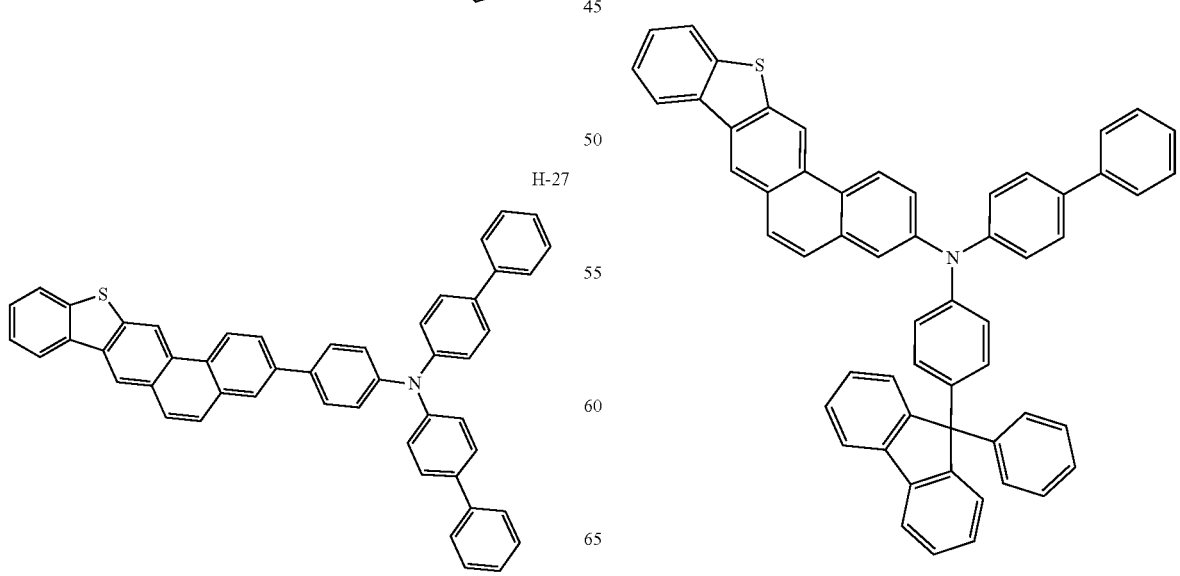

H-31
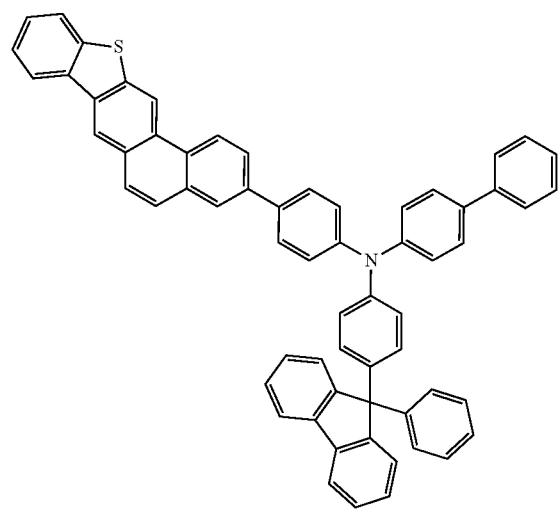
H-32
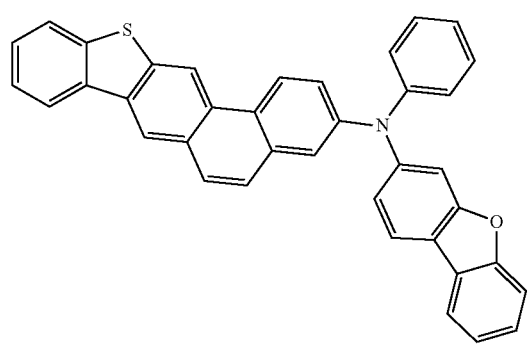 (note: placement approximate)
H-35
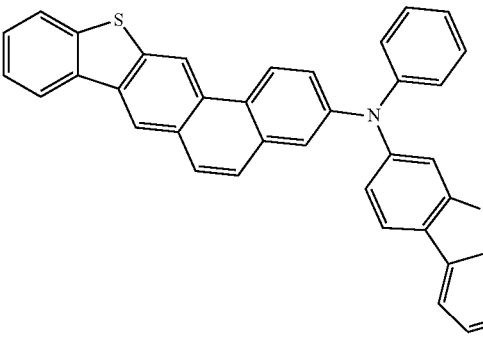
H-36
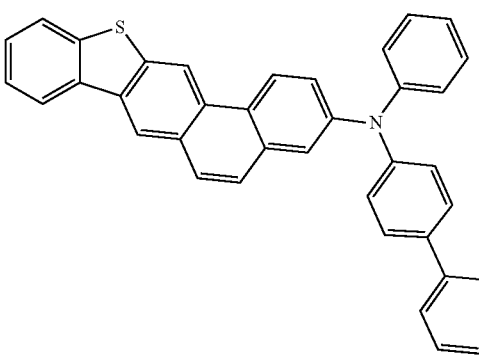
H-37
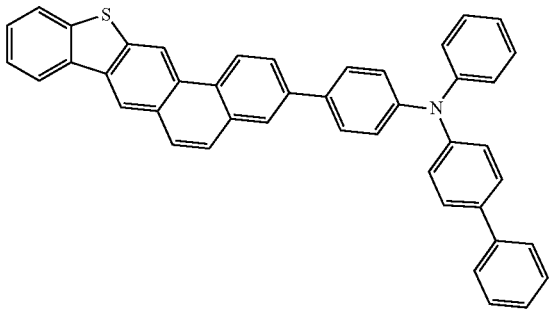
H-38
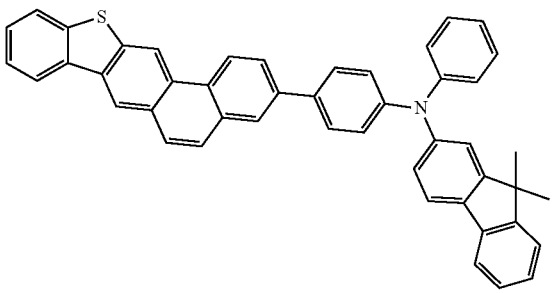

H-39
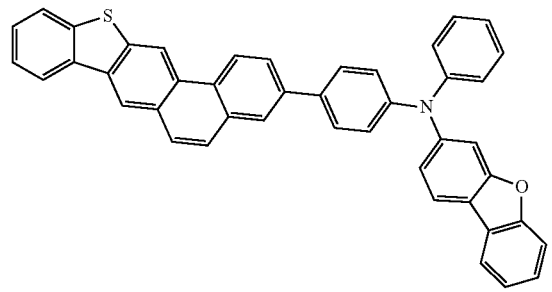
H-40
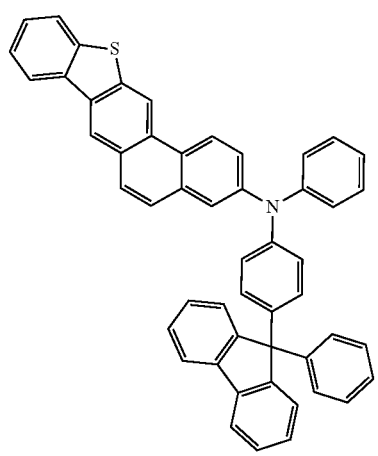
H-41
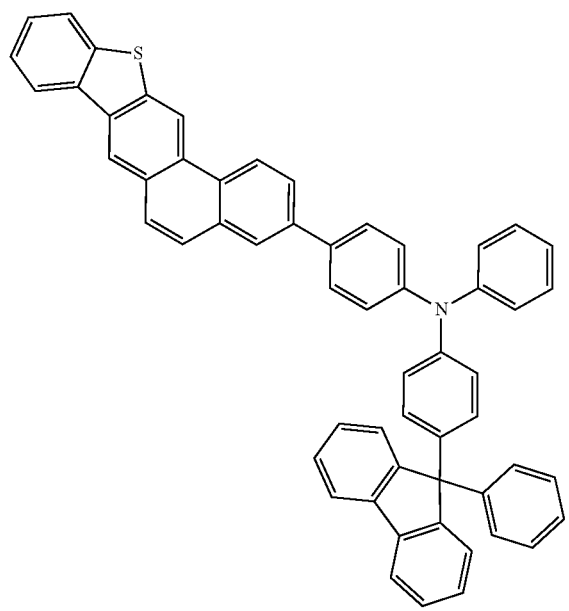
H-42
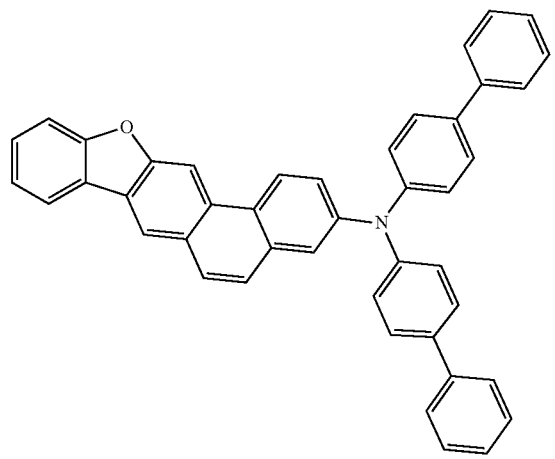
H-43
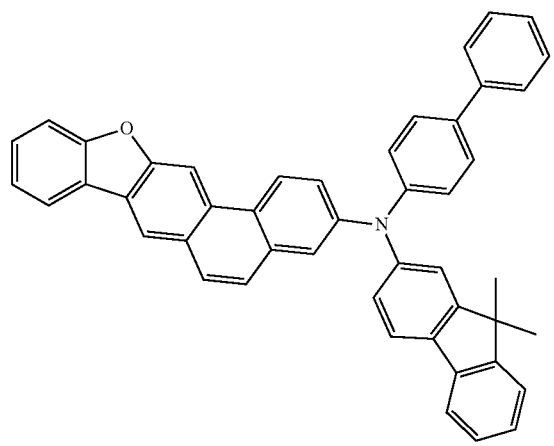
H-44
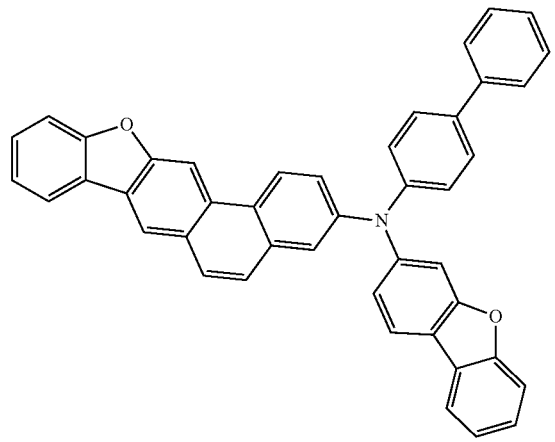

H-45
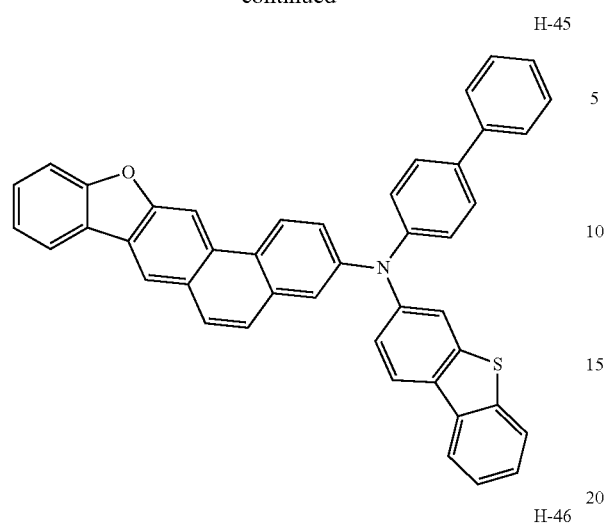
H-46
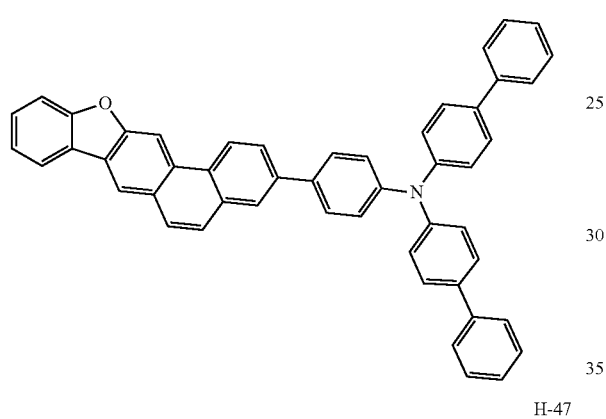
H-47
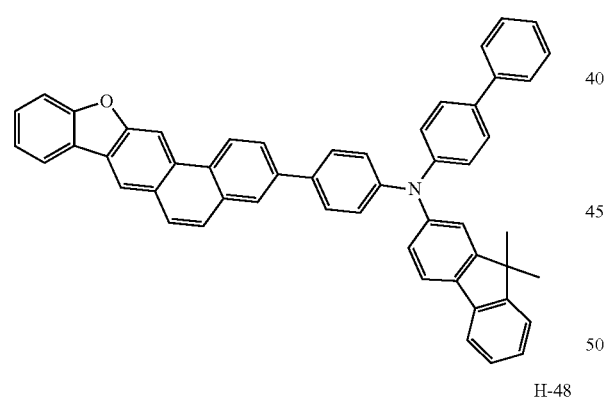
H-48
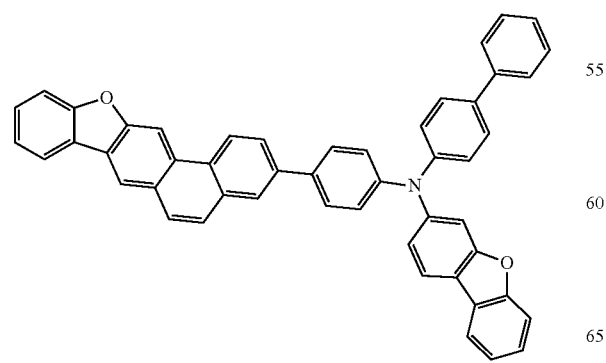
H-49
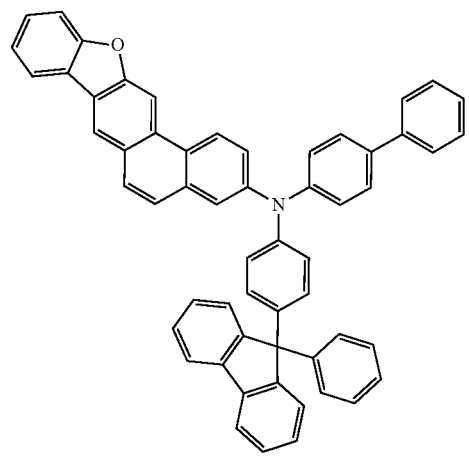
H-50
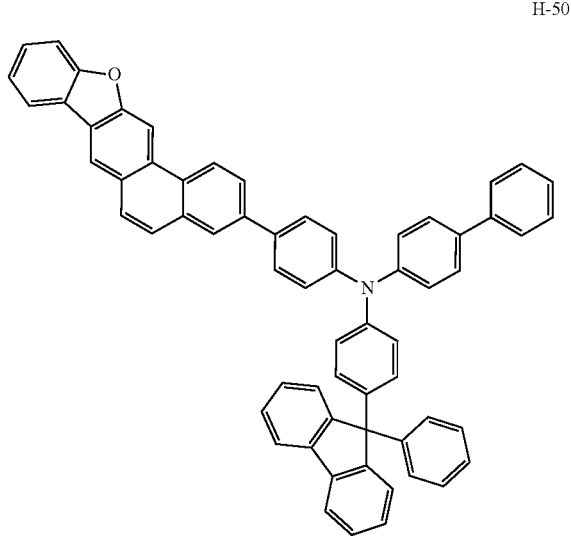
H-51
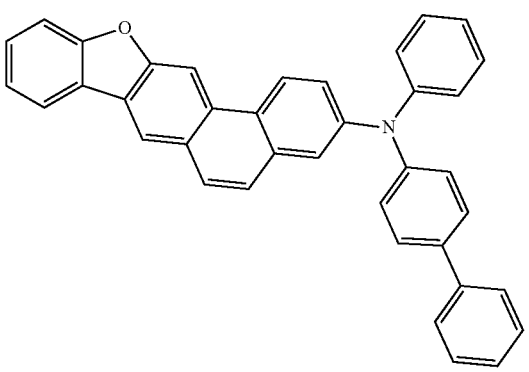

229
-continued
H-52
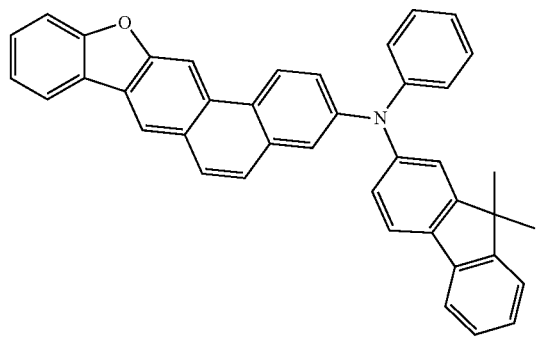
H-53
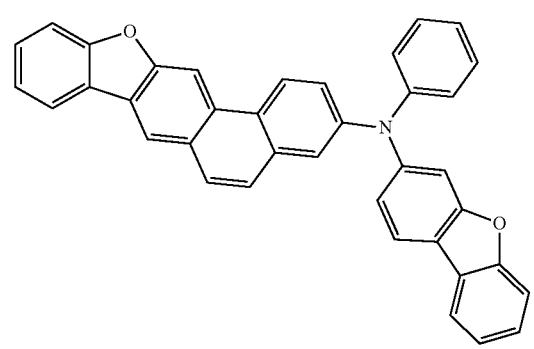
H-54
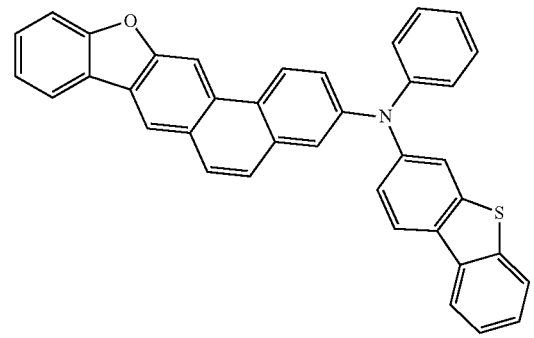
H-55
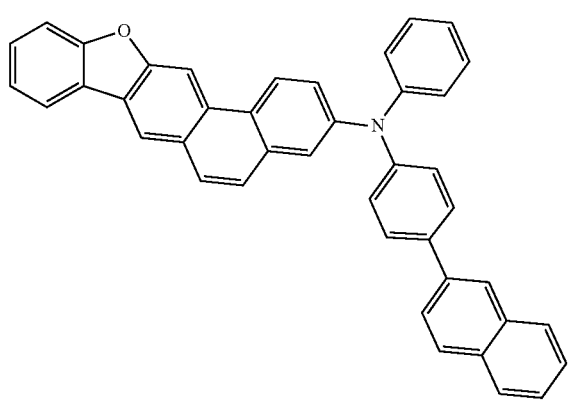
230
-continued
H-56
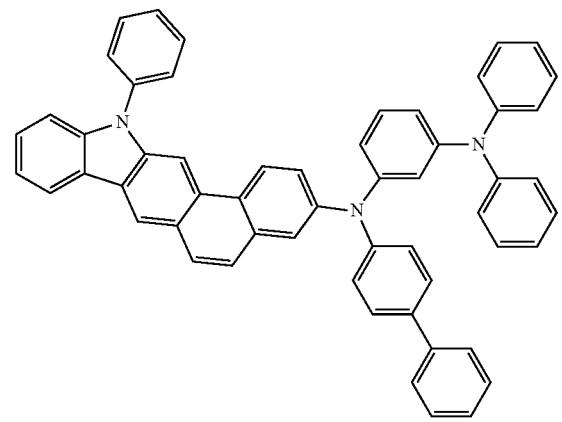
H-57
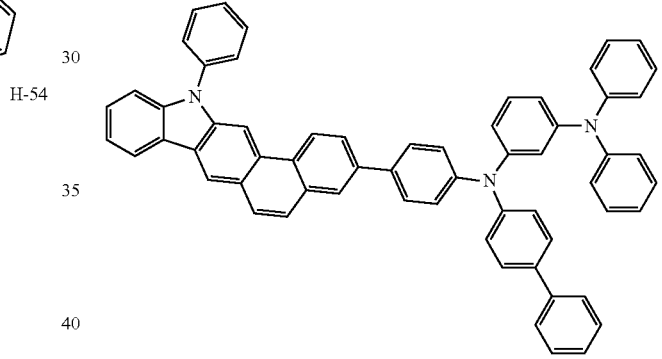
H-58
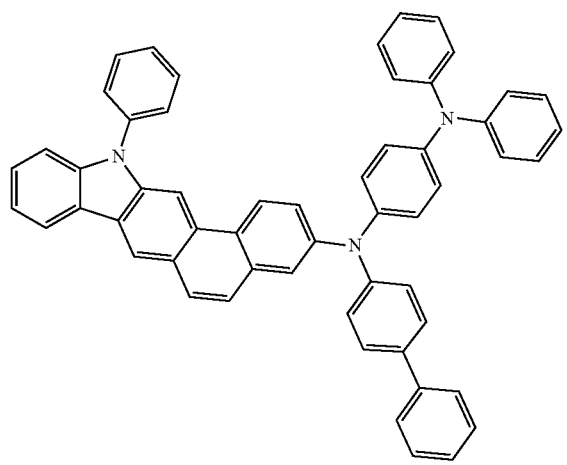

H-59
H-60
H-61
H-62
H-63
H-64
H-65
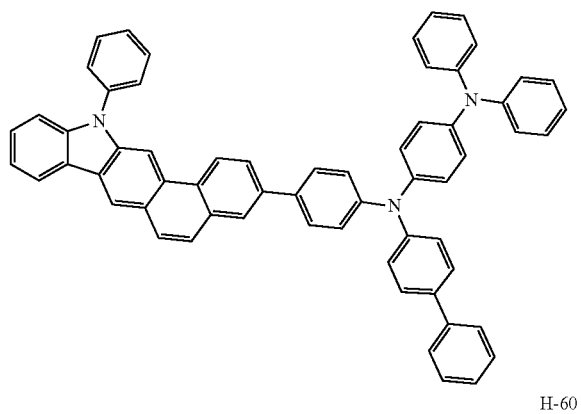
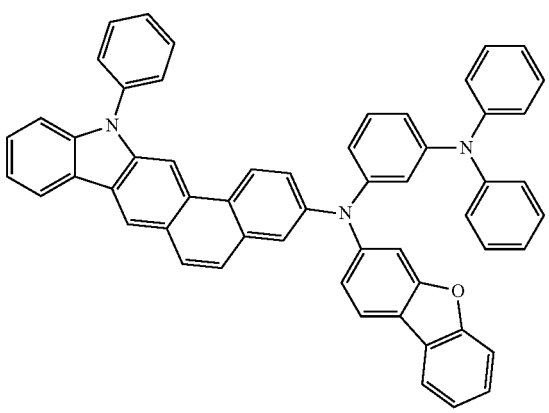
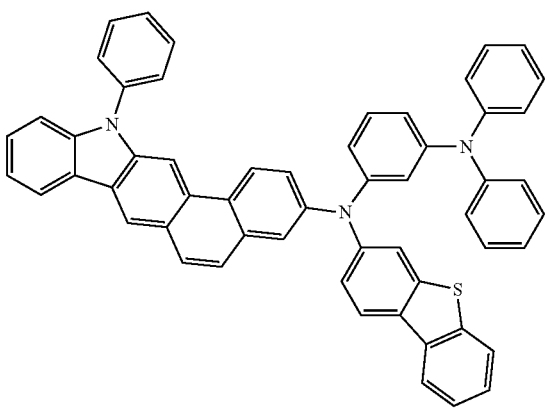
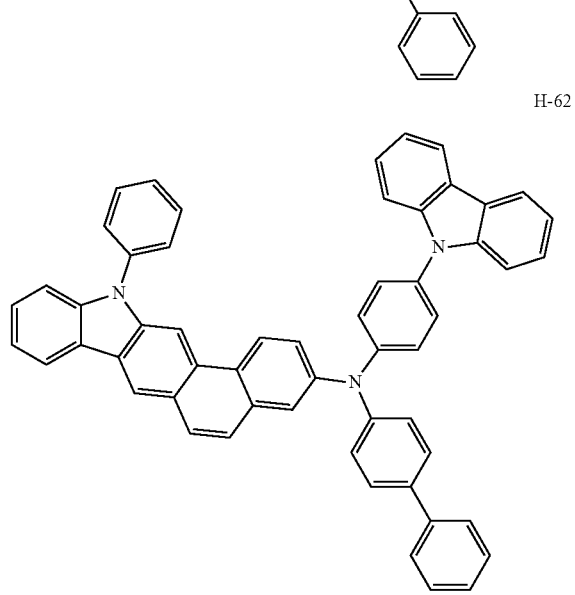

H-66
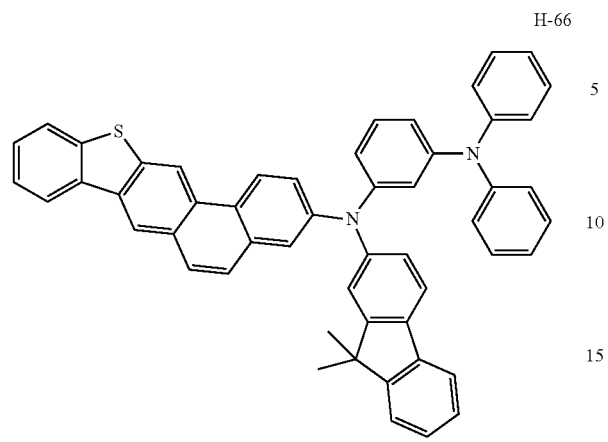
H-67
H-68
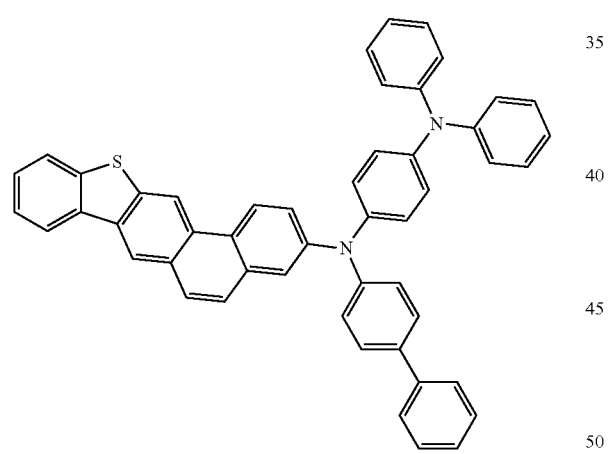
H-69
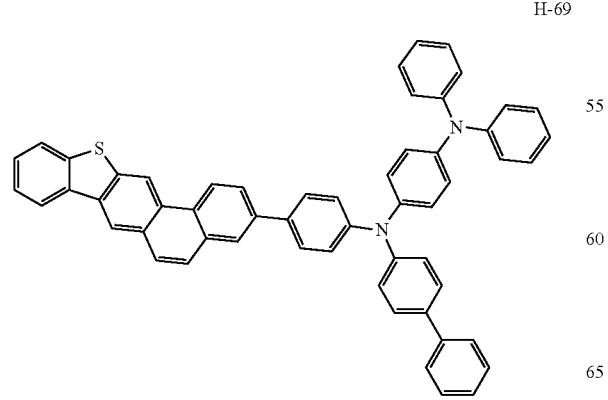
H-70
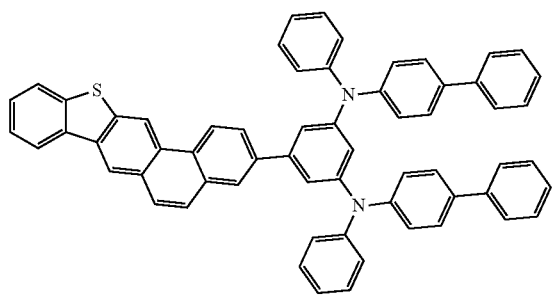
H-71
H-72
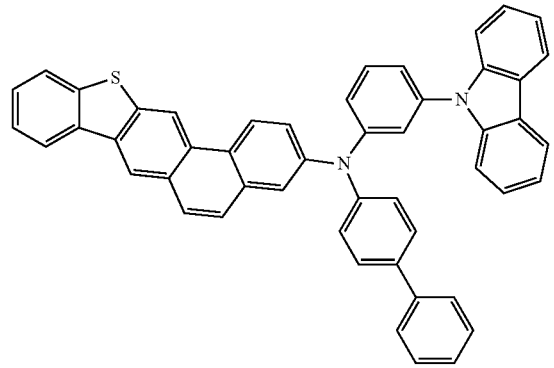
H-73
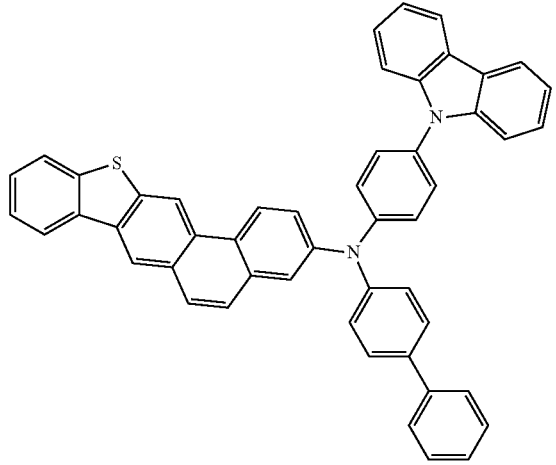

H-74
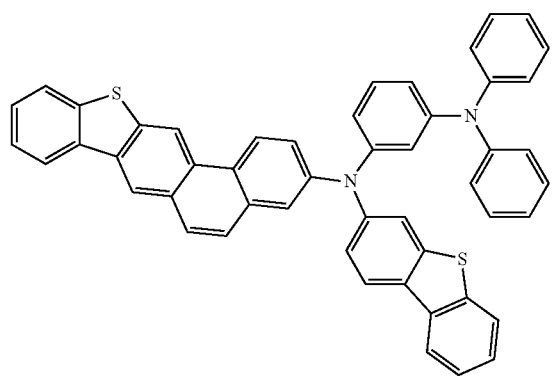
H-75
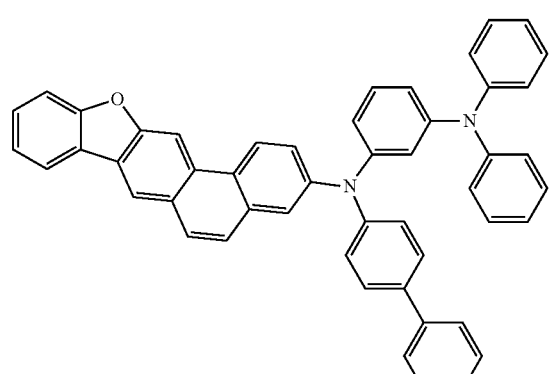
H-76
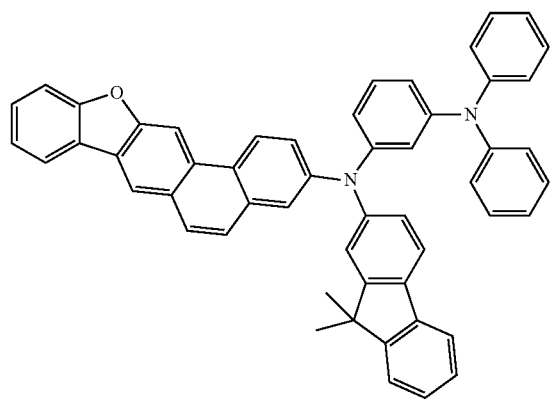
H-77
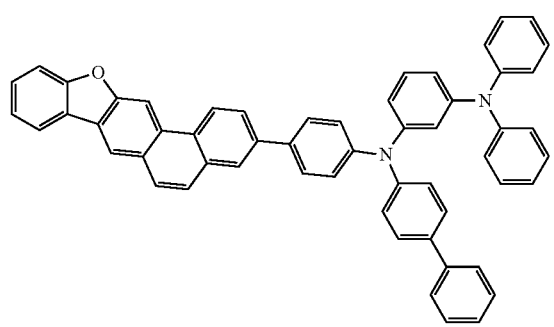
H-78
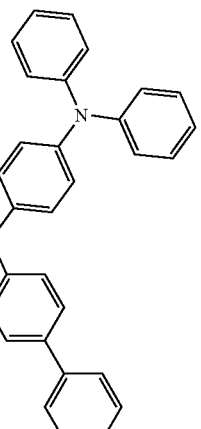
H-79
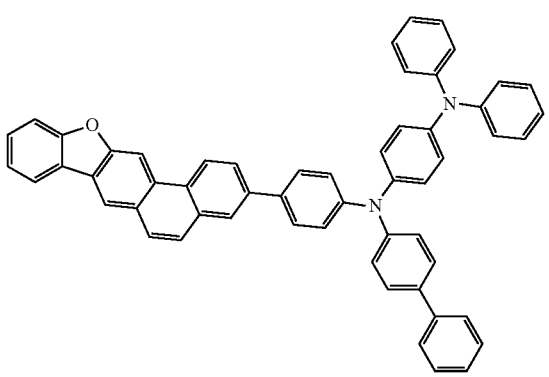
H-80
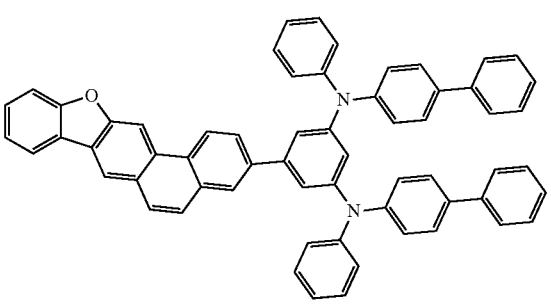
H-81
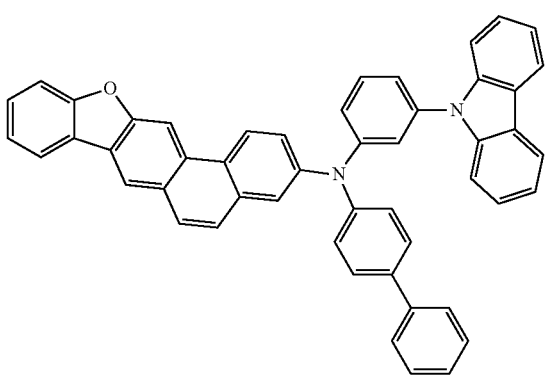

H-82
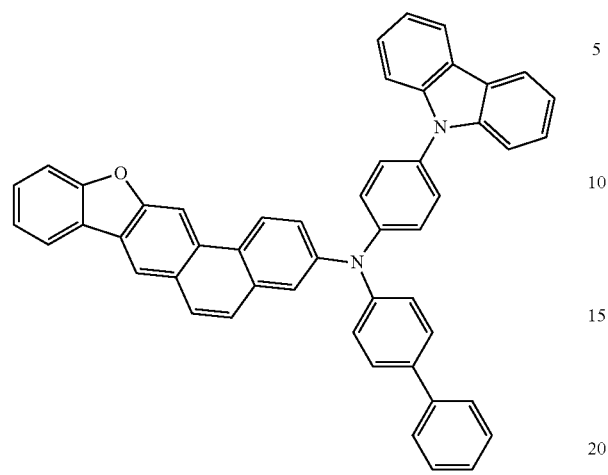
H-83
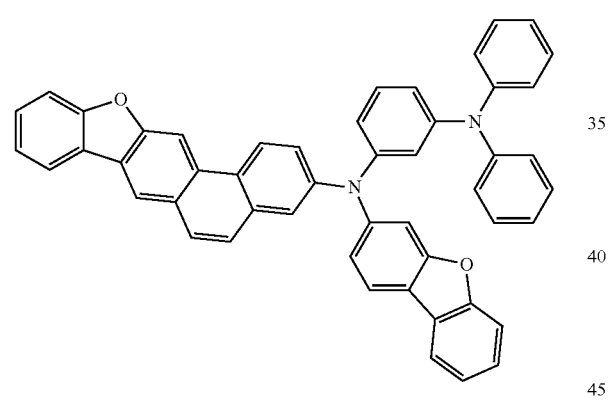
H-84
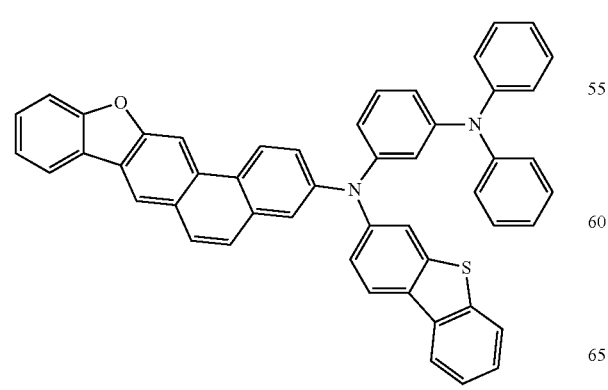
H-85
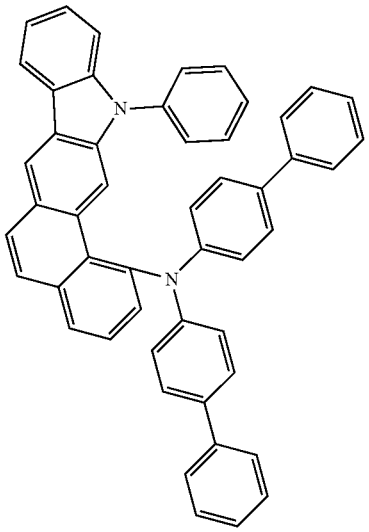
H-86
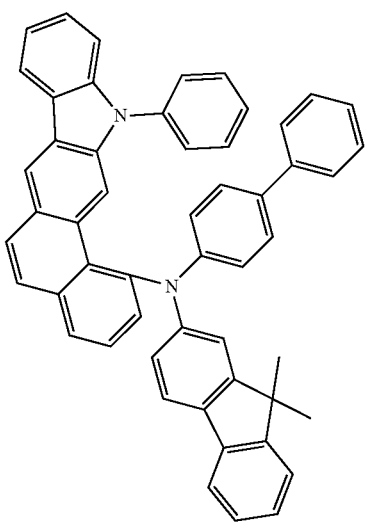
H-87
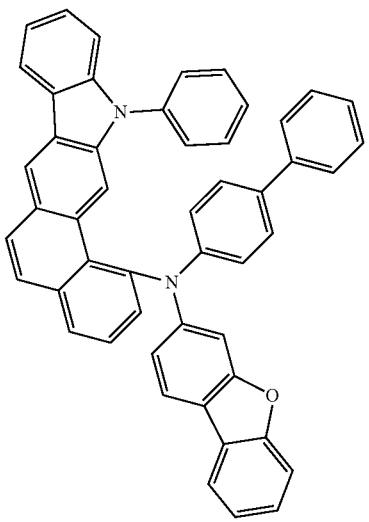

H-88
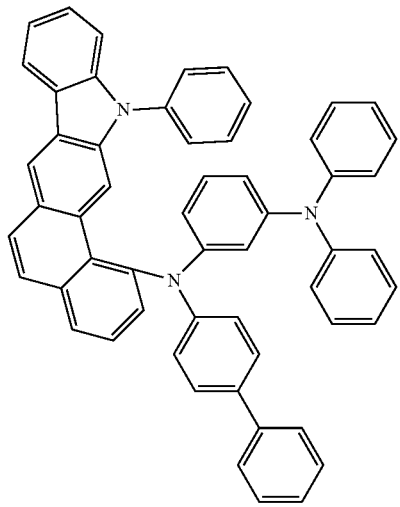
H-89
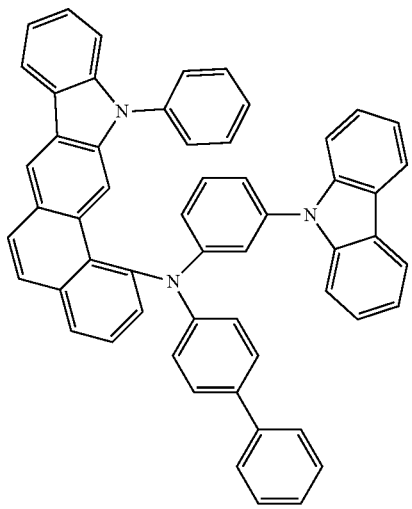
H-90
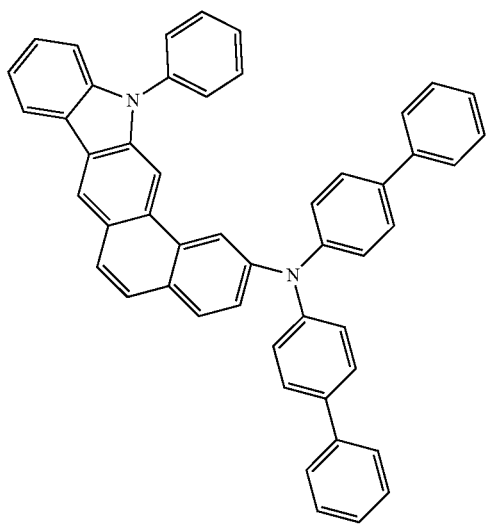
H-91
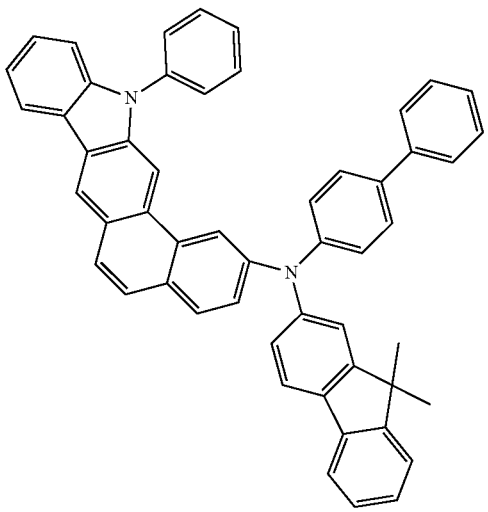
H-92
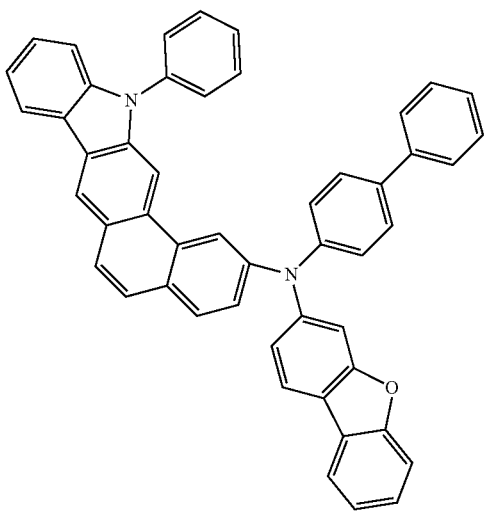
H-93
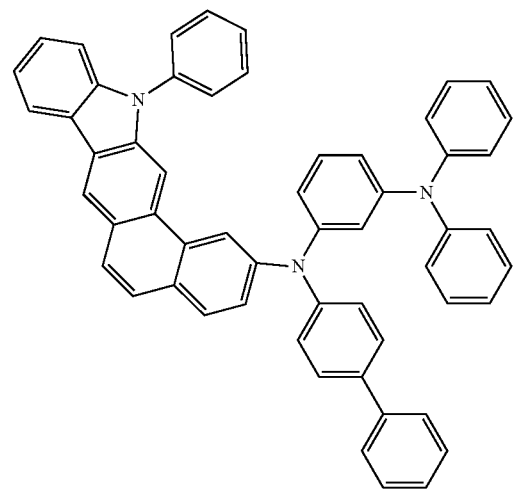

H-94
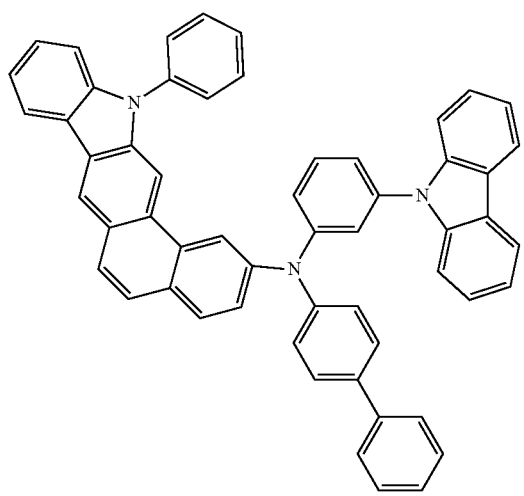
H-95
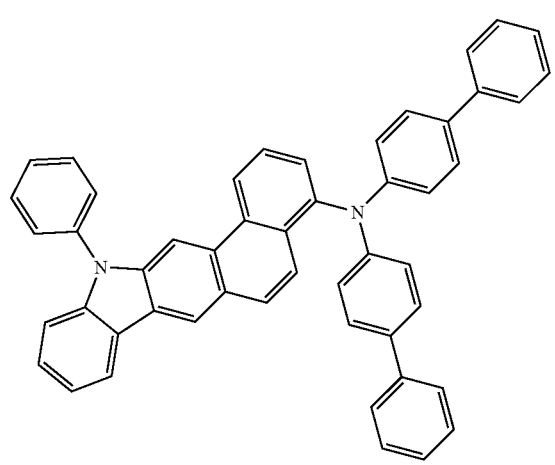
H-96
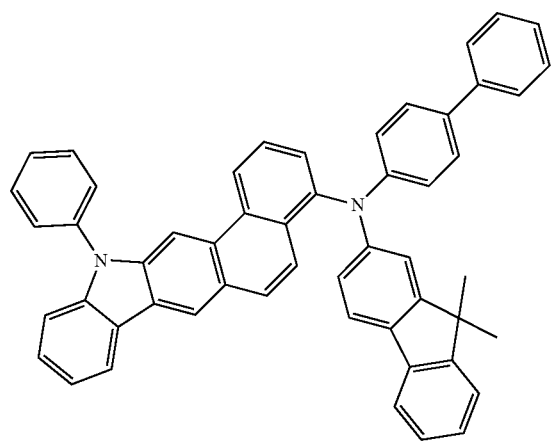
H-97
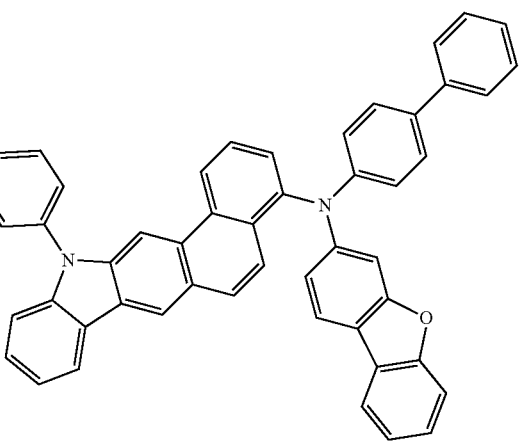
H-98
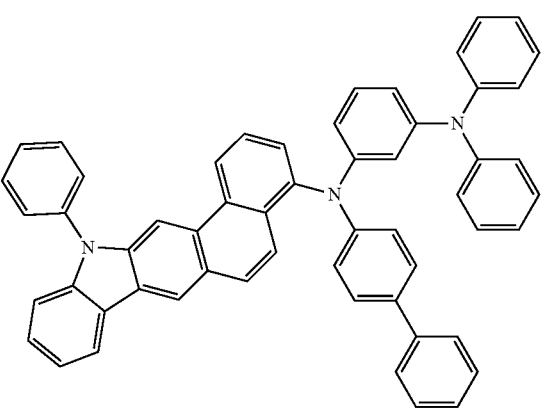
H-99
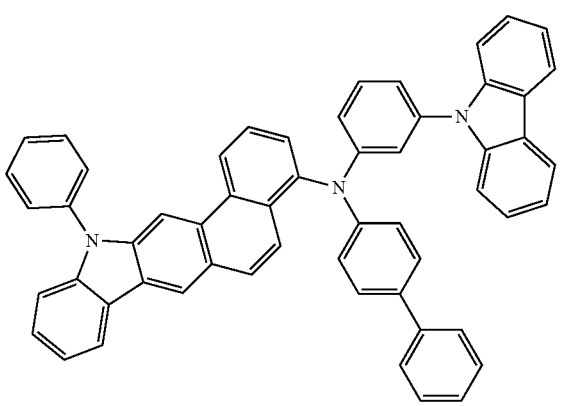

H-100
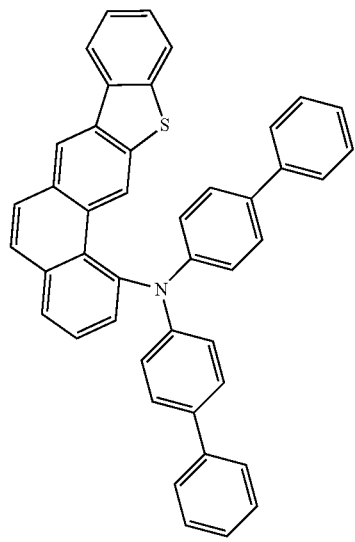
H-101
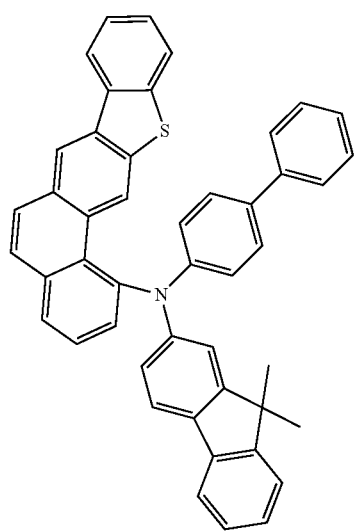
H-102
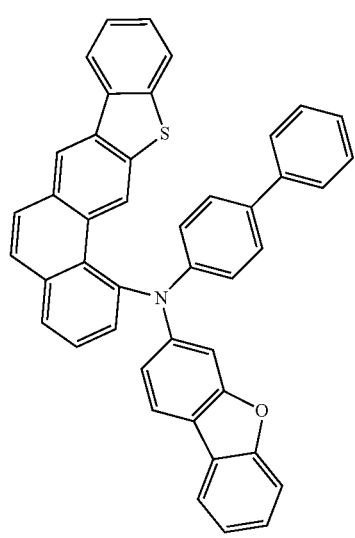
H-103
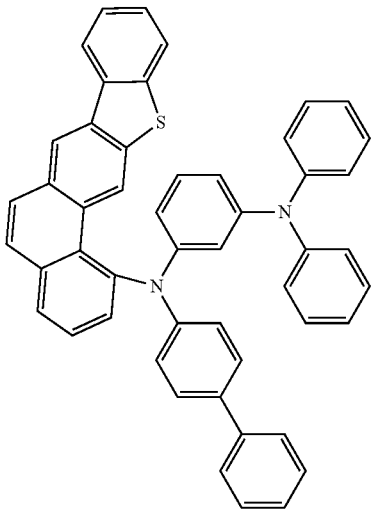
H-104
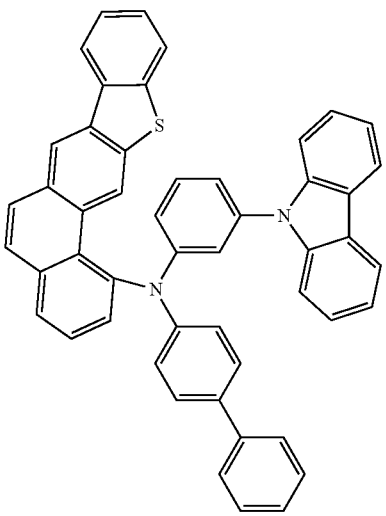
H-105
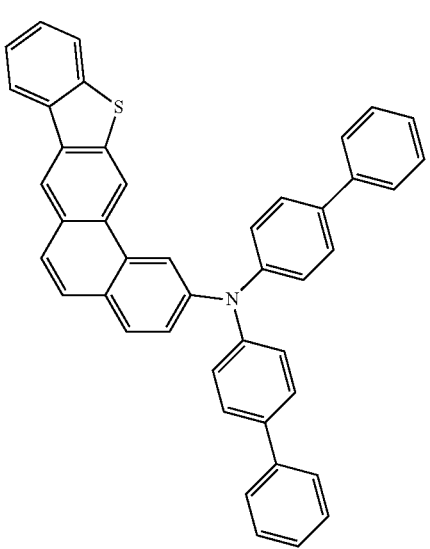

245
-continued
H-106
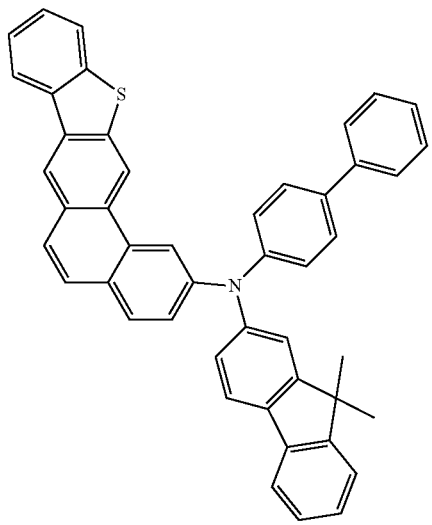
H-107
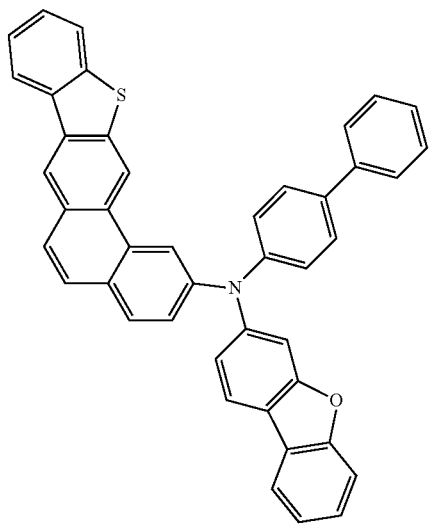
H-108
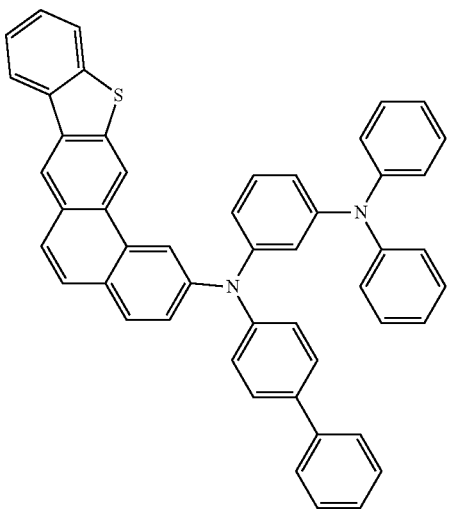
246
-continued
H-109
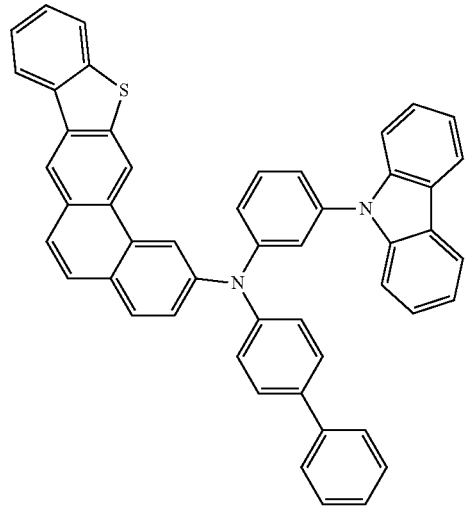
H-110
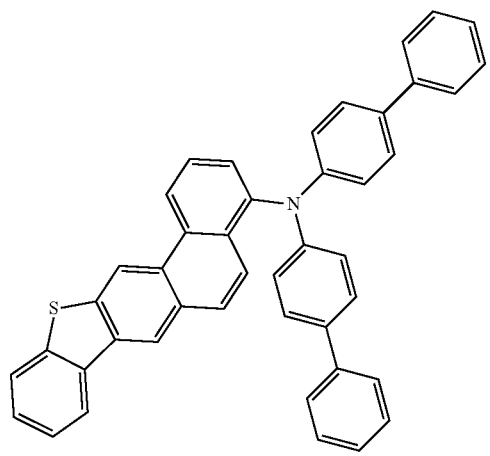
H-111
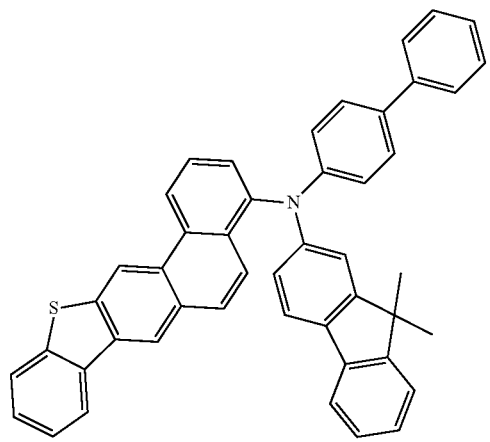

H-112
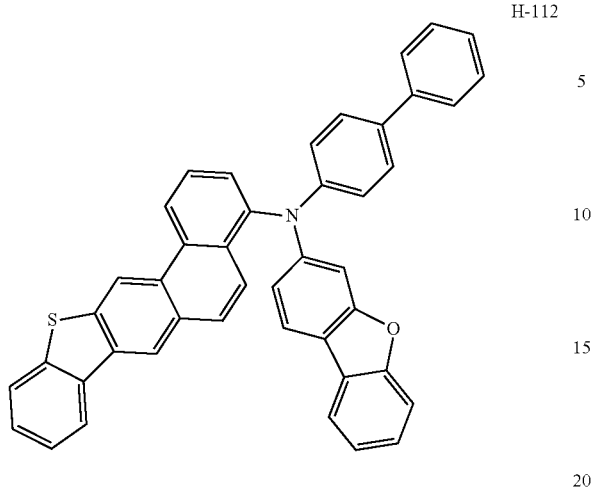
H-115
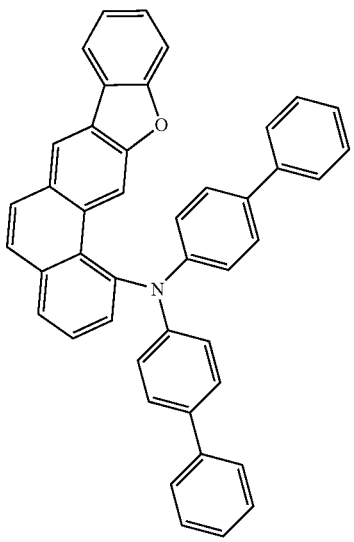
H-113
H-116
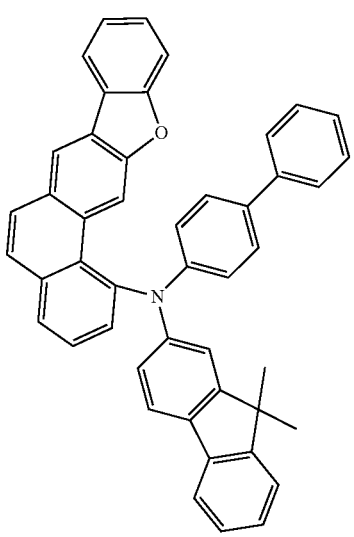
H-114
H-117
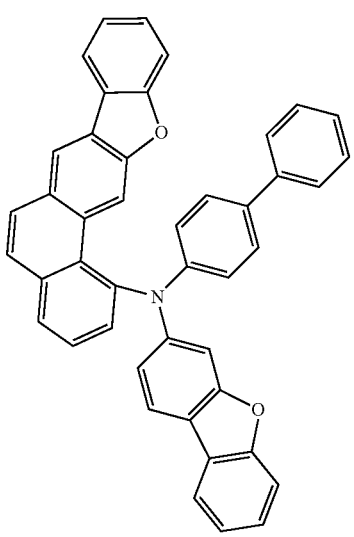

H-118
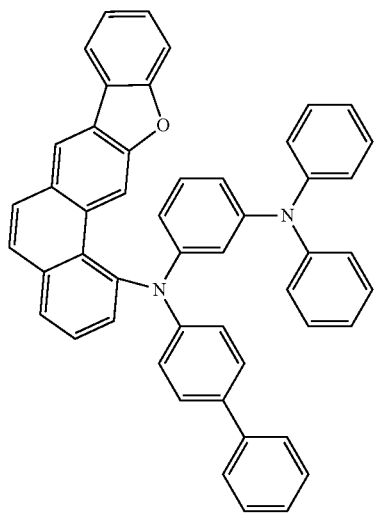
H-119
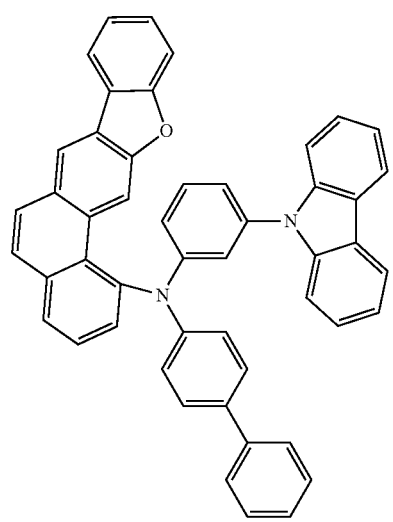
H-120
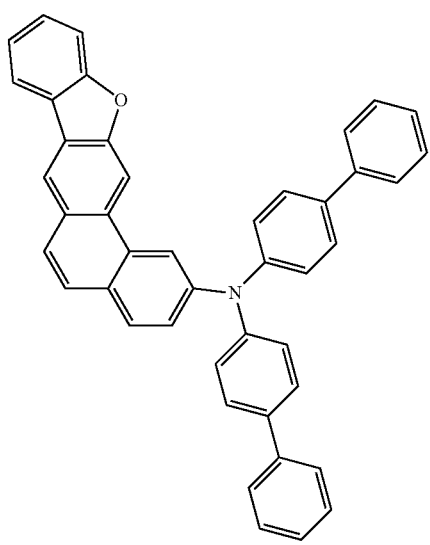
H-121
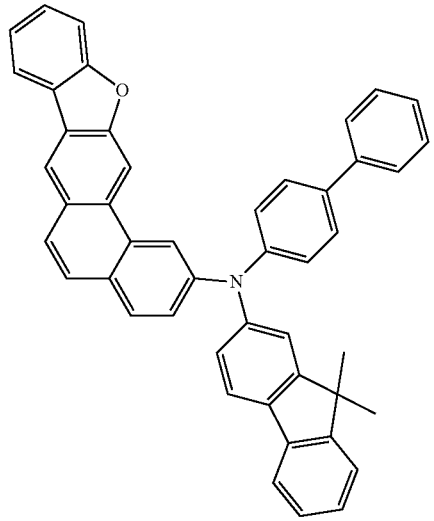
H-122
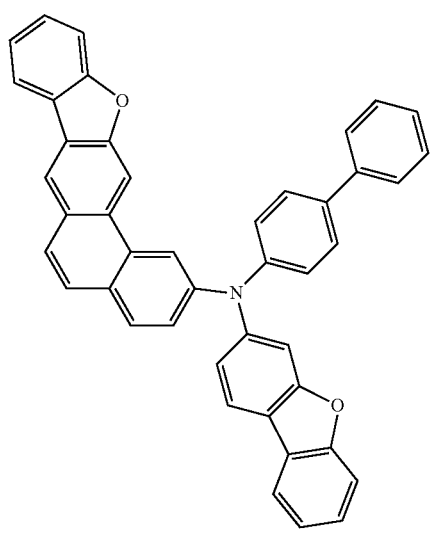
H-123
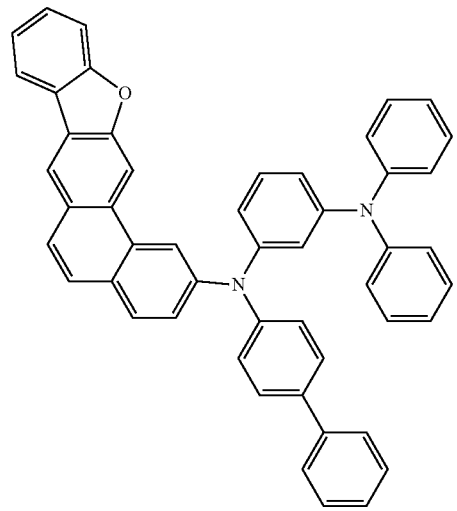

H-124

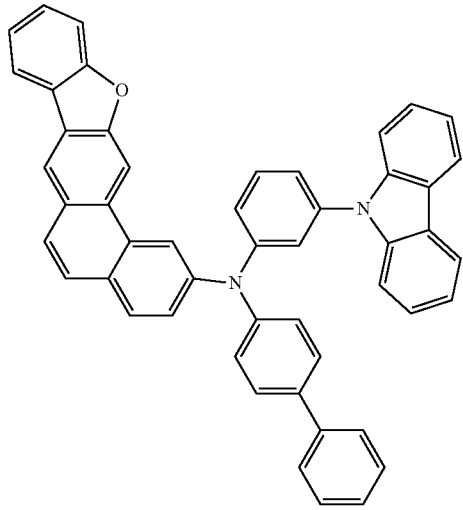

H-125

H-126

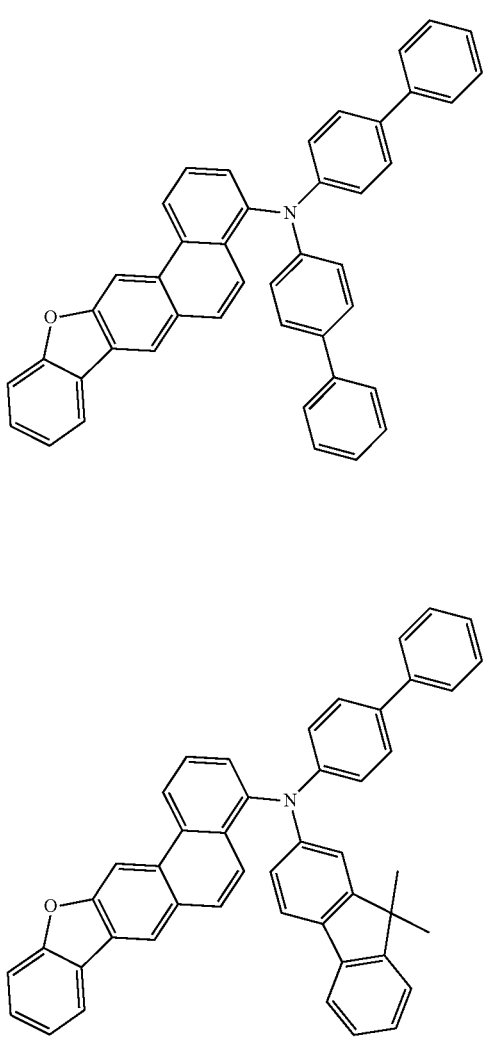

H-127

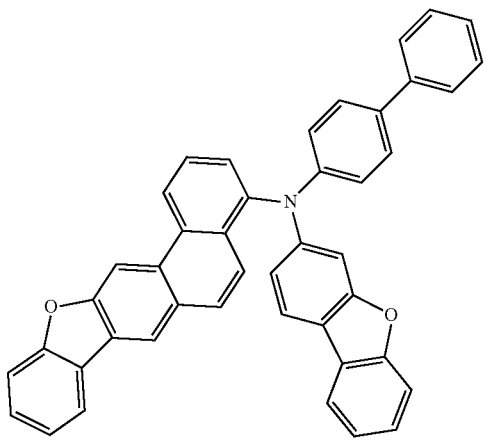

H-128

H-129

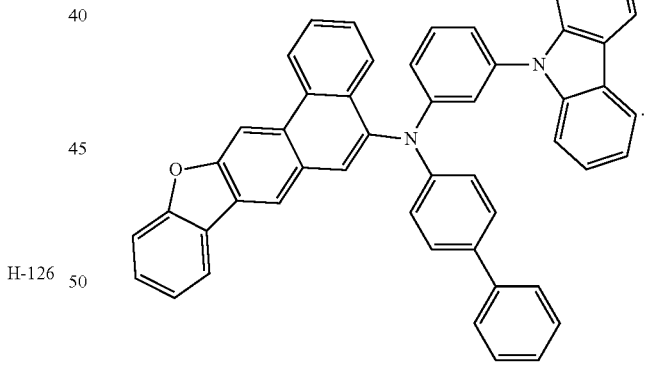

13. An organic optoelectronic device, comprising
an anode and a cathode facing each other,
at least one organic layer between the anode and the cathode,
wherein the at least one organic layer comprises the composition for an organic optoelectronic device of claim 1.

14. The organic optoelectronic device of claim 13, wherein:
the at least one organic layer comprises a light emitting layer, and
the light emitting layer comprises the composition for an organic optoelectronic device.

15. The organic optoelectronic device of claim 14, wherein the first compound for an organic optoelectronic device and the second compound for organic optoelectronic device are each a phosphorescent host of the light emitting layer.

16. The organic optoelectronic device of claim 14, wherein the composition for an organic optoelectronic device is a red light emitting composition.

17. An organic optoelectronic device, comprising: an anode and a cathode facing each other, at least one organic layer between the anode and the cathode, wherein the at least one organic layer comprises the compound for an organic optoelectronic device of claim 12.

18. The organic optoelectronic device of claim 17, wherein:
- the at least one organic layer comprises a light emitting layer, and a hole auxiliary layer between the anode and the light emitting layer,
- the hole auxiliary layer comprises a hole transport layer between the anode and the light emitting layer, and a hole transport auxiliary layer between the hole transport layer and the light emitting layer, and
- the hole transport auxiliary layer comprises the compound for an organic optoelectronic device.

19. A display device comprising the organic optoelectronic device of claim 17.

* * * * *